(12) United States Patent
Stoessel et al.

(10) Patent No.: US 9,169,282 B2
(45) Date of Patent: Oct. 27, 2015

(54) METAL COMPLEXES

(75) Inventors: Philipp Stoessel, Frankfurt (DE);
Holger Heil, Frankfurt am Main (DE);
Dominik Joosten, Frankfurt (DE);
Christof Pflumm, Frankfurt (DE); Anja Gerhard, Egelsbach (DE); Esther Breuning, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 1045 days.

(21) Appl. No.: 13/147,439

(22) PCT Filed: Jan. 14, 2010

(86) PCT No.: PCT/EP2010/000177
§ 371 (c)(1),
(2), (4) Date: Aug. 2, 2011

(87) PCT Pub. No.: WO2010/086089
PCT Pub. Date: Aug. 5, 2010

(65) Prior Publication Data
US 2011/0284799 A1    Nov. 24, 2011

(30) Foreign Application Priority Data
Feb. 2, 2009    (DE) .................... 10 2009 007 038

(51) Int. Cl.
| | | |
|---|---|---|
| H01L 51/54 | (2006.01) | |
| C09K 11/06 | (2006.01) | |
| C07F 19/00 | (2006.01) | |
| C07F 1/00 | (2006.01) | |
| C07F 1/08 | (2006.01) | |
| C07F 15/00 | (2006.01) | |
| C09B 57/00 | (2006.01) | |
| C09B 57/10 | (2006.01) | |
| H01L 51/00 | (2006.01) | |
| H01L 51/50 | (2006.01) | |

(52) U.S. Cl.
CPC . *C07F 19/00* (2013.01); *C07F 1/00* (2013.01); *C07F 1/08* (2013.01); *C07F 15/0033* (2013.01); *C07F 15/0086* (2013.01); *C09B 57/00* (2013.01); *C09B 57/001* (2013.01); *C09B 57/007* (2013.01); *C09B 57/008* (2013.01); *C09B 57/10* (2013.01); *C09K 11/06* (2013.01); *H01L 51/0085* (2013.01); *H01L 51/0087* (2013.01); *H01L 51/0091* (2013.01); C09K 2211/1029 (2013.01); C09K 2211/1044 (2013.01); C09K 2211/1048 (2013.01); C09K 2211/1051 (2013.01); C09K 2211/1074 (2013.01); C09K 2211/185 (2013.01); C09K 2211/188 (2013.01); H01L 51/0037 (2013.01); H01L 51/0059 (2013.01); H01L 51/5016 (2013.01); H01L 2251/308 (2013.01); Y02E 10/549 (2013.01)

(58) Field of Classification Search
CPC ............ C07F 15/0033; C07F 15/0006; C07F 15/002; C07F 15/0046; C07F 15/006; C07F 15/0073; C07F 15/0086; C07F 15/02; C07F 15/04; C07F 15/06; C07F 1/00; C07F 1/08; H01L 51/0083–51/0089; H01L 51/5016; H01L 51/0091; H01L 51/50; H01L 51/5012; C09K 11/06; C09K 2211/1044; C09K 2211/1059; C09K 2211/1074; C09K 2211/182; C09K 2211/183; C09K 2211/185; C09K 2211/187
See application file for complete search history.

(56) References Cited

U.S. PATENT DOCUMENTS

| | | | |
|---|---|---|---|
| 2,743,274 | A | 4/1956 | VanSlyke et al. |
| 3,704,300 | A | 11/1972 | Hardtmann |
| 3,887,566 | A | 6/1975 | Rodway et al. |
| 4,539,507 | A | 9/1985 | VanSlyke et al. |
| 5,151,629 | A | 9/1992 | VanSlyke |
| 5,621,131 | A | 4/1997 | Kreuder et al. |
| 5,840,217 | A | 11/1998 | Lupo et al. |
| 6,169,163 | B1 | 1/2001 | Woo et al. |
| 6,458,909 | B1 | 10/2002 | Spreitzer et al. |
| 6,653,438 | B1 | 11/2003 | Spreitzer et al. |
| 7,345,301 | B2 | 3/2008 | Gerhard et al. |
| 7,723,455 | B2 | 5/2010 | Becker et al. |
| 2005/0069729 | A1 | 3/2005 | Ueda et al. |
| 2005/0123795 | A1* | 6/2005 | Lussier et al. ............... 428/690 |
| 2005/0171076 | A1 | 8/2005 | Meggers et al. |
| 2005/0227112 | A1 | 10/2005 | Ise et al. |
| 2006/0019942 | A1 | 1/2006 | Meggers et al. |
| 2006/0058494 | A1 | 3/2006 | Busing et al. |

(Continued)

FOREIGN PATENT DOCUMENTS

| | | |
|---|---|---|
| DE | 2206012 | 8/1972 |
| DE | 2166398 | 1/1974 |

(Continued)

OTHER PUBLICATIONS

Hennig, H., et al., "Coordination tendencies of acidic amino groups. 12. EPR investigations on cationic copper(II) chelates of 5mino-2-methyl-3H-imidazo[4,5-h]quinoline," Zeitschrift fuer Chemie (1971), vol. 11, No. 3, pp. 115-117, Sekt. Chem., Karl-Marx-Univ., Leipzig, Fed. Rep. Ger. XP-002589524. (Article is not in the English language but can be found in the International Search Report).

(Continued)

*Primary Examiner* — Michael H Wilson
(74) *Attorney, Agent, or Firm* — Drinker Biddle & Reath LLP

(57) ABSTRACT

The present invention relates to metal complexes and to electronic devices, in particular organic electroluminescent devices, comprising these metal complexes.

38 Claims, No Drawings

(56) References Cited

U.S. PATENT DOCUMENTS

| | | |
|---|---|---|
| 2006/0063027 A1 | 3/2006 | Vestweber et al. |
| 2006/0142604 A1 | 6/2006 | Bach et al. |
| 2006/0175958 A1 | 8/2006 | Gerhard et al. |
| 2006/0220004 A1* | 10/2006 | Stossel et al. ............... 257/40 |
| 2006/0252936 A1 | 11/2006 | Stossel et al. |
| 2006/0284140 A1 | 12/2006 | Breuning et al. |
| 2007/0135635 A1 | 6/2007 | Stossel et al. |
| 2007/0176147 A1 | 8/2007 | Buesing et al. |
| 2007/0205714 A1 | 9/2007 | Busing et al. |
| 2007/0231598 A1 | 10/2007 | Busing et al. |
| 2007/0249834 A1 | 10/2007 | Stossel et al. |
| 2007/0281182 A1 | 12/2007 | Schulte et al. |
| 2008/0027220 A1 | 1/2008 | Stossel et al. |
| 2008/0312396 A1 | 12/2008 | Stoessel et al. |
| 2009/0134384 A1 | 5/2009 | Stoessel et al. |
| 2009/0134784 A1 | 5/2009 | Lin et al. |
| 2009/0163545 A1 | 6/2009 | Goldfarb |
| 2009/0167166 A1 | 7/2009 | Bach et al. |
| 2009/0302742 A1 | 12/2009 | Komori et al. |
| 2009/0302752 A1 | 12/2009 | Parham et al. |
| 2010/0102305 A1 | 4/2010 | Heun et al. |
| 2010/0141125 A1 | 6/2010 | Otsu et al. |
| 2010/0141126 A1 | 6/2010 | Otsu et al. |
| 2010/0187977 A1 | 7/2010 | Kai et al. |
| 2010/0227978 A1 | 9/2010 | Stoessel et al. |
| 2010/0244009 A1 | 9/2010 | Parham et al. |
| 2011/0068304 A1 | 3/2011 | Parham et al. |
| 2011/0105778 A1 | 5/2011 | Stoessel et al. |
| 2011/0121274 A1 | 5/2011 | Parham et al. |
| 2011/0140043 A1 | 6/2011 | Stoessel et al. |

FOREIGN PATENT DOCUMENTS

| | | |
|---|---|---|
| DE | 102008033943 | 1/2010 |
| DE | 102008036982 | 2/2010 |
| DE | 102008056688 | 5/2010 |
| EP | 652273 | 5/1995 |
| EP | 0 676 461 | 10/1995 |
| EP | 0 707 020 | 4/1996 |
| EP | 0 842 208 | 5/1998 |
| EP | 0 894 107 | 2/1999 |
| EP | 1 028 136 | 8/2000 |
| EP | 1205527 | 5/2002 |
| EP | 1617710 | 1/2006 |
| EP | 1617711 | 1/2006 |
| EP | 1731584 | 12/2006 |
| GB | 1327311 | 8/1973 |
| JP | 2002110357 A | 4/2002 |
| JP | 2004131464 A | 4/2004 |
| JP | 2004/288381 | 10/2004 |
| JP | 2005317516 A | 11/2005 |
| JP | 2005-347160 | 12/2005 |
| WO | WO-92/18552 | 10/1992 |
| WO | WO-98/27136 | 6/1998 |
| WO | WO-00/22026 | 4/2000 |
| WO | WO-02/060910 | 8/2002 |
| WO | WO-2004/013080 | 2/2004 |
| WO | WO-2004/037887 | 5/2004 |
| WO | WO-2004/041901 | 5/2004 |
| WO | WO-2004/058911 | 7/2004 |
| WO | WO-2004/070772 | 8/2004 |
| WO | WO-2004/081017 | 9/2004 |
| WO | WO-2004/085449 | 10/2004 |
| WO | WO-2004/093207 | 10/2004 |
| WO | WO-2004/113468 | 12/2004 |
| WO | WO-2005/011013 | 2/2005 |
| WO | WO-2005/014689 | 2/2005 |
| WO | WO-2005/039246 | 4/2005 |
| WO | WO-2005/040302 | 5/2005 |
| WO | WO-2005/042548 | 5/2005 |
| WO | WO-2005/104264 | 11/2005 |
| WO | WO-2005/111113 | 11/2005 |
| WO | WO-2005/111172 | 11/2005 |
| WO | WO-2005/113563 | 12/2005 |
| WO | WO-2006/003000 | 1/2006 |
| WO | WO-2006/005627 | 1/2006 |
| WO | WO-2006/008069 | 1/2006 |
| WO | WO-2006/117052 | 11/2006 |
| WO | WO-2007/063754 | 6/2007 |
| WO | WO-2007/065523 | 6/2007 |
| WO | WO-2007/095118 | 8/2007 |
| WO | WO-2007095118 A2 | 8/2007 |
| WO | WO-2007/137725 | 12/2007 |
| WO | WO-2008/056746 | 5/2008 |
| WO | WO-2008/086851 | 7/2008 |
| WO | WO-2008/140114 | 11/2008 |
| WO | WO-2008/143059 | 11/2008 |
| WO | WO-2008140114 A1 | 11/2008 |
| WO | WO-2008143059 A1 | 11/2008 |
| WO | WO-2008/156879 | 12/2008 |
| WO | WO-2009/062578 | 5/2009 |

OTHER PUBLICATIONS

English Translation of Japanese Office Action for Application No. 2011-54668, dated Feb. 4, 2014.

Henning, H. et al., "Chelate-forming dye couplers, III. Synthesis and properties of blue-green couplers with imidazo[4,5-h]-quinoline as the complex-forming group", Journal fuer Praktische Chemie (Leipzig), vol. 317, No. 5, (1975), pp. 853-860.

Henning, H. et al., Coordination tendencies of acidic amino groups. 12. EPR 5-amino-2-methyl-3H-imidazo[4,5-h]quinoline, Zeitschrift fuer Chemie, vol. 11, No. 3, (1971), pp. 115-117.

Karshtedt, D. et al., "Stoichiometric and Catalytic Arene Activations by Platinum Complexes Containing Bidentate Monoanionic Nitrogen-Based Ligands", Organometallics, vol. 25, No. 7, (2006), pp. 1801-1811.

Lee, J. et al., "An Unusual Coordination Mode for Amides: Lone-Pair Binding via Nitrogen", Inorganic Chemistry, vol. 34, No. 25, (1995), pp. 6295-6301.

Wu, F. et al., "Bidentate Ligands That Contain Pyrrole in Place of Pyridine", Inorg. Chem., vol. 39, No. 3, (2000), pp. 584-590.

* cited by examiner

METAL COMPLEXES

CROSS-REFERENCE TO RELATED APPLICATIONS

This application is a national stage application (under 35 U.S.C. §371) of PCT/EP2010/000177, filed Jan. 14, 2010, which claims benefit of Germany application 10 2009 007 038.9, filed Feb. 2, 2009.

BACKGROUND OF THE INVENTION

The structure of organic electroluminescent devices (OLEDs) in which organic semiconductors are employed as functional materials is described, for example, in U.S. Pat. No. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs which exhibit triplet emission, in particular with respect to efficiency, operating voltage and lifetime. This applies, in particular, to OLEDs which emit in the relatively short-wave range, i.e. green and in particular blue. Thus, no blue-emitting triplet emitters which meet the technical requirements for industrial use are known to date.

In accordance with the prior art, the triplet emitters employed in phosphorescent OLEDs are, in particular, iridium complexes. An improvement in these OLEDs has been achieved by employing metal complexes containing polypodal ligands or cryptates, as a consequence of which the complexes have higher thermal stability, which results in a longer lifetime of the OLEDs (WO 04/081017, WO 05/113563, WO 06/008069). However, these complexes are not suitable for blue emission, in particular for saturated deep-blue emission.

The prior art furthermore discloses iridium complexes which contain imidazophenanthridine derivatives or diimidazoquinazoline derivatives as ligands (WO 07/095,118). These complexes can result in blue phosphorescence on use in organic electroluminescent devices, depending on the precise structure of the ligand. Here too, further improvements are desirable with respect to efficiency, operating voltage and lifetime. In particular, there is also a need for improvement here with respect to the colour coordinates in order to be able to achieved deep-blue emission.

BRIEF SUMMARY OF THE INVENTION

The object of the present invention is therefore to provide novel metal complexes which are suitable as emitters for use in OLEDs. In particular, the object is to provide emitters which are suitable for blue-phosphorescent OLEDs.

Surprisingly, it has been found that certain metal chelate complexes described in greater detail below achieve this object and result in improvements in the organic electroluminescent device, in particular with respect to the operating voltage, the efficiency and the emission colour. The present invention therefore relates to these metal complexes and to organic electroluminescent devices which comprise these complexes.

The invention thus relates to a compound of the formula (1)

$$M(L)_n(L')_m \qquad \text{formula (1)}$$

where the compound of the general formula (1) contains a moiety $M(L)_n$ of the formula (2) or formula (3):

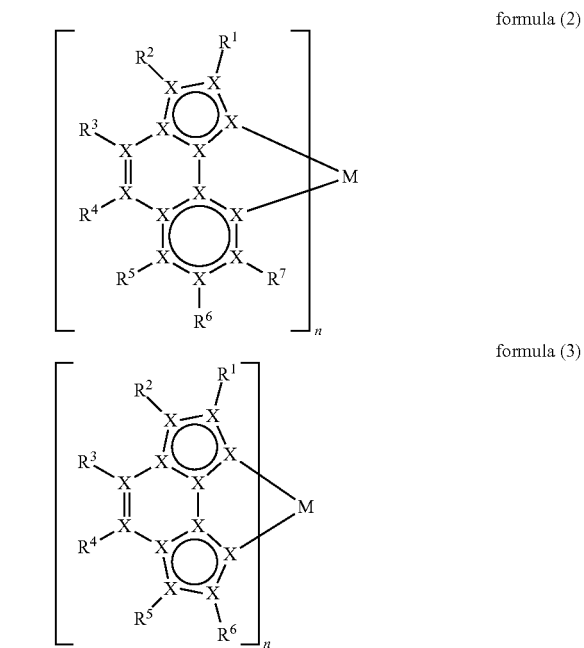

where the following applies to the symbols and indices used:

M is a metal;

X is selected on each occurrence, identically or differently, from the group consisting of C, N and B; and all X together represent a $14\pi$ electron system;

$R^1$ to $R^7$ are on each occurrence, identically or differently, H, D, F, Cl, Br, I, $N(R^8)_2$, CN, $NO_2$, $Si(R^8)_3$, $B(OR^8)_2$, C(=O)$R^8$, P(=O)$(R^8)_2$, S(=O)$R^8$, $S(=O)_2R^8$, $OSO_2R^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, C≡C, $Si(R^8)_2$, $Ge(R^8)_2$, $Sn(R^8)_2$, C=O, C=S, C=Se, C=NR^8$, P(=O)$(R^8)$, SO, $SO_2$, $NR^8$, O, S or $CONR^8$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or an aralkyl or heteroaralkyl group having 5 to 60 aromatic ring atoms, which may be substituted by one or more radicals $R^8$, or a diarylamino group, diheteroarylamino group or arylheteroarylamino group having 10 to 40 aromatic ring atoms, which may be substituted by one or more radicals $R^8$; $R^1$ and $R^2$ and/or $R^2$ and $R^3$ and/or $R^4$ and $R^5$ and/or $R^8$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, aliphatic ring system with one another;

with the proviso that $R^1$ to $R^7$ represent a free electron pair if the group X to which these radicals $R^1$ to $R^7$ are bonded is a nitrogen atom with a saturated valence;

R⁸ is on each occurrence, identically or differently, H, D, F, Cl, Br, I, N(R⁹)₂, CN, NO₂, Si(R⁹)₃, B(OR⁹)₂, C(=O)R⁹, P(=O)(R⁹)₂, S(=O)R⁹, S(=O)₂R⁹, OSO₂R⁹, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which may be substituted by one or more radicals R⁹, where one or more non-adjacent CH₂ groups may be replaced by R⁹C=CR⁹, C≡C, Si(R⁹)₂, Ge(R⁹)₂, Sn(R⁹)₂, C=O, C=S, C=Se, C=NR⁹, P(=O)(R⁹), SO, SO₂, NR⁹, O, S or CONR⁹ and where one or more H atoms may be replaced by D, F, Cl, Br, I, CN or NO₂, or an aromatic or heteroaromatic ring system having 5 to 60 aromatic ring atoms, which may in each case be substituted by one or more radicals R⁹, or an aryloxy or heteroaryloxy group having 5 to 60 aromatic ring atoms, which may be substituted by one or more radicals R⁹, or an aralkyl or heteroaralkyl group having 5 to 60 aromatic ring atoms, which may be substituted by one or more radicals R⁹, or a diarylamino group, diheteroarylamino group or arylheteroarylamino group having 10 to 40 aromatic ring atoms, which may be substituted by one or more radicals R⁹; two or more adjacent radicals R⁸ here may form a mono- or polycyclic, aliphatic or aromatic ring system with one another;

R⁹ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R⁹ here may also form a mono- or polycyclic, aliphatic or aromatic ring system with one another;

L' is, identically or differently on each occurrence, any desired co-ligand;

n is 1, 2, 3 or 4;

m is 0, 1, 2, 3, 4, 5 or 6;

a plurality of ligands L here may also be linked to one another or L may be linked to L' via any desired bridge V, thus forming a tridentate, tetradentate, pentadentate or hexadentate ligand system.

A DETAILED DESCRIPTION OF THE INVENTION

Both the ligand L as a whole and also individual atoms X in the ligand L may also be charged here.

The indices n and m here are selected so that the coordination number on the metal M corresponds overall, depending on the metal, to the usual coordination number for this metal. This is usually the coordination number 4, 5 or 6 for transition metals, depending on the metal. It is generally known that metal coordination compounds have different coordination numbers, i.e. bind a different number of ligands, depending on the metal and on the oxidation state of the metal. Since the preferred coordination numbers of metals and metal ions in various oxidation states belong to the general expert knowledge of the person skilled in the art in the area of organometallic chemistry or coordination chemistry, it is readily possible for the person skilled in the art to use a suitable number of ligands, depending on the metal and its oxidation state and depending on the precise structure of the ligand L, and thus to select the indices n and m suitably.

The ligands L are bidentate ligands, which bond to the metal M via one carbon atom and one nitrogen atom or via two carbon atoms or via two nitrogen atoms. If the ligand bonds to the metal via two carbon atoms, the ligand preferably contains precisely two nitrogen atoms in the coordinating carbene ring. In a preferred embodiment of the invention, the ligand L bonds to the metal M via one carbon atom and one nitrogen atom.

All atoms X together form a 14π electron system. Each carbon atom here contributes 1π electron to the overall electron system. Each nitrogen atom which is only bonded in a 6-membered ring likewise contributes 1π electron to the overall electron system. Each nitrogen atom which is bonded simultaneously in a 5-membered ring and a 6-membered ring contributes 2π electrons to the overall electron system. Each nitrogen atom which is only bonded in a 5-membered ring contributes 1 or 2π electrons to the overall electron system. It depends on the bonding of the nitrogen in the 5-membered ring whether this nitrogen atom contributes 1 or 2π electrons to the overall electron system. Each boron atom contributes 0 or 1π electron to the overall electron system, depending on whether the boron atom is neutral or negatively charged. The circle in a ring in formulae (2) and (3) represents a 6π electron system, as is usually used for the representation of aromatic or heteroaromatic structures in organic chemistry. The following structures again explain when the nitrogen contributes 1 or 2π electrons (shown only as electrons in the scheme) to the overall π electron system:

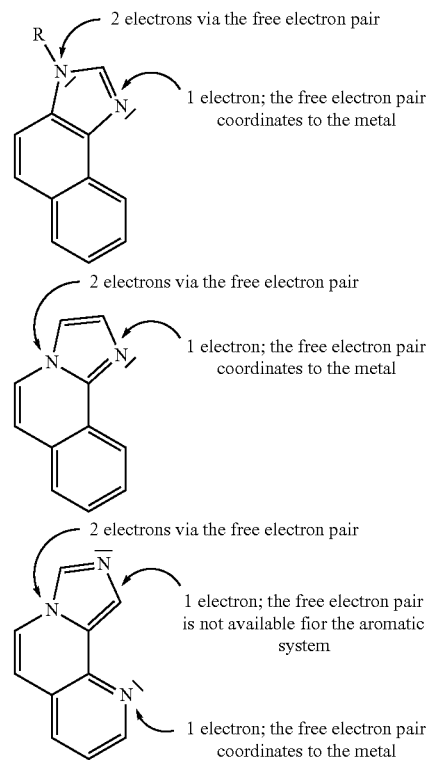

For the purposes of this invention, a nitrogen atom with a saturated valence is taken to mean a nitrogen atom which formally forms either one single bond and one double bond or three single bonds within the aromatic skeleton. In these cases, the radical R¹ to R⁷ which is bonded to this nitrogen atom represents a free electron pair. For the purposes of this invention, a nitrogen atom with an unsaturated valence is taken to mean, by contrast, a nitrogen atom which formally only forms two single bonds within the aromatic skeleton. In these cases, the radical from R¹ to R⁷ which is bonded to this nitrogen atom represents a radical as defined above and not a free electron pair. The following structures again explain what is taken to mean by a nitrogen atom with a saturated valence:

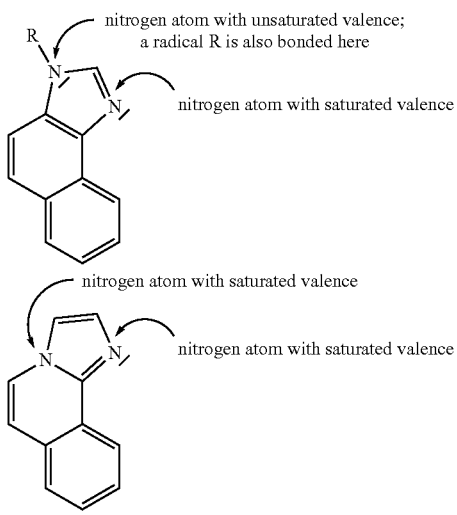

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

The ligands may also bond to the metal via a carbene carbon atom. For the purposes of this invention, a cyclic carbene is a cyclic group which bonds to the metal via a neutral C atom. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group for the purposes of this invention. In a preferred embodiment of the invention, the cyclic carbene which coordinates to the metal contains precisely two nitrogen atoms which bond to the carbene C atom, but no further nitrogen atoms.

For the purposes of this invention, an aromatic ring system contains 6 to 60 C atoms in the ring system. For the purposes of this invention, a heteroaromatic ring system contains 1 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to mean aromatic ring systems for the purposes of this invention, as are systems in which two or more aryl groups are interrupted, for example, by a linear or cyclic alkyl group or by a silyl group.

For the purposes of this invention, a cyclic alkyl, alkoxy or thioalkoxy group is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methyl-butyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charge of the ligands L and L' in such a way that they compensate for the charge of the complexed metal atom M.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal or for a main-group metal. If M stands for a main-group metal, it preferably stands for a metal from the third, fourth or fifth main group, in particular for tin.

Preference is given to compounds of the formula (1) in which M stands for a transition metal, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V); particular preference is given to Mo(0), W(0), Re(I), Ru(II), Os(II), Rh(III), Cu(I), Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', is (are) also coordinated to the metal M. If the index n=2, the index m=0.

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0.

In a preferred embodiment of the invention, the central ring of the ligand L contains at least one nitrogen atom. Preferred moieties of the formula (2) and of the formula (3) are thus the structures of the following formulae (2a) and (3a):

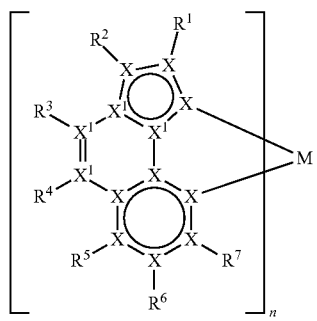

formula (2a)

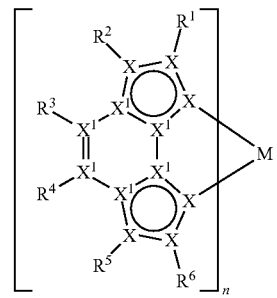

formula (3a)

where the symbols and indices used have the meanings given above and furthermore:

$X^1$ is, identically or differently on each occurrence, C or N, with the proviso that at least one group $X^1$ stands for N.

In a particularly preferred embodiment of the invention, the central ring of the ligand L contains at least one nitrogen atom which is bonded in two rings. Preferred moieties of the formula (2a) and of the formula (3a) are thus the structures of the following formulae (2b) and (3b):

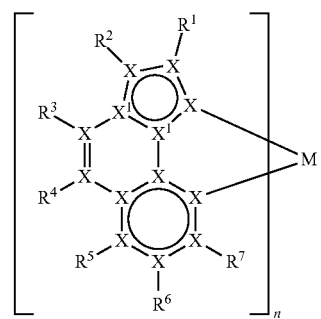

formula (2b)

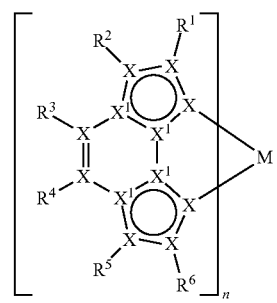

formula (3b)

where the symbols and indices used have the meanings given above.

In a preferred embodiment of the invention, the moieties of the formula (2) are selected from the structures of the following formulae (4), (5) and (6), and the moieties of the formula (3) are selected from the structures of the following formulae (7) and (8):

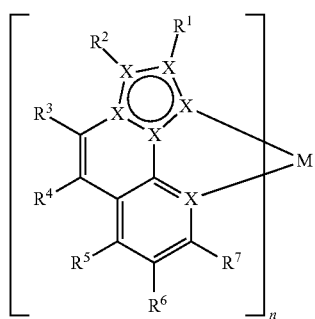
formula (4)
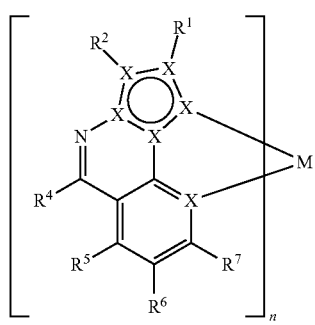
formula (5)
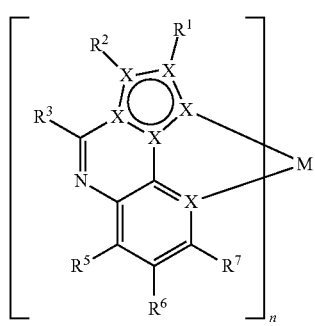
formula (6)
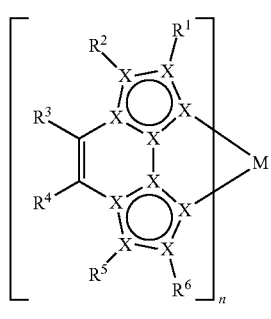
formula (7)
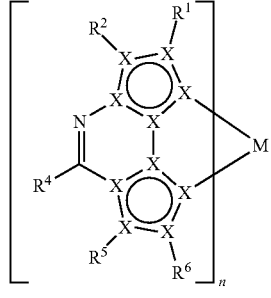
formula (8)
where the symbols and indices have the meanings indicated above.
In a particularly preferred embodiment of the invention, the moieties of the formulae (4) to (8) are selected from the structures of the following formulae (4a) to (8a) in which the central ring of the ligand has at least one nitrogen atom which is bonded in two rings:
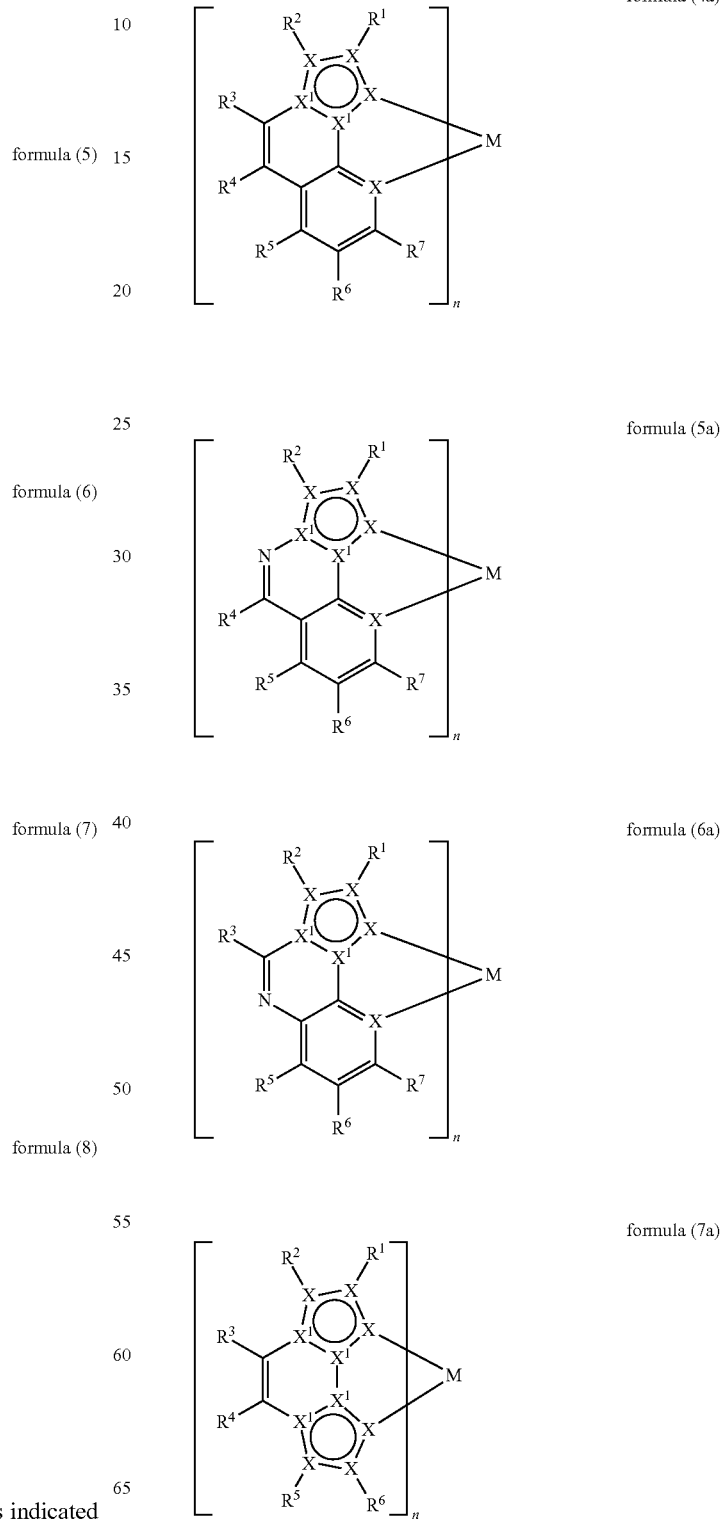

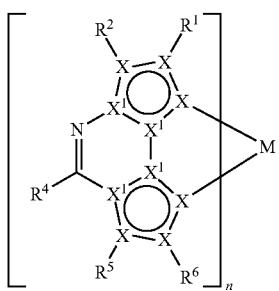
formula (8a)
where the symbols and indices have the meanings indicated above.
A particularly preferred embodiment of the moieties of the formulae (4) to (8) and (4a) to (8a) are the structures of the following formulae (9) to (77):
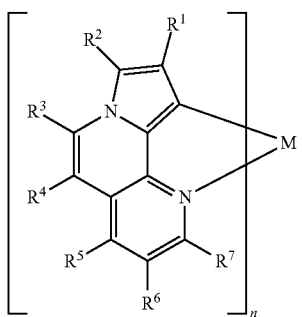
formula (9)
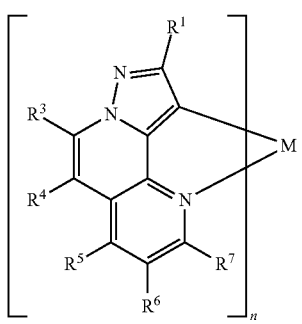
formula (10)
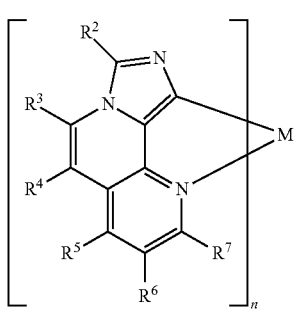
formula (11)
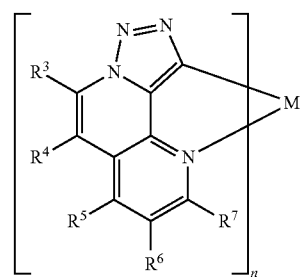
formula (12)
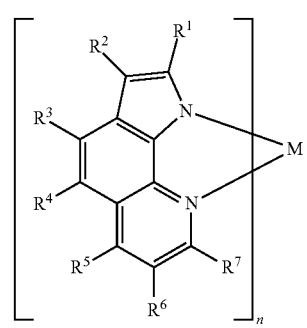
formula (13)
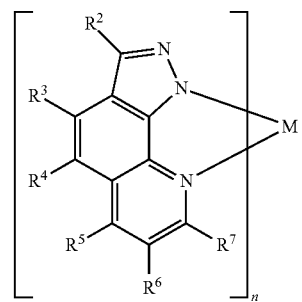
formula (14)
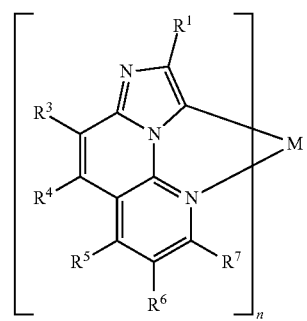
formula (15)
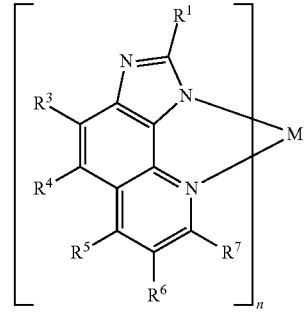
formula (16)

formula (17)
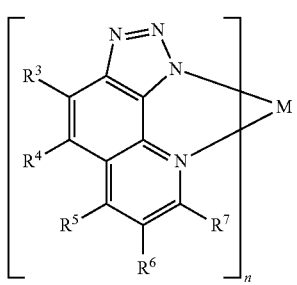
formula (18)
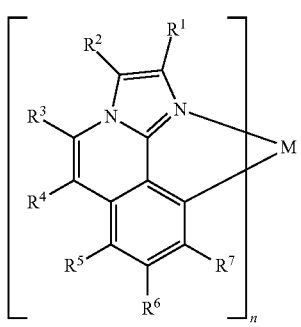
formula (19)
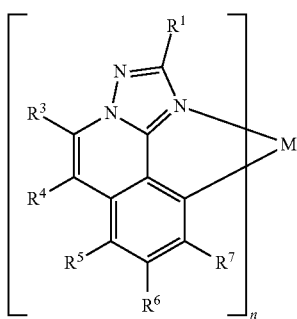
formula (20)
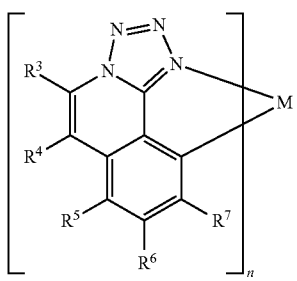
formula (21)
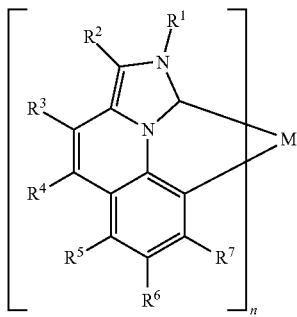
formula (22)
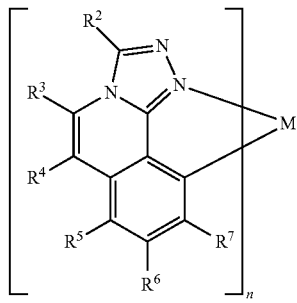
formula (23)
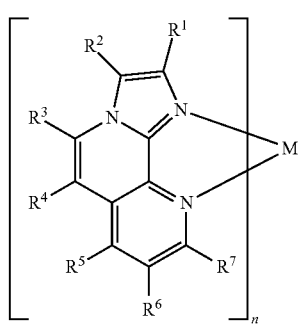
formula (24)
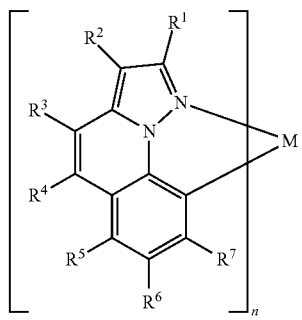
formula (25)
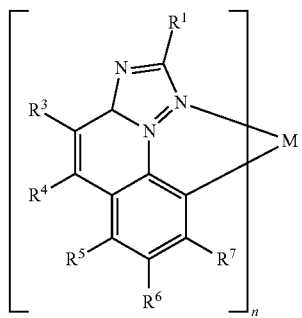
formula (26)
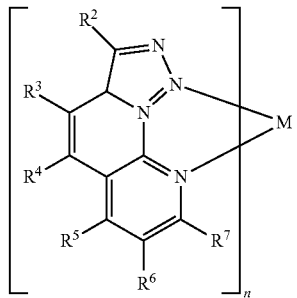

formula (27)
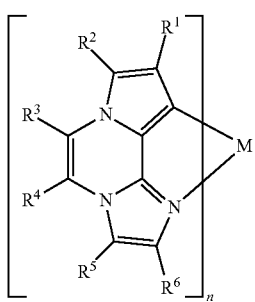
formula (28)
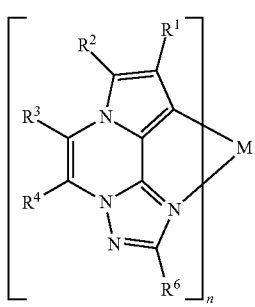
formula (29)
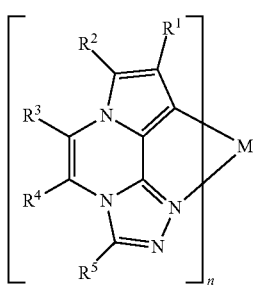
formula (30)
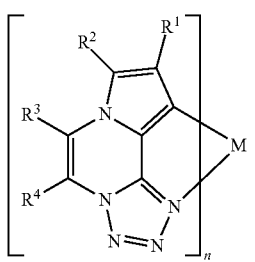
formula (31)
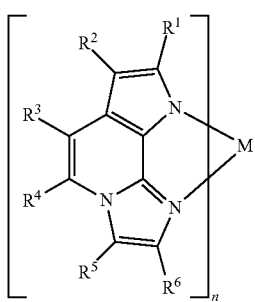
formula (32)
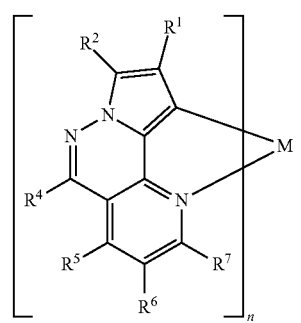
formula (33)
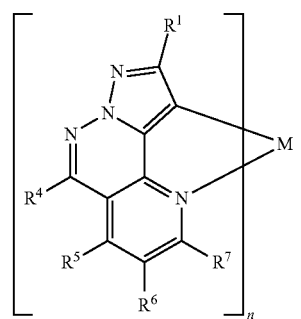
formula (34)
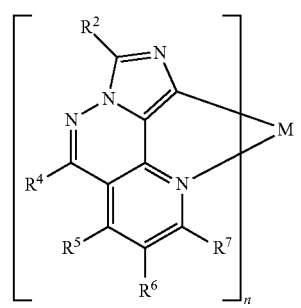
formula (35)
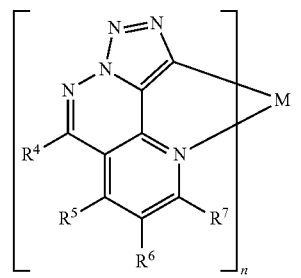
formula (36)
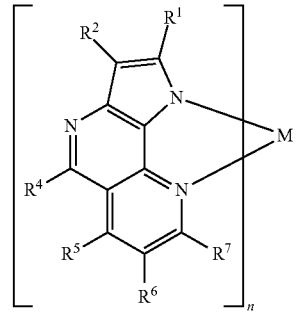

formula (37)
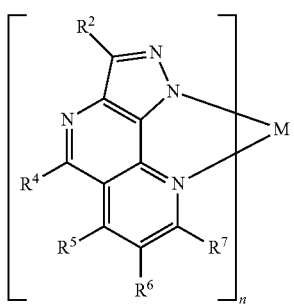
formula (38)
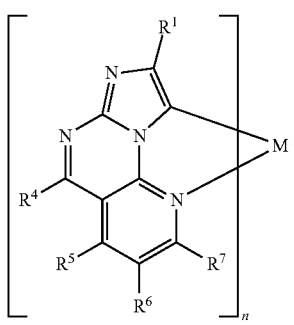
formula (39)
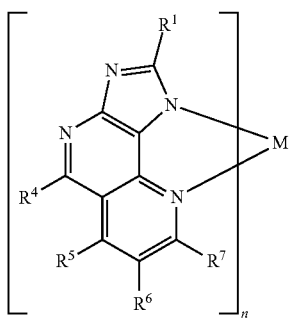
formula (40)
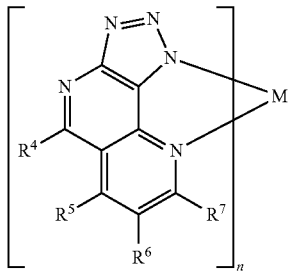
formula (41)
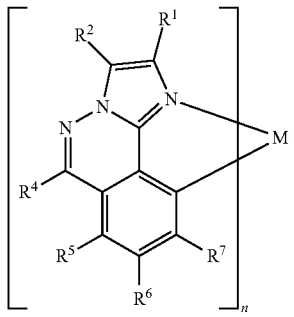
formula (42)
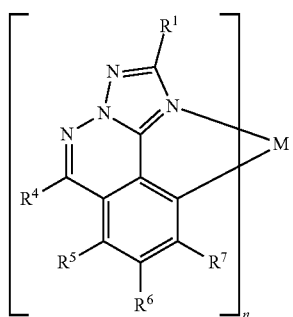
formula (43)
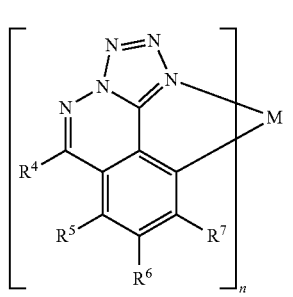
formula (44)
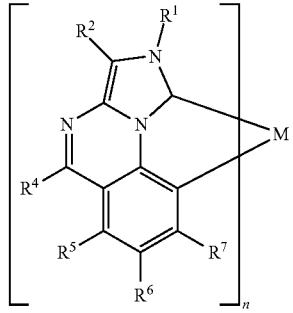
formula (45)
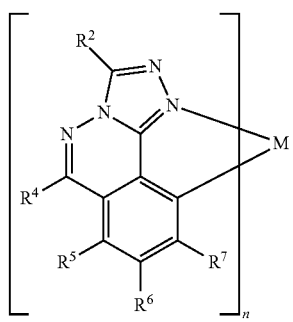
formula (46)
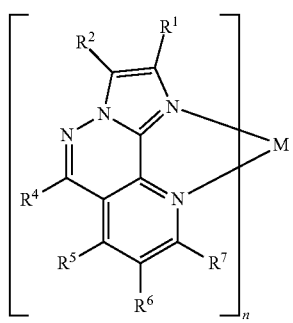

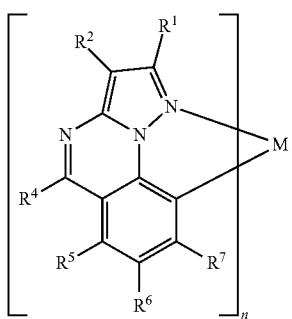
formula (47)
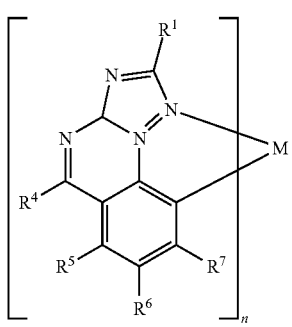
formula (48)
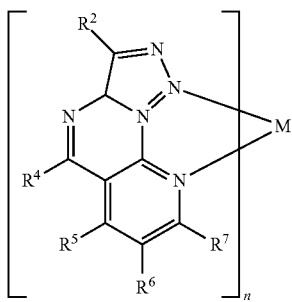
formula (49)
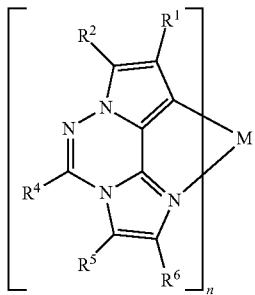
formula (50)
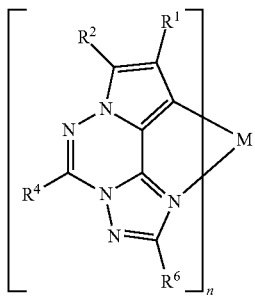
formula (51)
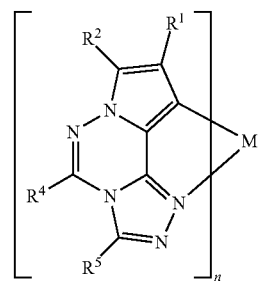
formula (52)
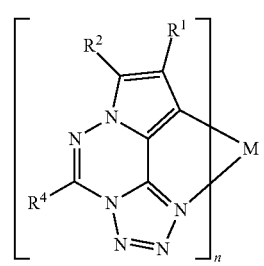
formula (53)
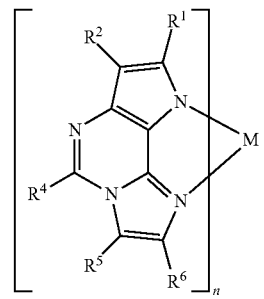
formula (54)
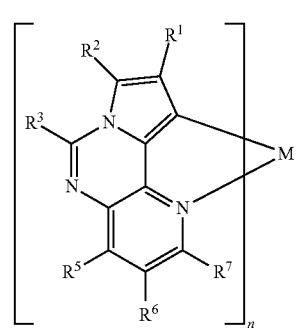
formula (55)
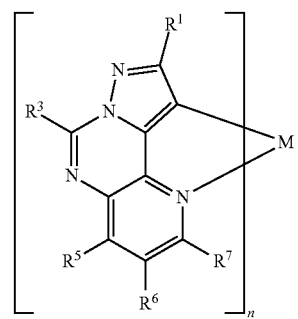
formula (56)

formula (57)
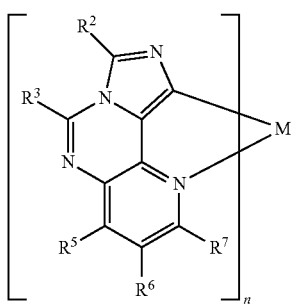
formula (58)
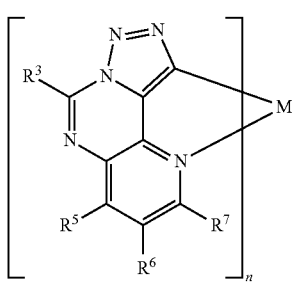
formula (59)
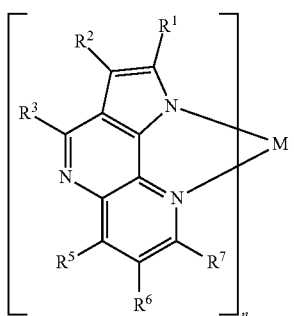
formula (60)
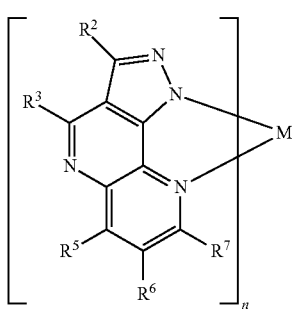
formula (61)
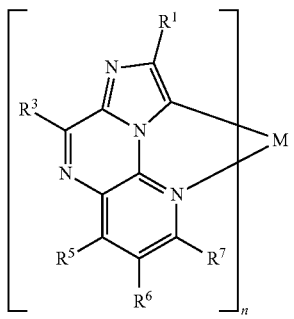
formula (62)
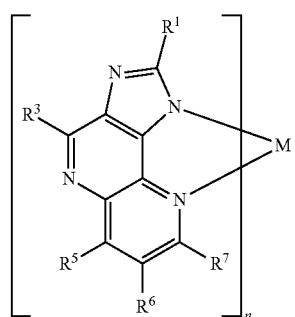
formula (63)
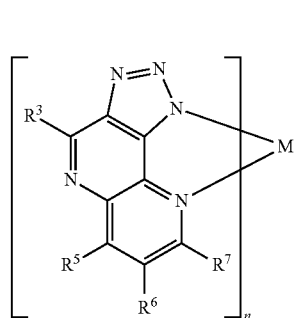
formula (64)
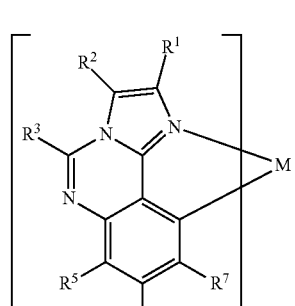
formula (65)
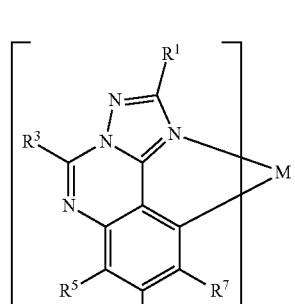
formula (66)
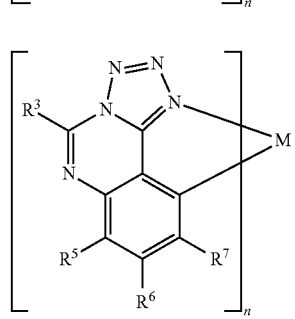

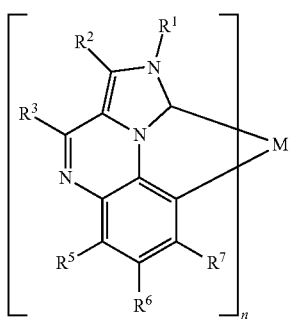
formula (67)
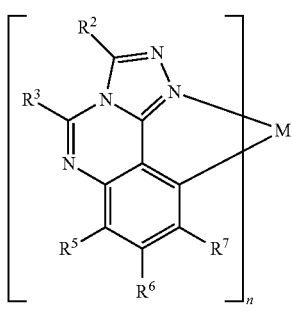
formula (68)
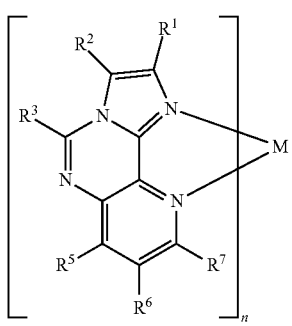
formula (69)
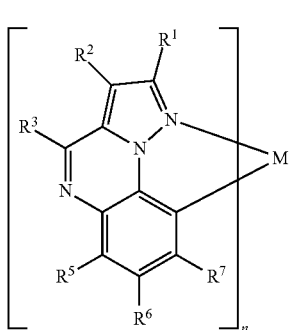
formula (70)
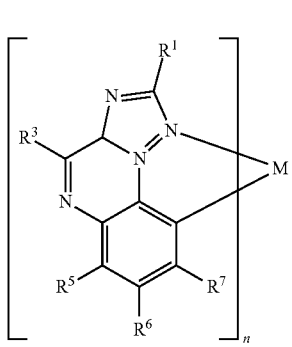
formula (71)
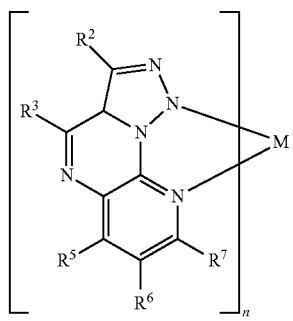
formula (72)
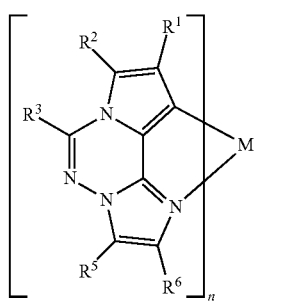
formula (73)
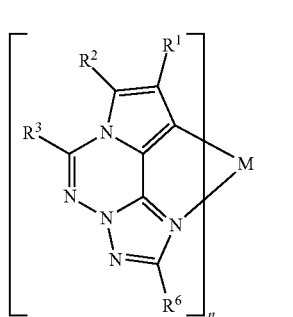
formula (74)
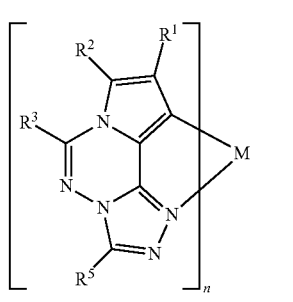
formula (75)
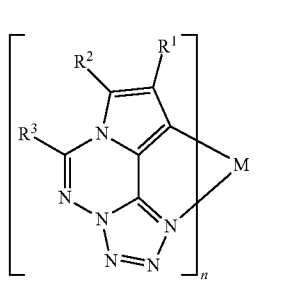
formula (76)

formula (77)

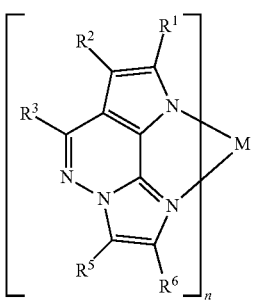

where the symbols and indices used have the meanings indicated above.

In a preferred embodiment of the invention, at least one of the substituents $R^1$, $R^2$, $R^3$ and/or $R^4$, particularly preferably $R^2$, $R^3$ and/or $R^4$, is not equal to hydrogen or deuterium. The substituent $R^2$ is very particularly preferably not equal to hydrogen or deuterium. In a very particularly preferred embodiment of the invention, the substituent $R^2$ is therefore not equal to hydrogen or deuterium and the substituents $R^3$ and $R^4$ are equal to hydrogen or deuterium or the substituent $R^3$ is equal to hydrogen or deuterium and the substituent $R^4$ is not equal to hydrogen or deuterium or the substituent $R^3$ is not equal to hydrogen or deuterium and the substituent $R^4$ is equal to hydrogen or deuterium. This preference is due to the higher stability of the corresponding metal complexes.

Furthermore, larger condensed structures are possible through cyclisation of the substituents. Thus, for example, structures of the following formulae (78) to (89) are obtainable:

formula (78)

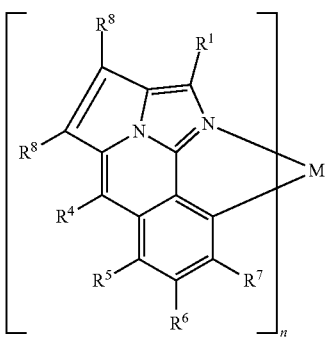

formula (79)

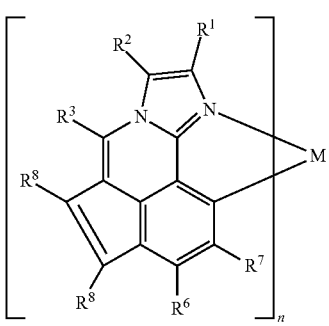

formula (80)

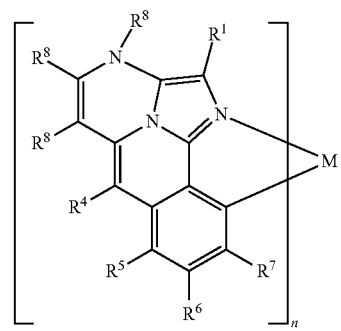

formula (81)

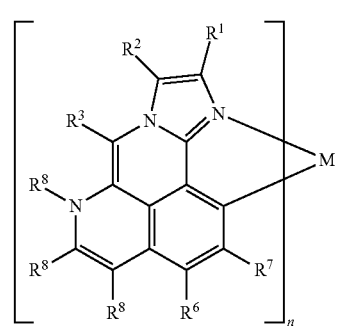

formula (82)

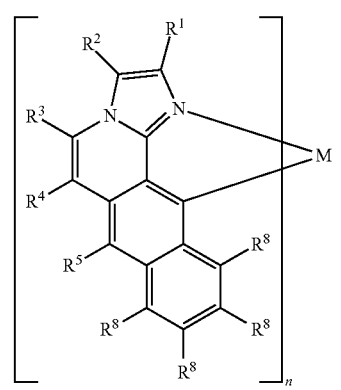

formula (83)

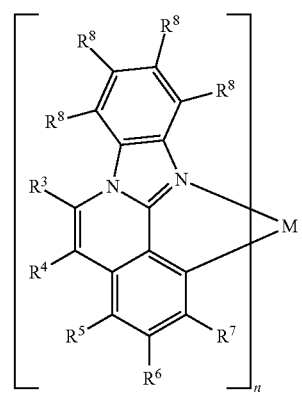

formula (84)

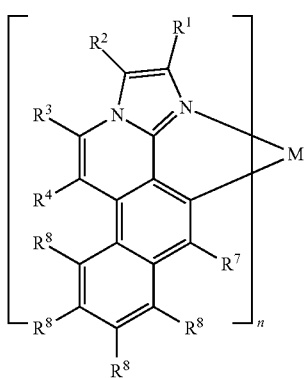

formula (87)

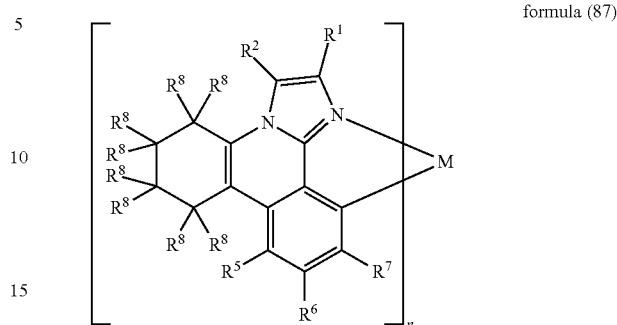

formula (88)

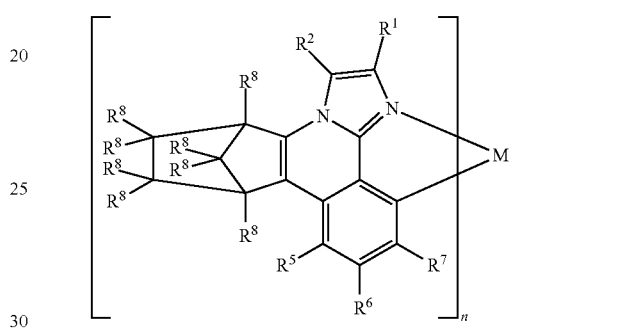

formula (85)

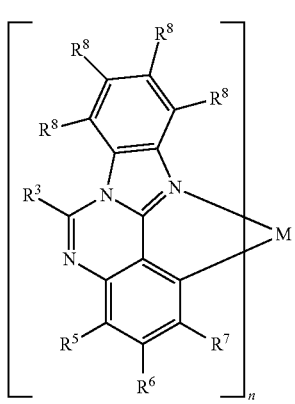

formula (89)

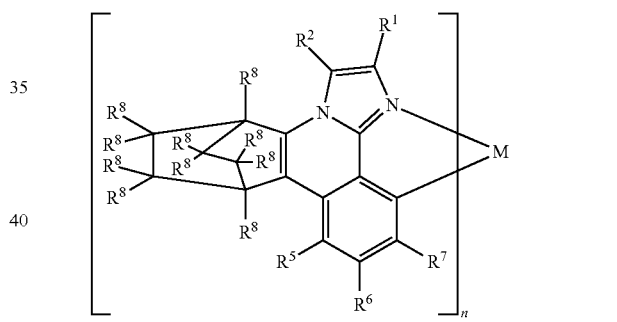

formula (86)

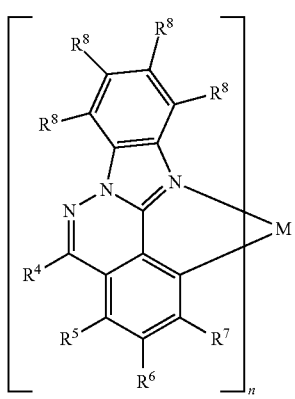

where the symbols and indices used have the meanings given above. $R^8$ in the formulae (78) to (89) preferably stands for H or an alkyl group having 1 to 5 C atoms, in particular for H or methyl.

The formulae (78) to (89) show merely by way of example on a specific ligand how corresponding larger condensed ring systems are accessible through cyclisation. Cyclisation is possible entirely analogously with the other structures according to the invention, for example with the structures of the formulae (9) to (77), without further inventive step.

It is furthermore possible for the substituent $R^6$ or $R^7$ which is in the orthoposition to the metal coordination to represent a coordinating group which likewise coordinates to the metal M. Preferred coordinating groups $R^7$ are aryl and heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties ML of the following formulae (90) to (97), for example, are accessible here:

formula (90)
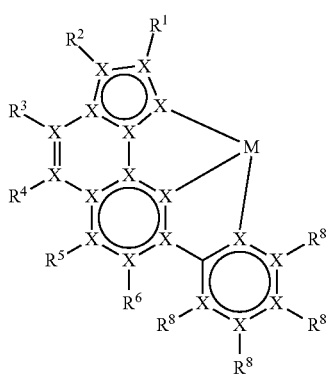
formula (91)
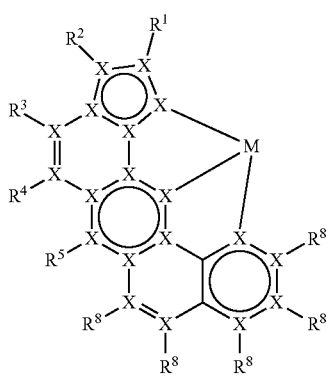
formula (92)
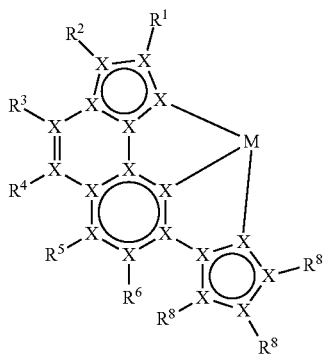
formula (93)
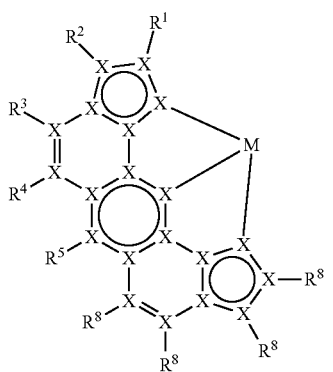
formula (94)
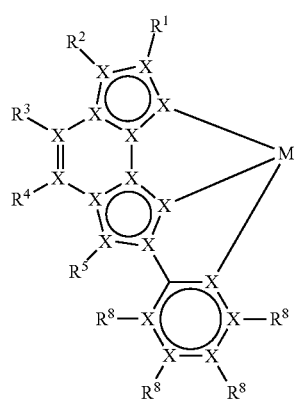
formula (95)
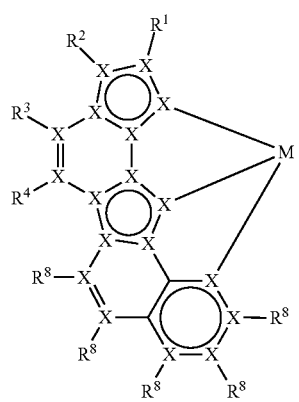
formula (96)
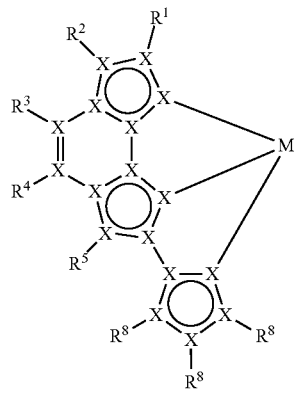
formula (97)
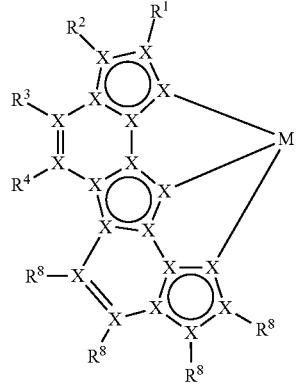
where the symbols used have the meanings given above. The preferences given above apply to the ligands.

The formulae (90) to (97) show merely by way of example how the substituent $R^6$ or $R^7$ can additionally coordinate to the metal. Other groups $R^6$ and $R^7$ which coordinate to the metal are also possible entirely analogously without further inventive step.

As described above, a bridging unit V which links this ligand L to one or more further ligands L or L' may also be present instead of one of the radicals $R^1$ to $R^7$. In a preferred embodiment of the invention, a bridging unit V is present instead of one of the radicals $R^1$ to $R^7$, in particular instead of $R^1$, $R^2$, $R^6$ or $R^7$, so that the ligands have a tridentate or polydentate or polypodal character. Formula (2) preferably contains a bridging unit V instead of $R^1$ or $R^7$ and formula (3) preferably contains a bridging unit V instead of $R^1$ or $R^6$. It is also possible for two such bridging units V to be present. This results in the formation of macrocyclic ligands or in the formation of cryptates.

Preferred structures containing polydentate ligands are the metal complexes of the following formulae (98) to (105):

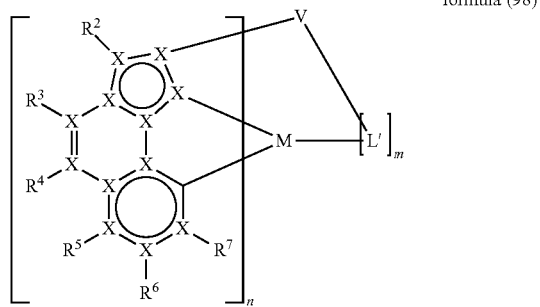

formula (98)

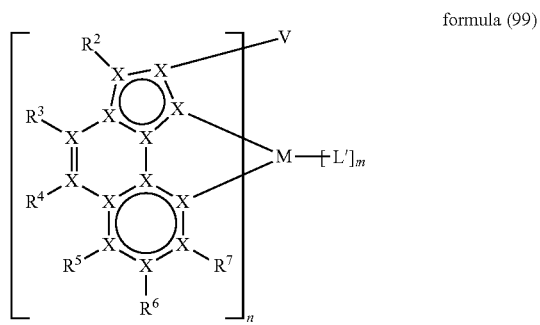

formula (99)

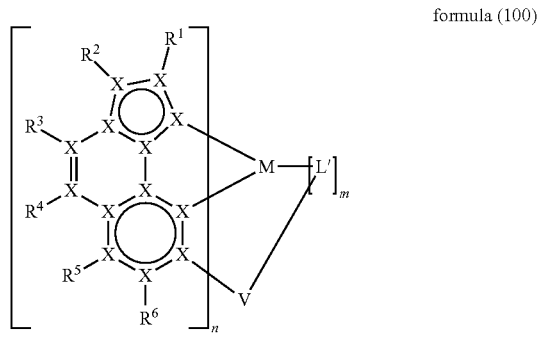

formula (100)

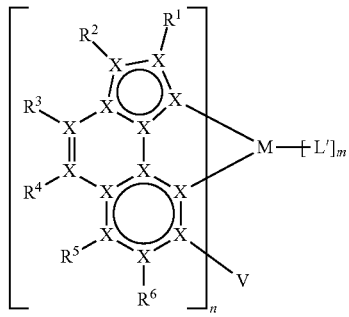

formula (101)

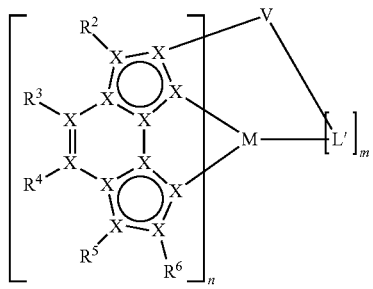

formula (102)

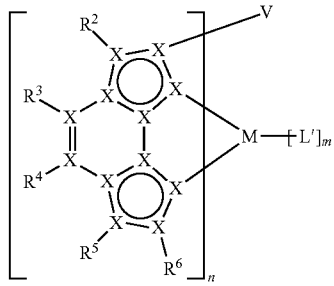

formula (103)

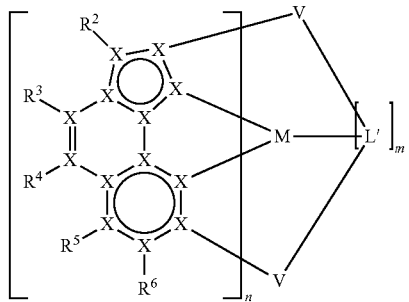

formula (104)

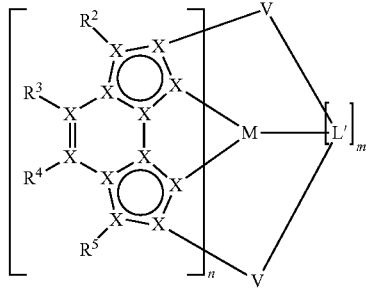

formula (105)

where the symbols used have the meanings given above, and V preferably represents a bridging unit containing 1 to 80 atoms from the third, fourth, fifth and/or sixth main group (IUPAC group 13, 14, 15 or 16) or a 3- to 6-membered homoor heterocycle which covalently bonds the part-ligands L to one another or covalently bonds L to L'. The bridging unit V here may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged. The charge of V is preferably selected so that overall a neutral complex forms. The preferences given above for the moiety $ML_n$ apply to the ligands.

The precise structure and chemical composition of the group V do not have a significant influence on the electronic properties of the complex since it is, in particular, the task of this group to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^8)^-$, $B(C(R^8)_2)_3$, $(R^8)B(C(R^8)_2)_3^-$, $B(O)_3$, $(R^8)B(O)_3^-$, $B(C(R^8)_2C(R^8)_2)_3$, $(R^8)B(C(R^8)_2C(R^8)_2)_3^-$, $B(C(R^8)_2O)_3$, $(R^8)B(C(R^8)_2O)_3^-$, $B(OC(R^8)_2)_3$, $(R^8)B(OC(R^8)_2)_3^-$, $C(R^8)$, $CO^-$, $CN(R^8)_2$, $(R^8)C(C(R^8)_2)_3$, $(R^8)C(O)_3$, $(R^8)C(C(R^8)_2C(R^8)_2)_3$, $(R^8)C(C(R^8)_2O)_3$, $(R^8)C(OC(R^8)_2)_3$, $(R^8)C(Si(R^8)_2)_3$, $(R^8)C(Si(R^8)_2C(R^8)_2)_3$, $(R^8)C(C(R^8)_2Si(R^8)_2)_3$, $(R^8)C(Si(R^8)_2Si(R^8)_2)_3$, $Si(R^8)$, $(R^8)Si(C(R^8)_2)_3$, $(R^8)Si(O)_3$, $(R^8)Si(C(R^8)_2C(R^8)_2)_3$, $(R^8)Si(OC(R^8)_2)_3$, $(R^8)Si(C(R^8)_2O)_3$, $(R^8)Si(Si(R^8)_2)_3$, $(R^8)Si(Si(R^8)_2C(R^8)_2)_3$, $(R^8)Si(C(R^8)_2Si(R^8)_2)_3$, $(R^8)Si(Si(R^8)_2Si(R^8)_2)_3$, N, NO, $N(R^8)^+$, $N(C(R^8)_2)_3$, $(R^8)N(C(R^8)_2)_3^+$, $N(C=O)_3$, $N(C(R^8)_2C(R^8)_2)_3$, $(R^8)N(C(R^8)_2C(R^8)_2)^+$, P, $P(R^8)^+$, PO, PS, PSe, PTe, $P(O)_3$, $PO(O)_3$, $P(OC(R^8)_2)_3$, $PO(OC(R^8)_2)_3$, $P(C(R^8)_2)_3$, $P(R^8)(C(R^8)_2)_3^+$, $PO(C(R^8)_2)_3$, $P(C(R^8)_2C(R^8)_2)_3$, $P(R^8)(C(R^8)_2C(R^8)_2)_3^+$, $PO(C(R^8)_2C(R^8)_2)_3$, As, $As(R^8)^+$, AsO, AsS, AsSe, AsTe, $As(O)_3$, $AsO(O)_3$, $As(OC(R^8)_2)_3$, $AsO(OC(R^8)_2)_3$, $As(C(R^8)_2)_3$, $As(R^8)(C(R^8)_2)_3^+$, $AsO(C(R^8)_2)_3$, $As(C(R^8)_2C(R^8)_2)_3$, $As(R^8)(C(R^8)_2C(R^8)_2)_3^+$, $AsO(C(R^8)_2C(R^8)_2)_3$, Sb, $Sb(R^8)^+$, SbO, SbS, SbSe, SbTe, $Sb(O)_3$, $SbO(O)_3$, $Sb(OC(R^8)_2)_3$, $SbO(OC(R^8)_2)_3$, $Sb(C(R^8)_2)_3$, $Sb(R^8)(C(R^8)_2)_3^+$, $SbO(C(R^8)_2)_3$, $Sb(C(R^8)_2C(R^8)_2)_3$, $Sb(R^8)(C(R^8)_2C(R^8)_2)_3^+$, $SbO(C(R^8)_2C(R^8)_2)_3$, Bi, $Bi(R^8)^+$, BiO, BiS, BiSe, BiTe, $Bi(O)_3$, $BiO(O)_3$, $Bi(OC(R^8)_2)_3$, $BiO(OC(R^8)_2)_3$, $Bi(C(R^8)_2)_3$, $Bi(R^8)(C(R^8)_2)_3^+$, $BiO(C(R^8)_2)_3$, $Bi(C(R^8)_2C(R^8)_2)_3$, $Bi(R^8)(C(R^8)_2C(R^8)_2)_3^+$, $BiO(C(R^8)_2C(R^8)_2)_3$, $S^+$, $S(C(R^8)_2)_3^+$, $S(C(R^8)_2C(R^8)_2)_3^+$, $Se^+$, $Se(C(R^8)_2)_3^+$, $Se(C(R^8)_2C(R^8)_2)_3^+$, $Te^+$, $Te(C(R^8)_2)_3^+$, $Te(C(R^8)_2C(R^8)_2)_3^+$, or a unit of the formula (106), (107), (108) or (109):

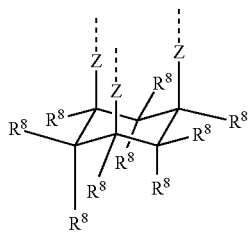

formula (106)

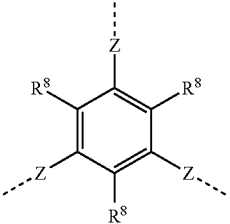

formula (107)

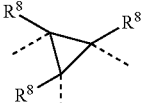

formula (108)

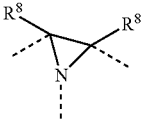

formula (109)

where the dashed bonds in each case indicate the bond to the part-ligands L or L', and Z is selected, identically or differently on each occurrence, from the group consisting of a single bond, O, S, S(=O), $S(=O)_2$, $NR^8$, $PR^8$, $P(=O)R^8$, $P(=NR^8)$, $C(R^8)_2$, C(=O), $C(=NR^8)$, $C(=C(R^8)_2)$, $Si(R^8)_2$ and $BR^8$. The other symbols used have the meanings given above.

If V is a divalent group, i.e. bridges two ligands L to one another or one ligand L to U, V is preferably selected, identically or differently on each occurrence, from the group consisting of $BR^8$, $B(R^8)_2^-$, $C(R^8)_2$, C(=O), $Si(R^8)_2$, $NR^B$, $PR^8$, $P(R^8)_2^+$, $P(=O)(R^8)$, $P(=S)(R^8)$, $AsR^8$, $As(=O)(R^8)$, $As(=S)(R^8)$, O, S, Se, or a unit of the formulae (110) to (119):

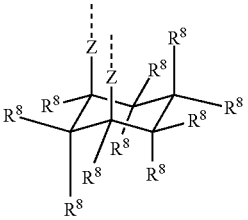

formula (110)

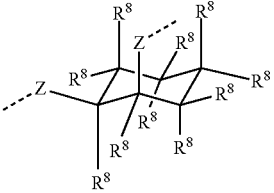

formula (111)

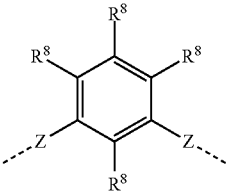

formula (112)

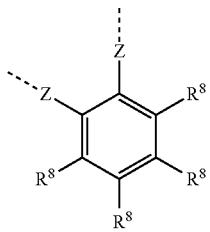

formula (113)

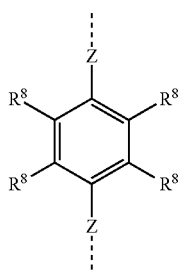

formula (114)

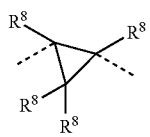

formula (115)

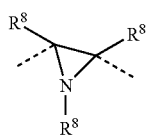

formula (116)

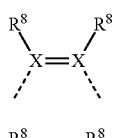

formula (117)

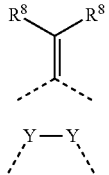

formula (118)

formula (119)

where the dashed bonds in each case indicate the bond to the part-ligands L or L', Y stands on each occurrence, identically or differently, for $C(R^8)_2$, $N(R^8)$, O or S, and the other symbols used each have the meanings mentioned above.

Preferred ligands L' as occur in formula (1) are described below. The ligand groups L' can also be selected correspondingly if they are bonded to L via a bridging unit V, as indicated in formulae (98) to (105).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl) phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-$C{\equiv}C^-$, tert-butyl-$C{\equiv}C^-$, arylacetylides, such as, for example, phenyl-$C{\equiv}C^-$, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C$\equiv$M, and nitrenes, which result in coordination in the form R—N$=$M, where R generally stands for a substituent, or $N^{3-}$.

Preferred neutral or mono- or dianionic bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or transN,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino) ethyl]-pyridine, 2-[1-(ethylimino)ethyl]pyridine, 2-[1-(iso-propylimino)ethyl]pyridine, 2-[1-(tert-butylimino)ethyl] pyridine, diimines, such as, for example, 1,2-bis (methylimino)ethane, 1,2-bis(ethylimino)ethane, 1,2-bis (iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino) ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino) ethane, bis(diphenylphosphino)propane, bis(diphenylphosphino)butane, bis(dimethylphosphino)methane, bis (dimethylphosphino)ethane, bis(dimethylphosphino)propane, bis(diethylphosphino)-methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)-methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl) borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals $R^1$ to $R^6$. A multiplicity of such ligands is known to the person skilled in the art in the area of phosphorescent electroluminescent devices, and he will be able, without inventive step, to select further ligands of this type as ligand L' for compounds of the formula (1). The combination of two groups as depicted by the following formulae (120) to (147) is generally particularly suitable for this purpose, where one group is preferably bonded via a neutral nitrogen atom or a carbene atom and the other group is preferably bonded via a negatively charged carbon atom or a negatively charged nitrogen atom. The ligand L' can then be formed from the groups of the formulae (120) to (147) through these groups bonding to one another in each case at the position denoted by #. The position at which the groups coordinate to the metal is denoted by *. These groups may also be bonded to the ligand L via one or two bridging units V.

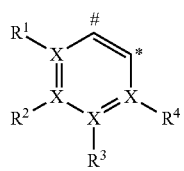

formula (120)

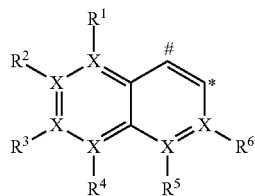

formula (121)

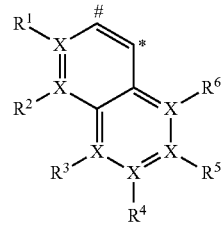

formula (122)

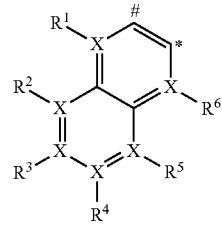

formula (123)

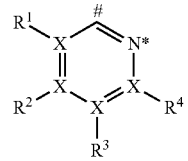

formula (124)

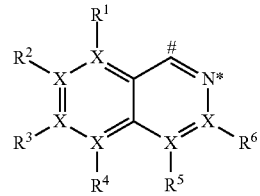

formula (125)

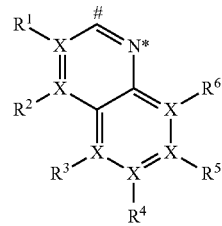

formula (126)

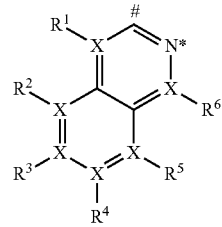

formula (127)

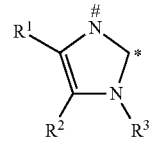

formula (128)

formula (129)
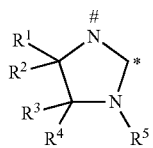
formula (130)
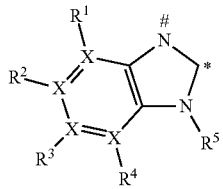
formula (131)
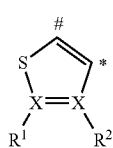
formula (132)
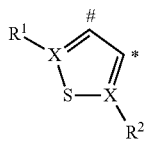
formula (133)
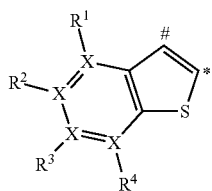
formula (134)
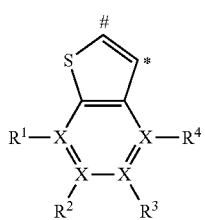
formula (135)
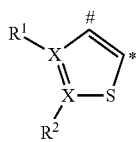
formula (136)
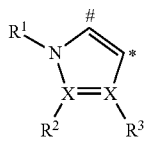
formula (137)
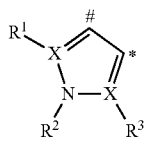
formula (138)
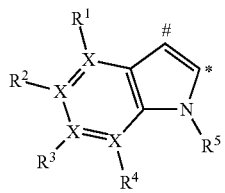
formula (139)
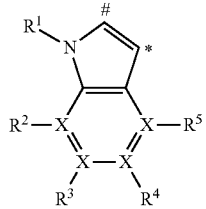
formula (140)
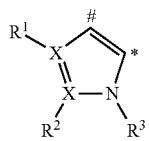
formula (141)
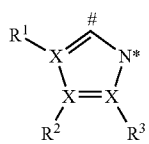
formula (142)
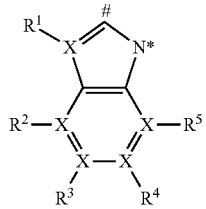
formula (143)
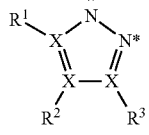
formula (144)
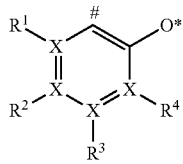
formula (145)
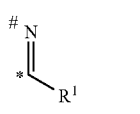
formula (146)
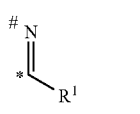

-continued

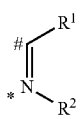

formula (147)

The symbols used here have the same meaning as described above, and preferably a maximum of three symbols X in each group stand for N, particularly preferably a maximum of two symbols X in each group stand for N, very particularly preferably a maximum of one symbol X in each group stands for N, especially preferably all symbols X stand for C.

Likewise preferred ligands L' are $\eta^5$-cyclopentadienyl, $\eta^5$-pentamethyl-cyclopentadienyl, $\eta^6$-benzene or $\eta^7$-cycloheptatrienyl, each of which may be substituted by one or more radicals $R^1$.

Likewise preferred ligands L' are 1,3,5-cis,cis-cyclohexane derivatives, in particular of the formula (148), 1,1,1-tri(methylene)methane derivatives, in particular of the formula (149), and 1,1,1-trisubstituted methanes, in particular of the formulae (150) and (151):

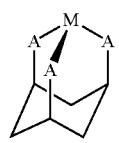

formula (148)

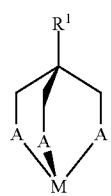

formula (149)

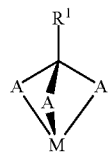

formula (150)

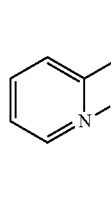

formula (151)

where the coordination to the metal M is shown in each of the formulae, $R^1$ has the meaning given above, and A stands, identically or differently on each occurrence, for $O^-$, $S^-$, $COO^-$, $P(R^1)_2$ or $N(R^1)_2$.

Preferred radicals $R^1$ to $R^7$ in the structures shown above are selected on each occurrence, identically or differently, from the group consisting of H, D, F, Br, $N(R^8)_2$, CN, $B(OR^8)_2$, $C(=O)R^8$, $P(=O)(R^8)_2$, a straight-chain alkyl group having 1 to 10 C atoms or an alkenyl or alkynyl group having 2 to 10 C atoms or a branched or cyclic alkyl group having 3 to 10 C atoms, each of which may be substituted by one or more radicals $R^8$, where one or more H atoms may be replaced by D or F, or an aromatic or heteroaromatic ring system having 5 to 14 aromatic ring atoms, which may in each case be substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, aliphatic ring system with one another. Particularly preferred radicals $R^1$ to $R^7$ are selected on each occurrence, identically or differently, from the group consisting of H, D, F, Br, CN, $B(OR^8)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here may also form a mono- or polycyclic, aliphatic, aromatic and/or benzo-fused ring system with one another; furthermore, $R^3$ and $R^4$ may form a mono- or polycyclic, aliphatic ring system with one another.

The complexes according to the invention can be facial or pseudofacial or they can be meridional or pseudomeridional.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (152), with metal ketoketonates of the formula (153) or with metal halides of the formula (154):

$$M(OR^8)_n$$

formula (152)

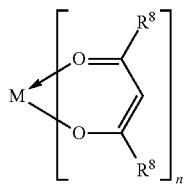

formula (153)

$$MHal_n$$

formula (154)

where the symbols M, n and $R^8$ have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 04/085449. $[IrCl_2(acac)_2]^-$, for example $Na[IrCl_2(acac)_2]$, is particularly suitable. A particularly preferred starting material is furthermore $Ir(acac)_3$.

Suitable platinum starting materials are, for example, $PtCl_2$, $K_2[PtCl_4]$, $PtCl_2(DMSO)_2$, $Pt(Me)_2(DMSO)_2$ or $PtCl_2$(benzonitrile)$_2$.

It is furthermore possible firstly to prepare a precursor of the metal complex and to introduce the bridge between the two coordinating aryl or heteroaryl rings in a further step. This is shown by way of example for a complex in the following scheme:

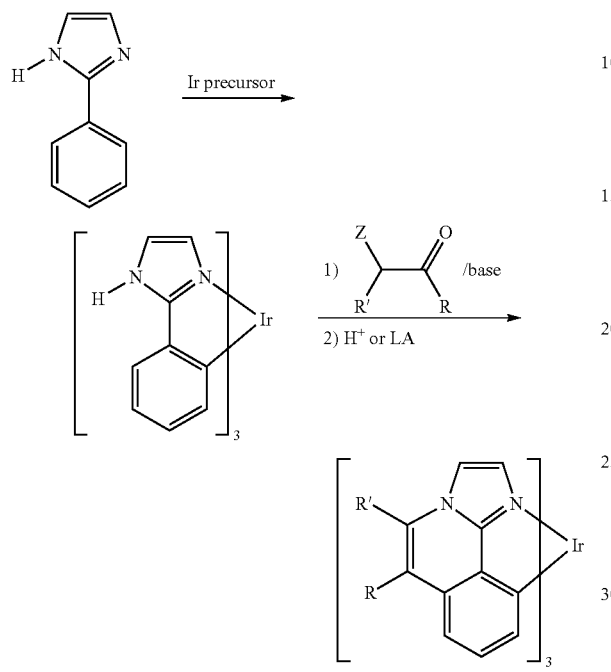

R, R' = radicals as defined
Z = Cl, Br, I, OMes, O(F₃Mes), OTos,
LA = Lewis acid, such as BZ₃, AlZ₃

The synthesis of the complexes is preferably carried out as described in WO 02/060910 and in WO 04/085449. Heteroleptic complexes can also be synthesised, for example, in accordance with WO 05/042548. The synthesis here can also be activated, for example, thermally, photochemically and/or by microwave radiation. In a preferred embodiment of the invention, the reaction is carried out in the melt without the use of an additional solvent. "Melt" here means that the ligand is in molten form, and the metal precursor is dissolved or suspended in this melt.

These processes give the compounds of the formula (1) according to the invention in high purity, preferably greater than 99% (determined by means of ¹H-NMR and/or HPLC).

The synthetic methods explained here facilitate, inter alia, the preparation of structures 1 to 357 according to the invention depicted below.

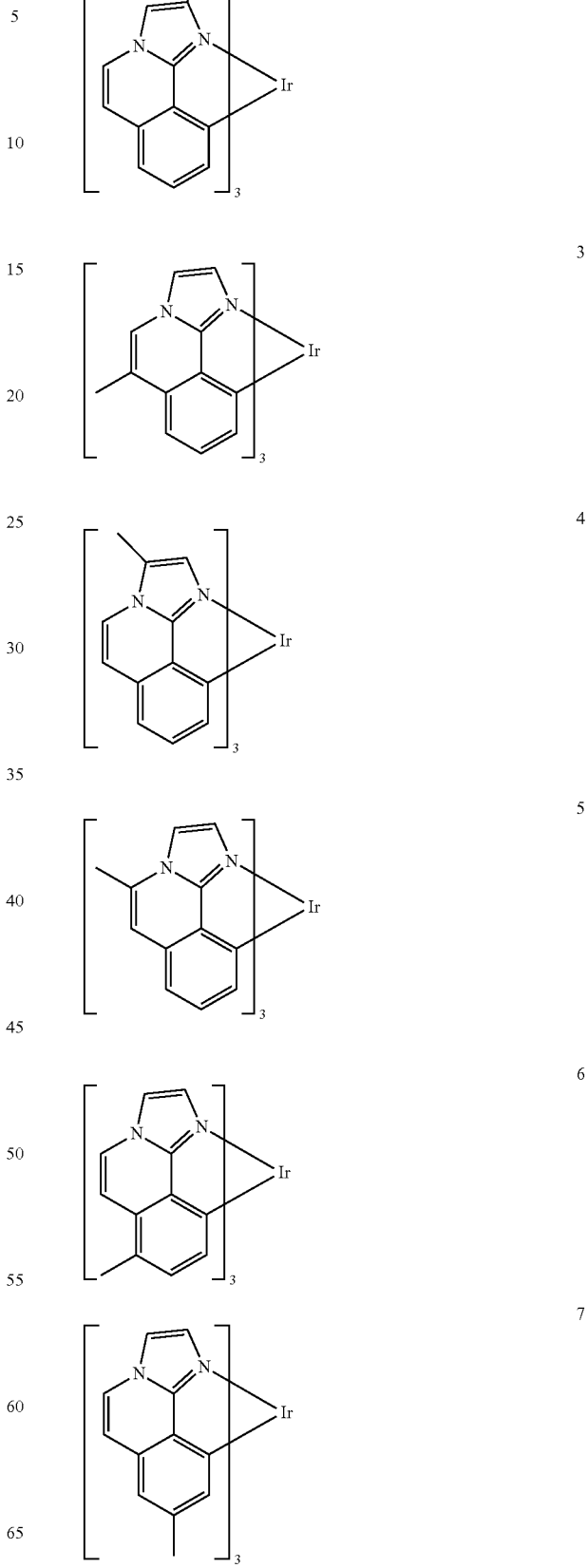

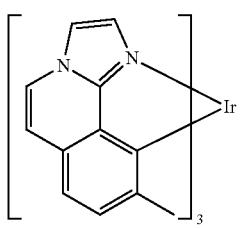 8
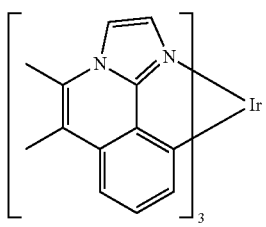 9
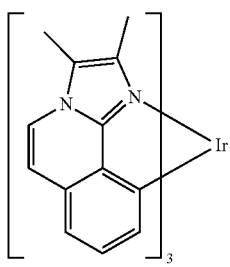 10
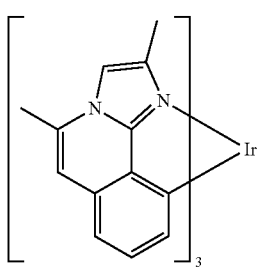 11
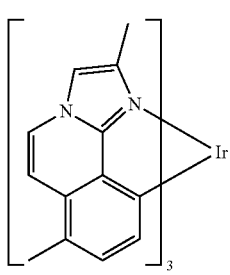 12
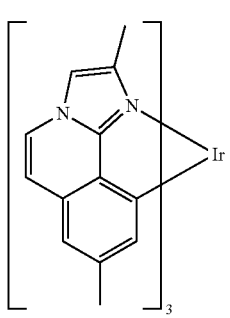 13
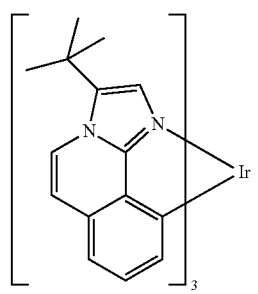 14
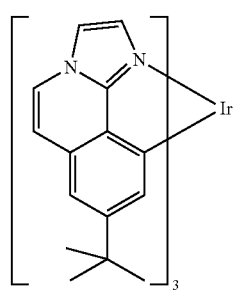 15
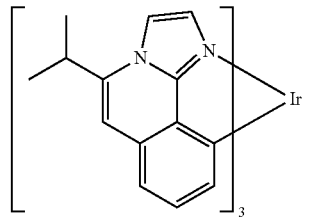 16
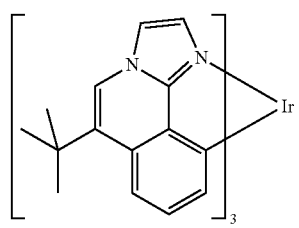 17
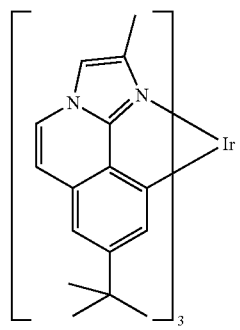 18

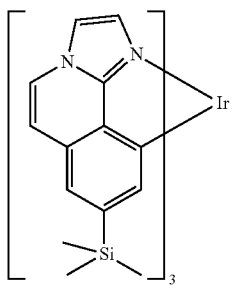
19
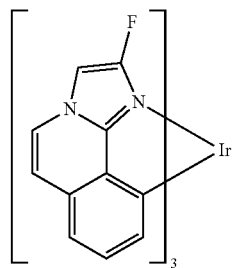
25
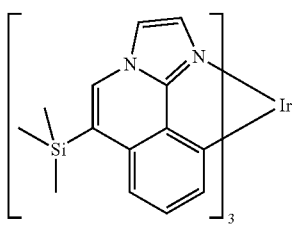
20
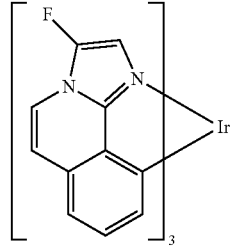
26
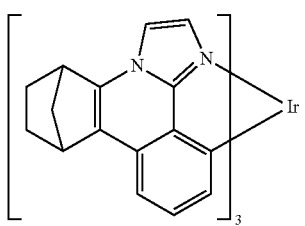
21
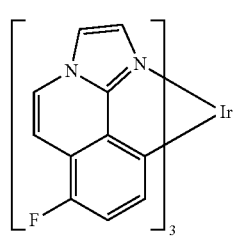
27
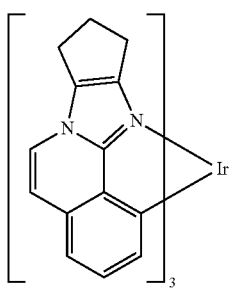
22
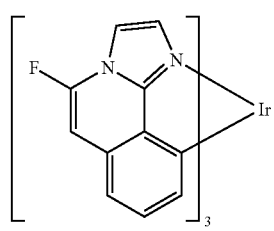
28
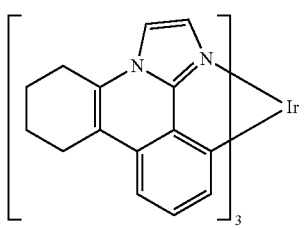
23
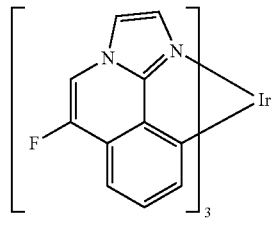
29
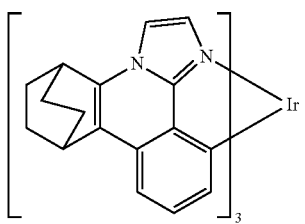
24
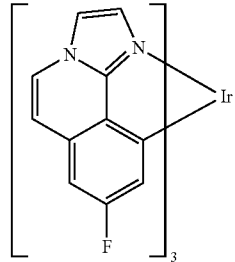
30

31
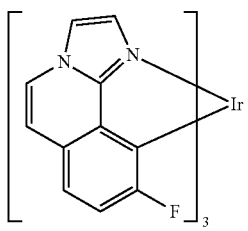
32
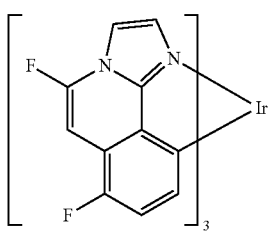
33
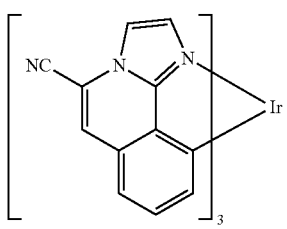
34
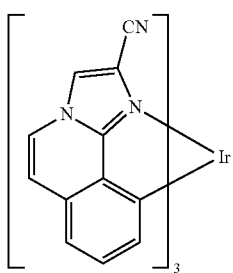
35
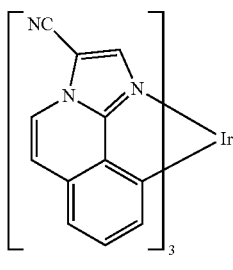
36
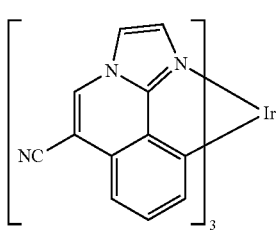
37
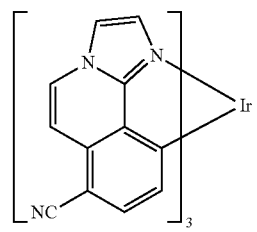
38
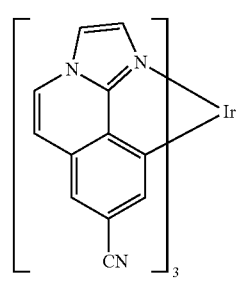
39
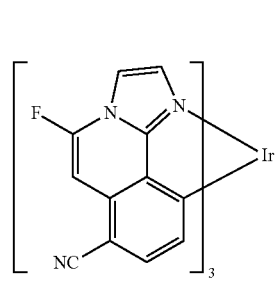
40
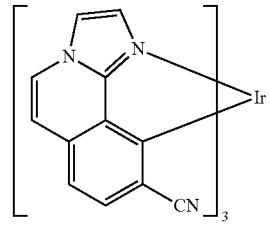
41
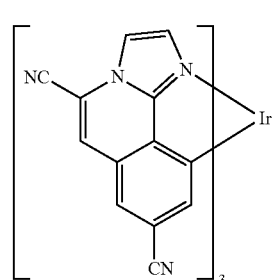
42
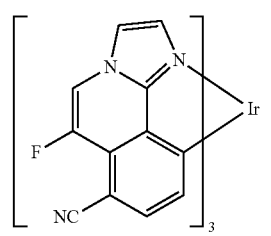

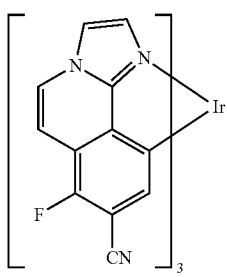
43
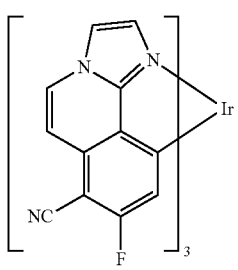
44
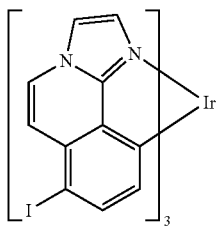
45
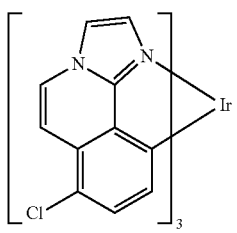
46
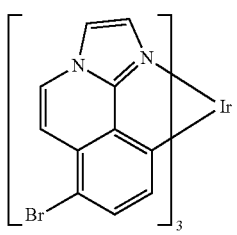
47
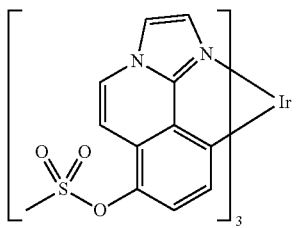
48
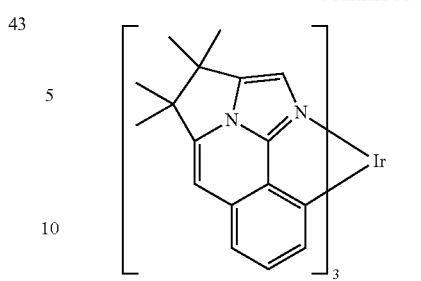
49
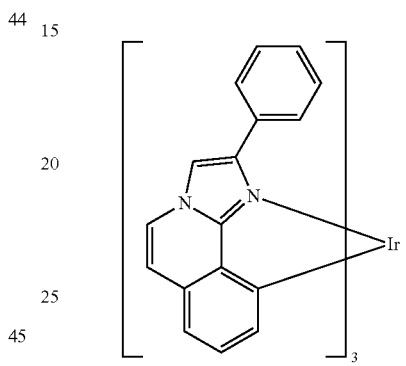
50
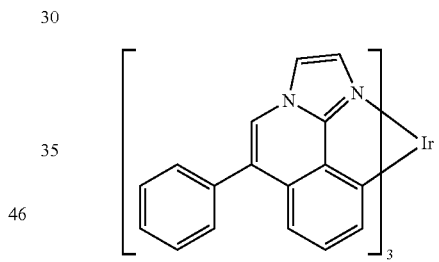
51
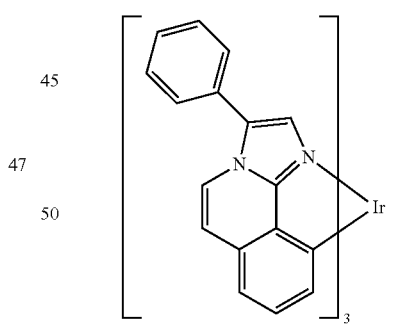
52
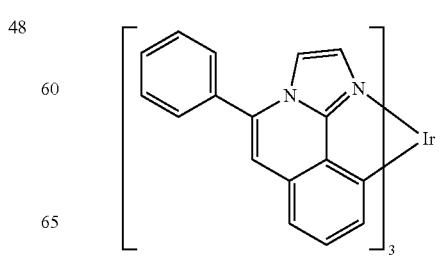
53

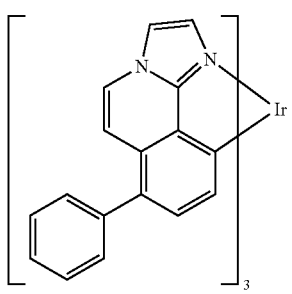
54
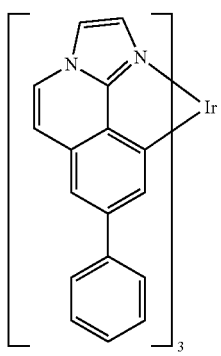
55
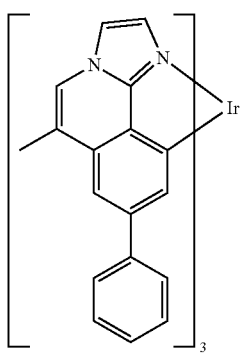
56
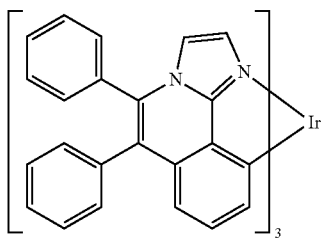
57
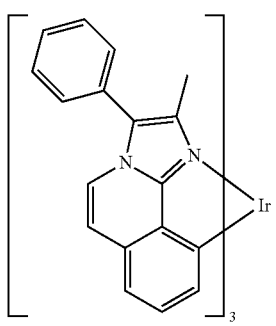
58
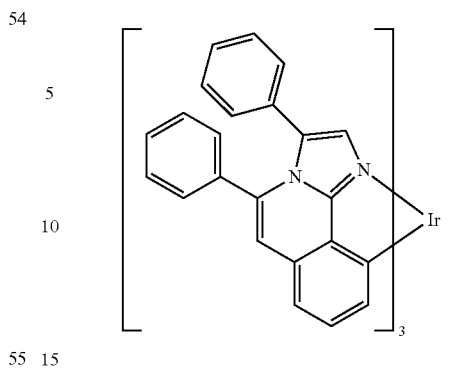
59
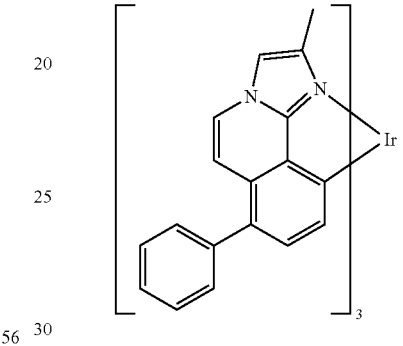
60
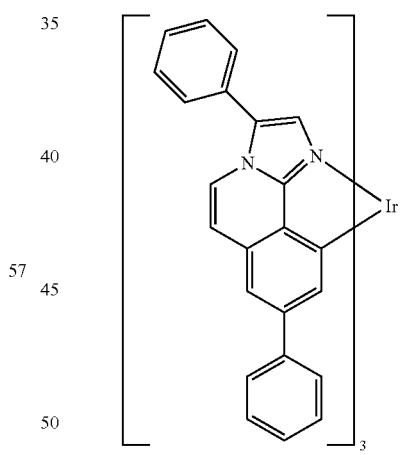
61
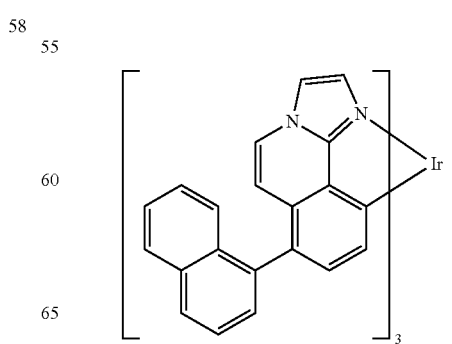
62

63
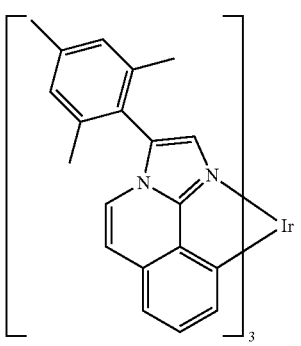
64
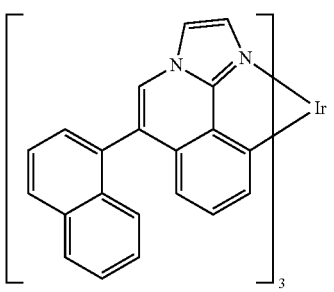
65
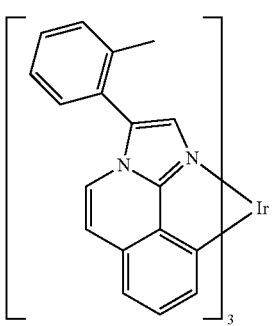
66
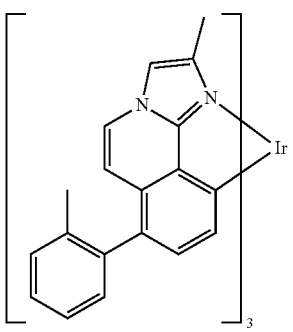
67
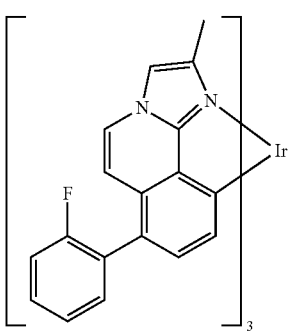
68
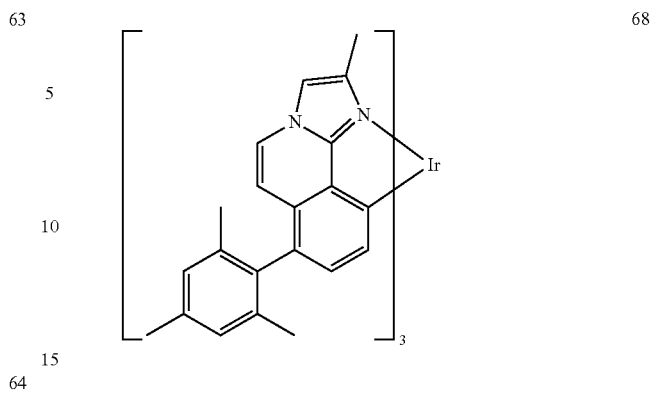
69
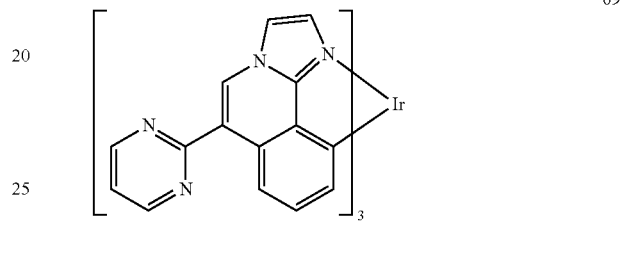
70
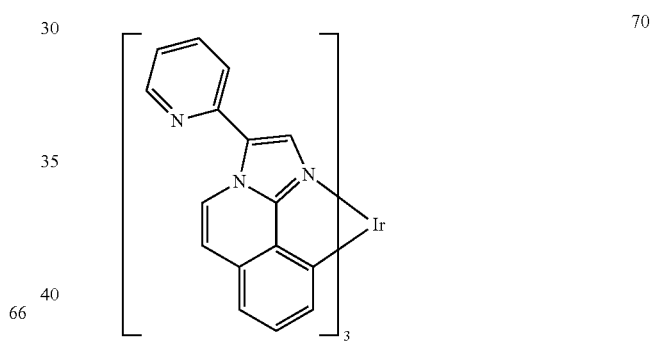
71
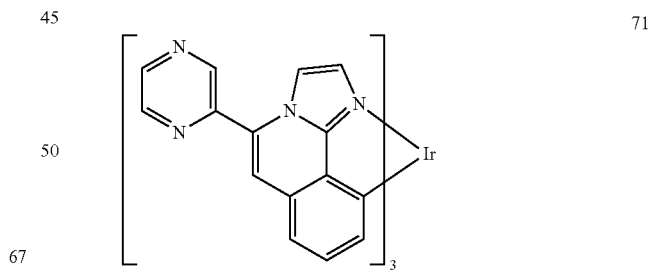
72
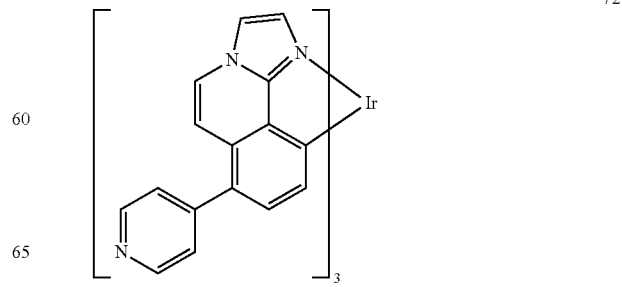

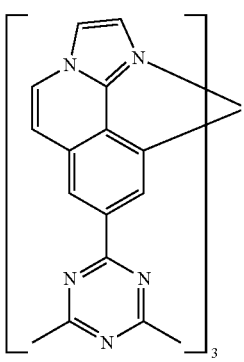
73
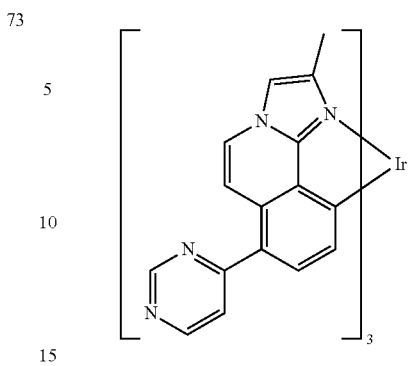
76
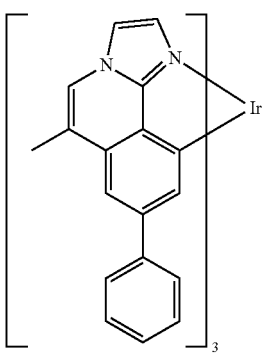
74
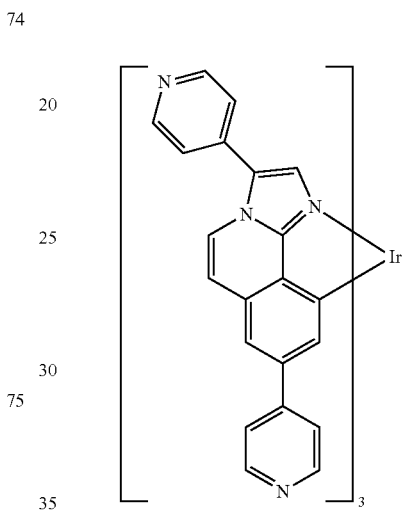
79
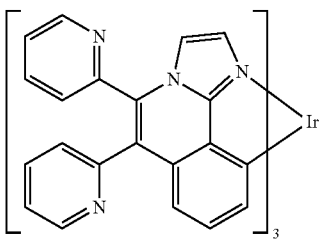
75
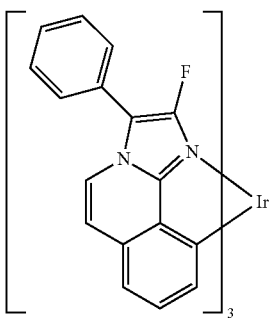
76
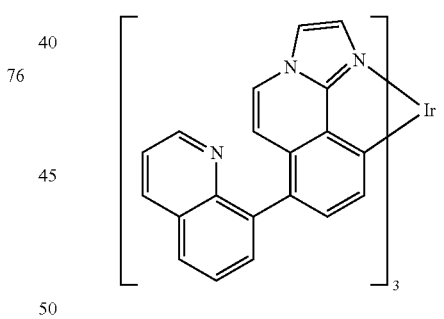
80
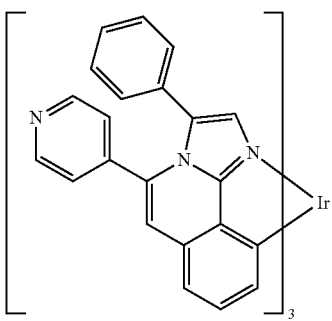
77
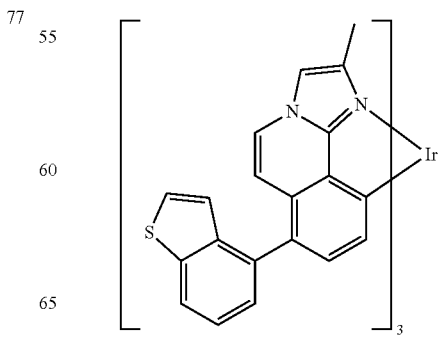
81

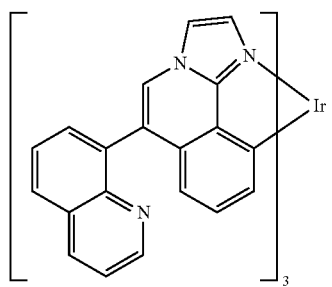
82
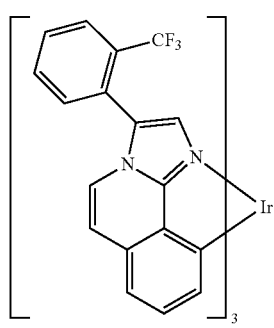
83
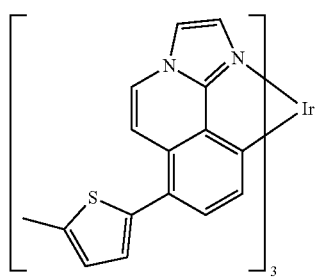
84
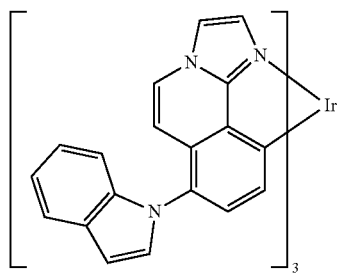
85
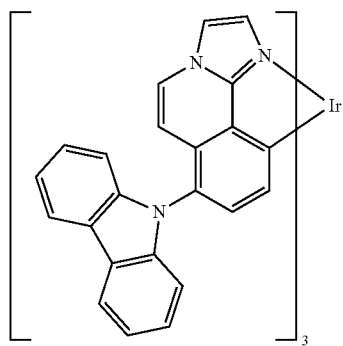
86
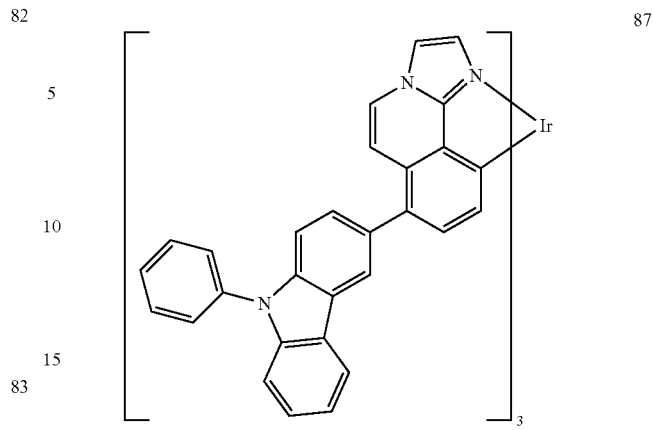
87
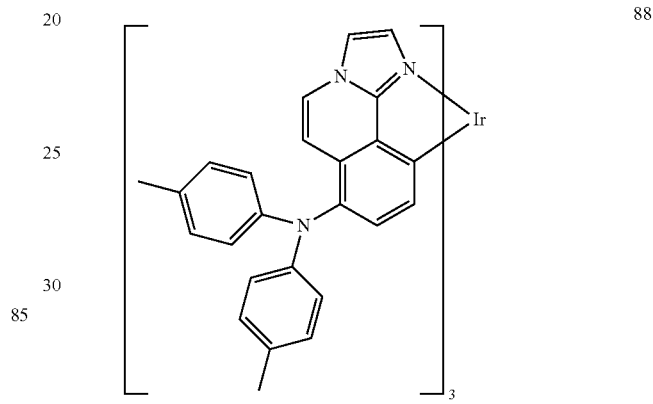
88
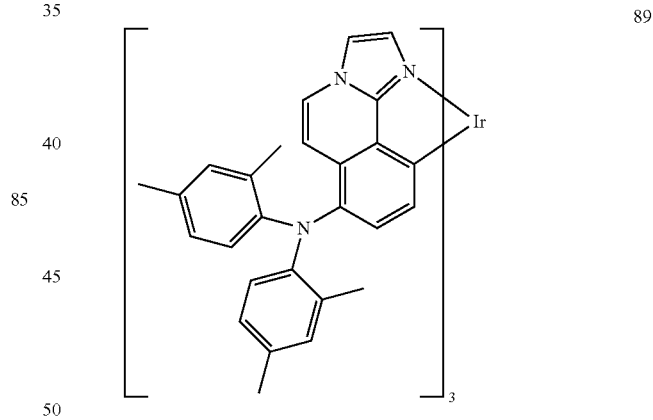
89
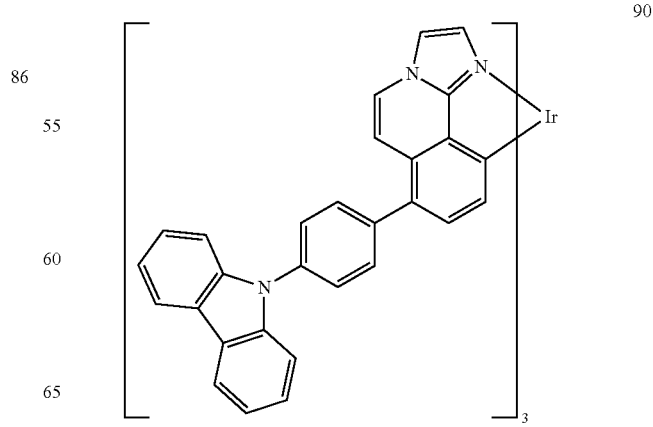
90

91
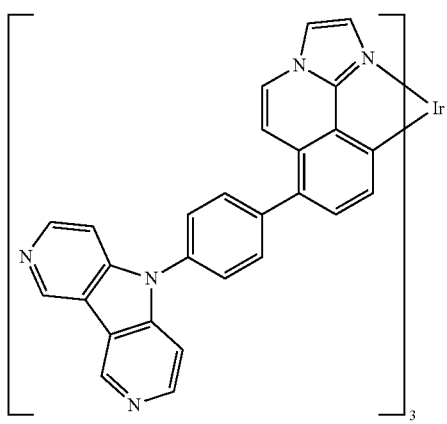
92
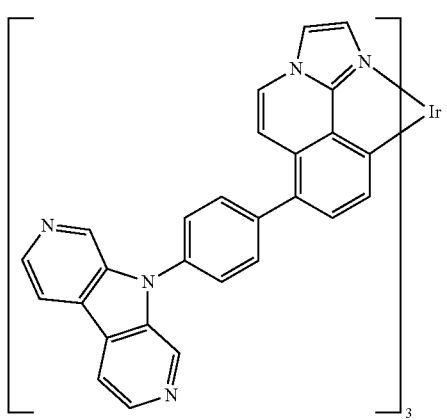
93
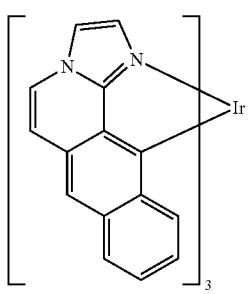
94
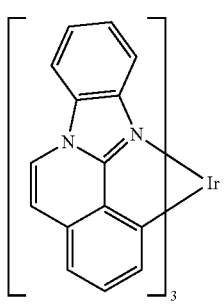
95
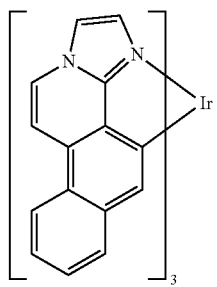
96
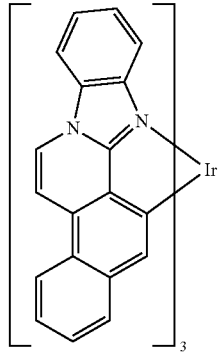
97
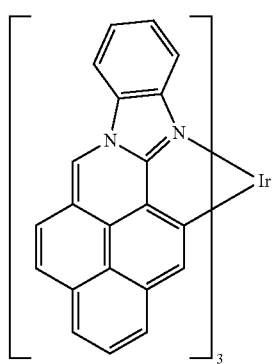
98
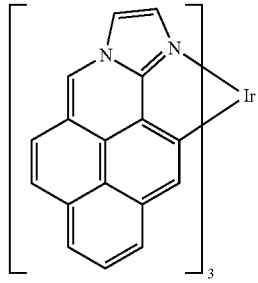
99
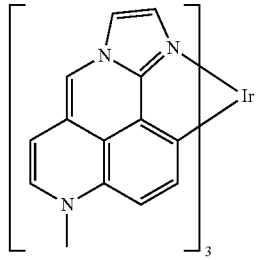

100 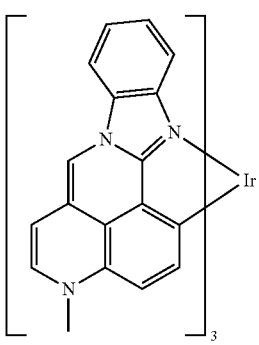
101 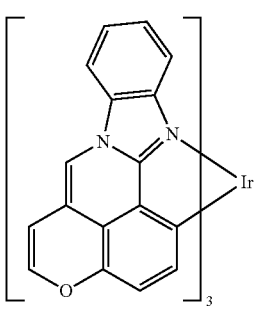
102 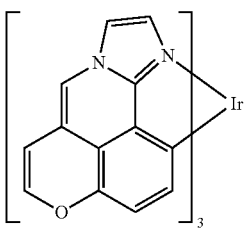
103 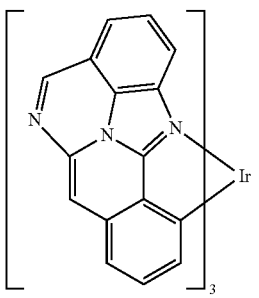
104 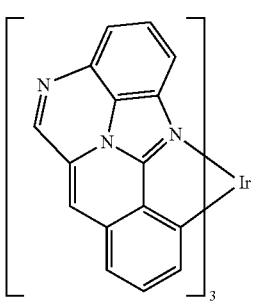
105 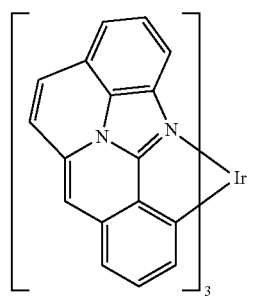
106 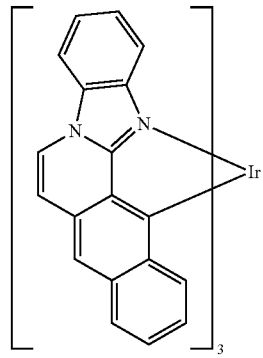
107 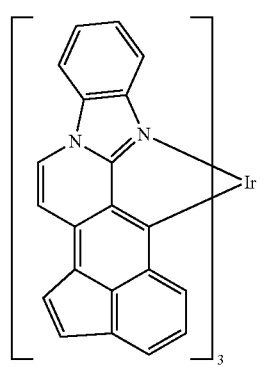
108 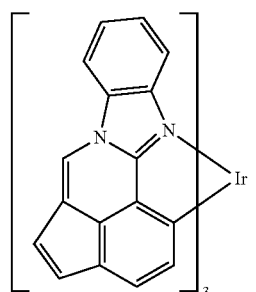
109 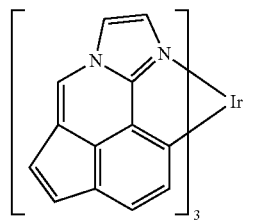

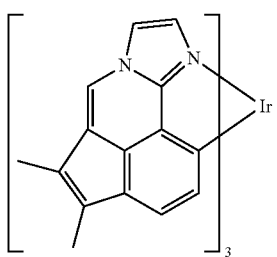
109
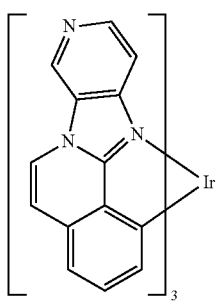
110
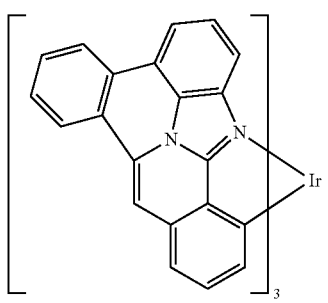
111
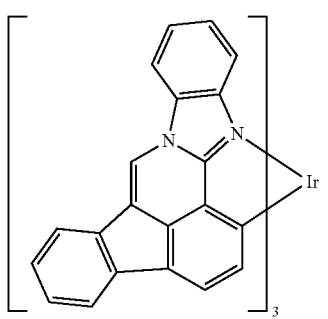
112
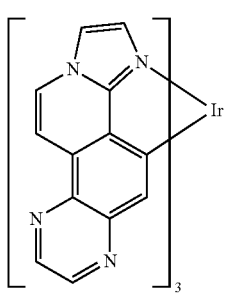
113
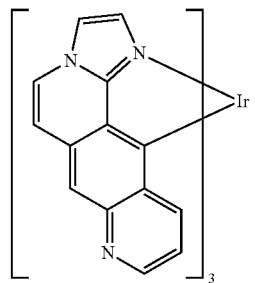
114
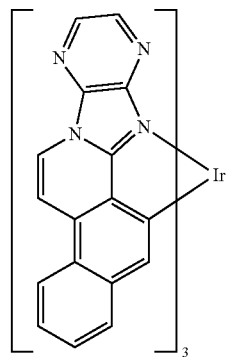
115
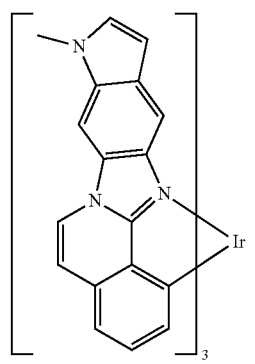
116
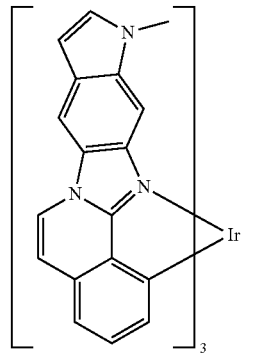
117

119 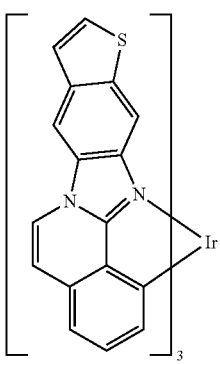
120 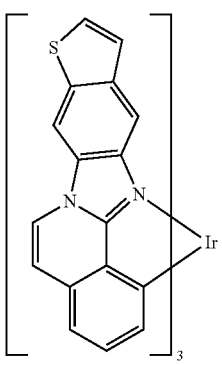
121 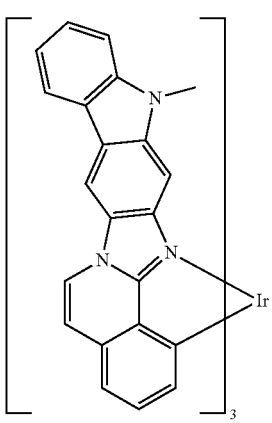
122 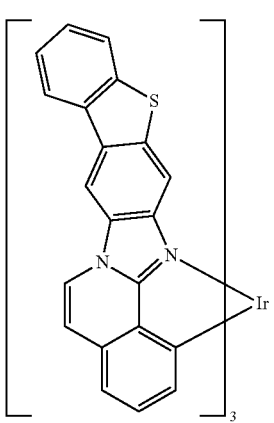
123 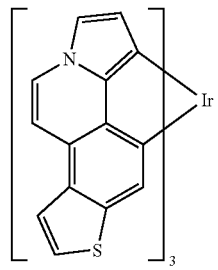
124 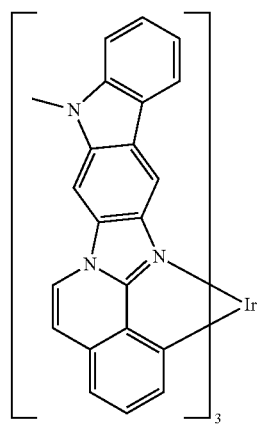
125 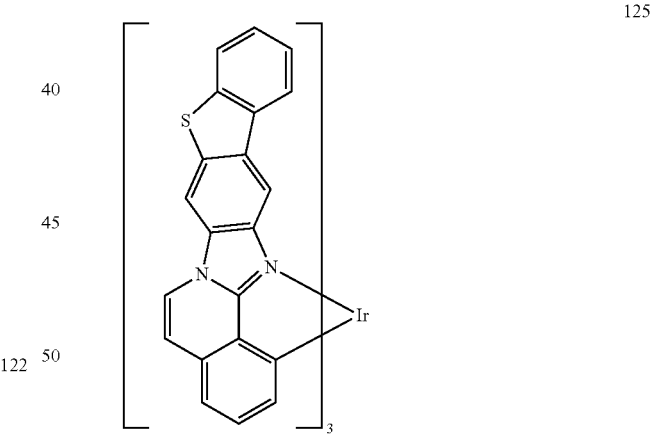
126 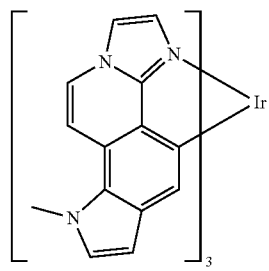

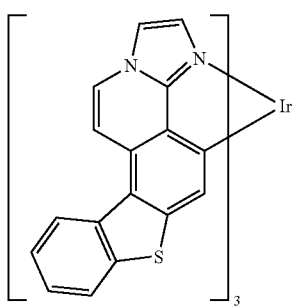
127
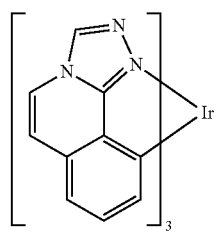
132
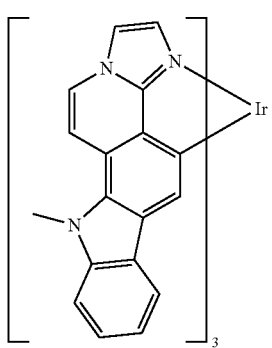
128
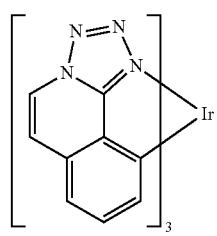
133
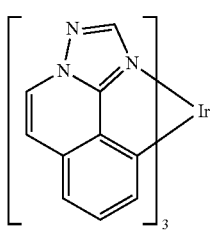
129
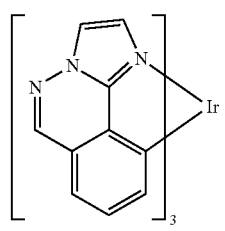
134
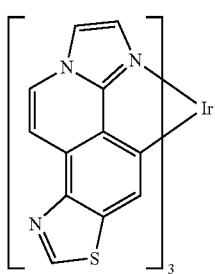
130
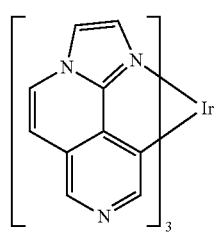
135
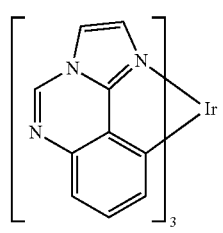
136
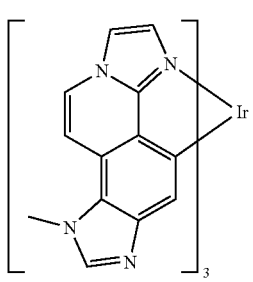
131
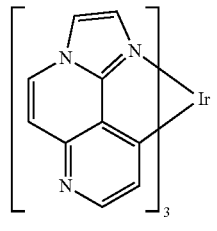
137
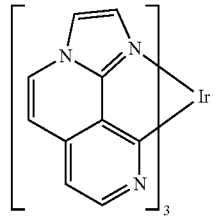
138

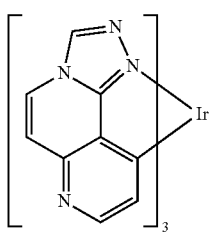
139
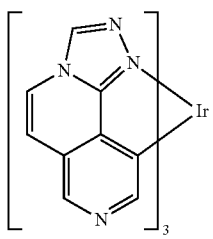 
140
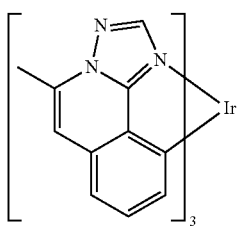
141
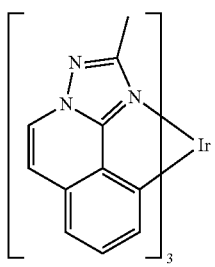
142
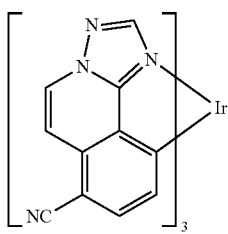
143
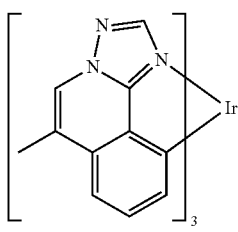
144
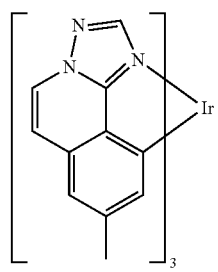
144
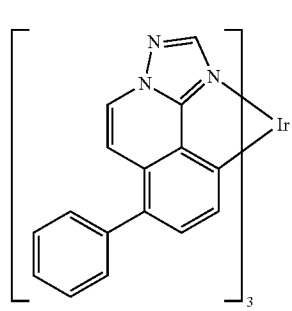
145
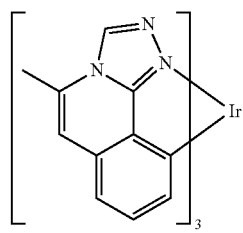
146
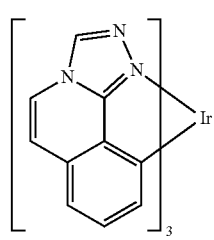
147
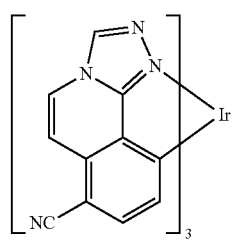
148
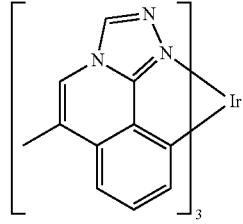
149

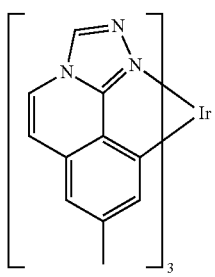 150
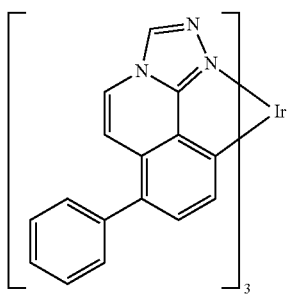 151
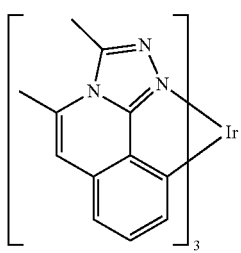 152
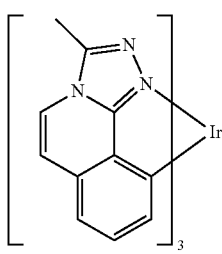 153
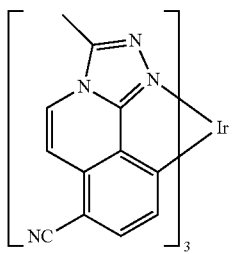 154
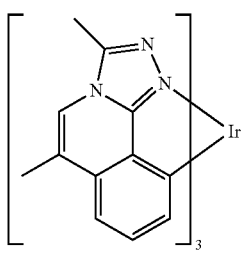 155
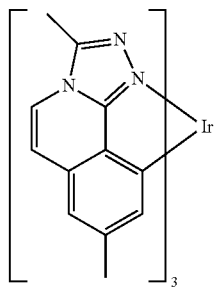 156
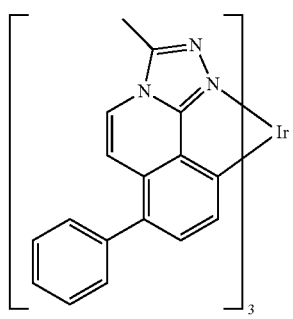 157
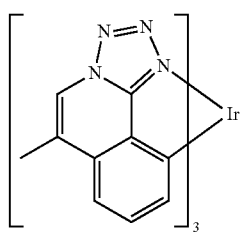 158
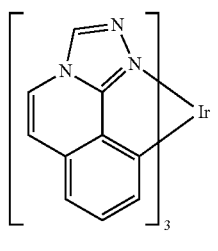 159
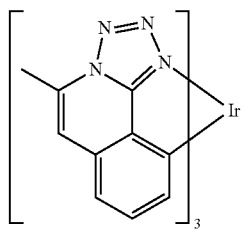 160
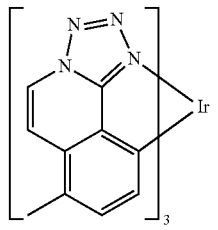 161

162
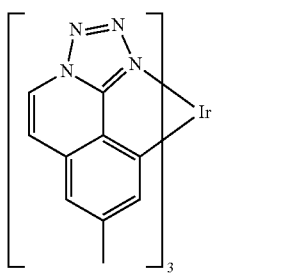
163
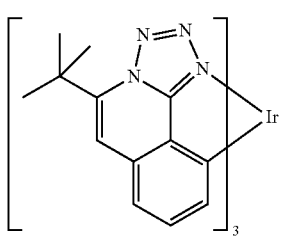
164
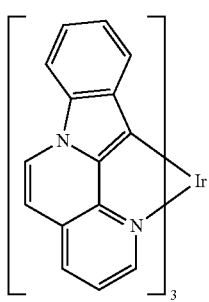
165
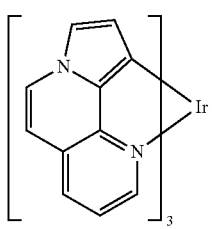
166
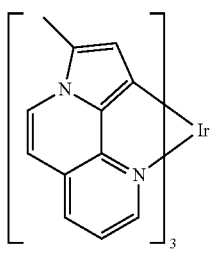
167
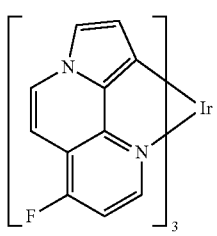
168
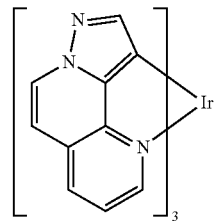
169
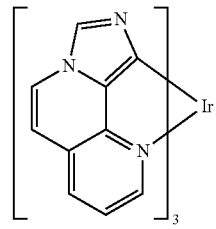
170
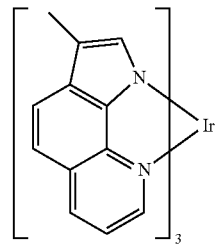
171
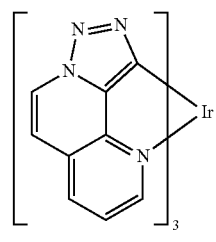
172
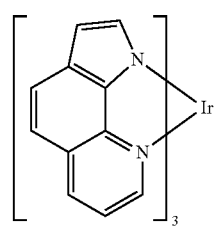
173
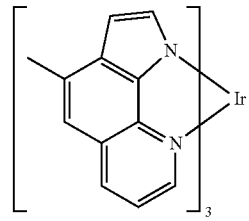
174
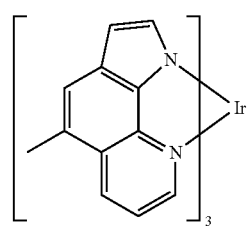

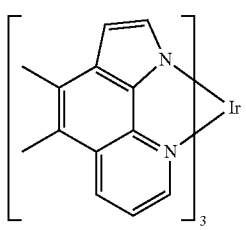 175
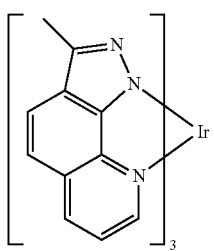 176
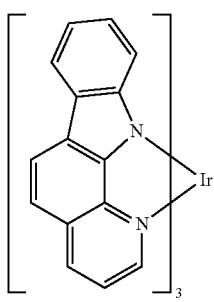 177
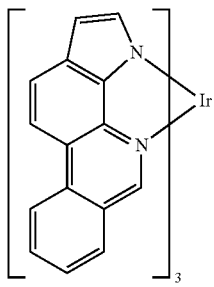 178
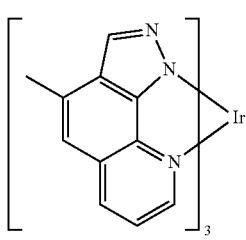 179
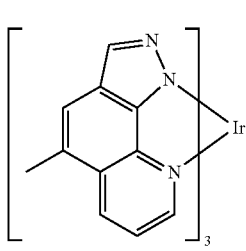 180
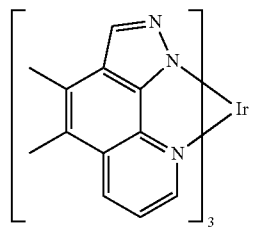 181
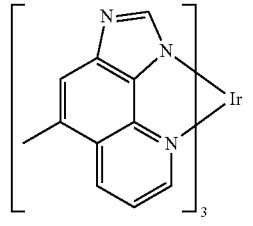 182
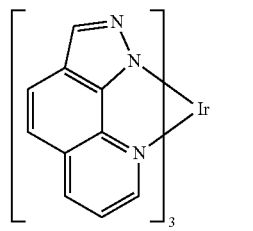 183
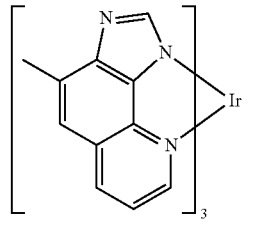 184
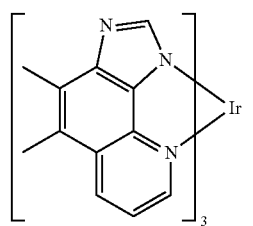 185
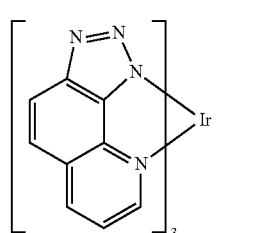 186
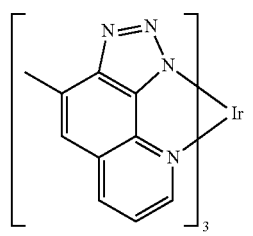 187

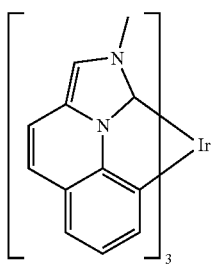
188
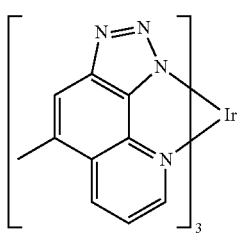
189
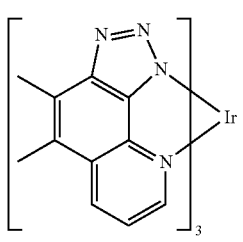
190
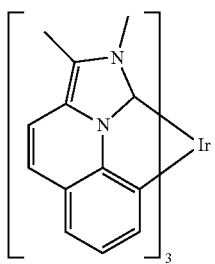
191
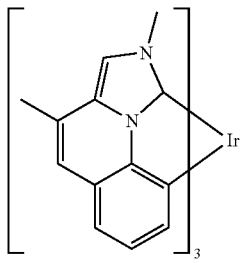
192
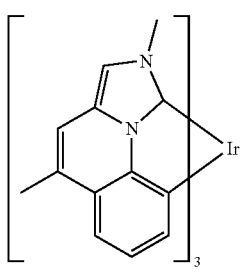
193
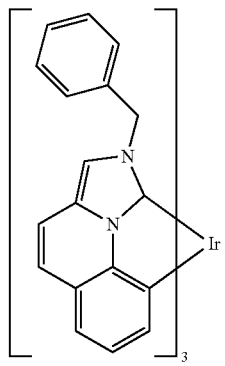
194
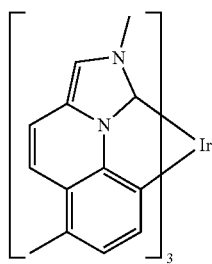
195
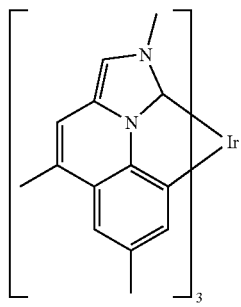
196
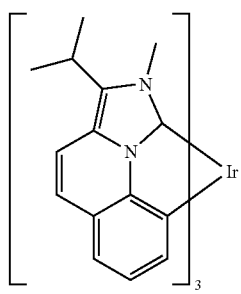
197
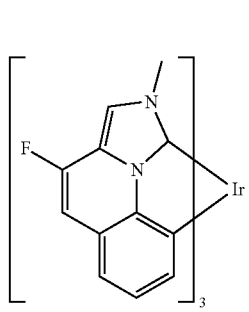
198

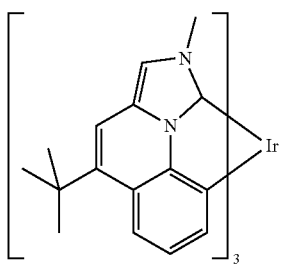
199
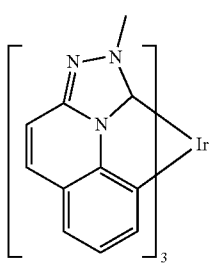
200
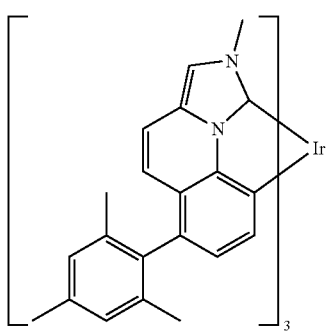
201
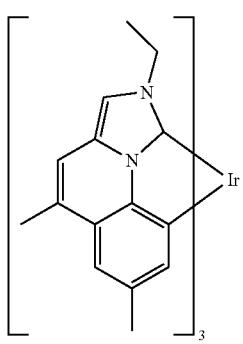
202
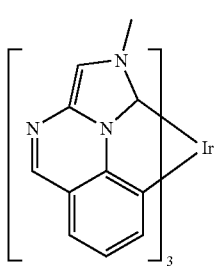
203
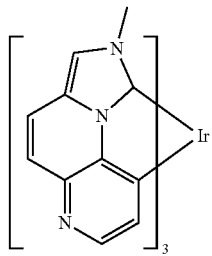
204
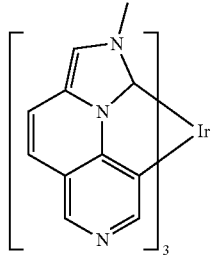
205
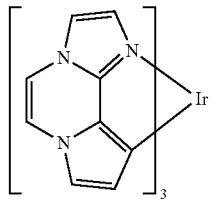
206
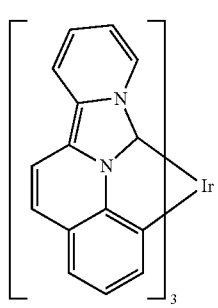
207
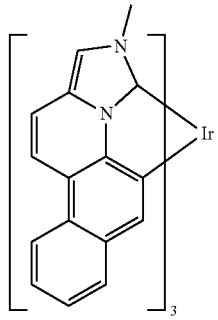
208
209

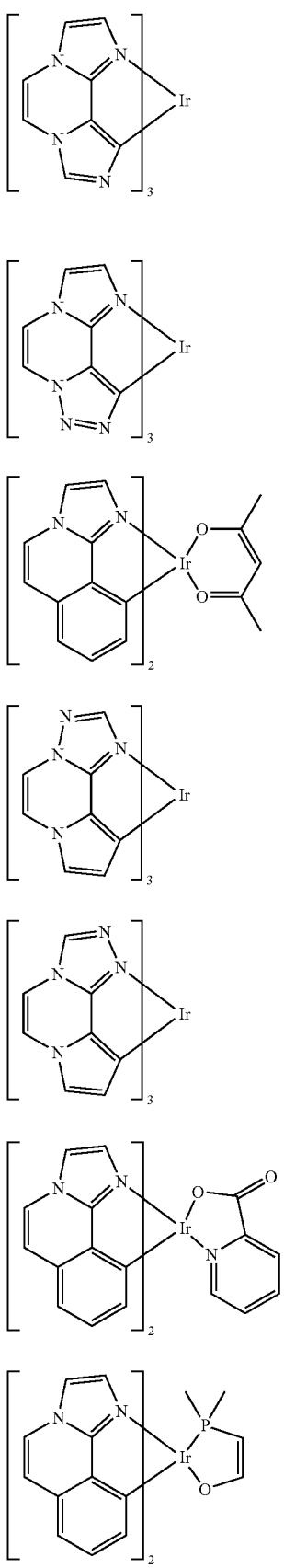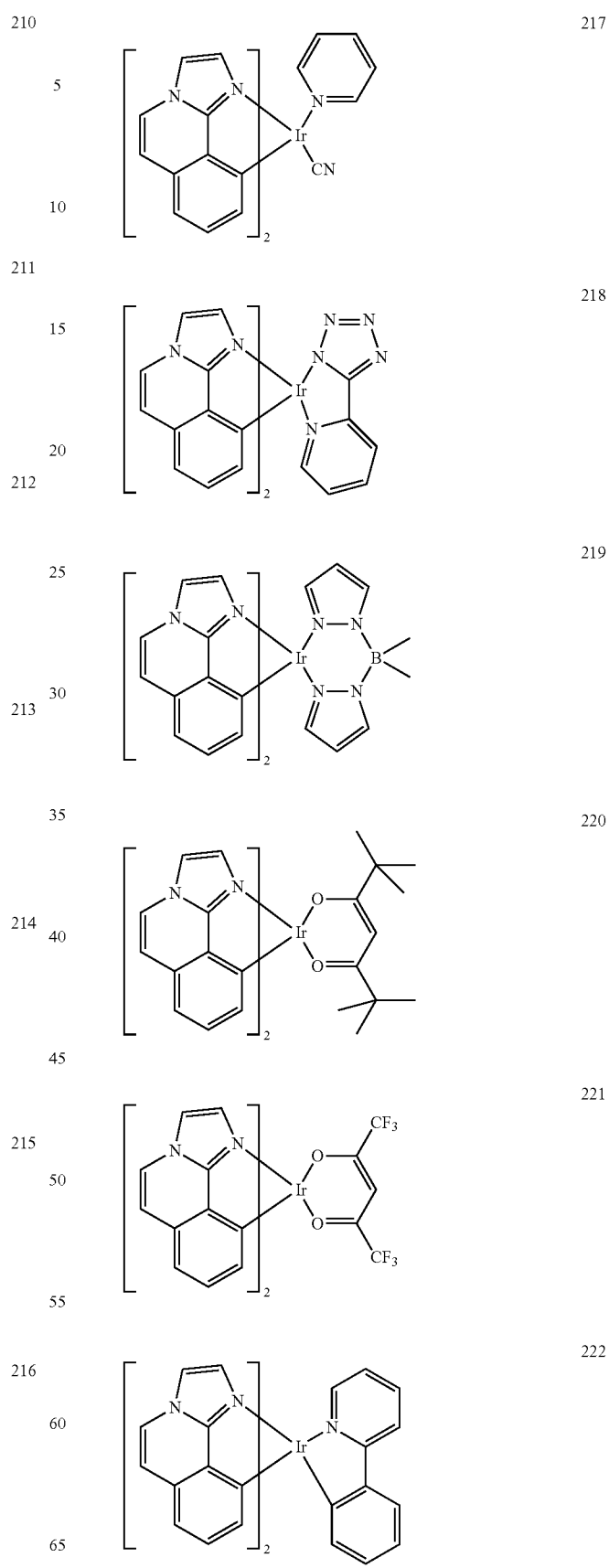

| | |
|---|---|
| 223 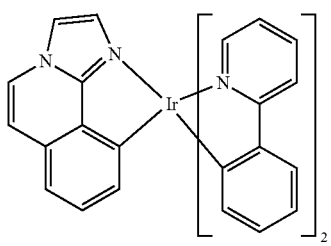 | 229 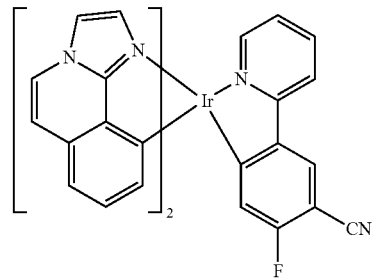 |
| 224 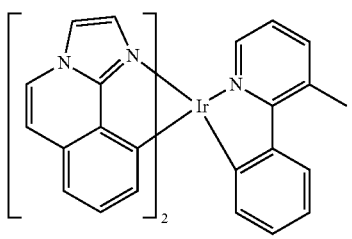 | 230 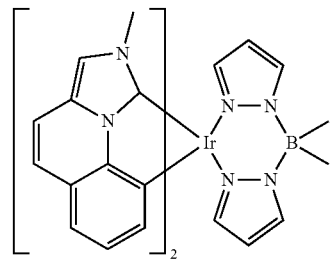 |
| 225 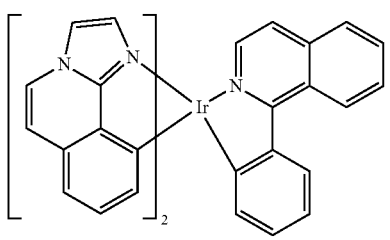 | 231 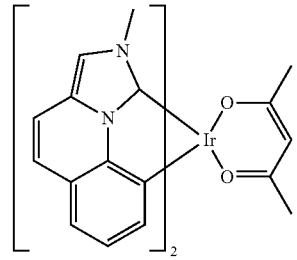 |
| 226 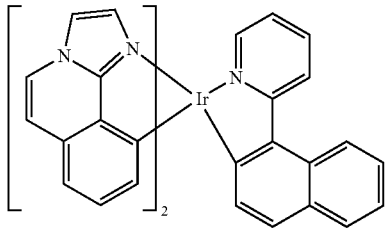 | 232 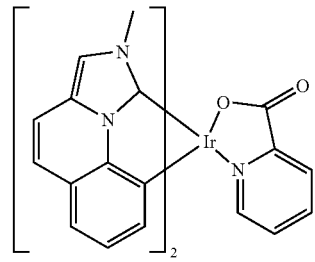 |
| 227 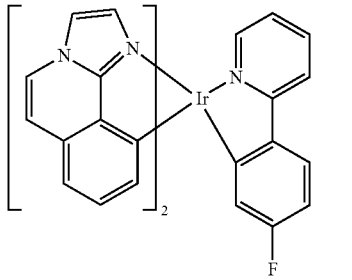 | 233 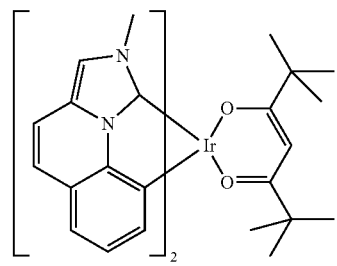 |
| 228 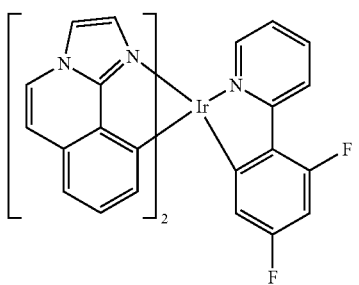 | 234 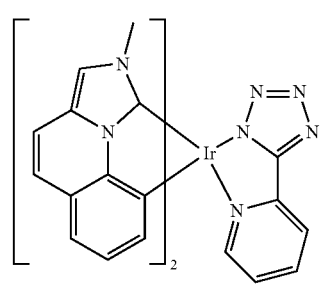 |

235
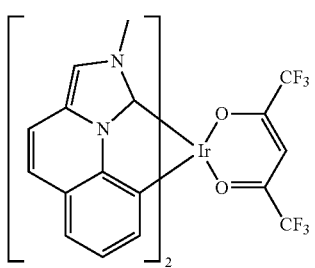
236
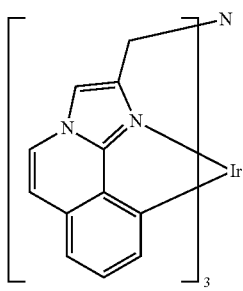
237
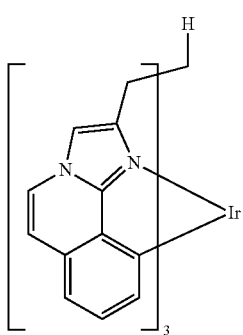
238
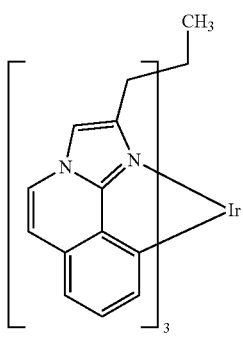
239
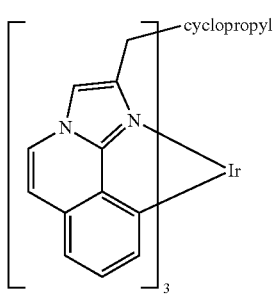
cyclopropyl = △
240
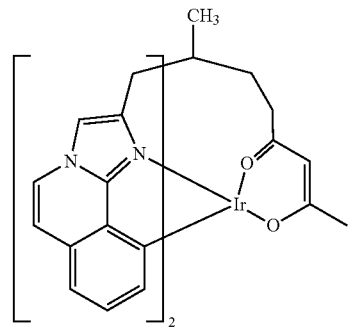
241
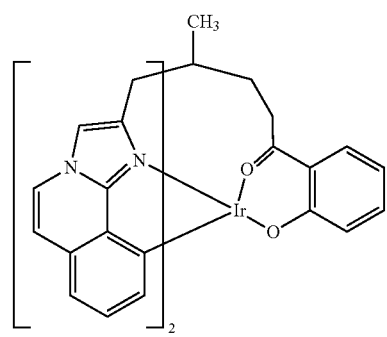
242
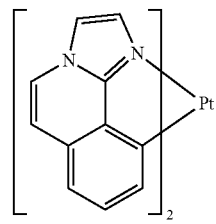
243
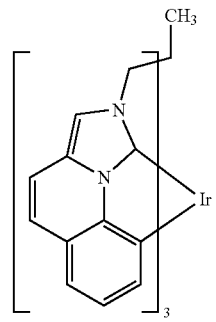
244
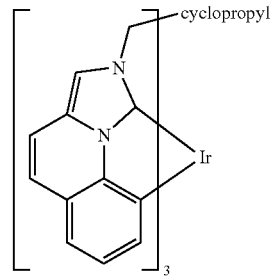
cyclopropyl = △

245 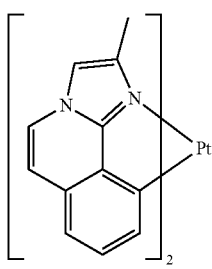
246 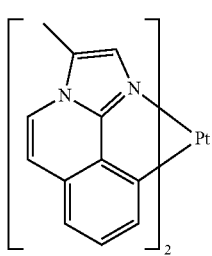
247 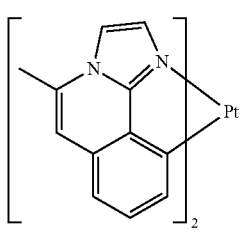
248 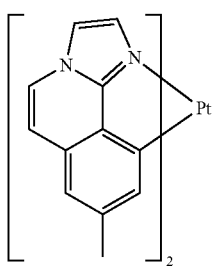
249 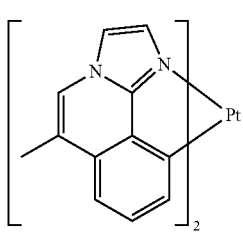
250 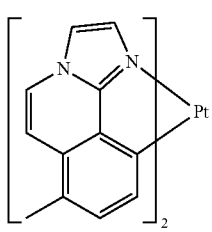
251 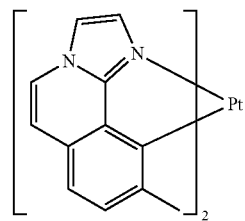
252 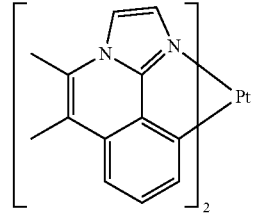
253 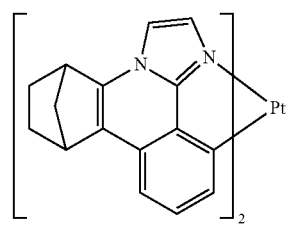
254 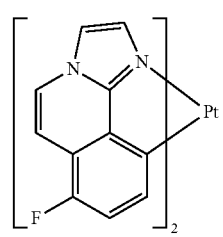
255 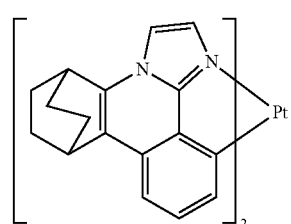
256 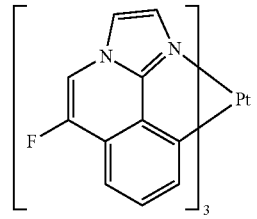

-continued
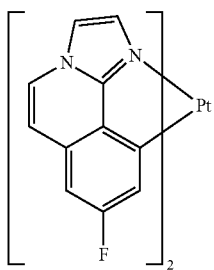
257
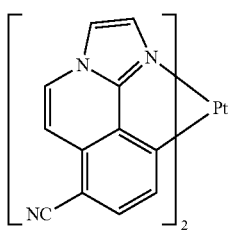
258
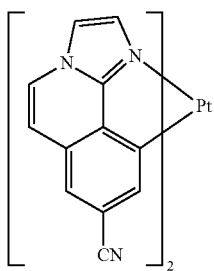
259
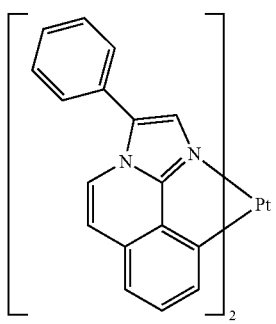
260
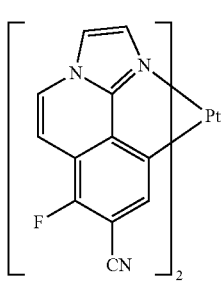
261
-continued
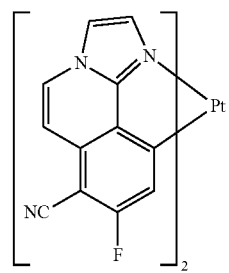
262
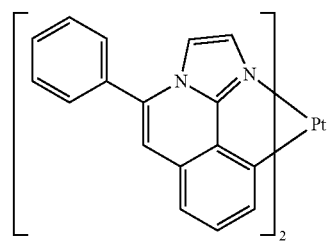
263
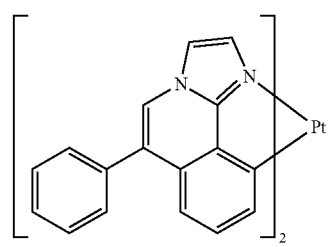
264
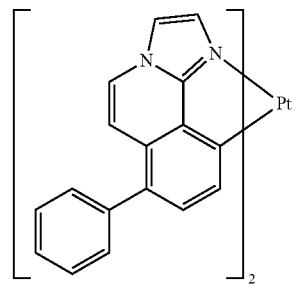
265
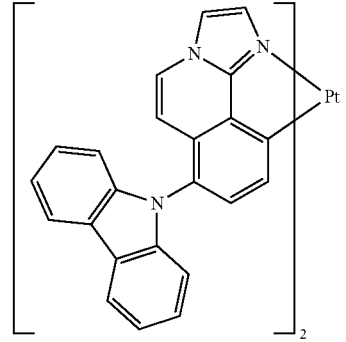
266

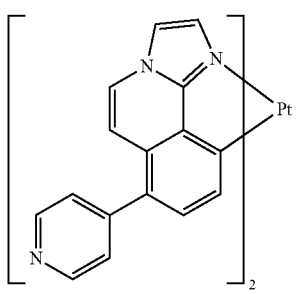
267
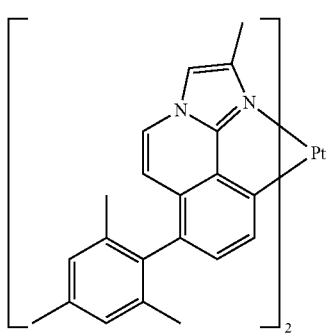
268
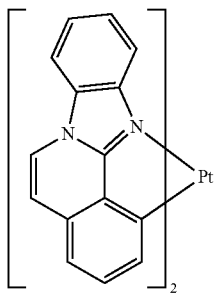
269
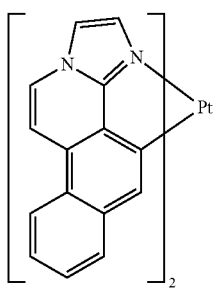
270
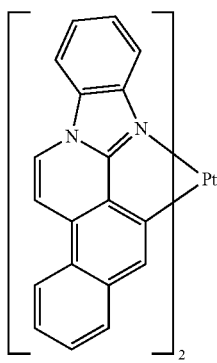
271
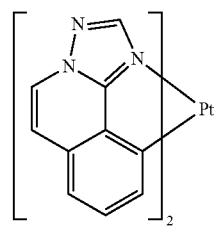
272
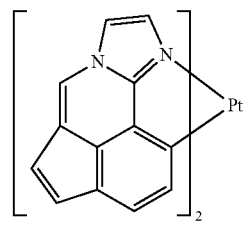
273
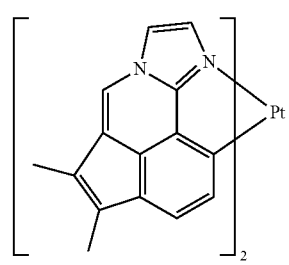
274
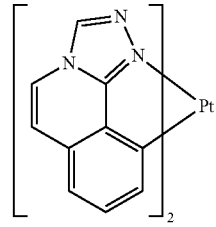
275
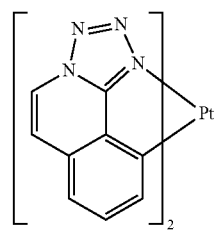
276
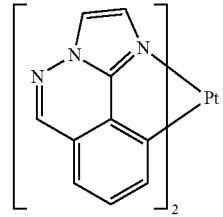
277

278 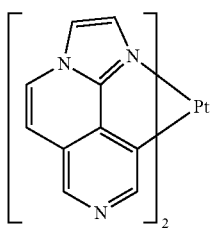
279 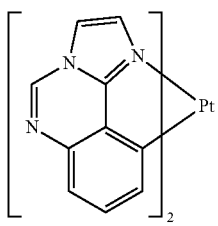
280 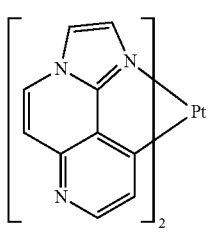
281 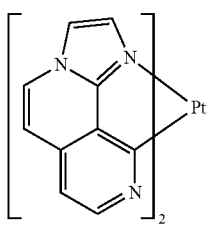
282 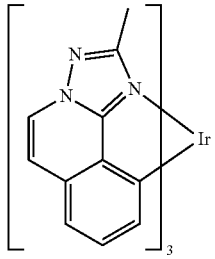
283 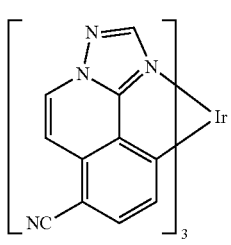
284 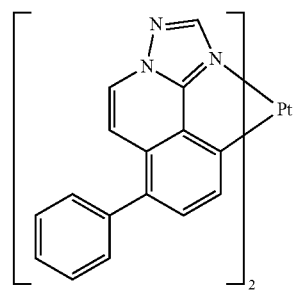
285 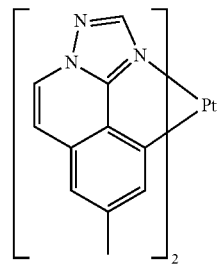
286 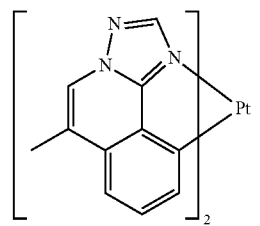
287 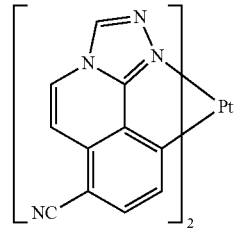
288 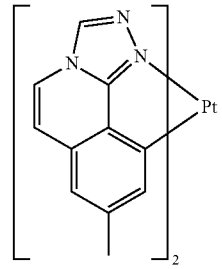
289 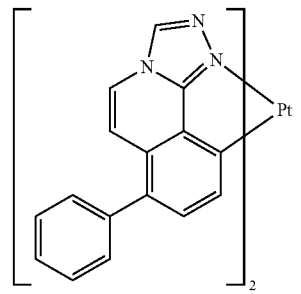

290 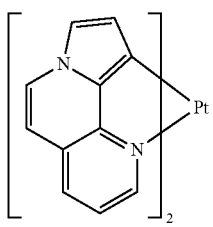
291 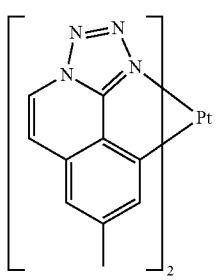
292 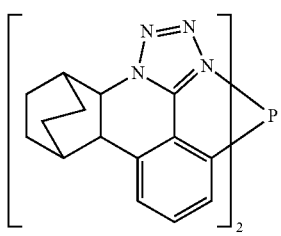
293 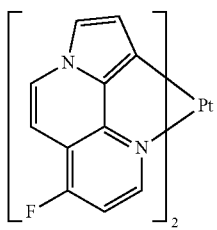
294 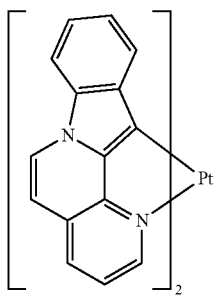
295 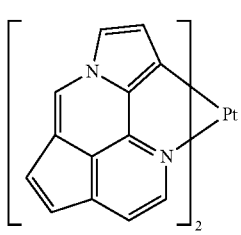
296 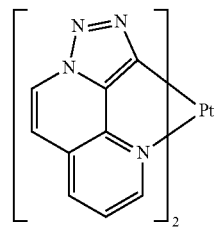
297 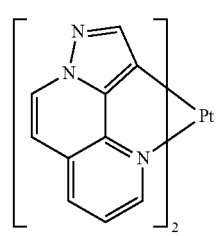
298 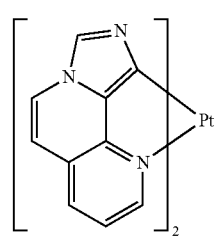
299 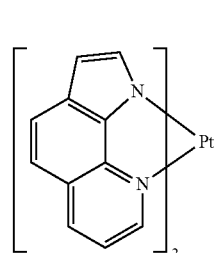
300 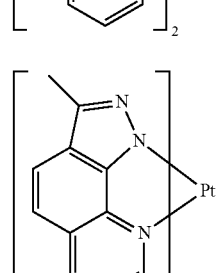
301 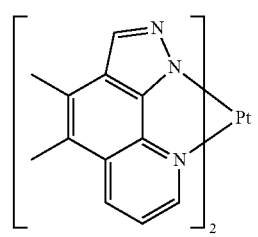

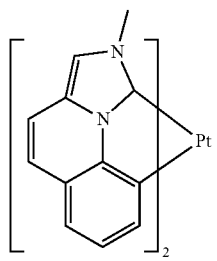
302
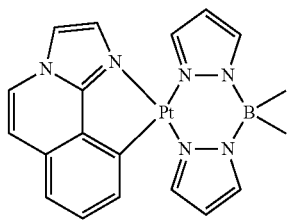
308
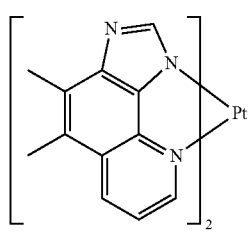
303
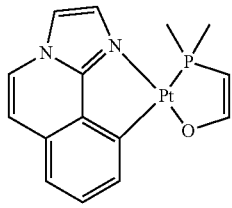
309
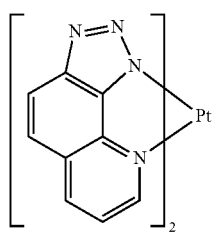
304
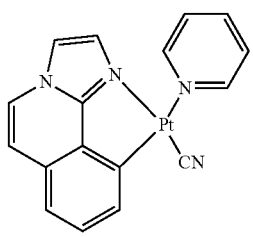
310
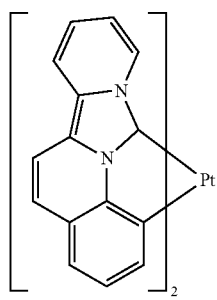
305
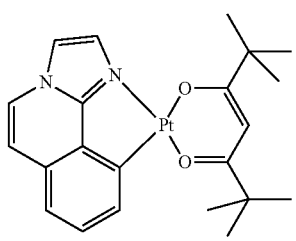
311
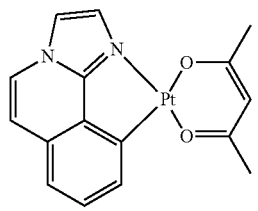
306
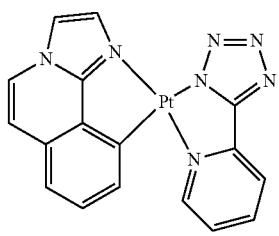
312
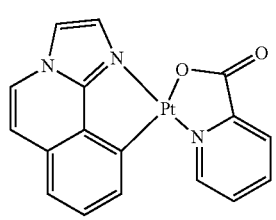
307
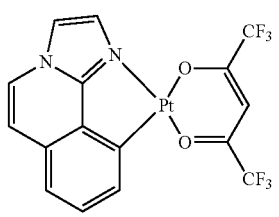
313

101
-continued
315
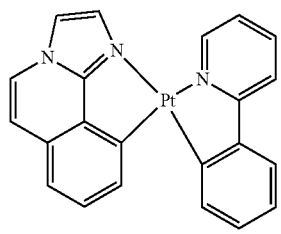
316
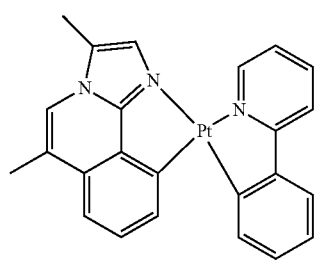
317
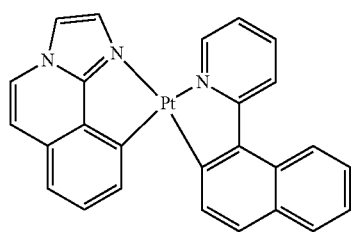
318
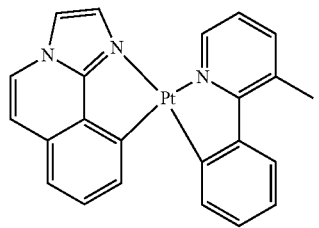
319
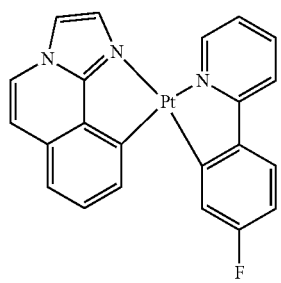
320
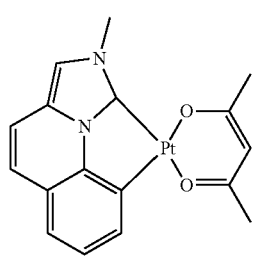
102
-continued
321
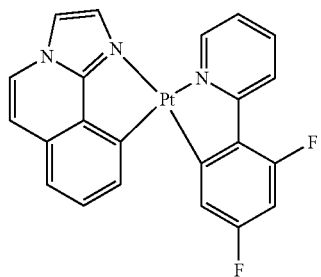
322
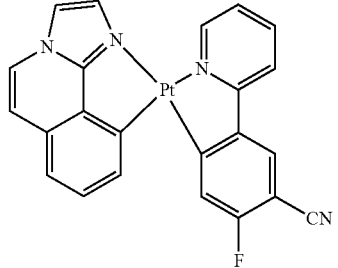
323
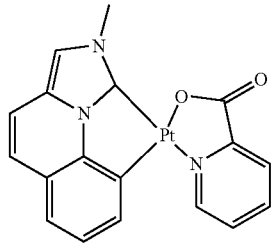
324
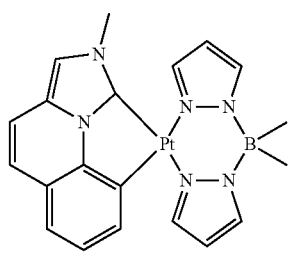
325
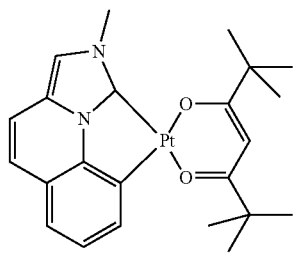
326
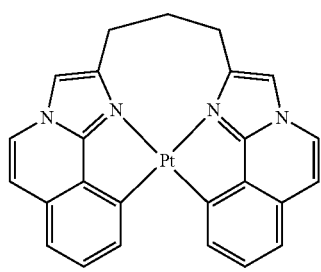

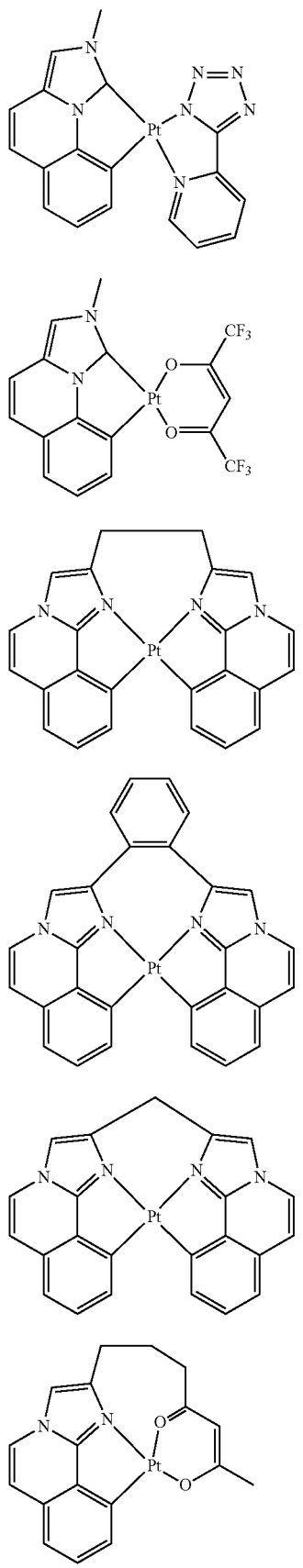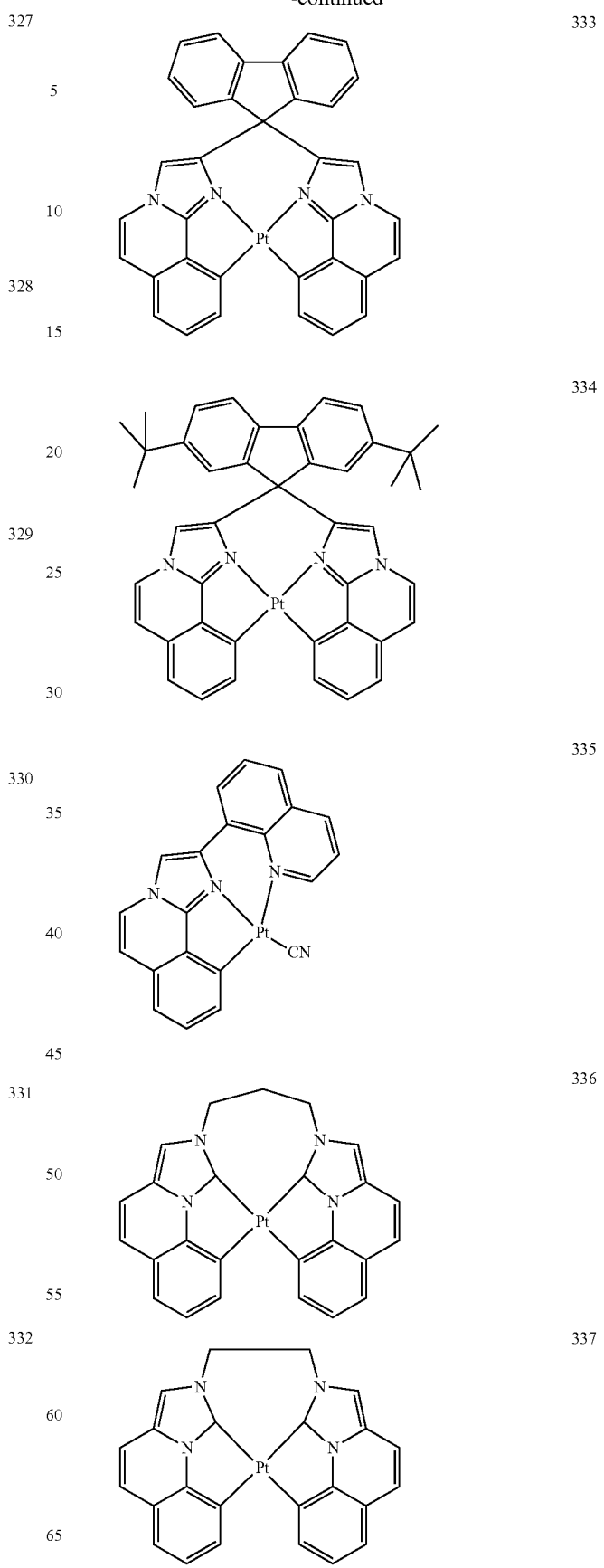

105
-continued
338 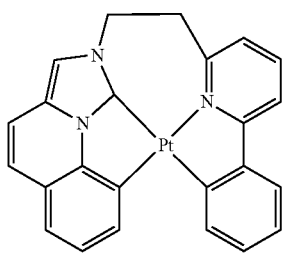
339 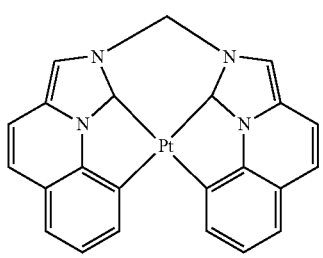
340 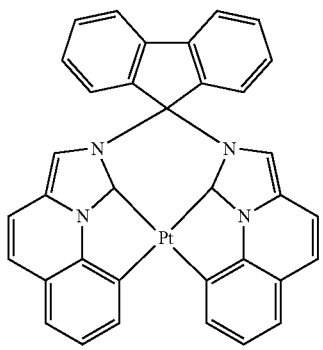
341 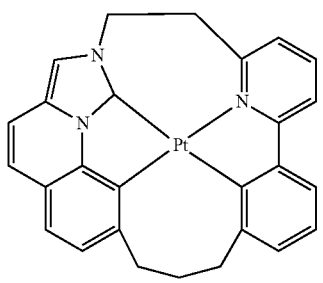
342 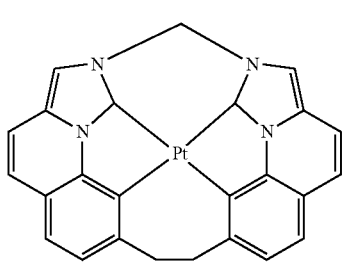
106
-continued
343 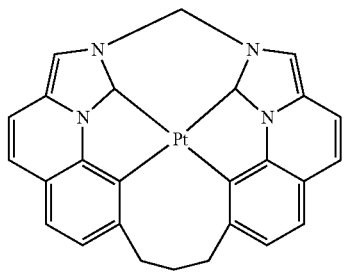
344 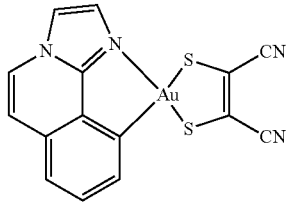
345 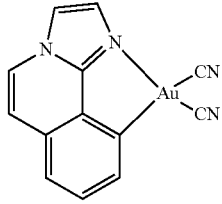
346 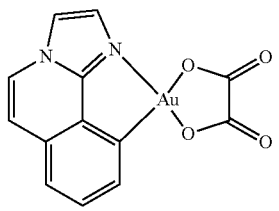
347 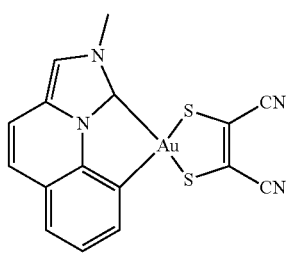
348 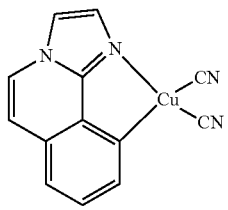
349 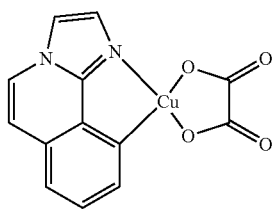

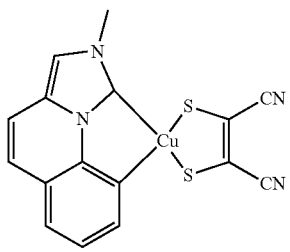
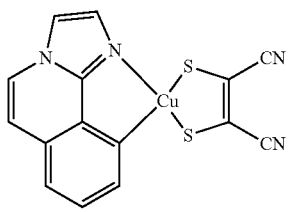
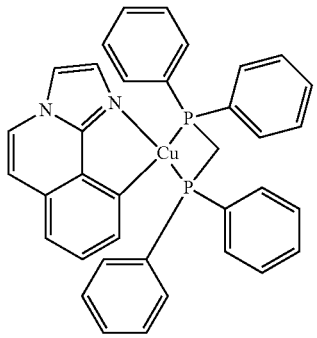
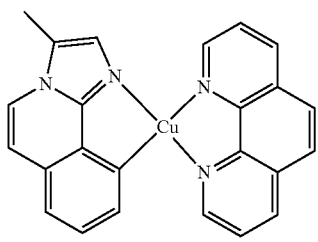
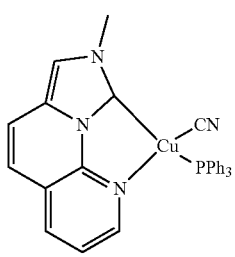
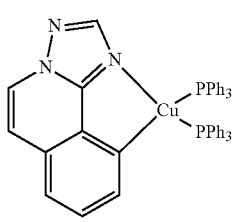

350

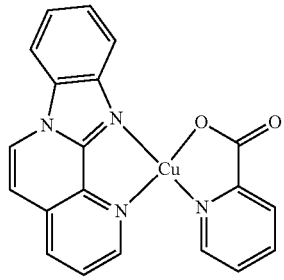

351

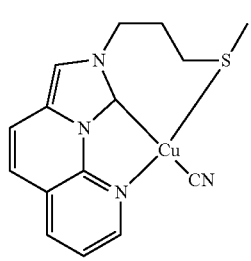

352

353

354

355

356

357

The compounds according to the invention can also be solubilised by suitable substitution, for example by alkyl groups, in particular branched alkyl groups, or optionally substituted aryl groups, for example xylyl, mesityl or branched terphenyl groups. These soluble compounds are particularly suitable for processing from solution, for example by printing processes.

The compounds according to the invention described above can also be used as recurring units in conjugated, partially conjugated or non-conjugated oligomers, polymers or dendrimers. For the purposes of this invention, an oligomer is taken to mean a compound having about 3 to 10 recurring units, which may be identical or different. The polymerisation here is preferably carried out via a bromine or boronic acid functionality. Thus, compounds of this type can be copolymerised, inter alia, into polyfluorenes (for example in accordance with EP 842208 or WO 00/22026), polyspirobifluorenes (for example in accordance with EP 707020 or EP 894107), polydihydrophenanthrenes (for example in accordance with WO 05/014689), polyindenofluorenes (for example in accordance with WO 04/041901 and WO 04/113468), polyphenanthrenes (for example in accordance with WO 05/104264), poly-para-phenylenes (for example in accordance with WO 92/18552), polycarbazoles (for example in accordance with WO 04/070772 or WO 04/113468), polyketones (for example in accordance with WO 05/040302), polysilanes (for example in accordance with WO 05/111113) or polythiophenes (for example in accordance with EP 1028136) or also into copolymers which comprise various of these units. They can either be incorporated into the side chain or into the main chain of the polymer here or can represent branching points of the polymer chains (for example in accordance with WO 06/003000).

The invention thus furthermore relates to oligomers, polymers or dendrimers comprising one or more of the compounds of the formula (1), where at least one of the radicals $R^1$ to $R^8$ defined above represents a bond to the polymer or dendrimer. The oligomers, polymers or dendrimers may be conjugated, partially conjugated or non-conjugated. For units of the formula (1), the same preferences as already described above apply in polymers and dendrimers. Apart from the units mentioned above, the oligomers, polymers or dendrimers may comprise further units selected, for example, from recurring units which have hole-transport properties or electron-transport properties. The materials or recurring units known in the prior art are suitable for this purpose.

The oligomers, polymers, copolymers and dendrimers mentioned above are distinguished by good solubility in organic solvents and high efficiency and stability in electroluminescent devices.

The compounds of the formula (1) according to the invention, in particular those which are functionalised by halogens, may furthermore also be further functionalised by common reaction types and thus converted into extended compounds of the formula (1). An example which may be mentioned here is functionalisation with arylboronic acids by the Suzuki method or with amines by the Hartwig-Buchwald method.

The complexes of the formula (1) described above or the preferred embodiments mentioned above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013), or systems which have more than three emitting layers. A hybrid system is also possible, where one or more layers fluoresce and one or more other layers phosphoresce.

In a preferred embodiment of the invention, the organic electroluminescent device comprises the compound of the formula (1) or the preferred embodiments mentioned above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99 and 1% by vol., preferably between 98 and 10% by vol., particularly preferably between 97 and 60% by vol., especially between 95 and 85% by vol., of the matrix material, based on the mixture as a whole comprising emitter and matrix material.

In general, the matrix material employed can be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl), m-CBP or the carbazole derivatives disclosed in WO 05/039246, US 2005/0069729, JP 2004/288381, EP 1205527, WO 08/086,851 or US 2009/0134784, indolocarbazole derivatives, for example in accordance with WO 07/063,754 or WO 08/056,746, indenocarbazole derivatives, azacarbazoles, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, diazasilole derivatives and diazaphosphole derivatives, for example in accordance with the unpublished application DE 102008056688.8, triazine derivatives, for example in accordance with the unpublished application DE 102008036982.9, WO 07/063,754 or WO 08/056,746, or zinc complexes, for example in accordance with EP 652273 or WO 09/062,578.

It may also be preferred to employ a plurality of different matrix materials as a mixture, in particular at least one electron-conducting matrix material and at least one hole-conducting matrix material. A preferred combination is, for example, the use of an aromatic ketone or a triazine derivative with a triarylamine derivative or a carbazole derivative as mixed matrix for the metal complex according to the invention.

It is furthermore preferred to employ a mixture of two or more triplet emitters together with a matrix. The triplet emitter having the shorter-wavelength emission spectrum serves as co-matrix for the triplet emitter having the longer-wavelength emission spectrum.

The compounds according to the invention can also be employed in other functions in the electronic device, for example as hole-transport material in a hole-injection or -transport layer, as charge-generation material or as electron-blocking material.

As cathode, preference is given to metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent in order either to facilitate irradiation of the organic material (O-SCs) or the coupling-out of light (OLEDs/PLEDs, O-LASERs). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et at., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments mentioned above.

The electronic devices according to the invention, in particular organic electroluminescent devices, are distinguished by the following surprising advantages over the prior art:
1. Organic electroluminescent devices comprising compounds of the formula (1) as emitting materials have an excellent lifetime.
2. Organic electroluminescent devices comprising compounds of the formula (1) as emitting materials have excellent efficiency.
3. The metal complexes according to the invention give access to organic electroluminescent devices which phosphoresce in the blue colour region. In particular, blue phosphorescence with good efficiencies and lifetimes can only be achieved with great difficulty in accordance with the prior art.

These advantages mentioned above are not accompanied by an impairment of the other electronic properties.

The invention is explained in greater detail by the following examples, without wishing to restrict it thereby. The person skilled in the art will be able to produce further electronic devices according to the invention from the descriptions without an inventive step and thus carry out the invention throughout the range claimed.

EXAMPLES

The following syntheses are, unless indicated otherwise, carried out under a protective-gas atmosphere in dried solvents. The metal complexes are additionally handled with exclusion of light. The solvents and reagents can be purchased from ALDRICH or ABCR.

A: Synthesis of the Ligands
1) Imidazo[2,1-a]isoquinoline systems
Synthesis of 1-aminoisoquinolines:

A mixture of 100 mmol of the 1-chloroisoquinoline derivative and 600 mmol of ammonium chloride in 100 ml of sulfolane is stirred at 200° C. for 20 h. 200 ml of water are added to the cooled mixture, and the mixture is stirred at room temperature for 1 h. The solid is filtered off with suction, washed once with 50 ml of water and subsequently suspended in a mixture of 50 ml of methanol and 150 ml of conc. ammonia solution. The suspension is stirred at room temperature for 20 h, and the solid is filtered off, washed three times with 50 ml of methanol/water 1:1, dried in vacuo and subjected to Kugelrohr distillation.

| Ex. | 1-Chloroisoquinoline derivative | 1-Aminoisoquinoline derivative | Yield |
|---|---|---|---|
| A1 | (structure) 24188-78-1 | (structure) | 74% |
| A2 | (structure) 15787-20-9 | (structure) | 67% |
| A3 | (structure) 55792-01-3 | (structure) | 61% |

Ligand Synthesis Variant A:

A vigorously stirred mixture of 100 mmol of the 1-aminoisoquinoline derivative, 150 mmol of the carbonyl component, 130 mmol of sodium hydrogencarbonate, 80 ml of ethanol and 15 ml of water is heated under reflux until the 1-aminoisoquinoline has reacted (aldehydes about 3-8 h, ketones about 30-100 h). The solvent is subsequently removed in vacuo, the residue is taken up in 500 ml of dichloromethane, and the mixture is washed three times with 200 ml of water. After the organic phase has been dried and the solvent has been removed in vacuo, the residue is chromatographed on silica gel (eluent: ethyl acetate/heptane mixtures). The resultant oils/solids are freed from low-boiling components in an oil-pump vacuum, by bulb-tube distillation or sublimation.

Ligand Synthesis Variant B:

A mixture of 100 mol of the 1-aminoisoquinoline derivative, 300 mol of the carbonyl component, 150 mol of sodium hydrogencarbonate, 150 ml of DMF and 30 g of glass beads (diameter 3 mm) is stirred at 130° C. for 24 h. The glass beads and salts are subsequently filtered off, the DMF is removed in vacuo, and the residue is chromatographed on silica gel (eluent: ethyl acetate/heptane mixtures). The resultant oils/solids are freed from low-boiling components in an oil-pump vacuum, by bulb-tube distillation or sublimation.

| Ex. | Variant | 1-Aminoisoquinoline derivative | Carbonyl component | Product | Yield |
|---|---|---|---|---|---|
| L1 | A | (structure) 1532-84-9 | (structure) 107-20-0 | (structure) | 84% |
| L2 | A | (structure) | (structure) 683-50-1 | (structure) | 79% |

-continued

| Ex. | Variant | 1-Amino-isoquinoline derivative | Carbonyl component | Product | Yield |
|---|---|---|---|---|---|
| L3 | A | 1-aminoisoquinoline | chloroacetone  78-95-5 | 1-methyl imidazo[2,1-a]isoquinoline | 81% |
| L4 | A | 1-aminoisoquinoline | 2-chlorobutanal  28832-55-5 | 3-ethyl imidazo[2,1-a]isoquinoline | 83% |
| L5 | A | 1-aminoisoquinoline | 3-chloro-2-butanone  4091-39-8 | 2,3-dimethyl imidazo[2,1-a]isoquinoline | 65% |
| L6 | A | 1-aminoisoquinoline | 3-chloro-5-methyl-2-hexanone  29585-17-9 | 3-isobutyl-2-methyl imidazo[2,1-a]isoquinoline | 76% |
| L7 | A | 1-aminoisoquinoline | 2-chloro-4,4-dimethylpentanal  29846-94-4 | 3-neopentyl imidazo[2,1-a]isoquinoline | 70% |

-continued

| Ex. | Variant | 1-Amino-isoquinoline derivative | Carbonyl component | Product | Yield |
|---|---|---|---|---|---|
| L8 | B | 1-aminoisoquinoline | 3-chlorobicyclo[2.2.1]heptan-2-one (61914-03-2) | fused polycyclic imidazo product | 54% |
| L9 | B | 1-aminoisoquinoline | 2-chloro-3,3-dimethylbutanal | 3-tert-butylimidazo[2,1-a]isoquinoline | 85% |
| L10 | A | 4-methyl-1-aminoisoquinoline | chloroacetaldehyde | 5-methylimidazo[2,1-a]isoquinoline | 91% |
| L11 | A | 4-methyl-1-aminoisoquinoline | 2-chloropropanal | 3,5-dimethylimidazo[2,1-a]isoquinoline | 90% |
| L12 | B | 4-methyl-1-aminoisoquinoline | 2-chloro-3,3-dimethylbutanal | 3-tert-butyl-5-methylimidazo[2,1-a]isoquinoline | 84% |

-continued
| Ex. | Variant | 1-Amino-isoquinoline derivative | Carbonyl component | Product | Yield |
|---|---|---|---|---|---|
| L13 | A | 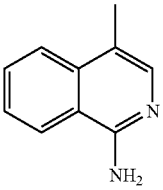 | 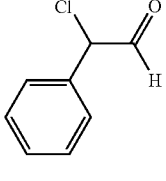 4638-79-3 | 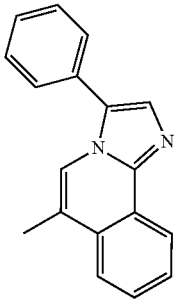 | 86% |
| L14 | A | 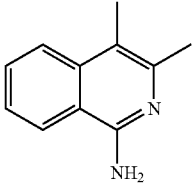 | 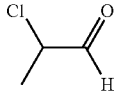 | 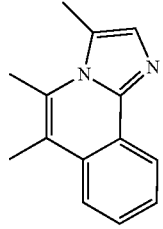 | 93% |
| L15 | A | 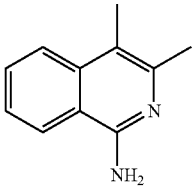 | 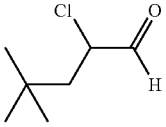 | 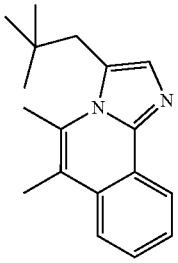 [SMILES: Cc1c(C)n2c(CC(C)(C)C)cnc2c2ccccc12] | 80% |
| L16 | B | 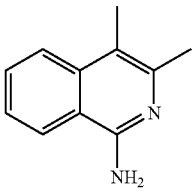 | 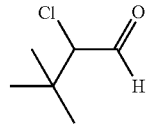 | 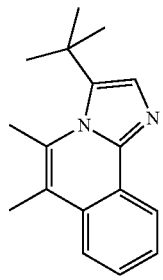 [SMILES: Cc1c(C)n2c(C(C)(C)C)cnc2c2ccccc12] | 68% |
| L17 | A | 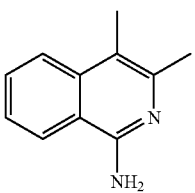 | 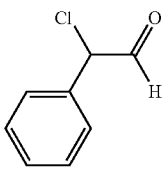 | 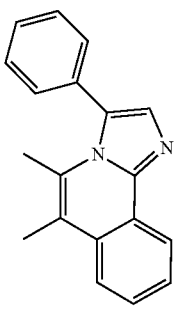 | 77% |

-continued
| Ex. | Variant | 1-Amino-isoquinoline derivative | Carbonyl component | Product | Yield |
|---|---|---|---|---|---|
| L18 | A | 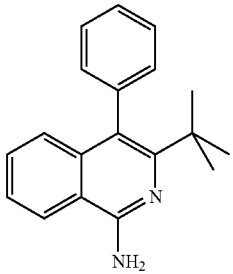 [SMILES: CC(C)(C)c1nc(N)c2ccccc2c1-c1ccccc1] | 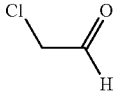 | 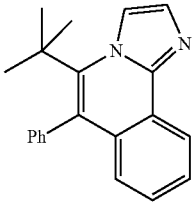 [SMILES: CC(C)(C)c1c(-c2ccccc2)c2ccccc2c2nccn12] | 88% |
| L19 | A | 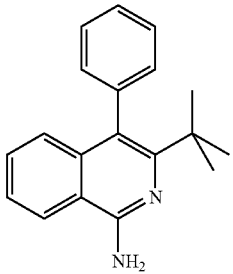 | 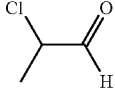 | 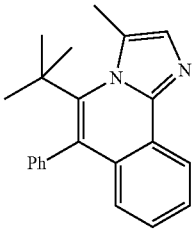 [SMILES: Cc1cnc2c3ccccc3c(-c3ccccc3)c(C(C)(C)C)n12] | 35% |
| L20 | B | 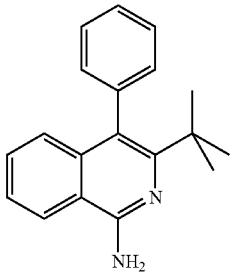 [SMILES: CC(C)(C)c1nc(N)c2ccccc2c1-c1ccccc1] | 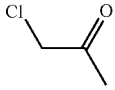 | 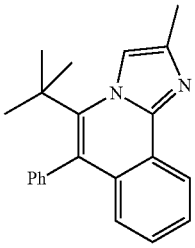 [SMILES: Cc1cn2c(C(C)(C)C)c(-c3ccccc3)c3ccccc3c2n1] | 72% |
| L21 | A | 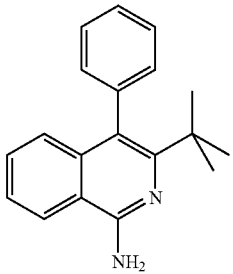 | 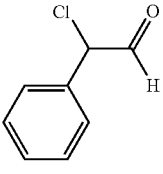 | 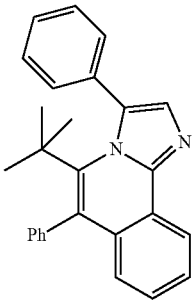 [SMILES: CC(C)(C)c1c(-c2ccccc2)c2ccccc2c2ncc(-c3ccccc3)n12] | 31% |
| L22 | A | 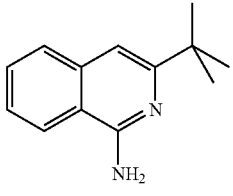 | 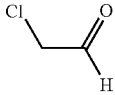 | 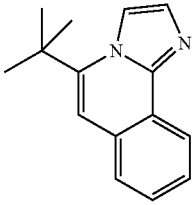 [SMILES: CC(C)(C)c1cc2ccccc2c2nccn12] 58814-41-8 | 91% |

-continued

| Ex. | Variant | 1-Amino-isoquinoline derivative | Carbonyl component | Product | Yield |
|---|---|---|---|---|---|
| L23 | B | | | | 73% |
| L24 | A | 55270-26-3 | | | 84% |
| L25 | A | | | | 84% |
| L26 | B | | | | 79% |
| L27 | A | | | | 80% |

| Ex. | Variant | 1-Amino-isoquinoline derivative | Carbonyl component | Product | Yield |
|---|---|---|---|---|---|
| L28 | B | 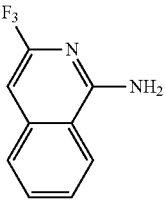 58814-43-0 | 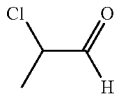 | 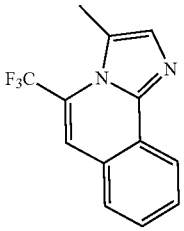 [SMILES: Cc1cnc2c3ccccc3cc(C(F)(F)F)n12] | 29% |
| L29 | A | 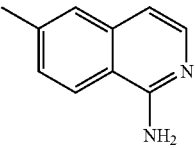 42398-74-3 | 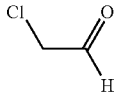 | 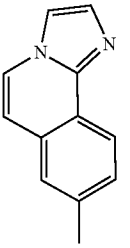 | 89% |
| L30 | A | 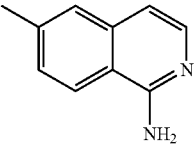 | 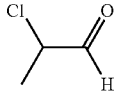 | 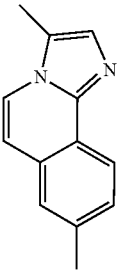 | 90% |
| L31 | A | 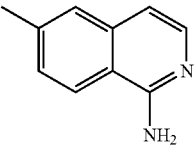 | 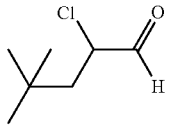 | 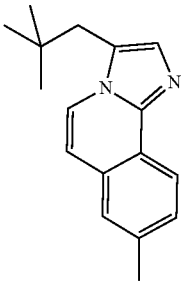 [SMILES: Cc1ccc2c(ccn3c(CC(C)(C)C)cnc23)c1] | 82% |
| L32 | B | 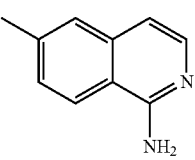 | 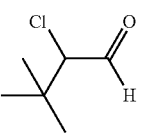 | 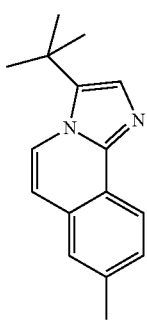 [SMILES: Cc1ccc2c(ccn3c(C(C)(C)C)cnc23)c1] | 71% |

-continued

| Ex. | Variant | 1-Amino-isoquinoline derivative | Carbonyl component | Product | Yield |
|---|---|---|---|---|---|
| L33 | A | 6-fluoro-1-aminoisoquinoline (CAS 009034-72-3) | 2-chloropropanal | 9-fluoro-3-methylimidazo[2,1-a]isoquinoline | 87% |
| L34 | A | 5-methyl-3-phenyl-1-aminoisoquinoline (CAS 58814-44-1) | 2-chloropropanal | 3-methyl-6-phenyl-10-methylimidazo[2,1-a]isoquinoline | 48% |
| L35 | A | 4-cyano-3-methyl-1-aminoisoquinoline (CAS 161468-33-3) | 2-chloropropanal | 3,5-dimethyl-6-cyanoimidazo[2,1-a]isoquinoline | 69% |
| L36 | A | 3-tert-butyl-1-aminoisoquinoline | 1,1,1-tris(chloroacetyl)methane (CAS 55756-20-2) | tris(5-tert-butylimidazo[2,1-a]isoquinolin-2-yl)methane | 41% |

Ligand Synthesis Variant C:

100 mmol of the 2-phenylimidazole derivative are initially introduced in 400 ml of triethylamine. 200 ml of the alkyne, 6 mmol of triphenylphosphine, 6 mmol of copper(I) iodide and 3 mmol of palladium(II) acetate are successively added with stirring. The reaction mixture is subsequently stirred at 80° C. for 20 h. After cooling, the reaction mixture is diluted with 400 ml of dichloromethane, the solids are separated off by filtration through a Celite bed, and the filtrate is evaporated to dryness. The residue is taken up in 300 ml of dichloromethane, and the solution is washed three times with 100 ml of conc. ammonia solution each time and three times with 100 ml of water each time and dried over magnesium sulfate. After the solvent has been removed in vacuo, the crude product is adsorbed onto silica gel (5 g per g of crude product) and packed into a silica-gel column. Byproducts are firstly removed using dichloromethane, then the solvent is switched to THF, and the product is eluted. The resultant oils/solids are freed from low-boiling components in an oil-pump vacuum, by bulb-tube distillation or sublimation.

| Ex. | 2-Phenylimidazole derivative | Alkyne | Product | Yield |
|---|---|---|---|---|
| L37 | 162356-38-9 | 536-74-3 | | 38% |
| L38 | 496807-43-3 | | | 51% |
| L39 | | 769-26-6 | | 44% |
| L40 | | | | 21% |
| L41 | | 40430-66-8 | | 17% |

Ligand Synthesis Variant D:

Synthesis of 3-bromoimidazo[2,1-a]isoquinolines:

105 mmol of N-bromosuccinimide are added in portions to a vigorously stirred solution, cooled to +5° C., of 100 mmol of the imidazo[2,1-a]isoquinoline derivative in 300 ml of THF at such a rate that the temperature does not exceed +10° C. When the addition is complete and after the reaction mixture has been warmed to room temperature, the mixture is diluted with 300 ml of dichloromethane, and the org. phase is washed five times with 500 ml of sat. sodium carbonate solution and dried over magnesium sulfate. The solvent is substantially removed in vacuo, 200 ml of n-heptane are added to the residue, and the mixture is stirred for 12 h. The resultant solid is filtered off, washed with n-heptane and dried in vacuo.

| Ex. | Imidazo[2,1-a]iso-quinoline derivative | 3-Bromoimidazo[2,1-a]-isoquinoline derivative | Yield |
|---|---|---|---|
| A4 | | | 81% |
| A5 | | | 79% |
| A6 | | | 76% |
| A7 | | | 64% |
| A8 | | | 80% |
| A9 | | | 45% |

Suzuki Coupling:

20 mmol of dicyclohexyl(2',6'-dimethoxy[1,1'-biphenyl]-2-yl)phosphine and 10 mmol of palladium(II) acetate are added to a vigorously stirred mixture of 100 mmol of the 3-bromoimidazo[2,1-a]isoquinoline derivative, 400 mmol of the boronic acid, 600 mmol of tripotassium phosphate (anhydrous) and 200 g of glass beads (diameter 3 mm) in 500 ml of toluene, and the mixture is stirred at 70° C. for 60 h. After cooling, the mixture is filtered through a Celite bed, and the organic phase is washed three times with 500 ml of water, dried over magnesium sulfate and then evaporated to dryness in vacuo. The residue is chromatographed on silica gel (eluent ethyl acetate/n-heptane). The resultant oils/solids are freed from low-boiling components and traces of metal in an oil-pump vacuum, by bulb-tube distillation or sublimation.

| Ex. | 3-Bromoimidazo-[2,1-a]isoquinoline derivative | Boronic acid | Product | Yield |
|---|---|---|---|---|
| L42 | | 98-80-6 | | 87% |

-continued
| Ex. | 3-Bromoimidazo-[2,1-a]isoquinoline derivative | Boronic acid | Product | Yield |
|---|---|---|---|---|
| L43 | 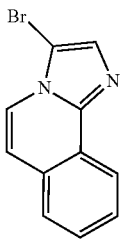 [SMILES: Brc1cnc2c3ccccc3ccn12] | 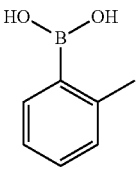<br>16419-60-6 | 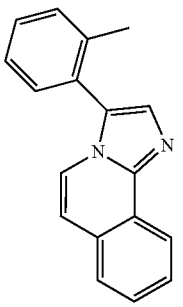 [SMILES: c1ccc(-c2cnc3c4ccccc4ccn23)cc1] | 80% |
| L44 | 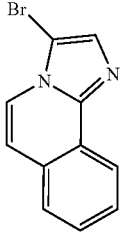 | 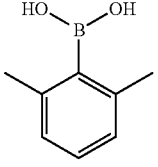<br>100379-00-8 | 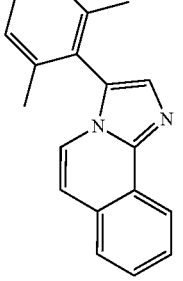 | 76% |
| L45 | 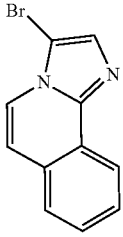 [SMILES: Brc1cnc2c3ccccc3ccn12] | 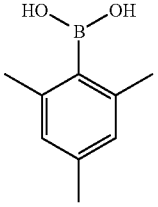<br>5980-97-2 | 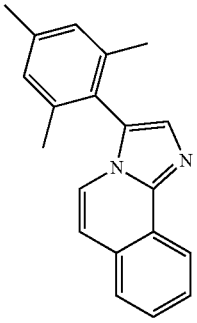 [SMILES: Cc1cc(C)c(-c2cnc3c4ccccc4ccn23)c(C)c1] | 59% |
| L46 | 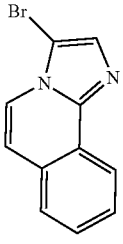 | 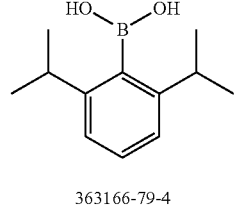<br>363166-79-4 | 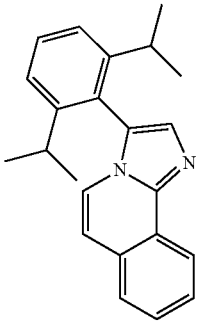 [SMILES: CC(C)c1cccc(C(C)C)c1-c1cnc2c3ccccc3ccn12] | 37% |

-continued

| Ex. | 3-Bromoimidazo-[2,1-a]isoquinoline derivative | Boronic acid | Product | Yield |
|---|---|---|---|---|
| L47 | | 1065663-52-6 | | 17% |
| L48 | | 197958-29-5 | | 83% |
| L49 | | | | 71% |
| L50 | | | | 66% |

| Ex. | 3-Bromoimidazo-[2,1-a]isoquinoline derivative | Boronic acid | Product | Yield |
|---|---|---|---|---|
| L51 | | | | 69% |
| L52 | | | | 57% |
| L53 | | | | 71% |
| L54 | | | | 23% |

Ligand Synthesis Variant E:

105 mmol, 62.6 ml of n-butyllithium (1.6 M in hexane) are added dropwise over the course of 5 min. to a vigorously stirred solution, cooled to −78° C., of 100 mmol of the 3-bromoimidazo[2,1-a]isoquinoline derivative in 1000 ml of diethyl ether. The mixture is stirred for a further 15 min., and 120 mmol of the electrophile are then added over the course of 2 min. After the mixture has been warmed to room temperature, the organic phase is washed once with 500 ml of water and dried over magnesium sulfate, and the solvent is removed in vacuo. The residue is chromatographed on silica gel (eluent ethyl acetate/n-heptane). The resultant oils/solids are freed from low-boiling components in an oil-pump vacuum, by bulb-tube distillation or sublimation.

| Ex. | 3-Bromoimidazo-[2,1-a]isoquinoline derivative | Electrophile | Product | Yield |
|---|---|---|---|---|
| L55 | 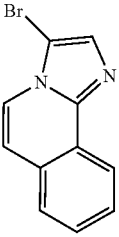 | H₃C—I | 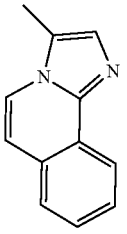 | 87% |
| L56 | 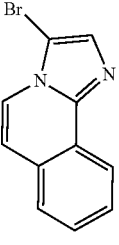 | D₃C—I | 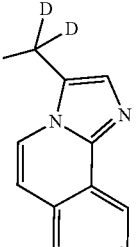 | 83% |
| L57 | 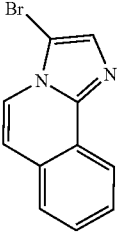 | 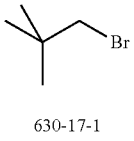<br>630-17-1 | 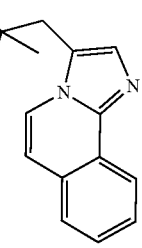 | 70% |
| L58 | 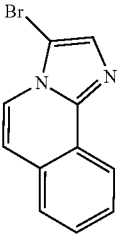 | 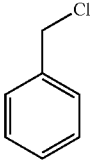 | 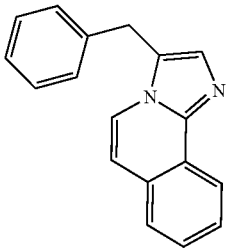 [SMILES: c1ccc(Cc2cnc3c4ccccc4ccn23)cc1] | 84% |
| L59 | 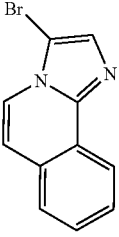 | 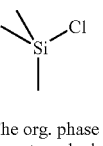<br>The org. phase is not washed with water. | 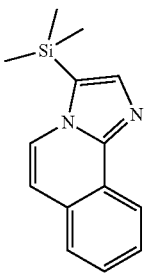 [SMILES: C[Si](C)(C)c1cnc2c3ccccc3ccn12] | 57% |

-continued

| Ex. | 3-Bromoimidazo-[2,1-a]isoquinoline derivative | Electrophile | Product | Yield |
|---|---|---|---|---|
| L60 | 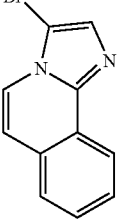 | 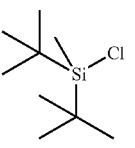<br>70892-81-8<br>The org. phase is not washed with water. | 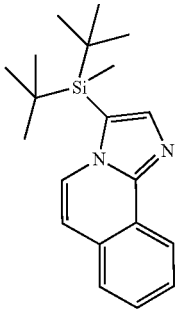 [SMILES: CC(C)(C)[Si](C)(c1cnc2c3ccccc3ccn12)C(C)(C)C] | 36% |
| L61 | 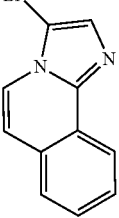 | 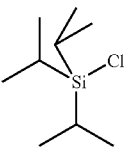<br>13154-24-0<br>The org. phase is not washed with water. | 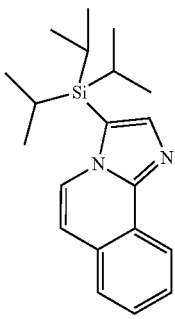 [SMILES: CC(C)[Si](c1cnc2c3ccccc3ccn12)(C(C)C)C(C)C] | 21% |
| L62 | 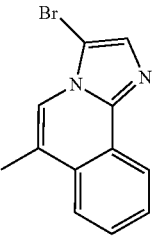 | 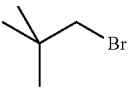 | 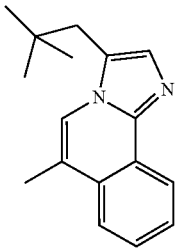 [SMILES: Cc1cn2c(CC(C)(C)C)cnc2c2ccccc12] | 74% |

Ligand Synthesis Variant F:

2 mmol of pentamethylcyclopentadienylrhodium(III) chloro dimer and 8 mmol of tetraphenylcyclopentadiene are added to a vigorously stirred mixture of 100 mmol of the 2-arylimidazole derivative, 120 mmol of the alkyne and 120 mmol of copper(II) acetate in 1000 ml of DMF, and the mixture is stirred at 80° C. for 20 h. After cooling, the mixture is filtered through a Celite bed, 1000 ml of dichloromethane are added to the organic phase, and the mixture is washed five times with 500 ml of water, dried over magnesium sulfate and then evaporated to dryness in vacuo. The residue is chromatographed on silica gel (eluent ethyl acetate/n-heptane). The resultant oils/solids are freed from low-boiling components in an oilpump vacuum, by bulb-tube distillation or sublimation.

| Ex. | 2-Arylimidazole derivative | Alkyne | Product | Yield |
|---|---|---|---|---|
| L63 | 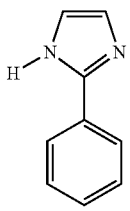 [SMILES: c1ccc(-c2ncc[nH]2)cc1]<br>670-96-2 | <br>501-65-5 | 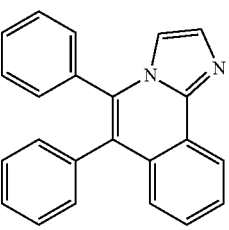 | 63% |
| L64 | 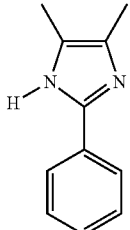<br>13682-20-7 | 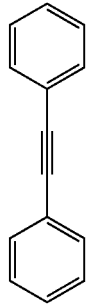 [SMILES: C(#Cc1ccccc1)c1ccccc1] | 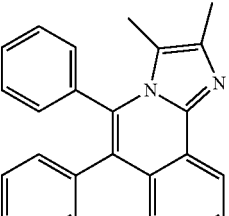 | 54% |
| L65 | 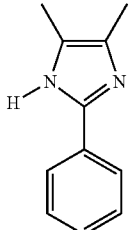 | 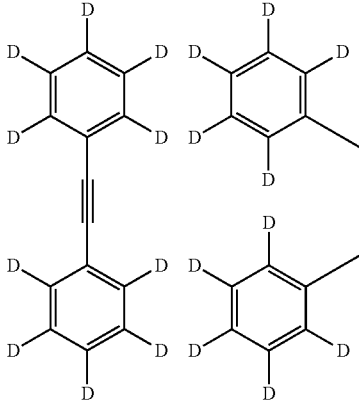<br>19339-46-9 | 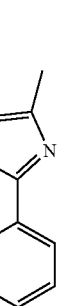 | 57% |
| L66 | 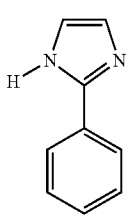 | 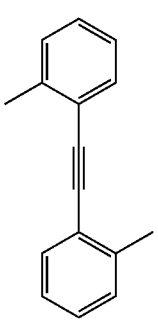<br>5294-03-1 | 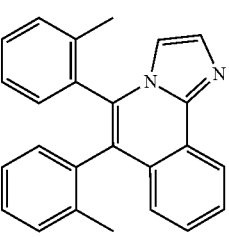 [SMILES: Cc1ccccc1-c1c(-c2ccccc2C)n2ccnc2c2ccccc12] | 61% |

-continued
| Ex. | 2-Arylimidazole derivative | Alkyne | Product | Yield |
|---|---|---|---|---|
| L67 | 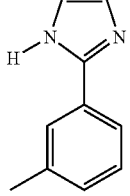 21202-37-9 | 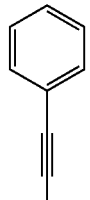 | 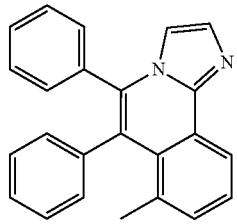 [SMILES: Cc1cccc2c1c(-c1ccccc1)c(-c1ccccc1)n1ccnc21] | 26% |
| L68 | 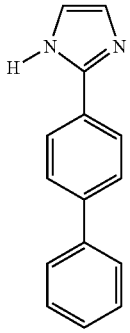 92437-07-5 | 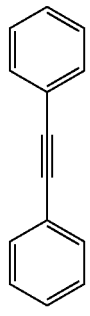 [SMILES: C(#Cc1ccccc1)c1ccccc1] | 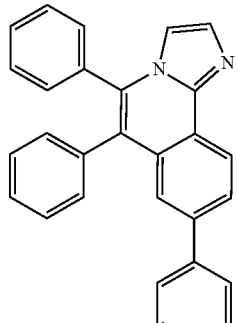 | 57% |
2) 1,2,4-Triazolo[3,4-a]isoquinoline systems
| Ex. | Literature | Product |
|---|---|---|
| L69 | G. S. Sidhu et al. J. Heterocyclic Chem. 1966, 3(2), 158. | 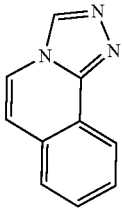 [SMILES: c1ccc2c(c1)ccn1cnnc21] |
| L70 | H. Reimlinger et al. Chem. Ber. 1970, 103, 1960. | 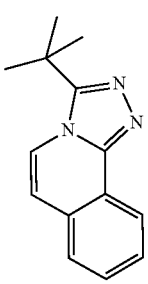 [SMILES: CC(C)(C)c1nnc2c3ccccc3ccn12] |
-continued
| Ex. | Literature | Product |
|---|---|---|
| L71 | Analogous to Ex. L70, but pivalic anhydride [1538-75-6] is employed instead of acetic anhydride | 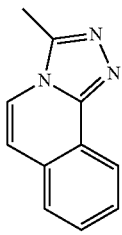 |
| L72 | H. Reimlinger et al. Chem. Ber. 1970, 103, 1960. | 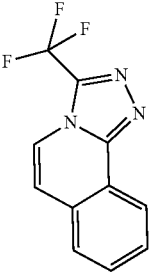 [SMILES: FC(F)(F)c1nnc2c3ccccc3ccn12] |

| Ex. | Literature | Product |
|---|---|---|
| L73 | H. Reimlinger et al. Chem. Ber. 1970, 103, 1960. | |

3) 1,2,4-Triazolo[5,1-a]isoquinoline systems

| Ex. | Literature | Product |
|---|---|---|
| L74 | Y.-I. Lin et al. J. Org. Chem., 1981, 46(15), 3123 | |
| L75 | C. N. Hoang et al. ARKIVOC, 2001, 2(2), 42-50 | |
| L76 | C. Hoogzand et al. Recueil des Travaux Chimiques des Pays-Bas 1971, 90(11), 1225-33 | |
| L77 | H. Reimlinger et al. Chem. Ber., 1971, 104(12), 3965-75 | |

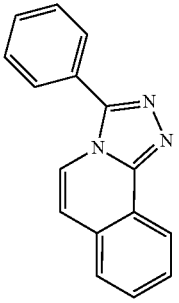 [SMILES: c1ccc(-c2nnc3c4ccccc4ccn23)cc1]

Suzuki Coupling:

20 mmol of dicyclohexyl(2',6'-dimethoxy[1,1'-biphenyl]-2-yl)phosphine and 10 mmol of palladium(II) acetate are added to a vigorously stirred mixture of 100 mmol of the bromo-1,2,4-triazolo[5,1-a]isoquinoline derivative, 400 mmol of the boronic acid, 600 mmol of tripotassium phosphate (anhydrous) and 200 g of glass beads (diameter 3 mm) in 500 ml of toluene, and the mixture is stirred at 70° C. for 60 h. After cooling, the mixture is filtered through a Celite bed, and the organic phase is washed three times with 500 ml of water, dried over magnesium sulfate and then evaporated to dryness in vacuo. The residue is chromatographed on silica gel (eluent ethyl acetate/n-heptane). The resultant oils/solids are freed from low-boiling components in an oil-pump vacuum, by bulb-tube distillation or sublimation.

| Ex. | Bromo-1,2,4-triazolo[5,1-a]isoquinoline derivative | Boronic acid | Product | Yield |
|---|---|---|---|---|
| L78 | | | | 47% |
| L79 | | | | 23% |

4) Tetraazolo[5,1-a]isoquinolines

| Ex. | Literature | Product |
|---|---|---|
| L80 | J. M. Keith, J. Org. Chem. 2006, 71(25), 9540. | (tetraazolo[5,1-a]isoquinoline structure) |
| L81 | H. Reimlinger, Chem. Ber. 1975, 108(12), 3780-6 | (Br-substituted tetraazolo[5,1-a]isoquinoline structure) |
| L82 | From bromide in accordance with Ex. L79 by Suzuki coupling analogously to process 3) 1,2,4-triazolo[5,1-a]isoquinoline systems | (mesityl-substituted structure) |

5) Benzimidazo[2,1-a]isoquinoline systems

Ligand Synthesis Variant A:

A vigorously stirred mixture of 500 mmol of the 1-chloroisoquinoline derivative, 600 mmol of the aniline, 1250 mmol of potassium carbonate, 200 g of glass beads (diameter 3 mm), 10 mmol of triphenylphosphine and 2 mmol of palladium(II) acetate in 1500 ml of o-xylene is heated under reflux for 3-48 h until the 1-chloroisoquinoline derivative has been consumed. After cooling, the mixture is filtered through a silica-gel bed and rinsed with 2000 ml of THF, and the filtrate is evaporated to dryness. The residue is dissolved in 100 ml of boiling ethyl acetate, and 800 ml of n-heptane are slowly added. After cooling, the solid that has crystallised out is filtered off with suction, washed twice with 100 ml of n-heptane each time and dried in vacuo. The resultant oils/solids are freed from low-boiling components in an oil-pump vacuum, by bulb-tube distillation or sublimation.

| Ex. | 1-Chloroisoquinoline derivative | Aniline | Product | Yield |
|---|---|---|---|---|
| L83 | 1-chloroisoquinoline | 2-bromoaniline (615-36-1) | benzimidazo[2,1-a]isoquinoline | 73% |
| L84 | 1-chloroisoquinoline | 2-bromo-3-methylaniline (54879-20-8) | methyl-benzimidazo[2,1-a]isoquinoline | 56% |

| Ex. | 1-Chloroiso-quinoline derivative | Aniline | Product | Yield |
|---|---|---|---|---|
| L85 | 1-chloroisoquinoline | 2-bromo-4-methylaniline (583-68-6) | benzimidazo-isoquinoline product | 67% |
| L86 | 1-chloroisoquinoline | 2-bromo-5-methylaniline (53078-85-6) | benzimidazo-isoquinoline product | 67% |
| L87 | 1-chloroisoquinoline | 2-bromo-4-tert-butylaniline (103273-01-4) | benzimidazo-isoquinoline product | 65% |
| L88 | 1-chloroisoquinoline | 2-bromo-4,5-dimethylaniline (22364-29-0) | benzimidazo-isoquinoline product | 61% |

-continued

| Ex. | 1-Chloroiso-quinoline derivative | Aniline | Product | Yield |
|---|---|---|---|---|
| L89 | (1-chloroisoquinoline) | 2-bromo-4-fluoroaniline<br>1003-98-1 | | 72% |
| L90 | (1-chloroisoquinoline) | 2-bromo-4-(trifluoromethyl)aniline<br>57946-63-1 | | 50% |
| L91 | (1-chloroisoquinoline) | 2-bromo-4-phenylaniline<br>41738-70-9 | | 69% |
| L92 | (1-chloroisoquinoline) | 3-bromo-4-aminopyridine<br>13534-98-0 | | 34% |
| L93 | (1-chloroisoquinoline) | 2-bromo-3-aminopyridine<br>39856-58-1 | | 41% |

-continued
| Ex. | 1-Chloroiso-quinoline derivative | Aniline | Product | Yield |
|---|---|---|---|---|
| L94 | 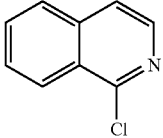 | 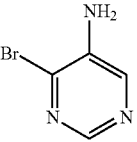 849353-34-0 | 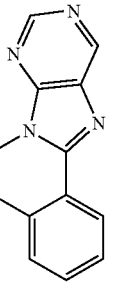 | 19% |
| L95 | 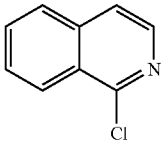 | 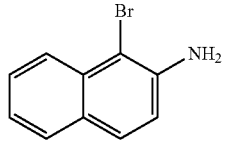 20191-75-7 | 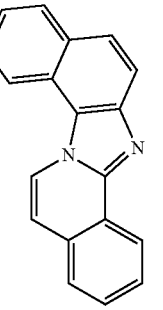 | 64% |
| L96 | 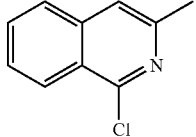 7115-16-4 | 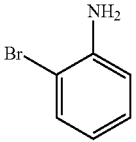 | 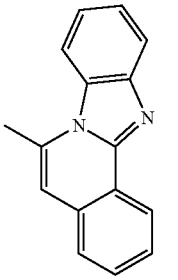 [SMILES: Cc1cc2ccccc2c2nc3ccccc3n12] | 71% |
| L97 | 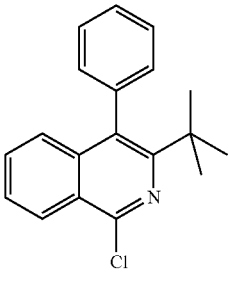 [SMILES: CC(C)(C)c1nc(Cl)c2ccccc2c1-c1ccccc1] |  | 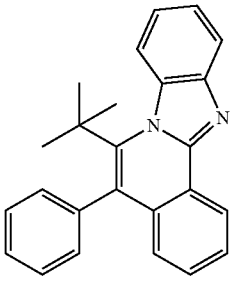 [SMILES: CC(C)(C)c1c(-c2ccccc2)c2ccccc2c2nc3ccccc3n12] | 29% |
| L98 | 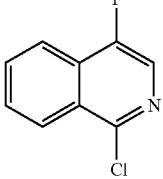 | 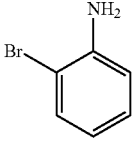 | 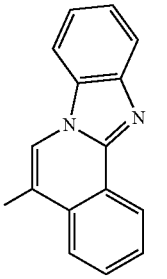 | 67% |

| Ex. | 1-Chloroiso-quinoline derivative | Aniline | Product | Yield |
|---|---|---|---|---|
| L99 | 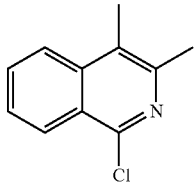 | 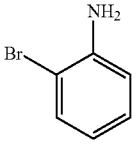 | 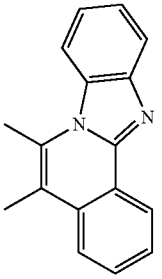 [SMILES: Cc1c(C)n2c3ccccc3nc2c2ccccc12] | 71% |
| L100 | 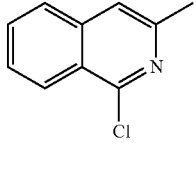 | 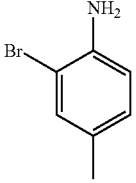 | 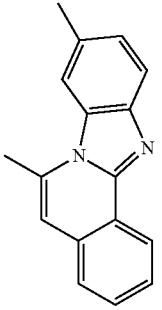 [SMILES: Cc1ccc2nc3c4ccccc4cc(C)n3c2c1] | 65% |
| L101 | 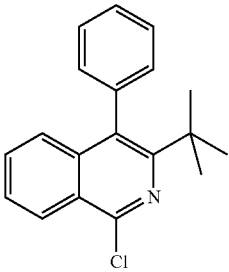 [SMILES: CC(C)(C)c1nc(Cl)c2ccccc2c1-c1ccccc1] | 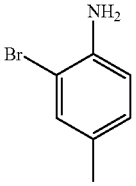 | 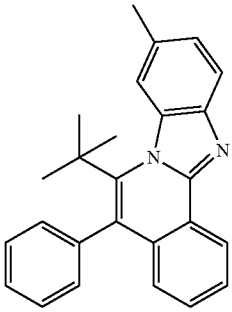 [SMILES: Cc1ccc2nc3c4ccccc4c(-c4ccccc4)c(C(C)(C)C)n3c2c1] | 34% |
| L102 | 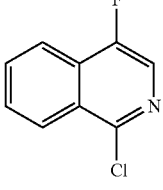<br>435278-06-1 | 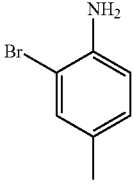 | 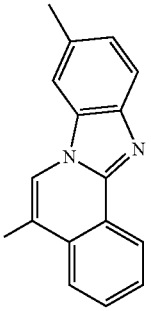 | 68% |
| L103 | 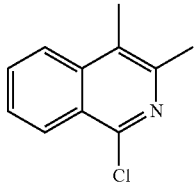 | 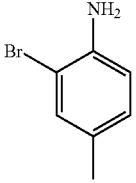 | 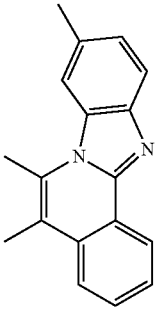 [SMILES: Cc1ccc2nc3c4ccccc4c(C)c(C)n3c2c1] | 60% |

-continued
| Ex. | 1-Chloroiso-quinoline derivative | Aniline | Product | Yield |
|---|---|---|---|---|
| L104 | 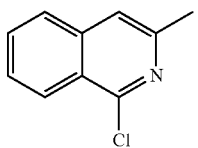 | 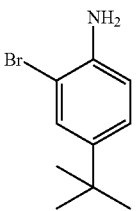 | 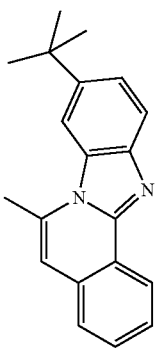 [SMILES: Cc1cc2ccccc2c2nc3ccc(C(C)(C)C)cc3n12] | 55% |
| L105 | 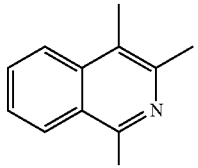 | 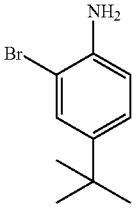 | 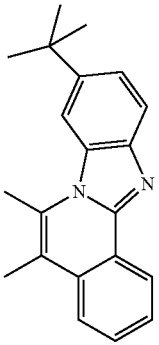 [SMILES: Cc1c(C)n2c3cc(C(C)(C)C)ccc3nc2c2ccccc12] | 69% |
| L106 | 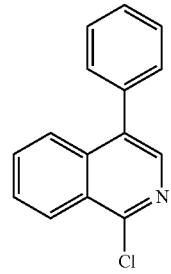 65810-96-0 | 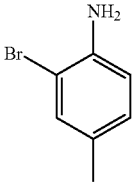 | 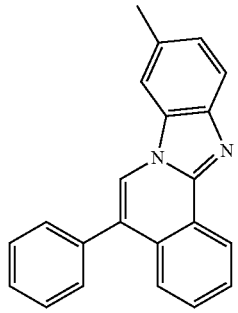 [SMILES: Cc1ccc2nc3c4ccccc4c(-c4ccccc4)cn3c2c1] | 63% |
| L107 | 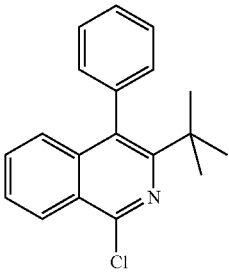 55792-01-3 | 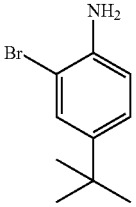 | 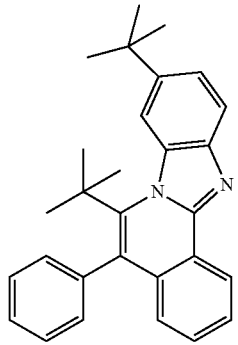 [SMILES: CC(C)(C)c1ccc2nc3c4ccccc4c(-c4ccccc4)c(C(C)(C)C)n3c2c1] | 28% |

-continued

| Ex. | 1-Chloroiso-quinoline derivative | Aniline | Product | Yield |
|---|---|---|---|---|
| L108 | 59500-31-2 | 2-bromo-4-methylaniline | | 22% |
| L109 | 102183-41-5 | 2-bromo-4-methylaniline | | 62% |
| L110 | 33279-84-4 | 2-bromo-4-methylaniline | | 31% |
| L111 | 32081-28-0 | 2-bromo-4-tert-butylaniline | | 74% |

-continued

| Ex. | 1-Chloroiso-quinoline derivative | Aniline | Product | Yield |
|---|---|---|---|---|
| L112 | 53491-80-8 | | | 19% |
| L113 | 132997-77-4 | | | 59% |
| L114 | 58839-98-8 | | | 44% |

Ligand Synthesis Variant B:

2 mmol of pentamethylcyclopentadienylrhodium(III) chloro dimer and 8 mmol of tetraphenylcyclopentadiene are added to a vigorously stirred mixture of 100 mmol of the 2-arylbenzimidazole derivative, 120 mmol of the alkyne and 120 mmol of copper(II) acetate in 1000 ml of DMF, and the mixture is stirred at 80° C. for 20 h. After cooling, the mixture is filtered through a Celite bed, 1000 ml of dichloromethane are added to the organic phase, and the mixture is washed five times with 500 ml of water, dried over magnesium sulfate and then evaporated to dryness in vacuo. The residue is chromatographed on silica gel (eluent ethyl acetate/n-heptane). The resultant oils/solids are freed from low-boiling components in an oil-pump vacuum, by bulb-tube distillation or sublimation.

| Ex. | 2-Arylbenzimidazole derivative | Alkyne | Product | Yield |
|---|---|---|---|---|
| L115 | 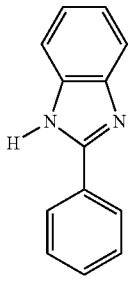 | 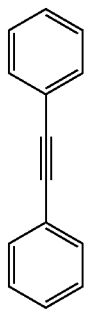 [SMILES: C(#Cc1ccccc1)c1ccccc1] | 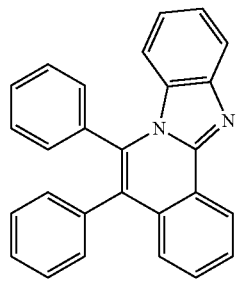 [SMILES: c1ccc(-c2c(-c3ccccc3)n3c4ccccc4nc3c3ccccc23)cc1] | 43% |
| L116 | 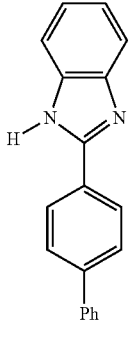 2562-77-8 | 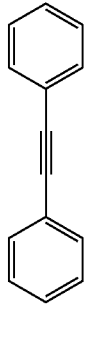 [SMILES: C(#Cc1ccccc1)c1ccccc1] | 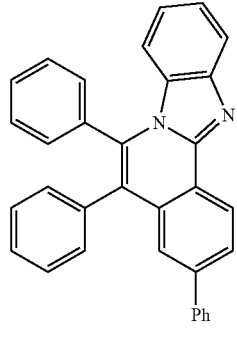 [SMILES: c1ccc(-c2ccc3c(c2)c(-c2ccccc2)c(-c2ccccc2)n2c4ccccc4nc32)cc1] | 45% |
| L117 | 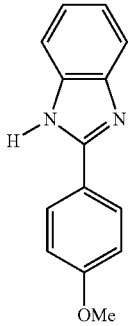 2620-81-7 | 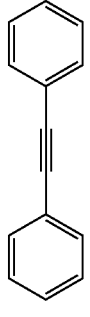 [SMILES: C(#Cc1ccccc1)c1ccccc1] | 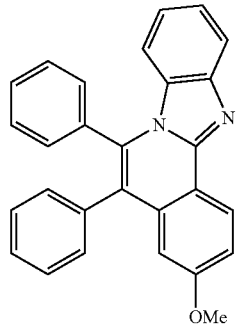 [SMILES: COc1ccc2c(c1)c(-c1ccccc1)c(-c1ccccc1)n1c3ccccc3nc21] | 37% |
| L118 | 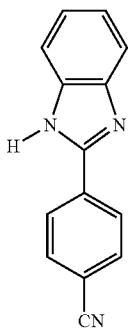 4110-15-0 | 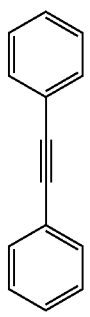 [SMILES: C(#Cc1ccccc1)c1ccccc1] | 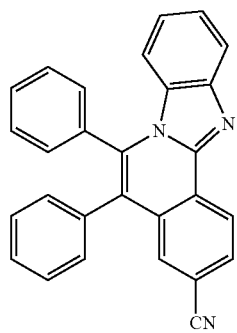 [SMILES: N#Cc1ccc2c(c1)c(-c1ccccc1)c(-c1ccccc1)n1c3ccccc3nc21] | 23% |

-continued
| Ex. | 2-Arylbenzimidazole derivative | Alkyne | Product | Yield |
|---|---|---|---|---|
| L119 | 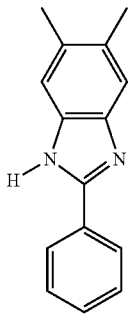<br>14313-45-2 | 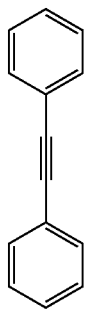 [SMILES: C(#Cc1ccccc1)c1ccccc1] | 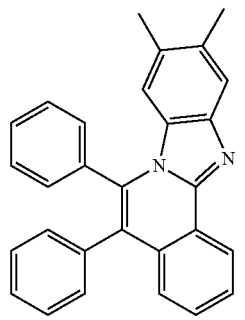 [SMILES: Cc1cc2nc3c4ccccc4c(-c4ccccc4)c(-c4ccccc4)n3c2cc1C] | 45% |
| L120 | 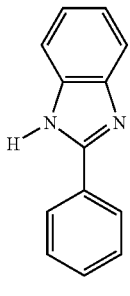 [SMILES: c1ccc(-c2nc3ccccc3[nH]2)cc1] | 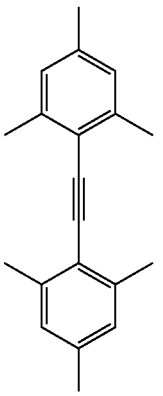<br>5806-58-6 | 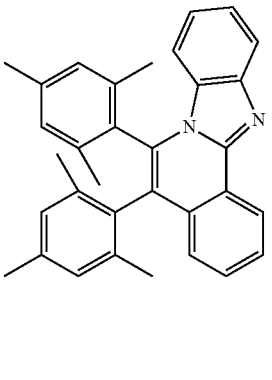 [SMILES: Cc1cc(C)c(-c2c(-c3c(C)cc(C)cc3C)n3c4ccccc4nc3c3ccccc23)c(C)c1] | 9% |
| L121 | 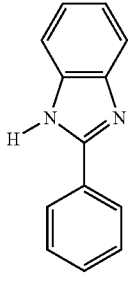 [SMILES: c1ccc(-c2nc3ccccc3[nH]2)cc1] | 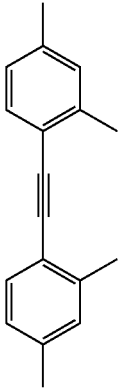<br>61440-87-7 | 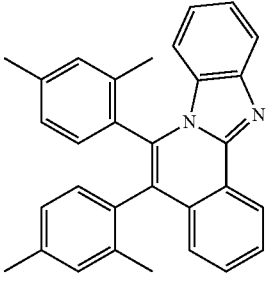 [SMILES: Cc1ccc(-c2c(-c3ccc(C)cc3C)n3c4ccccc4nc3c3ccccc23)c(C)c1] | 23% |
| L122 | 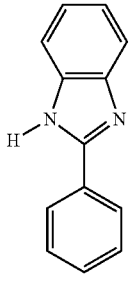 [SMILES: c1ccc(-c2nc3ccccc3[nH]2)cc1] | 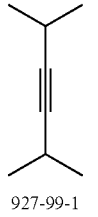<br>927-99-1 | 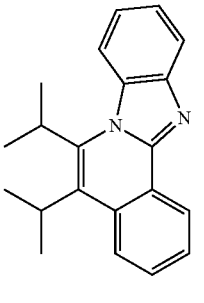 [SMILES: CC(C)c1c(C(C)C)n2c3ccccc3nc2c2ccccc12] | 6% |

-continued
| Ex. | 2-Arylbenz-imidazole derivative | Alkyne | Product | Yield |
|---|---|---|---|---|
| L123 | 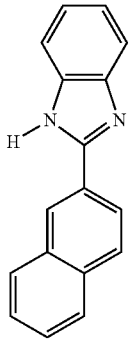<br>3367-02-0 | 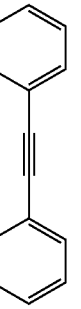 | 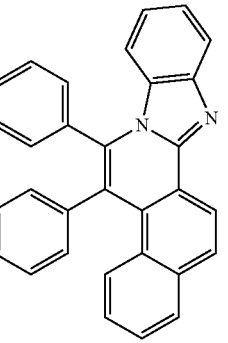 | 29% |
| L124 | 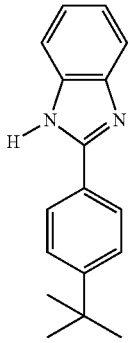<br>49671-76-3 | 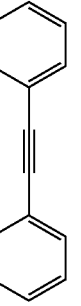 | 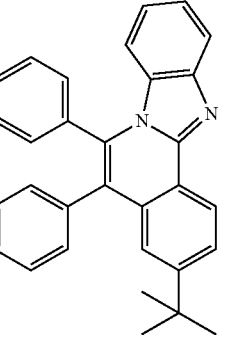 | 43% |
| L125 | 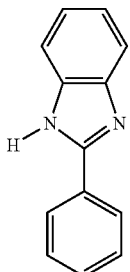 | 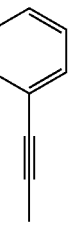<br>1001024-39-0 | 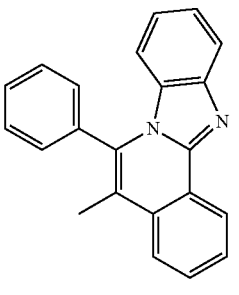 [SMILES: Cc1c(-c2ccccc2)n2c3ccccc3nc2c2ccccc12] | 13% |
| L126 | 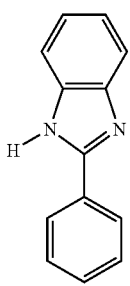 | 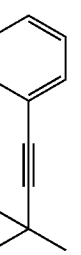<br>103239-12-9 | 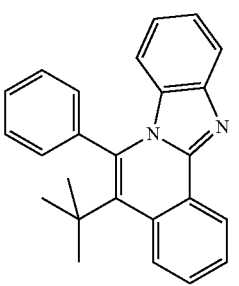 [SMILES: CC(C)(C)c1c(-c2ccccc2)n2c3ccccc3nc2c2ccccc12] | 16% |

Ligand Synthesis Variant C:

100 mmol of the 2-(2-bromophenyl)imidazole derivative are initially introduced in 300 ml of triethylamine and 200 ml of DMF. 200 ml of the alkyne, 5 mmol of triphenylphosphine, 5 mmol of copper(I) iodide and 2 mmol of palladium(II) acetate are successively added with stirring. The reaction mixture is subsequently stirred at 80° C. for 20 h. After cooling, the reaction mixture is diluted with 400 ml of dichloromethane, the solids are separated off by filtration through a Celite bed, and the filtrate is evaporated to dryness. The residue is taken up in 300 ml of dichloromethane, and the solution is washed three times with 100 ml of conc. ammonia solution each time and three times with 100 ml of water each time and dried over magnesium sulfate. The resultant oils/solids are freed from low-boiling components and traces of metal in an oil-pump vacuum, by bulb-tube distillation or sublimation.

| Ex. | 2-(2-Bromophenyl)-imidazole | Alkyne | Product | Yield |
|---|---|---|---|---|
| L127 | 13275-42-8 | | | 37% |
| L128 | 168209-94-7 | | | 34% |
| L129 | 1176128-00-9 | 769-26-6 | | 38% |
| L130 | | 769-26-6 | | 27% |

-continued

| Ex. | 2-(2-Bromo-phenyl)-imidazole | Alkyne | Product | Yield |
|---|---|---|---|---|
| L131 | 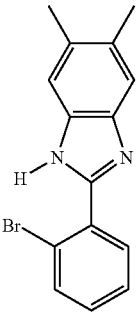 | 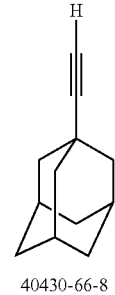   40430-66-8 | 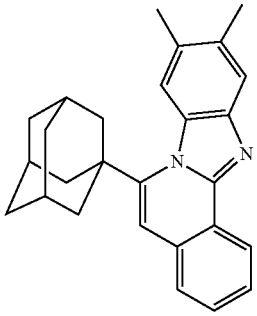 [SMILES: Cc1cc2nc3c4ccccc4cc(C45CC6CC(CC(C6)C4)C5)n3c2cc1C] | 9% |

6) Heteroimidazo[2,1-a]isoquinoline systems
Ligand Synthesis Variant A:

A vigorously stirred mixture of 500 mmol of the 1-chloroisoquinoline derivative, 520 mmol of the amine, 1250 mmol of potassium carbonate (1800 mmol in the case of hydrobromides), 200 g of glass beads (diameter 3 mm), 10 mmol of triphenylphosphine and 2 mmol of palladium(II) acetate in 1500 ml of o-xylene is heated under reflux for 3-36 h until the 1-chloroisoquinoline has been consumed. After cooling, the mixture is filtered through a silica-gel bed and rinsed with 2000 ml of THF, and the filtrate is evaporated to dryness. The residue is dissolved in 100 ml of boiling ethyl acetate, and 800 ml of n-heptane are slowly added. After cooling, the solid that has crystallised out is filtered off with suction, washed twice with 100 ml of n-heptane each time and dried in vacuo. If necessary, the crude product is recrystallised again from ethyl acetate/heptane. The resultant oils/solids are freed from low-boiling components in an oil-pump vacuum, by bulb-tube distillation or sublimation.

| Ex. | 1-Chloro-isoquinoline | Amine | Product | Yield |
|---|---|---|---|---|
| L132 | 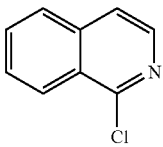 | 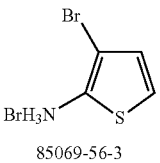   85069-56-3 | 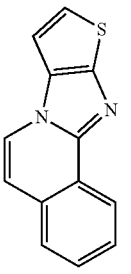 [SMILES: c1ccc2c(c1)ccn1c3ccsc3nc21] | 56% |
| L133 | 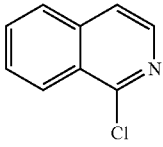 [SMILES: Clc1nccc2ccccc12] |    85069-58-5 | 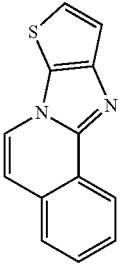 [SMILES: c1ccc2c(c1)ccn1c2nc2ccsc21] | 64% |

| Ex. | 1-Chloro-isoquinoline | Amine | Product | Yield |
|---|---|---|---|---|
| L134 | | 90490-37-2 | | 82% |
| L135 | | 344747-99-5 | | 78% |
| L136 | | 1104630-95-6 | | 26% |
| L137 | | 161833-43-8 | | 17% |
| L138 | | 85069-58-5 | | 45% |

| Ex. | 1-Chloro-isoquinoline | Amine | Product | Yield |
|---|---|---|---|---|
| L139 | (4-methyl, 3-methyl, 1-chloro isoquinoline) | 3-bromo-2-aminobenzothiophene 344747-99-5 | (fused benzothieno-imidazo-isoquinoline with two methyl groups) | 50% |

Ligand Synthesis Variant B:

A vigorously stirred mixture of 500 mmol of 1-aminoisoquinoline, 520 mmol of the dibromide, 1250 mmol of potassium carbonate, 200 g of glass beads (diameter 3 mm), 10 mmol of triphenylphosphine and 2 mmol of palladium(II) acetate in 1500 ml of o-xylene is heated under reflux for 3-12 h until the 1-aminoisoquinoline has been consumed. After cooling, the mixture is filtered through a silica-gel bed and rinsed with 2000 ml of THF, and the filtrate is evaporated to dryness. The residue is dissolved in 100 ml of boiling ethyl acetate, and 800 ml of n-heptane are slowly added. After cooling, the solid that has crystallised out is filtered off with suction, washed twice with 100 ml of n-heptane each time and dried in vacuo. If necessary, the crude product is recrystallised again from ethyl acetate/heptane. The resultant oils/solids are freed from low-boiling components in an oil-pump vacuum, by bulb-tube distillation or sublimation.

| Ex. | 1-Aminoiso-quinoline | Dibromide | Product | Yield |
|---|---|---|---|---|
| L140 | 1-aminoisoquinoline | 2,3-dibromobenzofuran 64150-61-4 | (benzofuro-imidazo-isoquinoline) | 22% |
| L141 | 1-aminoisoquinoline | 2,3-dibromo-1-methylindole 128746-62-3 | (N-methylindolo-imidazo-isoquinoline) | 19% |

7) 8H-Acenaphth[1',2':4,5]imidazo[2,1-a]benz[de]isoquinoline

Procedure analogous to 6) Heteroimidazo[2,1-a]isoquinoline systems, ligand synthesis variant B.

| Ex. | 1-Amino-isoquinoline | Dibromide | Product | Yield |
|---|---|---|---|---|
| L142 | | 13019-33-5 | | 25% |
| L143 | | | | 16% |

8) Imidazo[2,1-a]phthalazine systems

| Ex. | Literature | Product |
|---|---|---|
| L144 | A. D. C. Parenty et al. Synthesis 2008, 9, 1479 | |
| L145 | A. Heim-Riether et al. Synthesis 2009, 10, 1715-1719 | |
| L146 | DE 2206012 The base is liberated from the hydrochloride using solid potassium carbonate in EtOH. | |
| L147 | DE 2206012 | |
| L148 | U.S. Pat. No. 3,704,300 | |
| L149 | Analogously to Ex. L148 through the use of tert-butanol | |
| L150 | S. El-Feky et al. Polish Journal of Chemistry 1991, 65(9-10), 1645-57 | |
| L151 | D. Catarzi et al. Farmaco 1993, 48(4), 447-57 | |
| L152 | M. Razvi et al. Indian Journal of Chemistry, Section B: Organic Chemistry Including Medicinal Chemistry 1992, 31B(11), 788-9 | |

| Ex. | Literature | Product |
|---|---|---|
| L153 | V. A. Kuznetsov et al. Tetrahedron 2006, 62(42), 10018 | |

9) Imidazo[1,2-c]quinazoline systems

| Ex. | Literature | Product |
|---|---|---|
| L154 | P. Franchetti et al. Journal of Heterocyclic Chemistry 1970, 7(6), 1295 | |
| L155 | P. Franchetti et al. Journal of Heterocyclic Chemistry 1970, 7(6), 1295 | 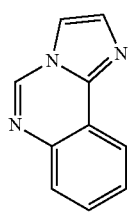 [SMILES: c1ccc2c(c1)ncn1ccnc21] |
| L156 | P. Franchetti et al. Journal of Heterocyclic Chemistry 1970, 7(6), 1295 | 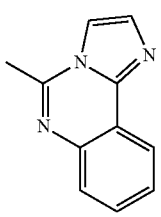 |
| L157 | P. Franchetti et al. Journal of Heterocyclic Chemistry 1970, 7(6), 1295 | 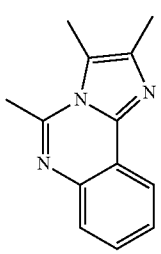 [SMILES: Cc1nc2c3ccccc3nc(C)n2c1C] |

| Ex. | Literature | Product |
|---|---|---|
| L158 | F. Claudi et al. Journal of Organic Chemistry 1974, 39(24), 3508 | 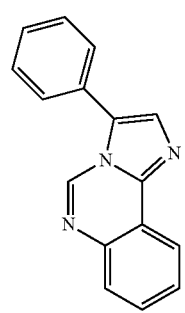 [SMILES: c1ccc(-c2cnc3c4ccccc4ncn23)cc1] |
| L159 | Analogously to Ex. 158 through the use of 2-mesitylaziridine [65855-33-6] instead of 2-phenylaziridine, Yield: 23% | 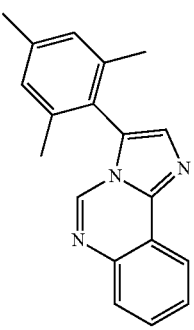 |
| L160 | J. Kalinowska-Torz et al. Acta Poloniae Pharmaceutica 1984, 41(2), 161 | 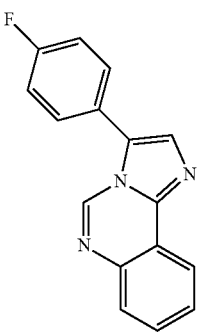 [SMILES: Fc1ccc(-c2cnc3c4ccccc4ncn23)cc1] |
| L161 | M. Cardellini et al. Farmaco, Edizione Scientifica 1975, 30(7), 536 | 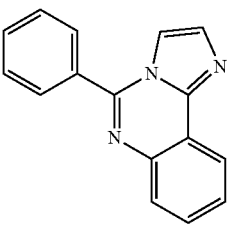 [SMILES: c1ccc(-c2nc3ccccc3c3nccn23)cc1] |
| L162 | M. Davis et al. Journal of the Chemical Society 1962, 945 | 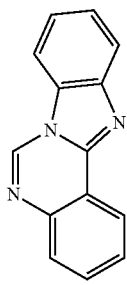 |

| Ex. | Literature | Product |
|---|---|---|
| L163 | D.-Q. Shi et al. Gaodeng Xuexiao Huaxue Xuebao 2007, 28(10), 1889 | 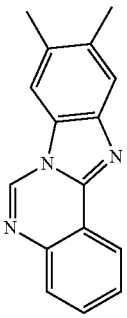 [SMILES: Cc1cc2nc3c4ccccc4ncn3c2cc1C] |
| L164 | M. Davis, Michael et al. Journal of the Chemical Society 1962, 945 | 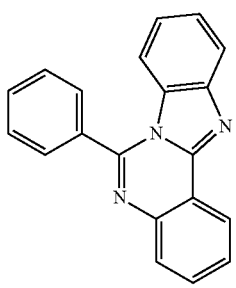 [SMILES: c1ccc(-c2nc3ccccc3c3nc4ccccc4n23)cc1] |
| L165 | A. V. Bogatskii et al. Ukrainskii Khimicheskii Zhurnal (Russian Edition) 1979, 45(3), 225 | 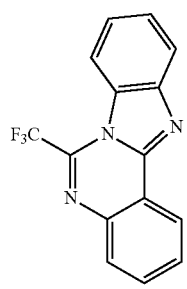 [SMILES: FC(F)(F)c1nc2ccccc2c2nc3ccccc3n12] |
| L166 | S. Vomero et al. Farmaco, Edizione Scientifica 1984, 39(5), 394 | 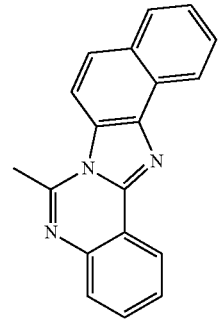 [SMILES: Cc1nc2ccccc2c2nc3c4ccccc4ccc3n12] |
| L167 | J. Padmaja et al. Indian Journal of Chemistry, Section B: Organic Chemistry Including Medicinal Chemistry 1988, 27B(10), 909 | 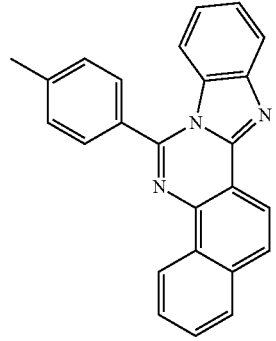 [SMILES: Cc1ccc(-c2nc3c4ccccc4ccc3c3nc4ccccc4n23)cc1] |
| L168 | J. Padmaja et al. Indian Journal of Chemistry, Section B: Organic Chemistry Including Medicinal Chemistry 1988, 27B(10), 909 | 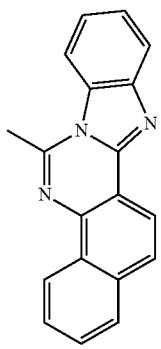 [SMILES: Cc1nc2c3ccccc3ccc2c2nc3ccccc3n12] |

Ligand Synthesis:

Preparation analogous to 1) Imidazo[2,1-a]isoquinoline systems.

| Ex. | Variant | Quinazol-4-ylamine | Carbonyl comp. | Product | Yield |
|---|---|---|---|---|---|
| L169 | A | 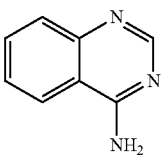 15018-66-3 | 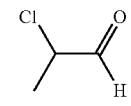 | 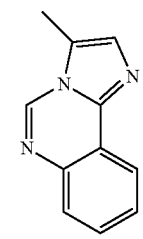 | 76% |

-continued
| Ex. | Variant | Quinazol-4-ylamine | Carbonyl comp. | Product | Yield |
|---|---|---|---|---|---|
| L170 | A | 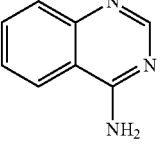 | 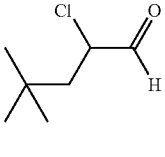 | 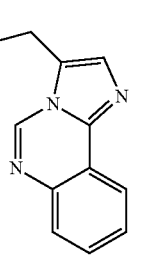 | 65% |
| L171 | A | 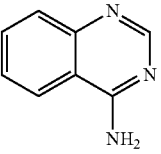 | 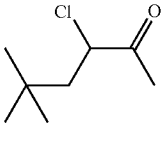 | 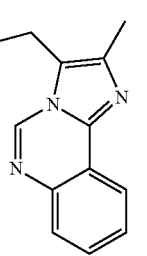 | 54% |
| L172 | A | 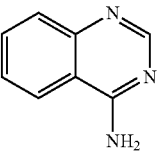 | 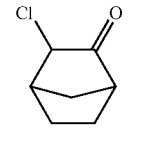 | 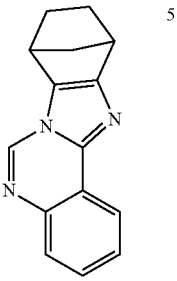 | 51% |
| L173 | B | 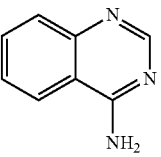 | 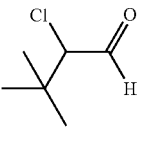 | 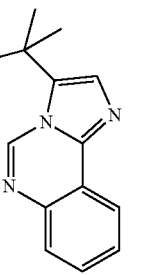 | 75% |
10) Imidazo[2,1-f][1,6]naphthyridine systems
| Ex. | Literature | Product |
|---|---|---|
| L174 | J. M. Chezal et al. Tetrahedron 2002, 58(2), 295 | 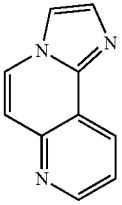 [SMILES: c1cnc2ccn3ccnc3c2c1] |
11) Pyrazolo[1,5-a]quinoline systems
| Ex. | Literature | Product |
|---|---|---|
| L175 | D. Barrett et al. Recent Research Developments in Organic Chemistry 1997, 1, 137 | 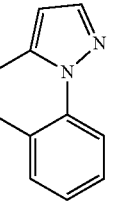 |

-continued

| Ex. | Literature | Product |
|---|---|---|
| L176 | H. Gnichtel et al.<br>Liebigs Annalen der Chemie 1981, 10, 1751 | 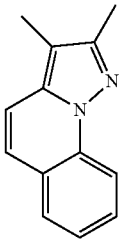 |
| L177 | R. E. Banks<br>Journal of Fluorine Chemistry 1980, 15(2), 179 | 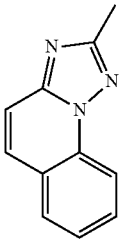 |
| L178 | Y. P. Reddy et al.<br>Indian Journal of Chemistry, Section B: Organic Chemistry Including Medicinal Chemistry 1988, 27B(6), 563 | 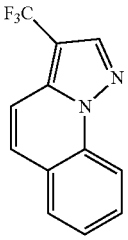 |
| L179 | Y. P. Reddy et al.<br>Indian Journal of Chemistry, Section B: Organic Chemistry Including Medicinal Chemistry 1988, 27B(6), 563 | 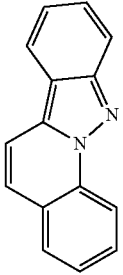 [SMILES: c1ccc2c(c1)ccc1c3ccccc3nn21] |

12) 1,2,4-Triazolo[1,5-a]quinoline systems

| Ex. | Literature | Product |
|---|---|---|
| L180 | S. Batori et al.<br>Heterocycles 1990, 31(2), 289 | 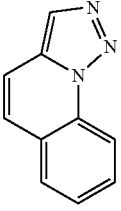 |

-continued

| Ex. | Literature | Product |
|---|---|---|
| L181 | C. N. Hoang, et al.<br>ARKIVOC 2001, 2(2), 42 | 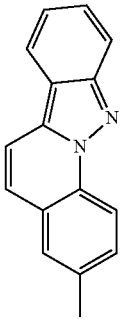 [SMILES: Cc1ccc2c(ccc3c4ccccc4nn23)c1] |

13) 1,2,3-Triazolo[1,5-a]quinoline systems

| Ex. | Literature | Product |
|---|---|---|
| L182 | Y. Tamura et al.<br>Journal of Heterocyclic Chemistry 1975, 12(3), 481 | 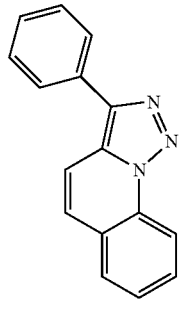 [SMILES: c1ccc(-c2nnn3c2ccc2ccccc23)cc1] |
| L183 | Y. Tamura et al.<br>Journal of Heterocyclic Chemistry 1975, 12(3), 481 | 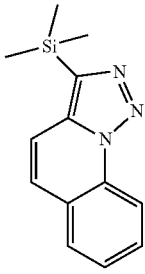 [SMILES: C[Si](C)(C)c1nnn2c1ccc1ccccc12] |
| L184 | R. Ballesteros-Garrido et al.<br>Tetrahedron 2009, 65(22), 4410 | 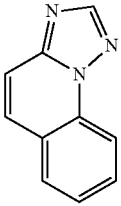 |

14) Tetraazolo[1,5-a]quinoline systems

| Ex. | Literature | Product |
|---|---|---|
| L185 | J. K. Laha<br>Synthesis 2008, 24, 4002 | 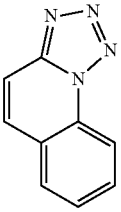 [SMILES: c1ccc2c(c1)ccc1nnnn12] |

189
-continued

| Ex. | Literature |
|---|---|
| L186 | U.S. Pat. No. 2743274 |
| L187 | DE 2166398 |
| L188 | C. W. Rees et al.<br>Journal of the Chemistry Society, Perkin Transactions 1: Organic and Bio-Organic Chemistry (1972-1999) 1976, 20, 2178 |

15) Imidazo[1,2-a][1,8]naphthyridine systems

| Ex. | Literature |
|---|---|
| L189 | A. Gueiffier et al.<br>Journal of Heterocyclic Chemistry 1997, 34(3), 765 |
| L190 | A. Gueiffier et al.<br>Journal of Heterocyclic Chemistry 1997, 34(3), 765 |

190

16) 1,2,4-Triazolo[4,3-a][1,8]naphthyridine systems

| Ex. | Literature |
|---|---|
| L191 | H. Shailaja Rani et al.<br>Indian Journal of Chemistry, Section B: Organic Chemistry Including Medicinal Chemistry 1996, 35B(2), 106 |

17) Pyrrolo[1,2-a][1,8]naphthyridine systems

| Ex. | Literature |
|---|---|
| L192 | I. Cardinaud et al.<br>Heterocycles 1993, 36(11), 2513 |

18) 1H-Pyrrolo[3,2-h]quinoline systems

| Ex. | Literature |
|---|---|
| L193 | M. Vlachou et al.<br>Heterocycles 2002, 57(1), 129 |
| L194 | Zh. F. Sergeeva et al.<br>Khimiya Geterotsiklicheskikh Soedinenii 1975, 12, 1656 |
| L195 | S. A. Yamashkin et al.<br>Khimiya Geterotsiklicheskikh Soedinenii 1995, 1, 58 |

| Ex. | Literature | Product |
|---|---|---|
| L196 | C. B. de Koning et al. Perkin 1 2000, 11, 1705 | 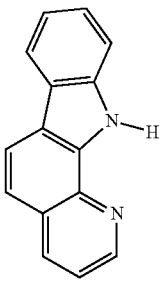 [SMILES: c1cnc2c(c1)ccc1c3ccccc3[nH]c12] |
| L197 | C. Galvez et al. Journal of Chemical Research, Synopses 1987, 1, 16 | 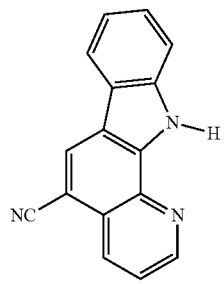 [SMILES: N#Cc1cc2c3ccccc3[nH]c2c2ncccc12] |
| L198 | N. P. Buu-Hoi et al. Journal of the Chemical Society [Section] C: Organic 1966, 1, 47 | 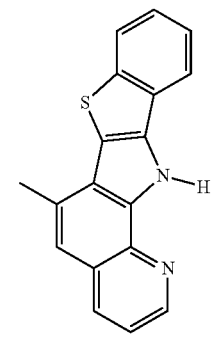 [SMILES: Cc1cc2cccnc2c2[nH]c3c4ccccc4sc3c12] |
| L199 | E. P. Baberkina et al. Zhurnal Organicheskoi Khimii 1991, 27(5), 1110 | 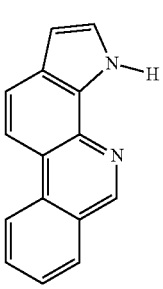 [SMILES: c1ccc2c(c1)cnc1c2ccc2cc[nH]c21] |

19) Imidazo[1,2-h][1,7]naphthyridine systems

| Ex. | Literature | Product |
|---|---|---|
| L200 | J. M. Chezal et al. Tetrahedron 2002, 58(2), 295 | 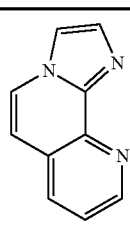 |
| L201 | M. Andaloussi et al. European Journal of Medicinal Chemistry 2008, 43(11), 2505 | 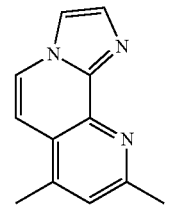 |

20) 1,8-Dihydropyrrolo[3,2-g]indoles

| Ex. | Literature | Product |
|---|---|---|
| L202 | A. Berlin et al. Journal of the Chemical Society, Chemical Communications 1987, 15, 1176 | 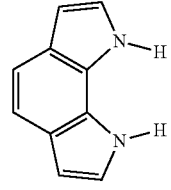 [SMILES: c1cc2ccc3cc[nH]c3c2[nH]1] |
| L203 | Schiavon, et al. Synthetic Metals 1989, 28(1-2), C199-C204 | 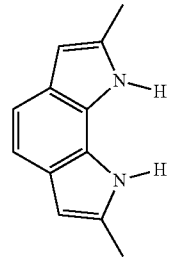 |

21) 1,8-Dihydrobenzo[1,2-d:3,4-d']diimidazoles

| Ex. | Literature | Product |
|---|---|---|
| L204 | A. Berlin et al. Journal of the Chemical Society, Chemical Communications 1987, 15, 1176 | 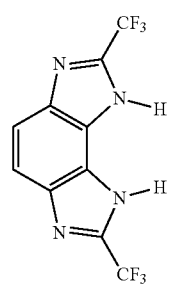 [SMILES: FC(F)(F)c1nc2ccc3nc(C(F)(F)F)[nH]c3c2[nH]1] |

22) Bridged imidazo[2,1-a]isoquinoline systems

The following ligands are prepared analogously to the imidazo[2,1-a]isoquinoline systems, variant A, from the 1-aminoisoquinoline derivatives and carbonyl components shown.

| Ex. | 1-Amino-isoquinoline derivative | Carbonyl component | Product | Yield |
|---|---|---|---|---|
| L205 | | 40630-12-4 | | 54% |
| L206 | | 72444-45-2 | | 55% |
| L207 | | 1087400-52-9 | | 63% |
| L208 | | | | 37% |

B: Synthesis of the Metal Complexes
1) Trishomoleptic Iridium Complexes:
Variant A:

A mixture of 12.5 mmol of the ligand, 2.5 mmol of sodium bis(acetylacetonato)dichloroiridate(III) [770720-50-8] in 5 ml of triethylene glycol is stirred at 240° C. for 24 h under a gentle stream of argon. After cooling, the mixture is diluted with 100 ml of 1N hydrochloric acid and extracted five times with 100 ml of dichloromethane. The org. phase is washed three times with 200 ml of water, dried over a mixture of sodium sulfate and sodium carbonate and then evaporated to dryness. The residue is chromatographed on silica gel (eluent dichloromethane), subsequently recrystallised from dichloromethane/hexane and then sublimed in vacuo.

| Ex. | Ligand | Ir complex | Yield |
|---|---|---|---|
| Ir(L1)₃ | L1 | | 19% |

-continued

| Ex. | Ligand | Ir complex | Yield |
|---|---|---|---|
| Ir(L74)$_3$ | L74 | (structure) | 23.9% |
| Ir(L69)$_3$ | L69 | (structure) | 12.0% |
| Ir(L80)$_3$ | L80 | (structure) | 3.4% |

Variant B:

A mixture of 10 mmol of tris(acetylacetonato)indium(III) [15635-87-7] and 60 mmol of the ligand is sealed in vacuo (10 mbar) in a 100 ml glass ampoule. The ampoule is conditioned for the stated time at the stated temperature, with the molten mixture being stirred with the aid of a magnetic stirrer. After cooling—ATTENTION: the ampoules are usually under pressure!—the ampoule is opened, and the sinter cake is stirred at 60° C. for 5 h with 200 g of glass beads (diameter 3 mm) in 500 ml of EtOH and mechanically digested in the process. After cooling, the fine suspension is decanted off from the glass beads, and the solid is filtered off with suction dried in vacuo. The dry solid is placed on a silica-gel bed with a depth of 10 cm in a hot extractor and then extracted with 1,2-dichloroethane or chlorobenzene. When the extraction is complete, the extraction medium is concentrated to about 50 ml in vacuo, 100 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Ir complex | Reaction temp./reaction time | Yield |
|---|---|---|---|---|
| Ir(L1)$_3$ | L1 | Ir(L1)$_3$ (structure) | 245° C./30 h | 5% |
| Ir(L2)$_3$ | L2 | Ir(L2)$_3$ | 245° C./30 h | 23% |
| Ir(L3)$_3$ | L3 | Ir(L3)$_3$ | 245° C./30 h | 13% |
| Ir(L4)$_3$ | L4 | Ir(L4)$_3$ | 245° C./30 h | 19% |
| Ir(L5)$_3$ | L5 | Ir(L5)$_3$ | 240° C./45 h | 65% |
| Ir(L6)$_3$ | L6 | Ir(L6)$_3$ | 240° C./48 h | 62% |
| Ir(L7)$_3$ | L7 | Ir(L7)$_3$ | 240° C./48 h | 38% |
| Ir(L8)$_3$ | L8 | Ir(L8)$_3$ | 240° C./48 h | 77% |
| Ir(L9)$_3$ | L9 | Ir(L9)$_3$ | 250° C./50 h | 59% |
| Ir(L10)$_3$ | L10 | Ir(L10)$_3$ | 245° C./30 h | 9% |
| Ir(L11)$_3$ | L11 | Ir(L11)$_3$ | 245° C./30 h | 23% |
| Ir(L12)$_3$ | L12 | Ir(L12)$_3$ | 245° C./30 h | 47% |
| Ir(L13)$_3$ | L13 | Ir(L13)$_3$ | 245° C./30 h | 51% |
| Ir(L14)$_3$ | L14 | Ir(L14)$_3$ | 245° C./26 h | 42% |
| Ir(L15)$_3$ | L15 | Ir(L15)$_3$ | 245° C./30 h | 41% |
| Ir(L16)$_3$ | L16 | Ir(L16)$_3$ | 245° C./40 h | 45% |
| Ir(L17)$_3$ | L17 | Ir(L17)$_3$ | 240° C./48 h | 32% |
| Ir(L18)$_3$ | L18 | Ir(L18)$_3$ | 240° C./48 h | 11% |
| Ir(L19)$_3$ | L19 | Ir(L19)$_3$ | 240° C./48 h | 38% |
| Ir(L20)$_3$ | L20 | Ir(L20)$_3$ | 240° C./48 h | 61% |
| Ir(L21)$_3$ | L21 | Ir(L21)$_3$ | 240° C./44 h | 35% |
| Ir(L22)$_3$ | L22 | Ir(L22)$_3$ | 245° C./20 h | 9% |
| Ir(L23)$_3$ | L23 | Ir(L23)$_3$ | 240° C./44 h | 40% |
| Ir(L24)$_3$ | L24 | Ir(L24)$_3$ | 245° C./20 h | 5% |
| Ir(L25)$_3$ | L25 | Ir(L25)$_3$ | 245° C./28 h | 31% |
| Ir(L26)$_3$ | L26 | Ir(L26)$_3$ | 245° C./32 h | 36% |
| Ir(L27)$_3$ | L27 | Ir(L27)$_3$ | 250° C./32 h | 39% |
| Ir(L28)$_3$ | L28 | Ir(L28)$_3$ | 240° C./44 h | 28% |
| Ir(L29)$_3$ | L29 | Ir(L29)$_3$ | 240° C./40 h | 4% |
| Ir(L30)$_3$ | L30 | Ir(L30)$_3$ | 240° C./40 h | 30% |
| Ir(L31)$_3$ | L31 | Ir(L31)$_3$ | 240° C./40 h | 43% |
| Ir(L32)$_3$ | L32 | Ir(L32)$_3$ | 240° C./40 h | 44% |

-continued

| Ex. | Ligand | Ir complex | Reaction temp./ reaction time | Yield |
|---|---|---|---|---|
| Ir(L33)₃ | L33 | Ir(L33)₃ | 245° C./ 28 h | 27% |
| Ir(L34)₃ | L34 | Ir(L34)₃ | 240° C./ 35 h | 36% |
| Ir(L35)₃ | L35 | Ir(L35)₃ | 240° C./ 32 h | 20% |
| Ir(L36)₃ | L36 | Ir(L36)₃ | 260° C./ 60 h | 15% |
| Ir(L37)₃ | L3 | Ir(L37)₃ | 270° C./ 48 h | 18% |
| Ir(L38)₃ | L38 | Ir(L38)₃ | 270° C./ 48 h | 48% |
| Ir(L39)₃ | L39 | Ir(L39)₃ | 270° C./ 48 h | 34% |
| Ir(L40)₃ | L40 | Ir(L40)₃ | 270° C./ 48 h | 76% |
| Ir(L41)₃ | L41 | Ir(L41)₃ | 270° C./ 48 h | 22% |
| Ir(L42)₃ | L42 | Ir(L42)₃ | 255° C./ 25 h | 47% |
| Ir(L43)₃ | L43 | Ir(L43)₃ | 250° C./ 60 h | 43% |
| Ir(L44)₃ | L44 | Ir(L44)₃ | 250° C./ 60 h | 55% |
| Ir(L45)₃ | L45 | Ir(L45)₃ | 250° C./ 60 h | 60% |
| Ir(L46)₃ | L46 | Ir(L46)₃ | 250° C./ 60 h | 34% |
| Ir(L47)₃ | L47 | Ir(L47)₃ | 260° C./ 35 h | 46% |
| Ir(L48)₃ | L48 | Ir(L48)₃ | 240° C./ 55 h | 17% |
| Ir(L49)₃ | L49 | Ir(L49)₃ | 250° C./ 60 h | 58% |
| Ir(L50)₃ | L50 | Ir(L50)₃ | 250° C./ 60 h | 61% |
| Ir(L51)₃ | L51 | Ir(L51)₃ | 250° C./ 38 h | 40% |
| Ir(L52)₃ | L52 | Ir(L52)₃ | 250° C./ 60 h | 68% |
| Ir(L53)₃ | L53 | Ir(L53)₃ | 250° C./ 43 h | 48% |
| Ir(L54)₃ | L54 | Ir(L54)₃ | 255° C./ 52 h | 31% |
| Ir(L55)₃ | L55 | Ir(L55)₃ | 245° C./ 30 h | 23% |
| Ir(L56)₃ | L56 | Ir(L56)₃ | 245° C./ 30 h | 21% |
| Ir(L57)₃ | L57 | Ir(L57)₃ | 245° C./ 50 h | 41% |
| Ir(L58)₃ | L58 | Ir(L58)₃ | 250° C./ 38 h | 34% |
| Ir(L59)₃ | L59 | Ir(L59)₃ | 240° C./ 18 h | 7% |
| Ir(L60)₃ | L60 | Ir(L60)₃ | 240° C./ 18 h | 22% |
| Ir(L61)₃ | L61 | Ir(L61)₃ | 240° C./ 22 h | 21% |
| Ir(L62)₃ | L62 | Ir(L62)₃ | 250° C./ 42 h | 40% |
| Ir(L63)₃ | L63 | Ir(L63)₃ | 275° C./ 48 h | 27% |
| Ir(L64)₃ | L64 | Ir(L64)₃ | 275° C./ 30 h | 61% |
| Ir(L65)₃ | L65 | Ir(L65)₃ | 275° C./ 30 h | 57% |
| Ir(L66)₃ | L66 | Ir(L66)₃ | 280° C./ 18 h | 44% |
| Ir(L67)₃ | L67 | Ir(L67)₃ | 280° C./ 22 h | 46% |
| Ir(L68)₃ | L68 | Ir(L68)₃ | 285° C./ 24 h | 41% |
| Ir(L69)₃ | L69 | Ir(L69)₃ | 250° C./ 32 h | 7% |
| Ir(L70)₃ | L70 | Ir(L70)₃ | 250° C./ 22 h | 11% |
| Ir(L71)₃ | L71 | Ir(L71)₃ | 275° C./ 16 h | 2% |
| Ir(L72)₃ | L72 | Ir(L72)₃ | 260° C./ 26 h | 23% |
| Ir(L73)₃ | L73 | Ir(L73)₃ | 260° C./ 18 h | 15% |

| Ex. | Ligand | Ir complex | Reaction temp./ reaction time | Yield |
|---|---|---|---|---|
| Ir(L74)$_3$ | L74 | 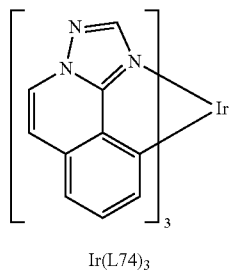 Ir(L74)$_3$ | 240° C./ 24 h | 13% |
| Ir(L75)$_3$ | L75 | Ir(L75)$_3$ | 240° C./ 24 h | 25% |
| Ir(L78)$_3$ | L78 | Ir(L78)$_3$ | 245° C./ 24 h | 15% |
| Ir(L79)$_3$ | L79 | Ir(L79)$_3$ | 245° C./ 30 h | 36% |
| Ir(L80)$_3$ | L80 | Ir(L80)$_3$ | 220° C./ 24 h | 3% |
| Ir(L82)$_3$ | L82 | Ir(L82)$_3$ | 230° C./ 24 h | 11% |
| Ir(L83)$_3$ | L83 | Ir(L83)$_3$ | 250° C./ 28 h | 72% |
| Ir(L84)$_3$ | L84 | Ir(L84)$_3$ | 250° C./ 28 h | 74% |
| Ir(L85)$_3$ | L85 | Ir(L85)$_3$ | 250° C./ 28 h | 69% |
| Ir(L86)$_3$ | L86 | Ir(L86)$_3$ | 250° C./ 24 h | 63% |
| Ir(L87)$_3$ | L87 | Ir(L87)$_3$ | 250° C./ 32 h | 70% |
| Ir(L88)$_3$ | L88 | Ir(L88)$_3$ | 250° C./ 20 h | 75% |
| Ir(L89)$_3$ | L89 | Ir(L89)$_3$ | 255° C./ 18 h | 65% |
| Ir(L90)$_3$ | L90 | Ir(L90)$_3$ | 245° C./ 29 h | 79% |
| Ir(L91)$_3$ | L91 | Ir(L91)$_3$ | 250° C./ 30 h | 70% |
| Ir(L92)$_3$ | L92 | Ir(L92)$_3$ | 270° C./ 24 h | 35% |
| Ir(L93)$_3$ | L93 | Ir(L93)$_3$ | 270° C./ 26 h | 38% |
| Ir(L94)$_3$ | L94 | Ir(L94)$_3$ | 270° C./ 24 h | 53% |
| Ir(L95)$_3$ | L95 | Ir(L95)$_3$ | 280° C./ 28 h | 72% |
| Ir(L96)$_3$ | L96 | Ir(L96)$_3$ | 265° C./ 24 h | 68% |
| Ir(L97)$_3$ | L97 | Ir(L97)$_3$ | 250° C./ 32 h | 66% |
| Ir(L98)$_3$ | L98 | Ir(L98)$_3$ | 250° C./ 20 h | 71% |
| Ir(L99)$_3$ | L99 | Ir(L99)$_3$ | 250° C./ 22 h | 77% |
| Ir(L100)$_3$ | L100 | Ir(L100)$_3$ | 245° C./ 32 h | 68% |
| Ir(L101)$_3$ | L101 | Ir(L101)$_3$ | 260° C./ 22 h | 70% |
| Ir(L102)$_3$ | L102 | Ir(L102)$_3$ | 250° C./ 22 h | 71% |
| Ir(L103)$_3$ | L103 | Ir(L103)$_3$ | 250° C./ 22 h | 70% |
| Ir(L104)$_3$ | L104 | Ir(L104)$_3$ | 255° C./ 26 h | 73% |
| Ir(L105)$_3$ | L105 | Ir(L105)$_3$ | 250° C./ 20 h | 67% |
| Ir(L106)$_3$ | L106 | Ir(L106)$_3$ | 255° C./ 25 h | 67% |
| Ir(L107)$_3$ | L107 | Ir(L107)$_3$ | 250° C./ 24 h | 65% |
| Ir(L108)$_3$ | L108 | Ir(L108)$_3$ | 275° C./ 18 h | 63% |
| Ir(L109)$_3$ | L109 | Ir(L109)$_3$ | 275° C./ 22 h | 58% |
| Ir(L110)$_3$ | L110 | Ir(L110)$_3$ | 275° C./ 24 h | 43% |
| Ir(L111)$_3$ | L111 | Ir(L111)$_3$ | 275° C./ 20 h | 57% |
| Ir(L112)$_3$ | L112 | Ir(L112)$_3$ | 255° C./ 16 h | 23% |
| Ir(L113)$_3$ | L113 | Ir(L113)$_3$ | 255° C./ 18 h | 26% |
| Ir(L114)$_3$ | L114 | Ir(L114)$_3$ | 260° C./ 16 h | 9% |
| Ir(L115)$_3$ | L115 | 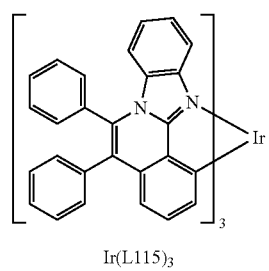 Ir(L115)$_3$ | 280° C./ 20 h | 76% |
| Ir(L116)$_3$ | L116 | Ir(L116)$_3$ | 280° C./ 22 h | 72% |
| Ir(L117)$_3$ | L117 | Ir(L117)$_3$ | 280° C./ 30 h | 78% |
| Ir(L118)$_3$ | L118 | Ir(L118)$_3$ | 270° C./ 20 h | 26% |
| Ir(L119)$_3$ | L119 | Ir(L119)$_3$ | 270° C./ 18 h | 19% |
| Ir(L120)$_3$ | L120 | Ir(L120)$_3$ | 285° C./ 40 h | 75% |
| Ir(L121)$_3$ | L121 | Ir(L121)$_3$ | 280° C./ 30 h | 74% |
| Ir(L122)$_3$ | L122 | Ir(L122)$_3$ | 280° C./ 22 h | 11% |
| Ir(L123)$_3$ | L123 | Ir(L123)$_3$ | 285° C./ 40 h | 69% |
| Ir(L124)$_3$ | L124 | Ir(L124)$_3$ | 280° C./ 36 h | 73% |

-continued

| Ex. | Ligand | Ir complex | Reaction temp./ reaction time | Yield |
|---|---|---|---|---|
| Ir(L125)$_3$ | L125 | Ir(L125)$_3$ | 265° C./ 40 h | 66% |
| Ir(L126)$_3$ | L126 | Ir(L126)$_3$ | 265° C./ 38 h | 64% |
| Ir(L127)$_3$ | L127 | Ir(L127)$_3$ | 265° C./ 40 h | 67% |
| Ir(L128)$_3$ | L128 | Ir(L128)$_3$ | 265° C./ 30 h | 44% |
| Ir(L129)$_3$ | L129 | Ir(L129)$_3$ | 265° C./ 60 h | 57% |
| Ir(L130)$_3$ | L130 | Ir(L130)$_3$ | 260° C./ 55 h | 62% |
| Ir(L131)$_3$ | L131 | Ir(L131)$_3$ | 245° C./ 45 h | 52% |
| Ir(L132)$_3$ | L132 | Ir(L132)$_3$ | 270° C./ 20 h | 15% |
| Ir(L133)$_3$ | L133 | Ir(L133)$_3$ | 275° C./ 30 h | 17% |
| Ir(L134)$_3$ | L134 | Ir(L134)$_3$ | 270° C./ 20 h | 34% |
| Ir(L135)$_3$ | L135 | Ir(L135)$_3$ | 270° C./ 20 h | 61% |
| Ir(L136)$_3$ | L136 | Ir(L136)$_3$ | 265° C./ 30 h | 56% |
| Ir(L137)$_3$ | L137 | Ir(L137)$_3$ | 275° C./ 24 h | 30% |
| Ir(L138)$_3$ | L138 | Ir(L138)$_3$ | 265° C./ 34 h | 23% |
| Ir(L139)$_3$ | L139 | Ir(L139)$_3$ | 270° C./ 47 h | 67% |
| Ir(L140)$_3$ | L140 | Ir(L140)$_3$ | 270° C./ 28 h | 53% |
| Ir(L141)$_3$ | L141 | Ir(L141)$_3$ | 270° C./ 28 h | 28% |
| Ir(L142)$_3$ | L142 | Ir(L142)$_3$ | 270° C./ 48 h | 47% |
| Ir(L143)$_3$ | L143 | Ir(L143)$_3$ | 265° C./ 64 h | 61% |
| Ir(L144)$_3$ | L144 | Ir(L144)$_3$ | 245° C./ 46 h | 7% |
| Ir(L145)$_3$ | L145 | Ir(L145)$_3$ | 250° C./ 36 h | 74% |
| Ir(L146)$_3$ | L146 | Ir(L146)$_3$ | 245° C./ 28 h | 13% |
| Ir(L147)$_3$ | L147 | Ir(L147)$_3$ | 265° C./ 35 h | 23% |
| Ir(L148)$_3$ | L148 | Ir(L148)$_3$ | 245° C./ 16 h | 5% |
| Ir(L149)$_3$ | L149 | Ir(L149)$_3$ | 245° C./ 26 h | 10% |
| Ir(L150)$_3$ | L150 | Ir(L150)$_3$ | 250° C./ 36 h | 7% |
| Ir(L151)$_3$ | L151 | Ir(L151)$_3$ | 255° C./ 42 h | 38% |
| Ir(L152)$_3$ | L152 | Ir(L152)$_3$ | 255° C./ 40 h | 77% |

203
-continued

| Ex. | Ligand | Ir complex | Reaction temp./ reaction time | Yield |
|---|---|---|---|---|
| Ir(L153)₃ | L153 | Ir(L153)₃ | 245° C./ 46 h | 74% |
| Ir(L154)₃ | L154 | 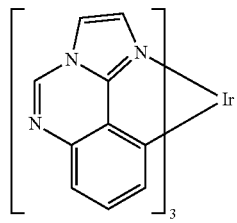 Ir(L154)₃ | 245° C./ 26 h | 11% |
| Ir(L155)₃ | L155 | Ir(L155)₃ | 245° C./ 30 h | 14% |
| Ir(L156)₃ | L156 | Ir(L156)₃ | 245° C./ 36 h | 65% |
| Ir(L157)₃ | L157 | Ir(L157)₃ | 245° C./ 36 h | 63% |
| Ir(L158)₃ | L158 | Ir(L158)₃ | 250° C./ 28 h | 48% |
| Ir(L159)₃ | L159 | Ir(L159)₃ | 245° C./ 30 h | 54% |
| Ir(L160)₃ | L160 | Ir(L160)₃ | 245° C./ 30 h | 50% |
| Ir(L161)₃ | L161 | Ir(L161)₃ | 240° C./ 38 h | 32% |
| Ir(L162)₃ | L162 | Ir(L162)₃ | 255° C./ 30h | 71% |
| Ir(L163)₃ | L163 | Ir(L163)₃ | 250° C./ 34 h | 69% |
| Ir(L164)₃ | L164 | Ir(L164)₃ | 255° C./ 30 h | 70% |
| Ir(L165)₃ | L165 | Ir(L165)₃ | 250° C./ 30 h | 59% |
| Ir(L166)₃ | L166 | Ir(L166)₃ | 255° C./ 40 h | 25% |
| Ir(L167)₃ | L167 | Ir(L167)₃ | 265° C./ 30 h | 38% |
| Ir(L168)₃ | L168 | Ir(L168)₃ | 270° C./ 35 h | 55% |
| Ir(L169)₃ | L169 | Ir(L169)₃ | 250° C./ 36 h | 42% |
| Ir(L170)₃ | L170 | 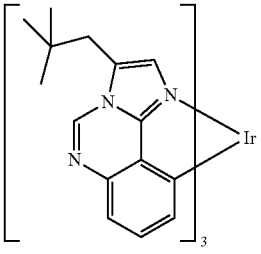 Ir(L170)₃ | 255° C./ 28 h | 33% |
| Ir(L171)₃ | L171 | Ir(L171)₃ | 255° C./ 30 h | 68% |
| Ir(L172)₃ | L172 | Ir(L172)₃ | 255° C./ 30 h | 71% |
| Ir(L173)₃ | L173 | Ir(L173)₃ | 255° C./ 30 h | 36% |

204
-continued

| Ex. | Ligand | Ir complex | Reaction temp./ reaction time | Yield |
|---|---|---|---|---|
| Ir(L174)₃ | L174 | 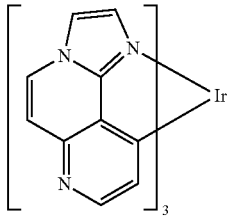 Ir(L174)₃ | 245° C./ 30 h | 6% |
| Ir(L175)₃ | L175 | 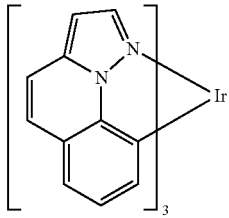 Ir(L175)₃ | 250° C./ 30 h | 3% |
| Ir(L176)₃ | L176 | Ir(L176)₃ | 250° C./ 34 h | 67% |
| Ir(L177)₃ | L177 | Ir(L177)₃ | 255° C./ 32 h | 48% |
| Ir(L178)₃ | L178 | Ir(L178)₃ | 260° C./ 30 h | 75% |
| Ir(L179)₃ | L179 | Ir(L179)₃ | 260° C./ 30 h | 74% |
| Ir(L180)₃ | L180 | 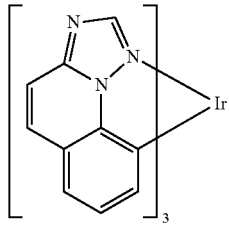 Ir(L180)₃ | 250° C./ 24 h | 26% |
| Ir(L181)₃ | L181 | Ir(L181)₃ | 250° C./ 24 h | 16% |
| Ir(L182)₃ | L182 | 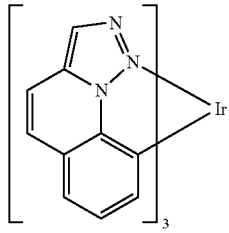 Ir(L182)₃ | 250° C./ 30 h | 17% |
| Ir(L183)₃ | L183 | Ir(L183)₃ | 260° C./ 20 h | 31% |
| Ir(L184)₃ | L184 | Ir(L184)₃ | 230° C./ 25 h | 23% |
| Ir(L185)₃ | L185 | Ir(L185)₃ | 230° C./ 18 h | 5% |

-continued

| Ex. | Ligand | Ir complex | Reaction temp./ reaction time | Yield |
|---|---|---|---|---|
| Ir(L186)₃ | L186 | Ir(L186)₃ | 235° C./ 20 h | 7% |
| Ir(L187)₃ | L187 | Ir(L187)₃ | 230° C./ 25 h | 8% |
| Ir(L188)₃ | L188 | Ir(L188)₃ | 240° C./ 25 h | 13% |
| Ir(L189)₃ | L189 | 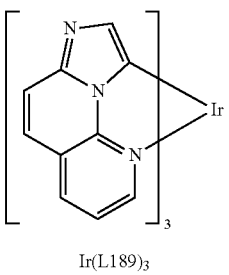 Ir(L189)₃ | 245° C./ 35 h | 9% |
| Ir(L190)₃ | L190 | Ir(L190)₃ | 245° C./ 26 h | 12% |
| Ir(L191)₃ | L191 | 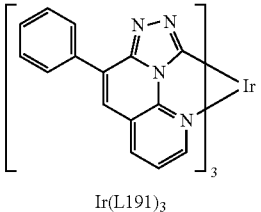 Ir(L191)₃ | 250° C./ 26 h | 26% |
| Ir(L192)₃ | L192 | 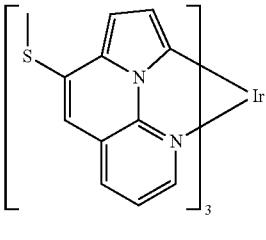 Ir(L192)₃ | 250° C./ 36 h | 8% |
| Ir(L193)₃ | L193 | 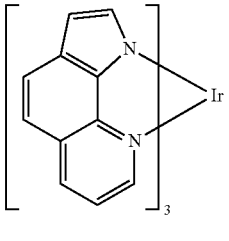 Ir(L193)₃ | 230° C./ 16 h | 6% |
| Ir(L194)₃ | L194 | Ir(L194)₃ | 230° C./ 16 h | 54% |
| Ir(L195)₃ | L195 | Ir(L195)₃ | 230° C./ 26 h | 71% |
| Ir(L196)₃ | L196 | Ir(L196)₃ | 250° C./ 36 h | 58% |
| Ir(L197)₃ | L197 | Ir(L197)₃ | 250° C./ 36 h | 27% |
| Ir(L198)₃ | L198 | Ir(L198)₃ | 255° C./ 46 h | 34% |
| Ir(L199)₃ | L199 | Ir(L199)₃ | 250° C./ 46 h | 17% |

Variant C: Ligand Synthesis on the Complex

A mixture of 10 mmol of tris(acetylacetonato)iridium(III) [15635-87-7] and 60 mmol of the imidazole derivative is sealed in vacuo ($10^{-3}$ mbar) in a 100 ml glass ampoule. The ampoule is conditioned for the stated time at the stated temperature, with the molten mixture being stirred with the aid of a magnetic stirrer. After cooling—ATTENTION: the ampoules are usually under pressure!—the ampoule is opened, and the sinter cake is stirred at 50° C. for 5 h with 100 g of glass beads (diameter 3 mm) in 300 ml of EtOH and mechanically digested in the process. After cooling, the fine suspension is decanted off from the glass beads, and the solid is filtered off with suction and dried in vacuo. The solid is suspended in a mixture of 90 ml of acetic acid and 10 ml of acetic anhydride, 1 ml of trifluoroacetic acid is added to the suspension, and the mixture is then heated under reflux for 1 h. After cooling, the solid is filtered off with suction, washed once with 20 ml of acetic acid and three times with 30 ml of ethanol each time and dried in vacuo. The dry solid is placed on a silicagel bed with a depth of 10 cm in a hot extractor and then extracted with 1,2-dichloroethane. When the extraction is complete, the extraction medium is concentrated to about 50 ml in vacuo, 100 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is sublimed. The sublimation is carried out in a high vacuum (p about $10^{-6}$ mbar) in the temperature range from about 350 to about 370° C.

| Example | Imidazole derivative | Ir complex | Yield |
|---|---|---|---|
| Ir(L83)₃ | 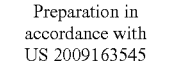 Preparation in accordance with US 2009163545 | 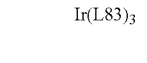 Ir(L83)₃ | 20% |

| Example | Imidazole derivative | Ir complex | Yield |
|---|---|---|---|
| Ir(L88)$_3$ | 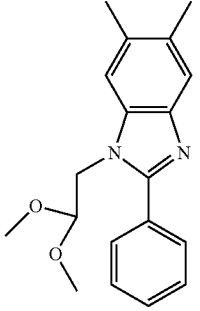 Preparation in accordance with US 2009163545 | 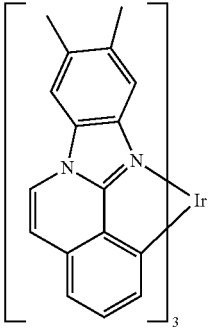 Ir(L88)$_3$ | 35% |

2) Heteroleptic Iridium Complexes:
Variant A:

A mixture of 10 mmol of sodium bis(acetylacetonato)dichloroiridate(III) [770720-50-8] and 21 mmol of the ligand is sealed in vacuo ($10^{-3}$ mbar) in a 50 ml glass ampoule. The ampoule is conditioned at 220-250° C. for 6-12 h, with the molten mixture being stirred with the aid of a magnetic stirrer. After cooling—ATTENTION: the ampoules are usually under pressure!—the ampoule is opened, and the sinter cake is stirred at 60° C. for 5 h with 200 g of glass beads (diameter 3 mm) in 500 ml of EtOH and mechanically digested in the process. After cooling, the fine suspension is decanted off from the glass beads, and the corresponding chloro dimer of the formula [Ir(L)$_2$Cl]$_2$ is filtered off with suction and dried in vacuo. The resultant crude chloro dimer of the formula [Ir(L)$_2$Cl]$_2$ is suspended in a mixture of 75 ml of 2-ethoxyethanol and 25 ml of water, and 13 mmol of the co-ligand or co-ligand compound and 15 mmol of sodium carbonate are added. After 20 h under reflux, a further 75 ml of water are added dropwise, the mixture is cooled, and the solid is filtered off with suction, washed three times with 50 ml of water each time and three times with 50 ml of methanol each time and dried in vacuo. The solid is placed on a silica-gel bed with a depth of 10 cm in a hot extractor and then extracted with dichloromethane or 1,2-dichloroethane. When the extraction is complete, the extraction medium is concentrated to about 50 ml in vacuo, 100 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Co-ligand | Ir complex | Yield |
|---|---|---|---|---|
| Ir(L5)$_2$(CL1) | L5 | 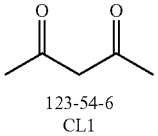 123-54-6 CL1 | 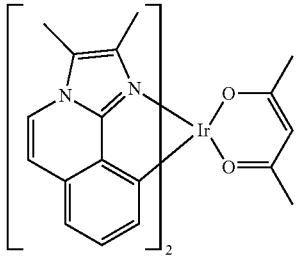 Ir(L5)$_2$(CL1) | 51% |
| Ir(L5)$_2$(CL2) | L5 | 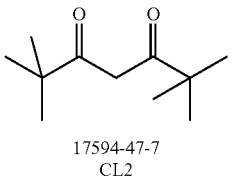 17594-47-7 CL2 | 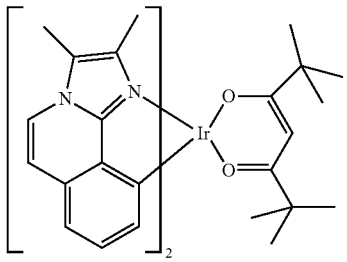 Ir(L5)$_2$(CL2) | 55% |

-continued

| Ex. | Ligand | Co-ligand | Ir complex | Yield |
|---|---|---|---|---|
| Ir(L5)₂(CL3) | L5 | 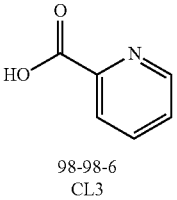 98-98-6 CL3 | 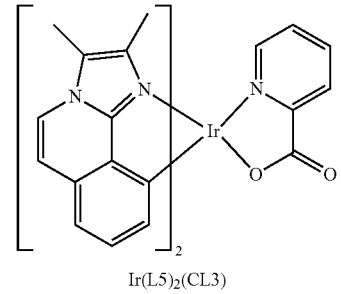 Ir(L5)₂(CL3) | 56% |
| Ir(L5)₂(CL4) | L5 | 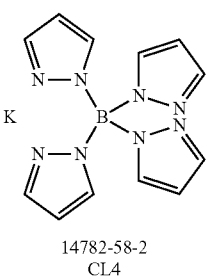 14782-58-2 CL4 | 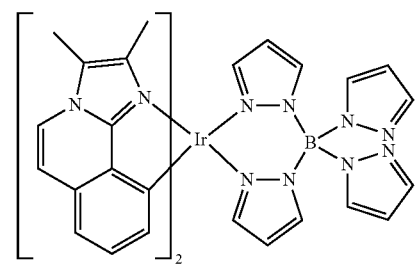 Ir(L5)₂(CL4) | 43% |
| Ir(L5)₂(L193) | L5 | L193 | 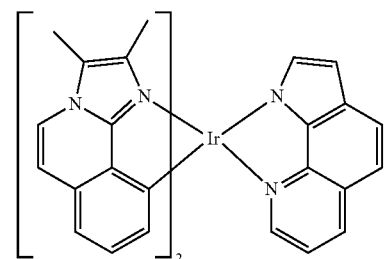 Ir(L5)₂(L193) | 61% |
| Ir(L7)₂(CL1) | L7 | CL1 | Ir(L7)₂(CL1) | 40% |
| Ir(L9)₂(CL1) | L9 | CL1 | Ir(L9)₂(CL1) | 55% |
| Ir(L15)₂(CL1) | L15 | CL1 | Ir(L15)₂(CL1) | 61% |
| Ir(L49)₂(CL1) | L49 | CL1 | Ir(L49)₂(CL1) | 37% |
| Ir(L83)₂(CL2) | L83 | CL2 | Ir(L83)₂(CL1) | 17% |
| Ir(L104)₂(CL2) | L104 | CL2 | Ir(L104)₂(CL2) | 41% |
| Ir(L105)₂(CL2) | L105 | CL2 | Ir(L105)₂(CL2) | 40% |
| Ir(L119)₂(CL3) | L119 | CL3 | Ir(L119)₂(CL3) | 23% |
| Ir(L130)₂(CL3) | L130 | CL3 | Ir(L130)₂(CL3) | 64% |
| r(L139)₂(CL3) | L139 | CL3 | Ir(L139)₂(CL3) | 58% |
| Ir(L163)₂(CL1) | L163 | CL1 | Ir(L163)₂(CL1) | 51% |
| Ir(L172)₂(L199) | L172 | L199 | Ir(L172)₂(L199) | 44% |

Variant B:

A mixture of 10 mmol of sodium bis(acetylacetonato)dichloroiridate(III) [770720-50-8] and 22 mmol of the ligand is sealed in vacuo ($10^{-3}$ mbar) in a 50 ml glass ampoule. The ampoule is conditioned at 220-250° C. for 6-12 h, with the molten mixture being stirred with the aid of a magnetic stirrer. After cooling—ATTENTION: the ampoules are usually under pressure!—the ampoule is opened, and the sinter cake is stirred at 60° C. for 5 h with 200 g of glass beads (diameter 3 mm) in 500 ml of EtOH and mechanically digested in the process. After cooling, the fine suspension is decanted off from the glass beads, and the corresponding crude chloro dimer of the formula [Ir(L)₂Cl]₂ is filtered off with suction and dried in vacuo. The crude chloro dimer of the formula [Ir(L)₂Cl]₂ is reacted further in accordance with WO 2007/065523, Example 5, in the presence of 75 mmol of N,N-dimethylglycine in a dioxane/water mixture. The resultant solids are placed on a silica-gel bed with a depth of 10 cm in a hot extractor and then extracted with dichloromethane or 1,2-dichloroethane. When the extraction is complete, the extraction medium is concentrated to about 50 ml in vacuo, 100 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Co-ligand | Ir complex | Yield |
|---|---|---|---|---|
| Ir(L1)$_2$(CL5) | L1 | 1008-89-5 CL5 | Ir(L1)$_2$(CL5) | 51% |
| Ir(L7)$_2$(CL5) | L7 | CL5 | Ir(L7)$_2$(CL5) | 72% |
| Ir(L7)$_2$(CL6) | L7 | 391604-55-0 CL6 | Ir(L7)$_2$(CL6) | 48% |
| Ir(L14)$_2$(CL7) | L14 | 1093072-00-4 CL7 | Ir(L14)$_2$(CL7) | 53% |
| Ir(L49)$_2$(CL7) | L49 | CL7 | Ir(L49)$_2$(CL7) | 57% |
| Ir(L83)$_2$(CL8) | L83 | 10273-90-2 CL8 | Ir(L83)$_2$(CL8) | 77% |
| Ir(L104)$_2$(CL8) | L104 | CL8 | Ir(L104)$_2$(CL8) | 82% |
| Ir(L105)$_2$(CL8) | L105 | CL8 | Ir(L105)$_2$(CL8) | 80% |
| Ir(L119)$_2$(CL8) | L119 | CL8 | Ir(L119)$_2$(CL8) | 69% |

-continued

| Ex. | Ligand | Co-ligand | Ir complex | Yield |
|---|---|---|---|---|
| Ir(L119)$_2$(CL9) | L119 | 51089-62-4 CL9 | Ir(L119)$_2$(CL9) | 73% |
| Ir(L130)$_2$(CL10) | L130 | 38210-35-4 CL10 | Ir(L130)$_2$(CL10) | 42% |
| Ir(L139)$_2$(CL7) | L139 | CL7 | Ir(L139)$_2$(CL7) | 55% |

Variant C:

A mixture of 10 mmol of sodium bis(acetylacetonato)dichloroiridate(III) [770720-50-8] and 21 mmol of the ligand is sealed in vacuo ($10^{-3}$ mbar) in a 50 ml glass ampoule. The ampoule is conditioned at 220-250° C. for 6-12 h, with the molten mixture being stirred with the aid of a magnetic stirrer. After cooling—ATTENTION: the ampoules are usually under pressure!—the ampoule is opened, and the sinter cake is stirred at 60° C. for 5 h with 200 g of glass beads (diameter 3 mm) in 500 ml of EtOH and mechanically digested in the process. After cooling, the fine suspension is decanted off from the glass beads, and the corresponding chloro dimer of the formula [Ir(L)$_2$Cl]$_2$ is filtered off with suction and dried in vacuo. The resultant crude chloro dimer of the formula [Ir(L)$_2$Cl]$_2$ is suspended in 100 ml of THF, 40 mmol of the co-ligand, 20 mmol of silver(I) trifluoroacetate and 80 mmol of potassium carbonate are added to the suspension, and the mixture is heated under reflux for 24 h. After cooling, the THF is removed in vacuo, and the solid is placed on a silica-gel bed with a depth of 10 cm in a hot extractor and then extracted with dichloromethane or 1,2-dichloroethane. When the extraction is complete, the extraction medium is concentrated to about 50 ml in vacuo, 100 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Co-ligand | Ir complex | Yield |
|---|---|---|---|---|
| Ir(L1)₂(CL5) | L1 | 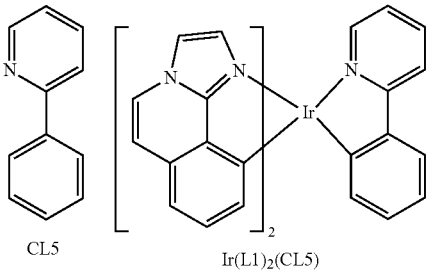 | | 83% |
| Ir(L12)₂(L7) | L12 | L7 | Ir(L12)₂(L7) | 31% |
| Ir(L12)₂(L32) | L12 | L32 | Ir(L12)₂(L32) | 43% |
| Ir(L12)₂(L51) | L12 | L51 | Ir(L12)₂(L51) | 45% |
| Ir(L51)₂(L12) | L51 | L12 | Ir(L51)₂(L12) | 32% |
| Ir(L79)₂(CL7) | L79 | CL7 | Ir(L79)₂(CL7) | 50% |
| Ir(L99)₂(L111) | L99 | L111 | Ir(L99)₂(L111) | 38% |
| Ir(L139)₂(CL8) | L139 | CL8 | Ir(L139)₂(CL8) | 41% |
| Ir(L164)₂(CL8) | L164 | CL8 | Ir(L164)₂(CL8) | 46% |

3) Bishomoleptic Platinum Complexes:

A mixture of 5 mmol of bis(benzonitrile)di(chloro)platinum(II) [14873-63-3], 20 mmol of the ligand, 20 mmol of lithium acetate and 20 ml of acetic acid is initially introduced in an ampoule. This is degassed via freeze-pumpthaw cycles, sealed in vacuo and then subjected to microwave radiation (Discover™ unit from CEM-GmbH, Kamp-Lintfort, Germany, magnetron frequency 2450 MHz, 150 W per litre) at 130° C. for 20 min. The reaction mixture is cooled and stirred into a mixture of 80 ml of EtOH and 20 ml of water, and the fine solid is filtered off with suction, washed three times with 20 ml of ethanol and dried in vacuo. The dry solid is placed on a silica-gel bed with a depth of 10 cm in a hot extractor and then extracted with THF. When the extraction is complete, the extraction medium is concentrated to about 30 ml in vacuo, 75 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Example | Ligand | Pt complex | Yield |
|---|---|---|---|
| Pt (L12)₂ | L12 | 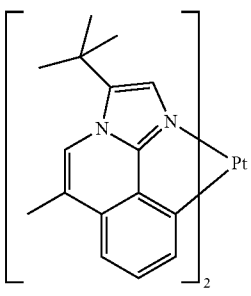 Pt (L12)₂ | 3% |
| Pt (L41)₂ | L41 | Pt (L41)₂ | 22% |
| Pt (L46)₂ | L46 | Pt (L46)₂ | 19% |
| Pt (L101)₂ | L101 | Pt (L101)₂ | 8% |
| Pt (L165)₂ | L165 | Pt (L165)₂ | 24% |

4) Platinum Complexes Containing Tetradentate Ligands:

A mixture of 5 mmol of bis(benzonitrile)di(chloro)platinum(II) [14873-63-3], 5 mmol of the ligand, 20 mmol of lithium acetate and 20 ml of acetic acid is initially introduced in an ampoule. This is degassed via freeze-pump-thaw cycles, sealed in vacuo and then subjected to microwave radiation (Discover™ unit from CEM-GmbH, Kamp-Lintfort, Germany, magnetron frequency 2450 MHz, 150 W per litre) at 130° C. for 20 min. The reaction mixture is cooled and stirred into a mixture of 80 ml of EtOH and 20 ml of water, and the fine solid is filtered off with suction, washed three times with 20 ml of ethanol and dried in vacuo. The dry solid is placed on a silica-gel bed with a depth of 10 cm in a hot extractor and then extracted with THF. When the extraction is complete, the extraction medium is concentrated to about 30 ml in vacuo, 75 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Example | Ligand | Pt complex | Yield |
|---|---|---|---|
| Pt (L205) | L205 | | 23% |
| Pt (L206) | L206 | | 17% |
| Pt (L207) | L207 | | 26% |
| Pt (L208) | L208 | | 31% |

5) Heteroleptic Platinum Complexes:

A mixture of 5 mmol of platinum(II) chloride, 6 mmol of the ligand and 0.5 mmol of tetra-n-butylammonium chloride in 10 ml of dichloromethane is heated under reflux for 12 h. After 50 ml of methanol have been added dropwise, the fine solid is filtered off with suction, washed twice with 10 ml of methanol and dried in vacuo. The resultant crude chloro dimer of the formula [Pt(L)Cl]$_2$ is suspended in a mixture of 45 ml of 2-ethoxyethanol and 15 ml of water, and 7 mmol of the co-ligand or co-ligand compound and 7 mmol of sodium carbonate are added. After 20 h under reflux, a further 75 ml of water are added dropwise, the mixture is cooled, and the solid is filtered off with suction, washed three times with 50 ml of water each time and three times with 50 ml of methanol each time and dried in vacuo. The dry solid is placed on a silica-gel bed with a depth of 10 cm in a hot extractor and then extracted with THF. When the extraction is complete, the extraction medium is concentrated to about 15 ml in vacuo, 75 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Co-ligand | Pt complex | Yield |
|---|---|---|---|---|
| Pt(L40)(CL1) | L40 | CL1 | Pt(L40)(CL1) | 32% |
| Pt(L66)(CL2) | L66 | CL2 | Pt(L66)(CL2) | 22% |
| Pt(L107)(CL1) | L107 | CL1 | Pt(L107)(CL1) | 13% |
| Pt(L107)(L196) | L107 | L196 | Pt(L107)(L196) | 17% |
| Pt(L107)(L199) | L107 | L199 | Pt(L107)(L199) | 28% |

6) Heteroleptic Gold Complexes:

A mixture of 5 mmol of dichloro[2-(2-pyridinyl)phenyl-C, N]gold, 6 mmol of the ligand and 10 mmol of triethylamine in 50 ml of THF is stirred at 50° C. for 20 h. After the reaction mixture has been concentrated to 10 ml and 50 ml of methanol have been added dropwise, the fine solid is filtered off with suction, washed twice with 10 ml of methanol and dried in vacuo. The dry solid is placed on a Celite bed with a depth of 10 cm in a hot extractor and then extracted with THF. When the extraction is complete, the extraction medium is concentrated to about 15 ml in vacuo, 75 ml of methanol are added to the suspension, and the mixture is stirred for a further 1 h. After the metal complex has been filtered off with suction and dried, its purity is determined by means of NMR and/or HPLC. If the purity is less than 99.9%, the hot extraction step is repeated, when a purity of >99.9% has been reached, the metal complex is conditioned or sublimed. The conditioning is carried out in a high vacuum (p about $10^{-6}$ mbar) in the temperature range from 200-300° C. The sublimation is carried out in a high vacuum (p about $10^{-6}$ mbar) in the temperature range from about 300 to about 420° C.

| Ex. | Ligand | Co-ligand | Au complex | Yield |
|---|---|---|---|---|
| Au(L202)(CL5) | L202 | CL5 | Au(L202)(CL5) | 42% |
| Au(L203)(CL5) | L203 | CL5 | Au(L203)(CL5) | 37% |
| Au(L204)(CL5) | L204 | CL5 | Au(L204)(CL5) | 11% |

7) Heteroleptic Copper Complexes:

A mixture of 5 mmol of tetrakis(acetonitrile)copper(I) tetrafluoroborate [15418-29-8], 5 mmol of the ligand, 5 mmol of the co-ligand and 6 mmol of triethylamine in 50 ml of THF is stirred at room temperature for 20 h. After the reaction mixture has been concentrated to 5 ml and 50 ml of methanol have been added dropwise, the fine solid is filtered off with suction, washed twice with 10 ml of methanol and dried in vacuo. The crude product is recrystallised twice from dichloromethane/methanol. The conditioning is carried out in a high vacuum (p about $10^{-6}$ mbar) at a temperature in the region of 200° C.

| Ex. | Ligand | Co-ligand | Cu complex | Yield |
|---|---|---|---|---|
| Cu(L194)(CL11) | L194 | 366-18-7 CL11 | Cu(L194)(CL11) | 63% |

| Ex. | Ligand | Co-ligand | Cu complex | Yield |
|---|---|---|---|---|
| Cu(L196)(CL11) | L196 | CL11 | Cu(L196)(CL11) | 48% |
| Cu(L195)(CL12) | | 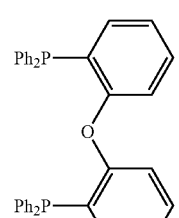 166330-10-5 CL12 | 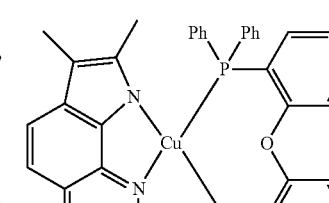 Cu(L195)(CL12) | 71% |

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in the following Examples 1 to 250 (see Tables 1 and 2). Glass plates coated with structured ITO (indium tin oxide) in a thickness of 150 nm are coated with 20 nm of PEDOT (poly(3,4-ethylenedioxy-2,5-thiophene), spin-coated from water, purchased from H.C. Starck, Goslar, Germany) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or materials in a certain volume proportion by co-evaporaSon. Information such as M3:M2:Ir(L1)$_3$ (55%:35%:10%) here means that the material M3 is present in the layer in a proportion by volume of 55%, M2 in a proportion of 35% and Ir(L1)$_3$ in a proportion of 10%. Analogously, the electron-transport layer may also consist of a mixture of two materials. The precise structure of the OLEDs is shown in Table 1. The materials used to produce the OLEDs are shown in Table 3.

The OLEDs are characterised by standard methods. For this purpose, the electroluminescence spectra, the current efficiency (measured in cd/A) and the voltage (measured in V at 1000 cd/m$^2$) are determined from current-voltage-luminance characteristic lines (IUL characteristic lines). For selected experiments, the lifetime is likewise determined. The lifetime is defined as the time after which the luminous density has dropped to a certain proportion from a certain initial luminous density. The term LD50 means that the lifetime indicated is the time at which the luminous density has dropped to 50% of the initial luminous density, i.e. from, for example, 4000 cd/m$^2$ to 2000 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is the usual figure here.

Use of Compounds According to the Invention as Emitter Materials And Hole-Transport Materials in Phosphorescent OLEDs The compounds according to the invention can be employed, inter alia, as phosphorescent emitter materials in the emission layer in OLEDs. The metal complexes containing the central atoms Ir, Pt, Au and Cu are used here. The compound Ir(ref)$_3$ is used as comparison in accordance with the prior art. It is furthermore shown that the compounds according to the invention can also be employed as hole-transporting materials. The results for the OLEDs are shown in Table 2.

TABLE 1

| | | | | Structure of the OLEDs | | | |
|---|---|---|---|---|---|---|---|
| Ex. | HTL1 thickness | HTL2 thickness | EBL thickness | EML thickness | HBL thickness | ETL thickness | EIL thickness |
| 1 | HTM1 20 nm | EBM1 5 m | EBM3 15 nm | M1:EBM3:Ir(L1)$_3$ (80%:10%:10%) 40 nm | M1 10 m | ETM1:LiQ (50%:50%) 20 nm | — |
| 2 | HTM1 20 nm | EBM1 5 m | EBM3 15 nm | M3:Ir(L1)$_3$ (90%:10%) 40 nm | — | ETM1:LiQ (50%:50%) 20 nm | — |
| 3 | HTM1 20 nm | EBM1 5 m | EBM3 15 nm | M4:EBM3:Ir(L1)$_3$ (68%:30%:2%) 40 m | M4 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 4 | HTM1 20 nm | EBM1 5 m | EBM3 15 nm | M4:EBM3:Ir(L1)$_3$ (28%:70%:2%) 40 m | M4 10 nm | ETM1:LiQ (50%:50%) 20 nm | — |
| 5 | HTM1 20 nm | EBM1 5 m | EBM3 15 nm | M2:Ir(L1)$_3$ (85%15%) 40 nm | M3 10 nm | ETM1:LiQ (50%:50%) 20 nm | — |
| 6 | HTM1 20 nm | EBM1 5 m | EBM2 15 nm | M5:Ir(L1)$_3$ (80%10%) 40 nm | M3 10 nm | Alq$_3$ | LiF |
| 7 | HTM1 20 nm | EBM1 5 m | EBM3 15 nm | M3:EBM3:Ir(L1)$_3$ (80%:10%:10%) 40 nm | M3 10 nm | ETM1:LiQ (50%:50%) 20 nm | — |
| 8 | HTM1 20 nm | EBM1 5 m | EBM3 15 nm | M3:EBM3:Ir(L2)$_3$ (80%:10%:10%) 40 nm | M3 10 nm | ETM1:LiQ (50%:50%) 20 nm | — |
| 9 | HTM1 20 nm | EBM1 5 m | EBM3 15 nm | M3:EBM3:Ir(L3)$_3$ (80%:10%:10%) 40 nm | M3 10 nm | ETM1:LiQ (50%:50%) 20 nm | — |
| 10 | HTM1 20 nm | EBM1 5 m | EBM3 15 nm | M3:EBM3:Ir(L4)$_3$ (80%:10%:10%) 40 nm | M3 10 nm | ETM1:LiQ (50%:50%) 20 nm | — |
| 11 | HTM1 20 nm | EBM1 5 m | EBM3 15 nm | M3:EBM3:Ir(L5)$_3$ (80%:10%:10%) 40 nm | M3 10 nm | ETM1:LiQ (50%:50%) 20 nm | — |
| 12 | HTM1 20 nm | EBM1 5 m | EBM3 15 nm | M3:EBM3:Ir(L6)$_3$ (80%:10%:10%) 40 nm | M3 10 nm | ETM1:LiQ (50%:50%) 20 nm | — |
| 13 | HTM1 20 nm | EBM1 5 m | EBM3 15 nm | M3:EBM3:Ir(L7)$_3$ (80%:10%:10%) 40 nm | M3 10 nm | ETM1:LiQ (50%:50%) 20 nm | — |
| 14 | HTM1 20 nm | EBM1 5 m | EBM3 15 nm | M3:EBM3:Ir(L8)$_3$ (80%:10%:10%) 40 nm | M3 10 nm | ETM1:LiQ (50%:60%) 20 nm | — |
| 15 | HTM1 20 nm | EBM1 5 m | EBM3 15 nm | M3:EBM3:Ir(L9)$_3$ (80%:10%:10%) 40 nm | M3 10 nm | ETM1:LiQ (50%:50%) 20 nm | — |
| 16 | HTM1 20 nm | EBM1 5 m | EBM3 15 nm | M3:EBM3:Ir(L10)$_3$ (80%:10%:10%) 40 nm | M3 10 nm | ETM1:LiQ (50%:50%) 20 nm | — |
| 17 | HTM1 20 nm | EBM1 5 m | EBM3 15 nm | M3:EBM3:Ir(L11)$_3$ (80%:10%:10%) 40 nm | M3 10 nm | ETM1:LiQ (50%:50%) 20 nm | — |
| 18 | HTM1 20 nm | EBM1 5 m | EBM3 15 nm | M3:EBM3:Ir(L12)$_3$ (80%:10%:10%) 40 nm | M3 10 nm | ETM1:LiQ (50%:50%) 20 nm | — |
| 19 | HTM1 20 nm | EBM1 5 m | EBM3 15 nm | M3:EBM3:Ir(L13)$_3$ (80%:10%:10%) 40 nm | M3 10 nm | ETM1:LiQ (50%:50%) 20 nm | — |
| 20 | HTM1 20 nm | EBM1 5 m | EBM3 15 nm | M3:EBM3:Ir(L14)$_3$ (80%:10%:10%) 40 nm | M3 10 nm | ETM1:LiQ (50%:50%) 20 nm | — |
| 21 | HTM1 20 nm | EBM1 5 m | EBM3 15 nm | M3:EBM3:Ir(L15)$_3$ (80%:10%:10%) 40 nm | M3 10 nm | ETM1:LiQ (50%:50%) 20 nm | — |
| 22 | HTM1 20 nm | EBM1 5 m | EBM3 15 nm | M3:EBM3:Ir(L16)$_3$ (80%:10%:10%) 40 nm | M3 10 nm | ETM1:LiQ (50%:50%) 20 nm | — |
| 23 | HTM1 20 nm | EBM1 5 m | EBM3 15 nm | M3:EBM3:Ir(L17)$_3$ (80%:10%:10%) 40 nm | M3 10 nm | ETM1:LiQ (50%:50%) 20 nm | — |
| 24 | HTM1 20 nm | EBM1 5 m | EBM3 15 nm | M3:EBM3:Ir(L18)$_3$ (80%:10%:10%) 40 nm | M3 10 nm | ETM1:LiQ (50%:50%) 20 nm | — |
| 25 | HTM1 20 nm | EBM1 5 m | EBM3 15 nm | M3:EBM3:Ir(L19)$_3$ (80%:10%:10%) 40 nm | M3 10 nm | ETM1:LiQ (50%:50%) 20 nm | — |
| 26 | HTM1 20 nm | EBM1 5 m | EBM3 15 nm | M3:EBM3:Ir(L20)$_3$ (80%:10%:10%) 40 nm | M3 10 nm | ETM1:LiQ (50%:50%) 20 nm | — |
| 27 | HTM1 20 nm | EBM1 5 m | EBM3 15 nm | M3:EBM3:Ir(L21)$_3$ (80%:10%:10%) 40 nm | M3 10 nm | ETM1:LiQ (50%:50%) 20 nm | — |
| 28 | HTM1 20 nm | EBM1 5 m | EBM3 15 nm | M3:EBM3:Ir(L22)$_3$ (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 29 | HTM1 20 nm | EBM1 5 m | EBM3 15 nm | M3:EBM3:Ir(L23)$_3$ (80%:10%:10%) 40 nm | M3 10 nm | ETM1:LiQ (50%:50%) 20 nm | — |
| 30 | HTM1 20 nm | EBM1 5 m | EBM3 15 nm | M3:EBM3:Ir(L24)$_3$ (80%:10%:10%) 40 nm | M3 10 nm | ETM1:LiQ (50%:50%) 20 nm | — |
| 31 | HTM1 20 nm | EBM1 5 m | EBM3 15 nm | M3:EBM3:Ir(L25)$_3$ (80%:10%:10%) 40 nm | M3 10 nm | ETM1:LiQ (50%:50%) 20 nm | — |
| 32 | HTM1 20 nm | EBM1 5 m | EBM3 15 nm | M3:EBM3:Ir(L26)$_3$ (80%:10%:10%) 40 nm | M3 10 nm | ETM1:LiQ (50%:50%) 20 nm | — |
| 33 | HTM1 20 nm | EBM1 5 m | EBM3 15 nm | M3:EBM3:Ir(L27)$_3$ (80%:10%:10%) 40 nm | M3 10 nm | ETM1:LiQ (50%:50%) 20 nm | — |
| 34 | HTM1 20 nm | EBM1 5 m | EBM3 15 nm | M3:EBM3:Ir(L28)$_3$ (80%:10%:10%) 40 nm | M3 10 nm | ETM1:LiQ (50%:50%) 20 nm | — |
| 35 | HTM1 20 nm | EBM1 5 m | EBM3 15 nm | M3:EBM3:Ir(L29)$_3$ (80%:10%:10%) 40 nm | M3 10 nm | ETM1:LiQ (50%:50%) 20 nm | — |
| 36 | HTM1 20 nm | EBM1 5 m | EBM3 15 nm | M3:EBM3:Ir(L30)$_3$ (80%:10%:10%) 40 nm | M3 10 nm | ETM1:LiQ (50%:50%) 20 nm | — |
| 37 | HTM1 20 nm | EBM1 5 m | EBM3 15 nm | M3:EBM3:Ir(L31)$_3$ (80%:10%:10%) 40 nm | M3 10 nm | ETM1:LiQ (50%:50%) 20 nm | — |
| 38 | HTM1 20 nm | EBM1 5 m | EBM3 15 nm | M3:EBM3:Ir(L32)$_3$ (80%:10%:10%) 40 nm | M3 10 nm | ETM1:LiQ (50%:50%) 20 nm | — |
| 39 | HTM1 20 nm | EBM1 5 m | EBM3 15 nm | M3:EBM3:Ir(L33)$_3$ (80%:10%:10%) 40 nm | M3 10 nm | ETM1:LiQ (50%:50%) 20 nm | — |
| 40 | HTM1 20 nm | EBM1 5 m | EBM3 15 nm | M3:EBM3:Ir(L34)$_3$ (80%:10%:10%) 40 nm | M3 10 nm | ETM1:LiQ (50%:50%) 20 nm | — |
| 41 | HTM1 20 nm | EBM1 5 m | EBM3 15 nm | M3:EBM3:Ir(L35)$_3$ (80%:10%:10%) 40 nm | M3 10 nm | ETM1:LiQ (50%:50%) 20 nm | — |
| 42 | HTM1 20 nm | EBM1 5 m | EBM3 15 nm | M3:EBM3:Ir(L36)$_3$ (80%:10%:10%) 40 nm | M3 10 nm | ETM1:LiQ (50%:50%) 20 nm | — |
| 43 | HTM1 20 nm | EBM1 5 m | EBM3 15 nm | M3:EBM3:Ir(L37)$_3$ (80%:10%:10%) 40 nm | M3 10 nm | ETM1:LiQ (50%:50%) 20 nm | — |
| 44 | HTM1 20 nm | EBM1 5 m | EBM3 15 nm | M3:EBM3:Ir(L38)$_3$ (80%:10%:10%) 40 nm | M3 10 nm | ETM1:LiQ (50%:50%) 20 nm | — |
| 45 | HTM1 20 nm | EBM1 5 m | EBM3 15 nm | M3:EBM3:Ir(L39)$_3$ (80%:10%:10%) 40 nm | M3 10 nm | ETM1:LiQ (50%:50%) 20 nm | — |
| 46 | HTM1 20 nm | EBM1 5 m | EBM3 15 nm | M3:EBM3:Ir(L40)$_3$ (80%:10%:10%) 40 nm | M3 10 nm | ETM1:LiQ (50%:50%) 20 nm | — |
| 47 | HTM1 20 nm | EBM1 5 m | EBM3 15 nm | M3:EBM3:Ir(L41)$_3$ (80%:10%:10%) 40 nm | M3 10 nm | ETM1:LiQ (50%:50%) 20 nm | — |
| 48 | HTM1 20 nm | EBM1 5 m | EBM3 15 nm | M3:EBM3:Ir(L42)$_3$ (80%:10%:10%) 40 nm | M3 10 nm | ETM1:LiQ (50%:50%) 20 nm | — |
| 49 | HTM1 20 nm | EBM1 5 m | EBM3 15 nm | M3:EBM3:Ir(L43)$_3$ (80%:10%:10%) 40 nm | M3 10 nm | ETM1:LiQ (50%:50%) 20 nm | — |
| 50 | HTM1 20 nm | EBM1 5 m | EBM3 15 nm | M3:EBM3:Ir(L44)$_3$ (80%:10%:10%) 40 nm | M3 10 nm | ETM1:LiQ (50%:50%) 20 nm | — |
| 51 | HTM1 20 nm | EBM1 5 m | EBM3 15 nm | M3:EBM3:Ir(L45)$_3$ (80%:10%:10%) 40 nm | M3 10 nm | ETM1:LiQ (50%:50%) 20 nm | — |
| 52 | HTM1 20 nm | EBM1 5 m | EBM3 15 nm | M3:EBM3:Ir(L46)$_3$ (80%:10%:10%) 40 nm | M3 10 nm | ETM1:LiQ (50%:50%) 20 nm | — |
| 53 | HTM1 20 nm | EBM1 5 m | EBM3 15 nm | M3:EBM3:Ir(L47)$_3$ (80%:10%:10%) 40 nm | M3 10 nm | ETM1:LiQ (50%:50%) 20 nm | — |

TABLE 1-continued

| | | | Structure of the OLEDs | | | |
|---|---|---|---|---|---|---|
| Ex. | HTL1 thickness | HTL2 thickness | EBL thickness | EML thickness | HBL thickness | ETL thickness | EIL thickness |
| 54 | HTM1 20 nm | EBM1 5 m | EBM3 15 nm | M3:EBM3:Ir(L48)₃ (80%:10%:10%) 40 nm | M3 10 nm | ETM1:LiQ (50%:50%) 20 nm | — |
| 55 | HTM1 20 nm | EBM1 5 m | EBM3 15 nm | M3:EBM3:Ir(L49)₃ (80%:10%:10%) 40 nm | M3 10 nm | ETM1:LiQ (50%:50%) 20 nm | — |
| 56 | HTM1 20 nm | EBM1 5 m | EBM3 15 nm | M3:EBM3:Ir(L50)₃ (80%:10%:10%) 40 nm | M3 10 nm | ETM1:LiQ (50%:50%) 20 nm | — |
| 57 | HTM1 20 nm | EBM1 5 m | EBM3 15 nm | M3:EBM3:Ir(L51)₃ (80%:10%:10%) 40 nm | M3 10 nm | ETM1:LiQ (50%:50%) 20 nm | — |
| 58 | HTM1 20 nm | EBM1 5 m | EBM3 15 nm | M3:EBM3:Ir(L52)₃ (80%:10%:10%) 40 nm | M3 10 nm | ETM1:LiQ (50%:50%) 20 nm | — |
| 59 | HTM1 20 nm | EBM1 5 m | EBM3 15 nm | M3:EBM3:Ir(L53)₃ (80%:10%:10%) 40 nm | M3 10 nm | ETM1:LiQ (50%:50%) 20 nm | — |
| 60 | HTM1 20 nm | EBM1 5 m | EBM3 15 nm | M3:EBM3:Ir(L54)₃ (80%:10%:10%) 40 nm | M3 10 nm | ETM1:LiQ (50%:50%) 20 nm | — |
| 61 | HTM1 20 nm | EBM1 5 m | EBM3 15 nm | M3:EBM3:Ir(L56)₃ (80%:10%:10%) 40 nm | M3 10 nm | ETM1:LiQ (50%:50%) 20 nm | — |
| 62 | HTM1 20 nm | EBM1 5 m | EBM3 15 nm | M3:EBM3:Ir(L58)₃ (80%:10%:10%) 40 nm | M3 10 nm | ETM1:LiQ (50%:50%) 20 nm | — |
| 63 | HTM1 20 nm | EBM1 5 m | EBM3 15 nm | M3:EBM3:Ir(L59)₃ (80%:10%:10%) 40 nm | M3 10 nm | ETM1:LiQ (50%:50%) 20 nm | — |
| 64 | HTM1 20 nm | EBM1 5 m | EBM3 15 nm | M3:EBM3:Ir(L60)₃ (80%:10%:10%) 40 nm | M3 10 nm | ETM1:LiQ (50%:50%) 20 nm | — |
| 65 | HTM1 20 nm | EBM1 5 m | EBM3 15 nm | M3:EBM3:Ir(L61)₃ (80%:10%:10%) 40 nm | M3 10 nm | ETM1:LiQ (50%:50%) 20 nm | — |
| 66 | HTM1 20 nm | EBM1 5 m | EBM3 15 nm | M3:EBM3:Ir(L62)₃ (80%:10%:10%) 40 nm | M3 10 nm | ETM1:LiQ (50%:50%) 20 nm | — |
| 67 | HTM1 20 nm | EBM1 5 m | EBM3 15 nm | M3:EBM3:Ir(L63)₃ (80%:10%:10%) 40 nm | M3 10 nm | ETM1:LiQ (50%:50%) 20 nm | — |
| 68 | HTM1 20 nm | EBM1 5 m | EBM3 15 nm | M3:EBM3:Ir(L64)₃ (80%:10%:10%) 40 nm | M3 10 nm | ETM1:LiQ (50%:50%) 20 nm | — |
| 69 | HTM1 20 nm | EBM1 5 m | EBM3 15 nm | M3:EBM3:Ir(L65)₃ (80%:10%:10%) 40 nm | M3 10 nm | ETM1:LiQ (50%:50%) 20 nm | — |
| 70 | HTM1 20 nm | EBM1 5 m | EBM3 15 nm | M3:EBM3:Ir(L66)₃ (80%:10%:10%) 40 nm | M3 10 nm | ETM1:LiQ (50%:50%) 20 nm | — |
| 71 | HTM1 20 nm | EBM1 5 m | EBM3 15 nm | M3:EBM3:Ir(L69)₃ (80%:10%:10%) 40 nm | M3 10 nm | ETM1:LiQ (50%:50%) 20 nm | — |
| 72 | HTM1 20 nm | EBM1 5 m | EBM3 15 nm | M3:EBM3:Ir(L70)₃ (80%:10%:10%) 40 nm | M3 10 nm | ETM1:LiQ (50%:50%) 20 nm | — |
| 73 | HTM1 20 nm | EBM1 5 m | EBM3 15 nm | M3:EBM3:Ir(L71)₃ (80%:10%:10%) 40 nm | M3 10 nm | ETM1:LiQ (50%:50%) 20 nm | — |
| 74 | HTM1 20 nm | EBM1 5 m | EBM3 15 nm | M3:EBM3:Ir(L72)₃ (80%:10%:10%) 40 nm | M3 10 nm | ETM1:LiQ (50%:50%) 20 nm | — |
| 75 | HTM1 20 nm | EBM1 5 m | EBM3 15 nm | M3:EBM3:Ir(L73)₃ (80%:10%:10%) 40 nm | M3 10 nm | ETM1:LiQ (50%:50%) 20 nm | — |
| 76 | HTM1 20 nm | EBM1 5 m | EBM3 15 nm | M3:EBM3:Ir(L74)₃ (80%:10%:10%) 40 nm | M3 10 nm | ETM1:LiQ (50%:50%) 20 nm | — |
| 77 | HTM1 20 nm | EBM1 5 m | EBM3 15 nm | M3:EBM3:Ir(L75)₃ (80%:10%:10%) 40 nm | M3 10 nm | ETM1:LiQ (50%:50%) 20 nm | — |
| 78 | HTM1 20 nm | EBM1 5 m | EBM3 15 nm | M3:EBM3:Ir(L78)₃ (80%:10%:10%) 40 nm | M3 10 nm | ETM1:LiQ (50%:50%) 20 nm | — |

TABLE 1-continued

| | | | | Structure of the OLEDs | | | |
|---|---|---|---|---|---|---|---|
| Ex. | HTL1 thickness | HTL2 thickness | EBL thickness | EML thickness | HBL thickness | ETL thickness | EIL thickness |
| 79 | HTM1 20 nm | EBM1 5 m | EBM3 15 nm | M3:EBM3:Ir(L79)₃ (80%:10%:10%) 40 nm | M3 10 nm | ETM1:LiQ (50%:50%) 20 nm | — |
| 80 | HTM1 20 nm | EBM1 5 m | EBM3 15 nm | M3:EBM3:Ir(L80)₃ (80%:10%:10%) 40 nm | M3 10 nm | ETM1:LiQ (50%:50%) 20 nm | — |
| 81 | HTM1 20 nm | EBM1 5 m | EBM3 15 nm | M3:EBM3:Ir(L82)₃ (80%:10%:10%) 40 nm | M3 10 nm | ETM1:LiQ (50%:50%) 20 nm | — |
| 82 | HTM1 20 nm | EBM1 5 m | EBM3 15 nm | M3:EBM3:Ir(L83)3 (80%:10%:10%) 40 nm | M3 10 nm | ETM1:LiQ (50%:50%) 20 nm | — |
| 83 | HTM1 20 nm | EBM1 5 m | EBM3 15 nm | M3:Ir(L83)₃ (90%:10%) 40 nm | M3 10 nm | Alq₃ 20 nm | LiF |
| 84 | HTM1 20 nm | EBM1 5 m | EBM2 15 nm | M4:Ir(L83)₃ (90%:10%) 40 nm | M3 10 nm | Alq₃ 20 nm | LiF |
| 85 | HTM1 20 nm | EBM1 20 m | — | M4:Ir(L83)₃ (90%:10%) 40 nm | M6 10 nm | Alq₃ 20 nm | LiF |
| 86 | HTM1 20 nm | EBM1 20 m | — | EBM3:Ir(L83)₃ (90%:10%) 40 nm | M6 10 nm | Alq₃ 20 nm | LiF |
| 87 | HTM1 20 nm | EBM1 5 m | EBM2 15 nm | EBM2:M3:Ir(L83)₃ (60%:30%:10%) 40 nm | M3 10 nm | Alq₃ 20 nm | LiF |
| 88 | HTM1 20 nm | EBM1 5 m | EBM3 15 nm | M6:Ir(L83)₃ (90%:10%) 40 nm | M3 10 nm | Alq₃ 20 nm | LiF |
| 89 | HTM1 20 nm | EBM1 5 m | EBM2 15 nm | M6:EBM3:Ir(L83)₃ (80%:10%:10%) 40 nm | M3 10 nm | Alq₃ 20 nm | LiF |
| 90 | HTM1 20 nm | EBM1 5 m | EBM3 15 nm | M7:Ir(L83)₃ (95%:5%) 40 nm | M3 10 nm | Alq₃ 20 nm | LiF |
| 91 | HTM1 20 nm | EBM1 5 m | EBM3 15 nm | M3:EBM3:Ir(L84)₃ (80%:10%:10%) 40 nm | M3 10 nm | ETM1:LiQ (50%:50%) 20 nm | — |
| 92 | HTM1 20 nm | EBM1 5 m | EBM3 15 nm | M3:EBM3:Ir(L85)₃ (80%:10%:10%) 40 nm | M3 10 nm | ETM1:LiQ (50%:50%) 20 nm | — |
| 93 | HTM1 20 nm | EBM1 5 m | EBM3 15 nm | M3:EBM3:Ir(L86)₃ (80%:10%:10%) 40 nm | M3 10 nm | ETM1:LiQ (50%:50%) 20 nm | — |
| 94 | HTM1 20 nm | EBM1 5 m | EBM3 15 nm | M3:EBM3:Ir(L87)₃ (80%:10%:10%) 40 nm | M3 10 nm | ETM1:LiQ (50%:50%) 20 nm | — |
| 95 | HTM1 20 nm | EBM1 5 m | EBM3 15 nm | M3:EBM3:Ir(L88)₃ (80%:10%:10%) 40 nm | M3 10 nm | ETM1:LiQ (50%:50%) 20 nm | — |
| 96 | HTM1 20 nm | EBM1 5 m | EBM3 15 nm | M3:EBM3:Ir(L89)₃ (80%:10%:10%) 40 nm | M3 10 nm | ETM1:LiQ (50%:50%) 20 nm | — |
| 97 | HTM1 20 nm | EBM1 5 m | EBM3 15 nm | M3:EBM3:Ir(L90)₃ (80%:10%:10%) 40 nm | M3 10 nm | ETM1:LiQ (50%:50%) 20 nm | — |
| 98 | HTM1 20 nm | EBM1 5 m | EBM3 15 nm | M3:EBM3:Ir(L91)₃ (80%:10%:10%) 40 nm | M3 10 nm | ETM1:LiQ (50%:50%) 20 nm | — |
| 99 | HTM1 20 nm | EBM1 5 m | EBM3 15 nm | M3:EBM3:Ir(L92)₃ (80%:10%:10%) 40 nm | M3 10 nm | ETM1:LiQ (50%:50%) 20 nm | — |
| 100 | HTM1 20 nm | EBM1 5 m | EBM3 15 nm | M3:EBM3:Ir(L93)₃ (80%:10%:10%) 40 nm | M3 10 nm | ETM1:LiQ (50%:50%) 20 nm | — |
| 101 | HTM1 20 nm | EBM1 5 m | EBM3 15 nm | M3:EBM3:Ir(L94)₃ (80%:10%:10%) 40 nm | M3 10 nm | ETM1:LiQ (50%:50%) 20 nm | — |
| 102 | HTM1 20 nm | EBM1 5 m | EBM3 15 nm | M3:EBM3:Ir(L95)₃ (80%:10%:10%) 40 nm | M3 10 nm | ETM1:LiQ (50%:50%) 20 nm | — |
| 103 | HTM1 20 nm | EBM1 5 m | EBM3 15 nm | M3:EBM3:Ir(L96)₃ (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 104 | HTM1 20 nm | EBM1 5 m | EBM3 15 nm | M3:EBM3:Ir(L97)$_3$ (80%:10%:10%) 40 nm | M3 10 nm | ETM1:LiQ (50%:50%) 20 nm | — |
| 105 | HTM1 20 nm | EBM1 5 m | EBM3 15 nm | M3:EBM3:Ir(L98)$_3$ (80%:10%:10%) 40 nm | M3 10 nm | ETM1:LiQ (50%:50%) 20 nm | — |
| 106 | HTM1 20 nm | EBM1 5 m | EBM3 15 nm | M3:EBM3:Ir(L99)$_3$ (80%:10%:10%) 40 nm | M3 10 nm | ETM1:LiQ (50%:50%) 20 nm | — |
| 107 | HTM1 20 nm | EBM1 5 m | EBM3 15 nm | M3:EBM3:Ir(L100)$_3$ (80%:10%:10%) 40 nm | M3 10 nm | ETM1:LiQ (50%:50%) 20 nm | — |
| 108 | HTM1 20 nm | EBM1 5 m | EBM3 15 nm | M3:EBM3:Ir(L101)$_3$ (80%:10%:10%) 40 nm | M3 10 nm | ETM1:LiQ (50%:50%) 20 nm | — |
| 109 | HTM1 20 nm | EBM1 5 m | EBM3 15 nm | M3:EBM3:Ir(L102)$_3$ (80%:10%:10%) 40 nm | M3 10 nm | ETM1:LiQ (50%:50%) 20 nm | — |
| 110 | HTM1 20 nm | EBM1 5 m | EBM3 15 nm | M3:EBM3:Ir(L103)$_3$ (80%:10%:10%) 40 nm | M3 10 nm | ETM1:LiQ (50%:50%) 20 nm | — |
| 111 | HTM1 20 nm | EBM1 5 m | EBM3 15 nm | M3:EBM3:Ir(L104)$_3$ (80%:10%:10%) 40 nm | M3 10 nm | ETM1:LiQ (50%:50%) 20 nm | — |
| 112 | HTM1 20 nm | EBM1 5 m | EBM3 15 nm | M3:EBM3:Ir(L105)$_3$ (80%:10%:10%) 40 nm | M3 10 nm | ETM1:LiQ (50%:50%) 20 nm | — |
| 113 | HTM1 20 nm | EBM1 5 m | EBM3 15 nm | M3:EBM3:Ir(L106)$_3$ (80%:10%:10%) 40 nm | M3 10 nm | ETM1:LiQ (50%:50%) 20 nm | — |
| 114 | HTM1 20 nm | EBM1 5 m | EBM3 15 nm | M3:EBM3:Ir(L107)$_3$ (80%:10%:10%) 40 nm | M3 10 nm | ETM1:LiQ (50%:50%) 20 nm | — |
| 115 | HTM1 20 nm | EBM1 5 m | EBM3 15 nm | M3:EBM3:Ir(L112)$_3$ (80%:10%:10%) 40 nm | M3 10 nm | ETM1:LiQ (50%:50%) 20 nm | — |
| 116 | HTM1 20 nm | EBM1 5 m | EBM3 15 nm | M3:EBM3:Ir(L113)$_3$ (80%:10%:10%) 40 nm | M3 10 nm | ETM1:LiQ (50%:50%) 20 nm | — |
| 117 | HTM1 20 nm | EBM1 5 m | EBM3 15 nm | M3:EBM3:Ir(L114)$_3$ (80%:10%:10%) 40 nm | M3 10 nm | ETM1:LiQ (50%:50%) 20 nm | — |
| 118 | HTM1 20 nm | EBM1 5 m | EBM3 15 nm | M3:EBM3:Ir(L115)$_3$ (80%:10%:10%) 40 nm | M3 10 nm | ETM1:LiQ (50%:50%) 20 nm | — |
| 119 | HTM1 20 nm | EBM1 5 m | EBM3 15 nm | M3:EBM3:Ir(L118)$_3$ (80%:10%:10%) 40 nm | M3 10 nm | ETM1:LiQ (50%:50%) 20 nm | — |
| 120 | HTM1 20 nm | EBM1 5 m | EBM3 15 nm | M3:EBM3:Ir(L119)$_3$ (80%:10%:10%) 40 nm | M3 10 nm | ETM1:LiQ (50%:50%) 20 nm | — |
| 121 | HTM1 20 nm | EBM1 5 m | EBM3 15 nm | M3:EBM3:Ir(L120)$_3$ (80%:10%:10%) 40 nm | M3 10 nm | ETM1:LiQ (50%:50%) 20 nm | — |
| 122 | HTM1 20 nm | EBM1 5 m | EBM3 15 nm | M3:EBM3:Ir(L122)$_3$ (80%:10%:10%) 40 nm | M3 10 nm | ETM1:LiQ (50%:50%) 20 nm | — |
| 123 | HTM1 20 nm | EBM1 5 m | EBM3 15 nm | M3:EBM3:Ir(L125)$_3$ (80%:10%:10%) 40 nm | M3 10 nm | ETM1:LiQ (50%:50%) 20 nm | — |
| 124 | HTM1 20 nm | EBM1 5 m | EBM3 15 nm | M3:EBM3:Ir(L126)$_3$ (80%:10%:10%) 40 nm | M3 10 nm | ETM1:LiQ (50%:50%) 20 nm | — |
| 125 | HTM1 20 nm | EBM1 5 m | EBM3 15 nm | M3:EBM3:Ir(L127)$_3$ (80%:10%:10%) 40 nm | M3 10 nm | ETM1:LiQ (50%:50%) 20 nm | — |
| 126 | HTM1 20 nm | EBM1 5 m | EBM3 15 nm | M3:EBM3:Ir(L128)$_3$ (80%:10%:10%) 40 nm | M3 10 nm | ETM1:LiQ (50%:50%) 20 nm | — |
| 127 | HTM1 20 nm | EBM1 5 m | EBM3 15 nm | M3:EBM3:Ir(L129)$_3$ (80%:10%:10%) 40 nm | M3 10 nm | ETM1:LiQ (50%:50%) 20 nm | — |
| 128 | HTM1 20 nm | EBM1 5 m | EBM3 15 nm | M3:EBM3:Ir(L130)$_3$ (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 129 | HTM1 20 nm | EBM1 5 m | EBM3 15 nm | M3:EBM3:Ir(L131)$_3$ (80%:10%:10%) 40 nm | M3 10 nm | ETM1:LiQ (50%:50%) 20 nm | — |
| 130 | HTM1 20 nm | EBM1 5 m | EBM3 15 nm | M3:EBM3:Ir(L132)$_3$ (80%:10%:10%) 40 nm | M3 10 nm | ETM1:LiQ (50%:50%) 20 nm | — |
| 131 | HTM1 20 nm | EBM1 5 m | EBM3 15 nm | M3:EBM3:Ir(L133)$_3$ (80%:10%:10%) 40 nm | M3 10 nm | ETM1:LiQ (50%:50%) 20 nm | — |
| 132 | HTM1 20 nm | EBM1 5 m | EBM3 15 nm | M3:EBM3:Ir(L134)$_3$ (80%:10%:10%) 40 nm | M3 10 nm | ETM1:LiQ (50%:50%) 20 nm | — |
| 133 | HTM1 20 nm | EBM1 5 m | EBM3 15 nm | M3:EBM3:Ir(L135)$_3$ (80%:10%:10%) 40 nm | M3 10 nm | ETM1:LiQ (50%:50%) 20 nm | — |
| 134 | HTM1 20 nm | EBM1 5 m | EBM3 15 nm | M3:EBM3:Ir(L136)$_3$ (80%:10%:10%) 40 nm | M3 10 nm | ETM1:LiQ (50%:50%) 20 nm | — |
| 135 | HTM1 20 nm | EBM1 5 m | EBM3 15 nm | M3:EBM3:Ir(L137)$_3$ (80%:10%:10%) 40 nm | M3 10 nm | ETM1:LiQ (50%:50%) 20 nm | — |
| 136 | HTM1 20 nm | EBM1 5 m | EBM3 15 nm | M3:EBM3:Ir(L138)$_3$ (80%:10%:10%) 40 nm | M3 10 nm | ETM1:LiQ (50%:50%) 20 nm | — |
| 137 | HTM1 20 nm | EBM1 5 m | EBM3 15 nm | M3:EBM3:Ir(L139)$_3$ (80%:10%:10%) 40 nm | M3 10 nm | ETM1:LiQ (50%:50%) 20 nm | — |
| 138 | HTM1 20 nm | EBM1 5 m | EBM3 15 nm | M3:EBM3:Ir(L142)$_3$ (80%:10%:10%) 40 nm | M3 10 nm | ETM1:LiQ (50%:50%) 20 nm | — |
| 139 | HTM1 20 nm | EBM1 5 m | EBM3 15 nm | M3:EBM3:Ir(L144)$_3$ (80%:10%:10%) 40 nm | M3 10 nm | ETM1:LiQ (50%:50%) 20 nm | — |
| 140 | HTM1 20 nm | EBM1 5 m | EBM3 15 nm | M3:EBM3:Ir(L145)$_3$ (80%:10%:10%) 40 nm | M3 10 nm | ETM1:LiQ (50%:50%) 20 nm | — |
| 141 | HTM1 20 nm | EBM1 5 m | EBM3 15 nm | M3:EBM3:Ir(L146)$_3$ (80%:10%:10%) 40 nm | M3 10 nm | ETM1:LiQ (50%:50%) 20 nm | — |
| 142 | HTM1 20 nm | EBM1 5 m | EBM3 15 nm | M3:EBM3:Ir(L147)$_3$ (80%:10%:10%) 40 nm | M3 10 nm | ETM1:LiQ (50%:50%) 20 nm | — |
| 143 | HTM1 20 nm | EBM1 5 m | EBM3 15 nm | M3:EBM3:Ir(L148)$_3$ (80%:10%:10%) 40 nm | M3 10 nm | ETM1:LiQ (50%:50%) 20 nm | — |
| 144 | HTM1 20 nm | EBM1 5 m | EBM3 15 nm | M3:EBM3:Ir(L149)$_3$ (80%:10%:10%) 40 nm | M3 10 nm | ETM1:LiQ (50%:50%) 20 nm | — |
| 145 | HTM1 20 nm | EBM1 5 m | EBM3 15 nm | M3:EBM3:Ir(L150)$_3$ (80%:10%:10%) 40 nm | M3 10 nm | ETM1:LiQ (50%:50%) 20 nm | — |
| 146 | HTM1 20 nm | EBM1 5 m | EBM3 15 nm | M3:EBM3:Ir(L151)$_3$ (80%:10%:10%) 40 nm | M3 10 nm | ETM1:LiQ (50%:50%) 20 nm | — |
| 147 | HTM1 20 nm | EBM1 5 m | EBM3 15 nm | M3:EBM3:Ir(L152)$_3$ (80%:10%:10%) 40 nm | M3 10 nm | ETM1:LiQ (50%:50%) 20 nm | — |
| 148 | HTM1 20 nm | EBM1 5 m | EBM3 15 nm | M3:EBM3:Ir(L153)$_3$ (80%:10%:10%) 40 nm | M3 10 nm | ETM1:LiQ (50%:50%) 20 nm | — |
| 149 | HTM1 20 nm | EBM1 5 m | EBM3 15 nm | M3:EBM3:Ir(L154)$_3$ (80%:10%:10%) 40 nm | M3 10 nm | ETM1:LiQ (50%:50%) 20 nm | — |
| 150 | HTM1 20 nm | EBM1 5 m | EBM3 15 nm | M3:EBM3:Ir(L155)$_3$ (80%:10%:10%) 40 nm | M3 10 nm | ETM1:LiQ (50%:50%) 20 nm | — |
| 151 | HTM1 20 nm | EBM1 5 m | EBM3 15 nm | M3:EBM3:Ir(L156)$_3$ (80%:10%:10%) 40 nm | M3 10 nm | ETM1:LiQ (50%:50%) 20 nm | — |
| 152 | HTM1 20 nm | EBM1 5 m | EBM3 15 nm | M3:EBM3:Ir(L157)$_3$ (80%:10%:10%) 40 nm | M3 10 nm | ETM1:LiQ (50%:50%) 20 nm | — |
| 153 | HTM1 20 nm | EBM1 5 m | EBM3 15 nm | M3:EBM3:Ir(L158)$_3$ (80%:10%:10%) 40 nm | M3 10 nm | ETM1:LiQ (50%:50%) 20 nm | — |

TABLE 1-continued

| | | | Structure of the OLEDs | | | | |
|---|---|---|---|---|---|---|---|
| Ex. | HTL1 thickness | HTL2 thickness | EBL thickness | EML thickness | HBL thickness | ETL thickness | EIL thickness |
| 154 | HTM1 20 nm | EBM1 5 m | EBM3 15 nm | M3:EBM3:Ir(L159)$_3$ (80%:10%:10%) 40 nm | M3 10 nm | ETM1:LiQ (50%:50%) 20 nm | — |
| 155 | HTM1 20 nm | EBM1 5 m | EBM3 15 nm | M3:EBM3:Ir(L160)$_3$ (80%:10%:10%) 40 nm | M3 10 nm | ETM1:LiQ (50%:50%) 20 nm | — |
| 156 | HTM1 20 nm | EBM1 5 m | EBM3 15 nm | M3:EBM3:Ir(L161)$_3$ (80%:10%:10%) 40 nm | M3 10 nm | ETM1:LiQ (50%:50%) 20 nm | — |
| 157 | HTM1 20 nm | EBM1 5 m | EBM3 15 nm | M3:EBM3:Ir(L162)$_3$ (80%:10%:10%) 40 nm | M3 10 nm | ETM1:LiQ (50%:50%) 20 nm | — |
| 158 | HTM1 20 nm | EBM1 5 m | EBM3 15 nm | M3:EBM3:Ir(L163)$_3$ (80%:10%:10%) 40 nm | M3 10 nm | ETM1:LiQ (50%:50%) 20 nm | — |
| 159 | HTM1 20 nm | EBM1 5 m | EBM3 15 nm | M3:EBM3:Ir(L164)$_3$ (80%:10%:10%) 40 nm | M3 10 nm | ETM1:LiQ (50%:50%) 20 nm | — |
| 160 | HTM1 20 nm | EBM1 5 m | EBM3 15 nm | M3:EBM3:Ir(L165)$_3$ (80%:10%:10%) 40 nm | M3 10 nm | ETM1:LiQ (50%:50%) 20 nm | — |
| 161 | HTM1 20 nm | EBM1 5 m | EBM3 15 nm | M3:EBM3:Ir(L169)$_3$ (80%:10%:10%) 40 nm | M3 10 nm | ETM1:LiQ (50%:50%) 20 nm | — |
| 162 | HTM1 20 nm | EBM1 5 m | EBM3 15 nm | M3:EBM3:Ir(L170)$_3$ (80%:10%:10%) 40 nm | M3 10 nm | ETM1:LiQ (50%:50%) 20 nm | — |
| 163 | HTM1 20 nm | EBM1 5 m | EBM3 15 nm | M3:EBM3:Ir(L171)$_3$ (80%:10%:10%) 40 nm | M3 10 nm | ETM1:LiQ (50%:50%) 20 nm | — |
| 164 | HTM1 20 nm | EBM1 5 m | EBM3 15 nm | M3:EBM3:Ir(L172)$_3$ (80%:10%:10%) 40 nm | M3 10 nm | ETM1:LiQ (50%:50%) 20 nm | — |
| 165 | HTM1 20 nm | EBM1 5 m | EBM3 15 nm | M3:EBM3:Ir(L173)$_3$ (80%:10%:10%) 40 nm | M3 10 nm | ETM1:LiQ (50%:50%) 20 nm | — |
| 166 | HTM1 20 nm | EBM1 5 m | EBM3 15 nm | M3:EBM3:Ir(L174)$_3$ (80%:10%:10%) 40 nm | M3 10 nm | ETM1:LiQ (50%:50%) 20 nm | — |
| 167 | HTM1 20 nm | EBM1 5 m | EBM3 15 nm | M3:EBM3:Ir(L175)$_3$ (80%:10%:10%) 40 nm | M3 10 nm | ETM1:LiQ (50%:50%) 20 nm | — |
| 168 | HTM1 20 nm | EBM1 5 m | EBM3 15 nm | M3:EBM3:Ir(L176)$_3$ (80%:10%:10%) 40 nm | M3 10 nm | ETM1:LiQ (50%:50%) 20 nm | — |
| 169 | HTM1 20 nm | EBM1 5 m | EBM3 15 nm | M3:EBM3:Ir(L177)$_3$ (80%:10%:10%) 40 nm | M3 10 nm | ETM1:LiQ (50%:50%) 20 nm | — |
| 170 | HTM1 20 nm | EBM1 5 m | EBM3 15 nm | M3:EBM3:Ir(L178)$_3$ (80%:10%:10%) 40 nm | M3 10 nm | ETM1:LiQ (50%:50%) 20 nm | — |
| 171 | HTM1 20 nm | EBM1 5 m | EBM3 15 nm | M3:EBM3:Ir(L179)$_3$ (80%:10%:10%) 40 nm | M3 10 nm | ETM1:LiQ (50%:50%) 20 nm | — |
| 172 | HTM1 20 nm | EBM1 5 m | EBM3 15 nm | M3:EBM3:Ir(L180)$_3$ (80%:10%:10%) 40 nm | M3 10 nm | ETM1:LiQ (50%:50%) 20 nm | — |
| 173 | HTM1 20 nm | EBM1 5 m | EBM3 15 nm | M3:EBM3:Ir(L181)$_3$ (80%:10%:10%) 40 nm | M3 10 nm | ETM1:LiQ (50%:50%) 20 nm | — |
| 174 | HTM1 20 nm | EBM1 5 m | EBM3 15 nm | M3:EBM3:Ir(L182)$_3$ (80%:10%:10%) 40 nm | M3 10 nm | ETM1:LiQ (50%:50%) 20 nm | — |
| 175 | HTM1 20 nm | EBM1 5 m | EBM3 15 nm | M3:EBM3:Ir(L183)$_3$ (80%:10%:10%) 40 nm | M3 10 nm | ETM1:LiQ (50%:50%) 20 nm | — |
| 176 | HTM1 20 nm | EBM1 5 m | EBM3 15 nm | M3:EBM3:Ir(L184)$_3$ (80%:10%:10%) 40 nm | M3 10 nm | ETM1:LiQ (50%:50%) 20 nm | — |
| 177 | HTM1 20 nm | EBM1 5 m | EBM3 15 nm | M3:EBM3:Ir(L185)$_3$ (80%:10%:10%) 40 nm | M3 10 nm | ETM1:LiQ (50%:50%) 20 nm | — |
| 178 | HTM1 20 nm | EBM1 5 m | EBM3 15 nm | M3:EBM3:Ir(L186)$_3$ (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 179 | HTM1 20 nm | EBM1 5 m | EBM3 15 nm | M3:EBM3:Ir(L187)$_3$ (80%:10%:10%) 40 nm | M3 10 nm | ETM1:LiQ (50%:50%) 20 nm | — |
| 180 | HTM1 20 nm | EBM1 5 m | EBM3 15 nm | M3:EBM3:Ir(L188)$_3$ (80%:10%:10%) 40 nm | M3 10 nm | ETM1:LiQ (50%:50%) 20 nm | — |
| 181 | HTM1 20 nm | EBM1 5 m | EBM3 15 nm | M3:EBM3:Ir(L189)$_3$ (80%:10%:10%) 40 nm | M3 10 nm | ETM1:LiQ (50%:50%) 20 nm | — |
| 182 | HTM1 20 nm | EBM1 5 m | EBM3 15 nm | M3:EBM3:Ir(L190)$_3$ (80%:10%:10%) 40 nm | M3 10 nm | ETM1:LiQ (50%:50%) 20 nm | — |
| 183 | HTM1 20 nm | EBM1 5 m | EBM3 15 nm | M3:EBM3:Ir(L191)$_3$ (80%:10%:10%) 40 nm | M3 10 nm | ETM1:LiQ (50%:50%) 20 nm | — |
| 184 | HTM1 20 nm | EBM1 20 m | — | ETM1:Ir(L192)$_3$ (90%:10%) 40 nm | — | ETM1:LiQ (50%:50%) 20 nm | — |
| 185 | HTM1 20 nm | EBM1 20 m | — | ETM1:Ir(L193)$_3$ (90%:10%) 40 nm | — | ETM1:LiQ (50%:50%) 20 nm | — |
| 186 | HTM1 20 nm | EBM1 20 m | — | ETM1:Ir(L194)$_3$ (90%:10%) 40 nm | — | ETM1:LiQ (50%:50%) 20 nm | — |
| 187 | HTM1 20 nm | EBM1 20 m | — | ETM1:Ir(L195)$_3$ (90%:10%) 40 nm | — | ETM1:LiQ (50%:50%) 20 nm | — |
| 188 | HTM1 20 nm | EBM1 5 m | EBM3 15 nm | M3:EBM3:Ir(L200)$_3$ (80%:10%:10%) 40 nm | M3 10 nm | ETM1:LiQ (50%:50%) 20 nm | — |
| 189 | HTM1 20 nm | EBM1 5 m | EBM3 15 nm | M3:EBM3:Ir(L201)$_3$ (80%:10%:10%) 40 nm | M3 10 nm | ETM1:LiQ (50%:50%) 20 nm | — |
| 190 | HTM1 20 nm | EBM1 20 m | — | ETM1:Ir(L202)$_3$ (90%:10%) 40 nm | — | ETM1:LiQ (50%:50%) 20 nm | — |
| 191 | HTM1 20 nm | EBM1 20 m | — | ETM1:Ir(L203)$_3$ (90%:10%) 40 nm | — | ETM1:LiQ (50%:50%) 20 nm | — |
| 192 | HTM1 20 nm | EBM1 5 m | EBM3 15 nm | M3:EBM3:Ir(L204)$_3$ (80%:10%:10%) 40 nm | M3 10 nm | ETM1:LiQ (50%:50%) 20 nm | — |
| 193 | HTM1 20 nm | EBM1 5 m | EBM3 15 nm | M3:EBM3:Ir(L5)$_2$(CL1) (80%:10%:10%) 40 nm | M3 10 nm | ETM1:LiQ (50%:50%) 20 nm | — |
| 194 | HTM1 20 nm | EBM1 5 m | EBM3 15 nm | M3:EBM3:Ir(L5)$_2$(CL2) (80%:10%:10%) 40 nm | M3 10 nm | ETM1:LiQ (50%:50%) 20 nm | — |
| 195 | HTM1 20 nm | EBM1 5 m | EBM3 15 nm | M3:EBM3:Ir(L5)$_2$(CL3) (80%:10%:10%) 40 nm | M3 10 nm | ETM1:LiQ (50%:50%) 20 nm | — |
| 196 | HTM1 20 nm | EBM1 5 m | EBM3 15 nm | M3:EBM3:Ir(L5)$_2$(CL4) (80%:10%:10%) 40 nm | M3 10 nm | ETM1:LiQ (50%:50%) 20 nm | — |
| 197 | HTM1 20 nm | EBM1 20 m | — | ETM1:Ir(L5)$_2$(L193) (90%:10%) 40 nm | — | ETM1:LiQ (50%:50%) 20 nm | — |
| 198 | HTM1 20 nm | EBM1 5 m | EBM3 15 nm | M3:EBM3:Ir(L7)$_2$(CL1) (80%:10%:10%) 40 nm | M3 10 nm | ETM1:LiQ (50%:50%) 20 nm | — |
| 199 | HTM1 20 nm | EBM1 5 m | EBM3 15 nm | M3:EBM3:Ir(L9)$_2$(CL1) (80%:10%:10%) 40 nm | M3 10 nm | ETM1:LiQ (50%:50%) 20 nm | — |
| 200 | HTM1 20 nm | EBM1 5 m | EBM3 15 nm | M3:EBM3:Ir(L15)$_2$(CL1) (80%:10%:10%) 40 nm | M3 10 nm | ETM1:LiQ (50%:50%) 20 nm | — |
| 201 | HTM1 20 nm | EBM1 5 m | EBM3 15 nm | M3:EBM3:Ir(L49)$_2$(CL1) (80%:10%:10%) 40 nm | M3 10 nm | ETM1:LiQ (50%:50%) 20 nm | — |
| 202 | HTM1 20 nm | EBM1 5 m | EBM3 15 nm | M3:EBM3:Ir(L83)$_2$(CL2) (80%:10%:10%) 40 nm | M3 10 nm | ETM1:LiQ (50%:50%) 20 nm | — |
| 203 | HTM1 20 nm | EBM1 5 m | EBM3 15 nm | M3:EBM3:Ir(L104)$_2$(CL2) (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 204 | HTM1 20 nm | EBM1 5 m | EBM3 15 nm | M3:EBM3:Ir(L105)$_2$(CL2) (80%:10%:10%) 40 nm | M3 10 nm | ETM1:LiQ (50%:50%) 20 nm | — |
| 205 | HTM1 20 nm | EBM1 5 m | EBM3 15 nm | M3:EBM3:Ir(L119)$_2$(CL3) (80%:10%:10%) 40 nm | M3 10 nm | ETM1:LiQ (50%:50%) 20 nm | — |
| 206 | HTM1 20 nm | EBM1 5 m | EBM3 15 nm | M3:EBM3:Ir(L130)$_2$(CL3) (80%:10%:10%) 40 nm | M3 10 nm | ETM1:LiQ (50%:50%) 20 nm | — |
| 207 | HTM1 20 nm | EBM1 5 m | EBM3 15 nm | M3:EBM3:Ir(L139)$_2$(CL3) (80%:10%:10%) 40 nm | M3 10 nm | ETM1:LiQ (50%:50%) 20 nm | — |
| 208 | HTM1 20 nm | EBM1 5 m | EBM3 15 nm | M3:EBM3:Ir(L163)$_2$(CL3) (80%:10%:10%) 40 nm | M3 10 nm | ETM1:LiQ (50%:50%) 20 nm | — |
| 209 | HTM1 20 nm | EBM1 5 m | EBM3 15 nm | M3:EBM3:Ir(L172)$_2$(L199) (80%:10%:10%) 40 nm | M3 10 nm | ETM1:LiQ (50%:50%) 20 nm | — |
| 210 | HTM1 20 nm | EBM1 5 m | EBM3 15 nm | M3:EBM3:Ir(L1)$_2$(CL5) (80%:10%:10%) 40 nm | M3 10 nm | ETM1:LiQ (50%:50%) 20 nm | — |
| 211 | HTM1 20 nm | EBM1 5 m | EBM3 15 nm | M3:EBM3:Ir(L7)$_2$(CL5) (80%:10%:10%) 40 nm | M3 10 nm | ETM1:LiQ (50%:50%) 20 nm | — |
| 212 | HTM1 20 nm | EBM1 5 nm | EBM3 15 nm | M3:EBM3:Ir(L7)$_2$(CL6) (80%:10%:10%) 40 nm | M3 10 nm | ETM1:LiQ (50%:50%) 20 nm | — |
| 213 | HTM1 20 nm | EBM1 5 m | EBM3 15 nm | M3:EBM3:Ir(L15)$_2$(CL7) (80%:10%:10%) 40 nm | M3 10 nm | ETM1:LiQ (50%:50%) 20 nm | — |
| 214 | HTM1 20 nm | EBM1 5 m | EBM3 15 nm | M3:EBM3:Ir(L49)$_2$(CL7) (80%:10%:10%) 40 nm | M3 10 nm | ETM1:LiQ (50%:50%) 20 nm | — |
| 215 | HTM1 20 nm | EBM1 5 m | EBM3 15 nm | M3:EBM3:Ir(L83)$_2$(CL8) (80%:10%:10%) 40 nm | M3 10 nm | ETM1:LiQ (50%:50%) 20 nm | — |
| 216 | HTM1 20 nm | EBM1 5 m | EBM3 15 nm | M3:EBM3:Ir(L104)$_2$(CL8) (80%:10%:10%) 40 nm | M3 10 nm | ETM1:LiQ (50%:50%) 20 nm | — |
| 217 | HTM1 20 nm | EBM1 5 m | EBM3 15 nm | M3:EBM3:Ir(L105)$_2$(CL8) (80%:10%:10%) 40 nm | M3 10 nm | ETM1:LiQ (50%:50%) 20 nm | — |
| 218 | HTM1 20 nm | EBM1 5 m | EBM3 15 nm | M3:EBM3:Ir(L119)$_2$(CL8) (80%:10%:10%) 40 nm | M3 10 nm | ETM1:LiQ (50%:50%) 20 nm | — |
| 219 | HTM1 20 nm | EBM1 20 m | — | ETM1:Ir(L119)$_2$(CL9) (90%:10%) 40 nm | — | ETM1:LiQ (50%:50%) 20 nm | — |
| 220 | HTM1 20 nm | EBM1 20 m | — | ETM1:Ir(L130)$_2$(CL10) 90%:10%) 40 nm | — | ETM1:LiQ (50%:50%) 20 nm | — |
| 221 | HTM1 20 nm | EBM1 5 m | EBM3 15 nm | M3:EBM3:Ir(L139)$_2$(CL7) (80%:10%:10%) 40 nm | M3 10 nm | ETM1:LiQ (50%:50%) 20 nm | — |
| 222 | HTM1 20 nm | EBM1 5 m | EBM3 15 nm | M3:EBM3:Ir(L12)$_2$(L7) (80%:10%:10%) 40 nm | M3 10 nm | ETM1:LiQ (50%:50%) 20 nm | — |
| 223 | HTM1 20 nm | EBM1 5 m | EBM3 15 nm | M3:EBM3:Ir(L12)$_2$(L32) (80%:10%:10%) 40 nm | M3 10 nm | ETM1:LiQ (50%:50%) 20 nm | — |
| 224 | HTM1 20 nm | EBM1 5 m | EBM3 15 nm | M3:EBM3:Ir(L12)$_2$(L51) (80%:10%:10%) 40 nm | M3 10 nm | ETM1:LiQ (50%:50%) 20 nm | — |
| 225 | HTM1 20 nm | EBM1 5 m | EBM3 15 nm | M3:EBM3:Ir(L51)$_2$(L12) (80%:10%:10%) 40 nm | M3 10 nm | ETM1:LiQ (50%:50%) 20 nm | — |
| 226 | HTM1 20 nm | EBM1 5 m | EBM3 15 nm | M3:EBM3:Ir(L79)$_2$(CL7) (80%:10%:10%) 40 nm | M3 10 nm | ETM1:LiQ (50%:50%) 20 nm | — |
| 227 | HTM1 20 nm | EBM1 5 m | EBM3 15 nm | M3:EBM3:Ir(L99)$_2$(L111) (80%:10%:10%) 40 nm | M3 10 nm | ETM1:LiQ (50%:50%) 20 nm | — |
| 228 | HTM1 20 nm | EBM1 5 m | EBM3 15 nm | M3:EBM3:Ir(L139)$_2$(CL8) (80%:10%:10%) 40 nm | M3 10 nm | ETM1:LiQ (50%:50%) 20 nm | — |

TABLE 1-continued

Structure of the OLEDs

| Ex. | HTL1 thickness | HTL2 thickness | EBL thickness | EML thickness | HBL thickness | ETL thickness | EIL thickness |
|---|---|---|---|---|---|---|---|
| 229 | HTM1 20 nm | EBM1 5 m | EBM3 15 nm | M3:EBM3:Ir(L164)$_2$(CL8) (80%:10%:10%) 40 nm | M3 10 nm | ETM1:LiQ (50%:50%) 20 nm | — |
| 230 | HTM1 20 nm | EBM1 5 m | EBM3 15 nm | M3:EBM3:Pt(L12)$_2$ (80%:10%:10%) 40 nm | M3 10 nm | ETM1:LiQ (50%:50%) 20 nm | — |
| 231 | HTM1 20 nm | EBM1 5 m | EBM3 15 nm | M3:EBM3:Pt(L41)$_2$ (80%:10%:10%) 40 nm | M3 10 nm | ETM1:LiQ (50%:50%) 20 nm | — |
| 232 | HTM1 20 nm | EBM1 5 m | EBM3 15 nm | M3:EBM3:Pt(L46)$_2$ (80%:10%:10%) 40 nm | M3 10 nm | ETM1:LiQ (50%:50%) 20 nm | — |
| 233 | HTM1 20 nm | EBM1 5 m | EBM3 15 nm | M3:EBM3:Pt(L101)$_2$ (80%:10%:10%) 40 nm | M3 10 nm | ETM1:LiQ (50%:50%) 20 nm | — |
| 234 | HTM1 20 nm | EBM1 5 m | EBM3 15 nm | M3:EBM3:Pt(L165)$_2$ (80%:10%:10%) 40 nm | M3 10 nm | ETM1:LiQ (50%:50%) 20 nm | — |
| 235 | HTM1 20 nm | EBM1 5 m | EBM3 15 nm | M3:EBM3:Pt(L205) (80%:10%:10%) 40 nm | M3 10 nm | ETM1:LiQ (50%:50%) 20 nm | — |
| 236 | HTM1 20 nm | EBM1 5 m | EBM3 15 nm | M3:EBM3:Pt(L206) (80%:10%:10%) 40 nm | M3 10 nm | ETM1:LiQ (50%:50%) 20 nm | — |
| 237 | HTM1 20 nm | EBM1 5 m | EBM3 15 nm | M3:EBM3:Pt(L207) (80%:10%:10%) 40 nm | M3 10 nm | ETM1:LiQ (50%:50%) 20 nm | — |
| 238 | HTM1 20 nm | EBM1 5 m | EBM3 15 nm | M3:EBM3:Pt(L208) (80%:10%:10%) 40 nm | M3 10 nm | ETM1:LiQ (50%:50%) 20 nm | — |
| 239 | HTM1 20 nm | EBM1 5 m | EBM3 15 nm | M3:EBM3:Pt(L40)(CL1) (80%:10%:10%) 40 nm | M3 10 nm | ETM1:LiQ (50%:50%) 20 nm | — |
| 240 | HTM1 20 nm | EBM1 5 m | EBM3 15 nm | M3:EBM3:Pt(L66)(CL2) (80%:10%:10%) 40 nm | M3 10 nm | ETM1:LiQ (50%:50%) 20 nm | — |
| 241 | HTM1 20 nm | EBM1 5 m | EBM3 15 nm | M3:EBM3:Pt(L107)(CL1) (80%:10%:10%) 40 nm | M3 10 nm | ETM1:LiQ (50%:50%) 20 nm | — |
| 242 | HTM1 20 nm | EBM1 20 m | — | ETM1:Pt (L107)(L196) (90%:10%) 40 nm | — | ETM1:LiQ (50%:50%) 20 nm | — |
| 243 | HTM1 20 nm | EBM1 20 m | — | ETM1:Pt(L107)(L199) (90%:10%) 40 nm | — | ETM1:LiQ (50%:50%) 20 nm | — |
| 244 | HTM1 20 nm | EBM1 20 m | — | ETM1:Au(L202)(CL5) (90%:10%) 40 nm | — | ETM1:LiQ (50%:50%) 20 nm | — |
| 245 | HTM1 20 nm | EBM1 20 m | — | ETM1:Pt(L203)(CL5) (90%:10%) 40 nm | — | ETM1:LiQ (50%:50%) 20 nm | — |
| 246 | HTM1 20 nm | EBM1 20 m | — | ETM1:Pt(L204)(CL5) (90%:10%) 40 nm | — | ETM1:LiQ (50%:50%) 20 nm | — |
| 247 | HTM1 20 nm | EBM1 20 m | — | ETM1:Cu(L194)(CL11) (90%:10%) 40 nm | — | ETM1:LiQ (50%:50%) 20 nm | — |
| 248 | HTM1 20 nm | EBM1 20 m | — | ETM1:Pt (L196)(CL11) (90%:10%) 40 nm | — | ETM1:LiQ (50%:50%) 20 nm | — |
| 249 | HTM1 20 nm | EBM1 20 m | — | ETM1:Pt(L195)(CL12) (90%:10%) 40 nm | — | ETM1:LiQ (50%:50%) 20 nm | — |
| 250 | Ir(L83)$_3$ 20 nm | M2:Ir(L83)$_3$ (70%:30%) 20 nm | — | M2:Ir(L83)$_3$ (85%:15%) 40 nm | M3 10 nm | Alq$_3$ 20 nm | LiF |
| comp. | HTM1 20 nm | EBM1 5 m | EBM3 15 nm | M2:Ir(ref) (85%:15%) 40 nm | M3 10 nm | Alq$_3$ 20 nm | LiF |

TABLE 2

Use of compounds according to the invention as matrix materials in phosphorescent OLEDs

| Ex. | Voltage (V) 1000 cd/m² | Efficiency (cd/A) at 1000 cd/m² | CIE x/y at 1000 cd/m² | LD50 (h) at 1000 cd/m² |
|---|---|---|---|---|
| 1 | 6.1 | 9.4 | 0.34/0.52 | 1300 |
| 2 | 5.2 | 8.1 | 0.52/0.47 | 600 |
| 3 | 14.0 | 7.5 | 0.18/0.32 | 300 |
| 4 | 14.2 | 7.2 | 0.18/0.31 | 400 |
| 5 | 8.1 | 9.8 | 0.19/0.35 | 400 |
| 6 | 6.5 | 8.2 | 0.19/0.35 | 700 |
| 7 | 5.1 | 8.9 | 0.34/0.52 | 1200 |
| 8 | 6.2 | 15.0 | 0.29/0.52 | — |
| 9 | 5.0 | 18.2 | 0.27/0.48 | — |
| 10 | 6.0 | 19.3 | 0.26/0.47 | — |
| 11 | 5.5 | 15.5 | 0.29/0.53 | — |
| 12 | 5.8 | 20.3 | 0.23/0.45 | — |
| 13 | 5.7 | 22.5 | 0.25/0.46 | — |
| 14 | 4.8 | 19.9 | 0.27/0.46 | — |
| 15 | 5.3 | 22.3 | 0.26/0.47 | — |
| 16 | 5.7 | 27.6 | 0.29/0.52 | — |
| 17 | 4.9 | 29.3 | 0.28/0.50 | — |
| 18 | 6.1 | 9.3 | 0.16/0.24 | 300 |
| 19 | 5.1 | 28.6 | 0.29/0.52 | — |
| 20 | 4.9 | 11.2 | 0.19/0.35 | — |
| 21 | 5.0 | 14.5 | 0.19/0.35 | — |
| 22 | 4.7 | 16.7 | 0.16/0.30 | 600 |
| 23 | 4.9 | 17.3 | 0.19/0.35 | — |
| 24 | 5.3 | 16.9 | 0.18/0.31 | — |
| 25 | 5.2 | 16.7 | 0.18/0.34 | — |
| 26 | 5.5 | 17.3 | 0.19/0.35 | — |
| 27 | 5.0 | 22.7 | 0.21/0.39 | — |
| 28 | 5.0 | 14.9 | 0.20/0.41 | — |
| 29 | 4.9 | 19.0 | 0.21/0.38 | — |
| 30 | 5.2 | 14.7 | 0.18/0.32 | 700 |
| 31 | 5.5 | 16.9 | 0.19/0.34 | — |
| 32 | 4.6 | 21.3 | 0.21/0.38 | — |
| 33 | 4.8 | 13.9 | 0.20/0.36 | — |
| 34 | 5.3 | 16.7 | 0.18/0.32 | 500 |
| 35 | 4.8 | 18.3 | 0.18/0.31 | — |
| 36 | 4.7 | 16.3 | 0.17/0.31 | 300 |
| 37 | 5.6 | 22.5 | 0.21/0.36 | — |
| 38 | 5.0 | 25.8 | 0.21/0.35 | 800 |
| 39 | 4.9 | 15.6 | 0.17/0.30 | — |
| 40 | 5.8 | 12.9 | 0.20/0.36 | — |
| 41 | 5.3 | 13.9 | 0.16/0.25 | — |
| 42 | 4.9 | 18.6 | 0.20/0.39 | — |
| 43 | 5.5 | 15.5 | 0.21/0.36 | — |
| 44 | 5.0 | 23.2 | 0.23/0.40 | — |
| 45 | 4.9 | 25.6 | 0.21/0.36 | — |
| 46 | 5.1 | 27.1 | 0.22/0.38 | — |
| 47 | 4.7 | 24.9 | 0.18/0.31 | — |
| 48 | 5.3 | 22.9 | 0.21/0.38 | — |
| 49 | 4.9 | 23.1 | 0.20/0.37 | — |
| 50 | 4.8 | 20.3 | 0.19/0.34 | — |
| 51 | 4.8 | 19.7 | 0.19/0.33 | 400 |
| 52 | 4.9 | 20.1 | 0.17/0.26 | — |
| 53 | 5.3 | 21.1 | 0.17/0.26 | — |
| 54 | 5.2 | 23.1 | 0.20/0.38 | — |
| 55 | 4.9 | 19.9 | 0.19/0.32 | — |
| 56 | 4.7 | 22.3 | 0.18/0.32 | — |
| 57 | 5.6 | 16.7 | 0.20/0.39 | — |
| 58 | 7.3 | 24.1 | 0.20/0.35 | — |
| 59 | 5.6 | 22.1 | 0.21/0.36 | — |
| 60 | 4.8 | 16.7 | 0.22/0.38 | — |
| 61 | 5.7 | 19.3 | 0.23/0.40 | 700 |
| 62 | 5.5 | 23.5 | 0.25/0.43 | — |
| 63 | 4.5 | 19.5 | 0.19/0.33 | — |
| 64 | 4.8 | 22.6 | 0.17/0.28 | — |
| 65 | 5.1 | 19.7 | 0.19/0.34 | 200 |
| 66 | 5.5 | 19.0 | 0.21/0.38 | — |
| 67 | 4.9 | 24.9 | 0.28/0.52 | 17000 |
| 68 | 5.8 | 19.6 | 0.26/0.49 | 22000 |
| 69 | 5.2 | 22.7 | 0.28/0.48 | — |
| 70 | 5.4 | 20.6 | 0.21/0.35 | — |
| 71 | 4.7 | 22.4 | 0.19/0.32 | 1800 |
| 72 | 4.9 | 24.7 | 0.20/0.35 | — |
| 73 | 5.2 | 23.9 | 0.20/0.34 | — |
| 74 | 4.8 | 19.7 | 0.18/0.30 | — |
| 75 | 5.5 | 18.7 | 0.21/0.35 | — |
| 76 | 4.8 | 22.7 | 0.20/0.30 | 2800 |
| 77 | 6.1 | 24.6 | 0.21/0.40 | — |
| 78 | 5.5 | 20.7 | 0.19/0.26 | — |
| 79 | 5.1 | 19.6 | 0.20/0.32 | — |
| 80 | 8.5 | 15.7 | 0.25/0.43 | 1500 |
| 81 | 8:3 | 16.9 | 0.19/0.28 | — |
| 82 | 5.4 | 24.7 | 0.33/0.51 | 12000 |
| 83 | 6.2 | 23.0 | 0.34/0.51 | 7000 |
| 84 | 5.7 | 18.8 | 0.19/0.45 | 1200 |
| 85 | 6.0 | 14.1 | 0.20/0.46 | 700 |
| 86 | 7.4 | 11.3 | 0.17/0.40 | 200 |
| 87 | 4.9 | 20.7 | 0.26/0.47 | 600 |
| 88 | 8.9 | 7.3 | 0.23/0.45 | 2100 |
| 89 | 7.4 | 8.6 | 0.21/0.44 | 2600 |
| 90 | 5.8 | 37.2 | 0.25/0.49 | 100 |
| 91 | 5.4 | 22.7 | 0.26/0.47 | — |
| 92 | 5.6 | 36.5 | 0.23/0.45 | — |
| 93 | 5.1 | 24.9 | 0.22/0.45 | — |
| 94 | 4.8 | 26.7 | 0.20/0.44 | 2400 |
| 95 | 5.6 | 22.7 | 0.29/0.45 | — |
| 96 | 4.9 | 25.0 | 0.23/0.39 | — |
| 97 | 5.8 | 22.9 | 0.21/0.37 | — |
| 98 | 5.2 | 24.7 | 0.22/0.43 | — |
| 99 | 4.9 | 22.0 | 0.25/0.49 | — |
| 100 | 5.5 | 21.9 | 0.25/0.43 | — |
| 101 | 5.3 | 19.7 | 0.23/0.39 | — |
| 102 | 5.9 | 30.9 | 0.29/0.52 | — |
| 103 | 4.7 | 26.9 | 0.20/0.43 | — |
| 104 | 6.7 | 33.5 | 0.23/0.39 | — |
| 105 | 5.8 | 23.8 | 0.21/0.32 | — |
| 106 | 5.3 | 18.9 | 0.22/0.32 | — |
| 107 | 4.7 | 25.7 | 0.23/042 | — |
| 108 | 4.5 | 25.6 | 0.19/0.43 | 2800 |
| 109 | 5.5 | 28.8 | 0.21/0.32 | — |
| 110 | 5.3 | 32.6 | 0.21/0.32 | — |
| 111 | 4.9 | 26.9 | 0.30/0.46 | — |
| 112 | 6.7 | 29.0 | 0.29/0.43 | — |
| 113 | 5.2 | 26.4 | 0.26/0.43 | — |
| 114 | 6.3 | 23.9 | 0.23/0.43 | — |
| 115 | 5.0 | 22.7 | 0.19/0.36 | — |
| 116 | 4.8 | 19.8 | 0.21/0.32 | — |
| 117 | 5.7 | 31.0 | 0.29/0.52 | — |
| 118 | 5.2 | 29.8 | 0.30/0.55 | 25000 |
| 119 | 5.4 | 29.6 | 0.21/0.35 | — |
| 120 | 5.6 | 26.8 | 0.30/0.49 | — |
| 121 | 4.7 | 33.8 | 0.21/0.34 | — |
| 122 | 4.9 | 30.2 | 0.22/0.38 | — |
| 123 | 5.1 | 24.8 | 0.20/0.37 | — |
| 124 | 4.6 | 29.8 | 0.19/0.34 | — |
| 125 | 5.8 | 32.2 | 0.28/0.55 | 23000 |
| 126 | 4.4 | 29.8 | 0.26/0.42 | — |
| 127 | 5.3 | 30.7 | 0.23/0.38 | — |
| 128 | 6.0 | 23.8 | 0.22/0.36 | — |
| 129 | 5.8 | 26.8 | 0.21/0.30 | — |
| 130 | 5.0 | 26.5 | 0.19/0.34 | 1700 |
| 131 | 4.8 | 25.6 | 0.20/0.38 | — |
| 132 | 4.2 | 36.6 | 0.26/0.38 | — |
| 133 | 4.6 | 33.3 | 0.23/0.38 | — |
| 134 | 5.2 | 30.5 | 0.26/0.47 | — |
| 135 | 5.3 | 34.8 | 0.23/0.37 | — |
| 136 | 4.3 | 35.7 | 0.19/0.32 | — |
| 137 | 4.7 | 34.5 | 0.25/40 | — |
| 138 | 5.5 | 23.4 | 0.26/0.47 | — |
| 139 | 5.2 | 39.1 | 0.32/0.50 | 29000 |
| 140 | 4.6 | 40.3 | 0.35/0.59 | — |
| 141 | 4.3 | 32.0 | 0.30/0.50 | — |
| 142 | 4.8 | 29.9 | 0.29/0.59 | — |
| 143 | 5.3 | 33.5 | 0.28/0.50 | — |
| 144 | 5.1 | 29.8 | 0.27/0.45 | — |
| 145 | 4.9 | 38.9 | 0.30/0.55 | — |
| 146 | 4.7 | 37.6 | 0.26/0.46 | — |

TABLE 2-continued

Use of compounds according to the invention as matrix materials in phosphorescent OLEDs

| Ex. | Voltage (V) 1000 cd/m² | Efficiency (cd/A) at 1000 cd/m² | CIE x/y at 1000 cd/m² | LD50 (h) at 1000 cd/m² |
|---|---|---|---|---|
| 147 | 5.0 | 38.6 | 0.33/0.60 | — |
| 148 | 4.7 | 35.6 | 0.30/0.55 | — |
| 149 | 5.5 | 27.3 | 0.26/0.49 | 23000 |
| 150 | 5.3 | 29.3 | 0.26/0.45 | — |
| 151 | 5.1 | 30.5 | 0.25/0.50 | — |
| 152 | 4.9 | 34.0 | 0.23/0.37 | — |
| 153 | 4.9 | 33.4 | 0.26/0.49 | — |
| 154 | 4.2 | 39.8 | 0.23/0.26 | — |
| 155 | 4.8 | 26.8 | 0.20/0.28 | — |
| 156 | 5.0 | 28.1 | 0.19/0.25 | 3100 |
| 157 | 6.0 | 22.0 | 0.26/0.47 | — |
| 158 | 4.9 | 25.6 | 0.23/0.35 | — |
| 159 | 5.1 | 26.4 | 0.23/0.39 | — |
| 160 | 5.5 | 20.2 | 0.19/0.26 | — |
| 161 | 5.1 | 30.6 | 0.27/0.50 | 12000 |
| 162 | 4.6 | 36.5 | 0.23/0.35 | — |
| 163 | 4.5 | 32.7 | 0.24/0.37 | — |
| 164 | 4.9 | 29.6 | 0.22/0.40 | — |
| 165 | 4.8 | 32.3 | 0.24/0.42 | — |
| 166 | 5.3 | 22.7 | 0.19/0.29 | 1600 |
| 167 | 5.3 | 26.4 | 0.26/0.49 | 4500 |
| 168 | 5.0 | 25.3 | 0.21/0.38 | — |
| 169 | 4.8 | 22.0 | 0.19/0.28 | — |
| 170 | 5.2 | 30.5 | 0.28/0.51 | — |
| 171 | 5.6 | 33.5 | 0.29/0.52 | — |
| 172 | 4.8 | 32.3 | 0.27/0.52 | 15000 |
| 173 | 5.4 | 26.7 | 0.22/0.42 | — |
| 174 | 6.2 | 28.4 | 0.29/0.52 | 800 |
| 175 | 5.3 | 33.7 | 0.28/0.51 | — |
| 176 | 4.4 | 36.1 | 0.27/0.51 | — |
| 177 | 5.7 | 30.6 | 0.24/0.48 | 300 |
| 178 | 5.9 | 38.9 | 0.23/0.38 | — |
| 179 | 6.2 | 35.7 | 0.24/0.40 | — |
| 180 | 5.8 | 33.6 | 0.29/0.58 | — |
| 181 | 4.6 | 28.3 | 0.23/0.42 | 400 |
| 182 | 4.3 | 26.8 | 0.21/0.35 | — |
| 183 | 5.7 | 37.2 | 0.19/0.26 | 500 |
| 184 | 5.3 | 8.1 | 0.64/0.36 | — |
| 185 | 4.5 | 16.6 | 0.62/0.38 | 19000 |
| 186 | 4.8 | 7.9 | 0.68/0.32 | — |
| 187 | 5.5 | 10.5 | 0.67/0.33 | 32000 |
| 188 | 4.3 | 19.7 | 0.20/0.28 | — |
| 189 | 4.1 | 18.0 | 0.18/0.24 | — |
| 190 | 4.5 | 16.7 | 0.19/0.27 | — |
| 191 | 5.1 | 17.2 | 0.61/0.39 | 16700 |
| 192 | 4.7 | 16.5 | 0.63/0.37 | 22000 |
| 193 | 5.7 | 23.6 | 0.26/0.45 | — |
| 194 | 5.2 | 25.1 | 0.24/0.38 | 900 |
| 195 | 5.9 | 22.0 | 0.37/0.61 | 10000 |
| 196 | 5.2 | 23.1 | 0.22/0.28 | — |
| 197 | 4.2 | 19.6 | 0.61/0.39 | 22000 |
| 198 | 4.9 | 16.4 | 0.23/0.38 | — |
| 199 | 5.3 | 14.2 | 0.21/0.29 | — |
| 200 | 5.2 | 18.9 | 0.19/0.35 | 3200 |
| 201 | 4.6 | 19.0 | 0.18/0.32 | — |
| 202 | 6.2 | 26.8 | 0.23/0.45 | — |
| 203 | 5.1 | 29.0 | 0.29/0.42 | — |
| 204 | 6.2 | 25.4 | 0.28/0.51 | — |
| 205 | 5.6 | 35.7 | 0.33/0.58 | 21000 |
| 206 | 5.7 | 19.7 | 0.21/0.32 | — |
| 207 | 4.9 | 29.4 | 0.25/0.50 | — |
| 208 | 4.7 | 24.1 | 0.24/0.35 | — |
| 209 | 5.5 | 10.9 | 0.55/0.43 | 26000 |
| 210 | 4.2 | 30.5 | 0.28/0.55 | — |
| 211 | 4.7 | 16.0 | 0.21/0.28 | — |
| 212 | 5.3 | 12.1 | 0.19/0.23 | — |
| 213 | 4.9 | 17.3 | 0.20/0.25 | — |
| 214 | 5.7 | 19.5 | 0.23/0.40 | — |
| 215 | 4.8 | 45.8 | 0.30/0.60 | — |
| 216 | 4.9 | 13.2 | 0.26/0.49 | — |
| 217 | 5.0 | 30.1 | 0.29/0.51 | — |
| 218 | 5.2 | 32.2 | 0.30/0.59 | — |
| 219 | 4.7 | 12.8 | 0.67/0.33 | 35000 |
| 220 | 4.3 | 14.7 | 0.66/0.34 | — |
| 221 | 5.1 | 39.0 | 0.35/0.62 | — |
| 222 | 5.8 | 15.6 | 0.17/0.26 | 600 |
| 223 | 5.8 | 20.4 | 0.20/0.29 | — |
| 224 | 4.7 | 13.9 | 0.18/0.24 | — |
| 225 | 4.8 | 14.0 | 0.19/0.25 | — |
| 226 | 5.2 | 16.5 | 0.17/0.22 | — |
| 227 | 4.6 | 31.2 | 0.29/0.56 | — |
| 228 | 4.3 | 38.4 | 0.30/0.59 | — |
| 229 | 4.4 | 36.7 | 0.32/0.57 | 29000 |
| 230 | 5.6 | 19.1 | 0.25/0.47 | 600 |
| 231 | 5.2 | 17.4 | 0.23/0.35 | — |
| 232 | 6.7 | 13.1 | 0.19/0.28 | 1200 |
| 233 | 5.8 | 17.9 | 0.22/0.42 | — |
| 234 | 6.4 | 18.6 | 0.23/0.39 | — |
| 235 | 5.1 | 16.5 | 0.19/0.24 | 1100 |
| 236 | 8.0 | 8.9 | 0.25/0.45 | 600 |
| 237 | 5.2 | 14.0 | 0.22/0.28 | — |
| 238 | 4.9 | 11.2 | 0.23/0.32 | — |
| 239 | 5.5 | 16.4 | 0.25/0.35 | 5000 |
| 240 | 5.1 | 12.1 | 0.23/0.33 | — |
| 241 | 4.9 | 13.1 | 0.35/0.58 | — |
| 242 | 4.2 | 13.1 | 0.65/035 | 23000 |
| 243 | 5.9 | 11.1 | 0.66/0.33 | — |
| 244 | 6.3 | 20.5 | 0.62/0.38 | 1500 |
| 245 | 5.9 | 19.7 | 0.63/0.37 | 2500 |
| 246 | 5.3 | 14.3 | 0.59/0.37 | — |
| 247 | 4.8 | 17.3 | 0.58/0.36 | — |
| 248 | 5.2 | 14.2 | 0.63/0.37 | — |
| 249 | 4.7 | 8.6 | 0.64/0.36 | — |
| 250 | 6.2 | 21.4 | 0.34/0.51 | 500 |
| comp. | 6.7 | 9.6 | 0.18/0.30 | 300 |

TABLE 3

Structural formulae of the materials used

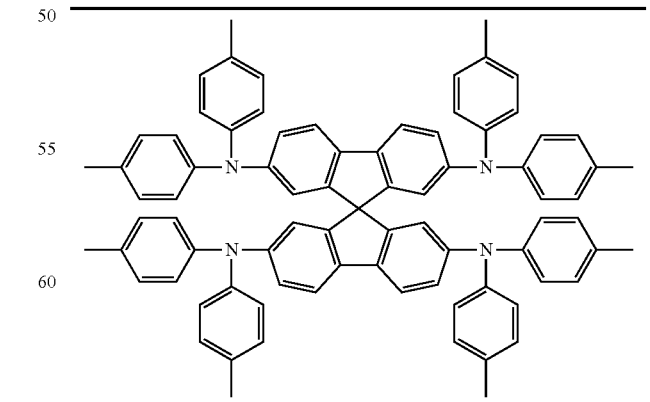

HTM1

TABLE 3-continued
Structural formulae of the materials used
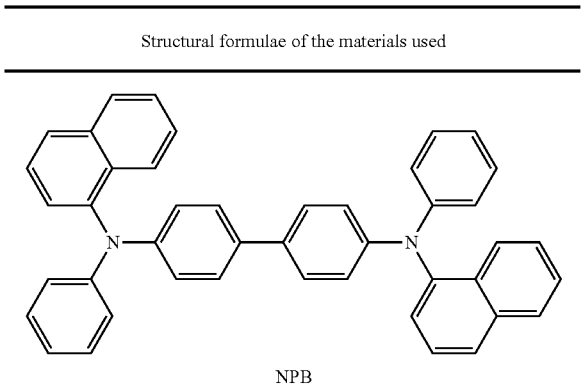
NPB
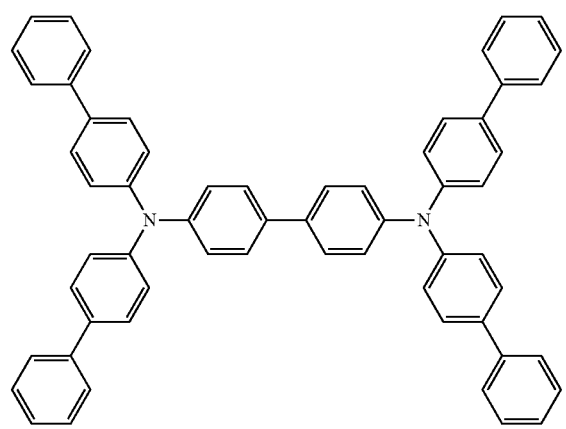
EBM1
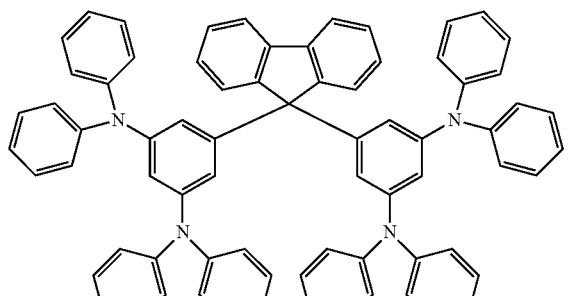
EBM2
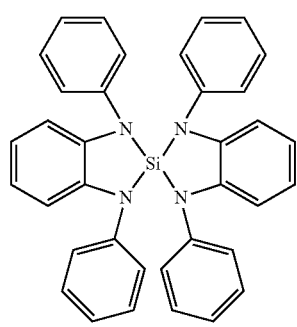
EBM3
TABLE 3-continued
Structural formulae of the materials used
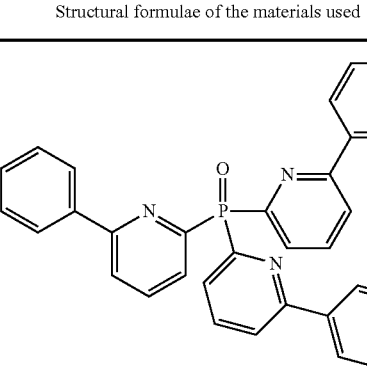
M1
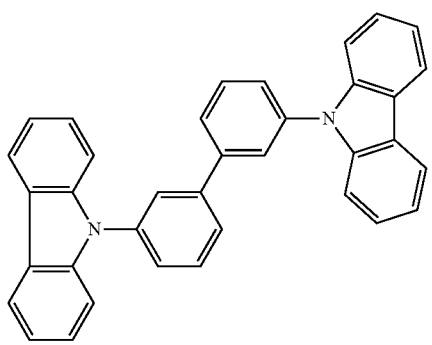
M2
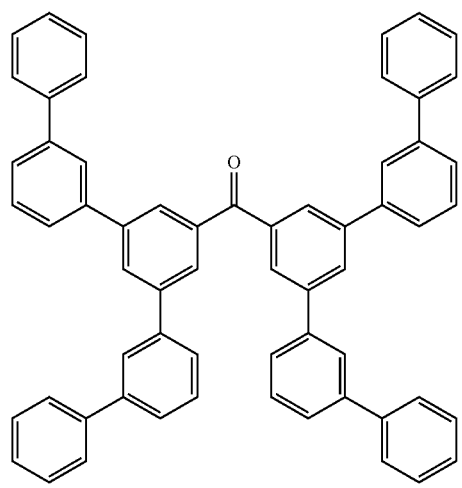
M3
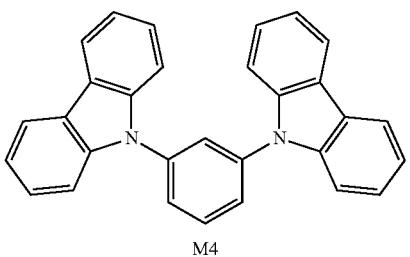
M4

TABLE 3-continued

Structural formulae of the materials used

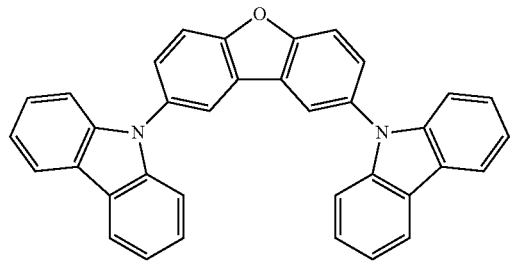

M5

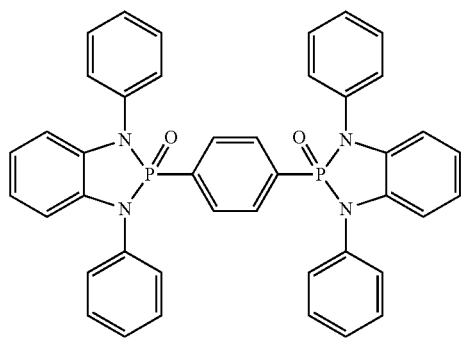

M6

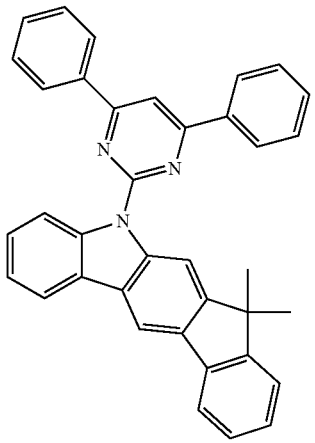

M7

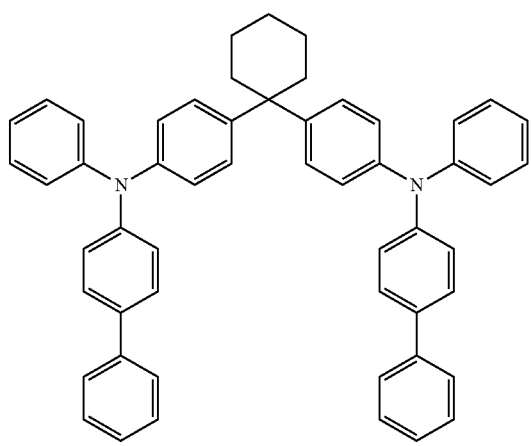

M8

TABLE 3-continued

Structural formulae of the materials used

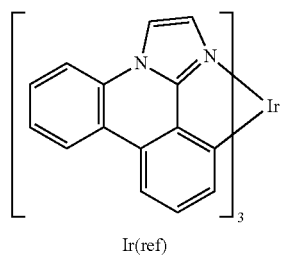

Ir(ref)

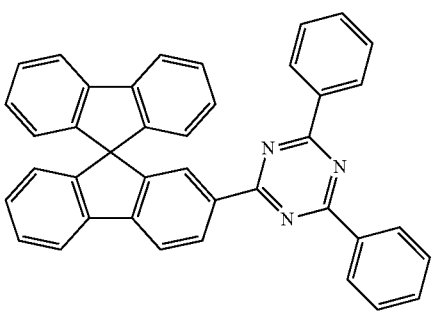

ETM1

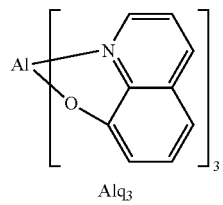

Alq3

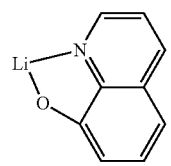

LiQ

Materials according to the invention can also be used from solution and in this case result in significantly simpler OLEDs compared with vacuum-processed OLEDs, but nevertheless having good properties.

The production of components of this type is based on the production of polymeric light-emitting diodes (PLEDs), which has already been described a number of times in the literature (for example in WO 2004/037887 A2). The structure is composed of substrate/ITO/PEDOT (80 nm)/interlayer/emission layer (80 nm)/cathode. The interlayer used serves for hole injection; in this case, HIL-012 from Merck is used. In the present case, the emitters according to the invention for the emission layer are dissolved in toluene besides the matrices. The typical solids content of such solutions is between 16 and 25 g/l if, as here, the layer thickness of 80 nm which is typical for a device is to be achieved by means of spin coating. The emission layer is applied by spin coating in an inert-gas atmosphere, in the present case argon, and dried by heating at 120° C. for 10 min. Finally, a cathode comprising barium and aluminium is applied by vacuum vapour deposition. The layers HBL and ETL used in the above-mentioned examples can also be applied between the EML and the cathode by vapour deposition, and the interlayer may also be replaced by one or more layers, which merely have to satisfy the condition of not being re-detached by the downstream processing step of EML deposition from solution.

The solution-processed devices are also characterised by standard methods in the matrices PS (polystyrene):M8:M1:Ir(LX)$_3$ (26%:14%:42%:20%), and the OLED examples given have not yet been optimised. Table 4 shows the data obtained. It is evident here that the materials according to the invention in the processed OLEDs result in efficient blue- to greenemitting OLEDs.

TABLE 4

Results with materials processed from solution

| Ex. | EML with emitter 80 nm | Voltage [V] at 100 cd/m$^2$ | Max. eff. [cd/A] | CIE (x, y) |
| --- | --- | --- | --- | --- |
| 251 | Ir(L67)$_3$ | 8.3 | 12.6 | 0.21/0.38 |
| 252 | Ir(L68)$_3$ | 8.6 | 10.6 | 0.22/0.41 |
| 253 | Ir(L108)$_3$ | 7.9 | 13.4 | 0.23/0.39 |
| 254 | Ir(L109)$_3$ | 7.7 | 11.3 | 0.24/0.45 |
| 255 | Ir(L110)$_3$ | 8.6 | 9.1 | 0.25/0.49 |
| 256 | Ir(L111)$_3$ | 7.6 | 14.7 | 0.24/0.43 |
| 257 | Ir(L116)$_3$ | 6.9 | 16.4 | 0.28/0.52 |
| 258 | Ir(L117)$_3$ | 7.1 | 14.8 | 0.27/0.50 |
| 259 | Ir(L121)$_3$ | 8.6 | 19.1 | 0.30/0.50 |
| 260 | Ir(L123)$_3$ | 9.5 | 20.6 | 0.32/0.59 |
| 261 | Ir(L124)$_3$ | 8.1 | 17.6 | 0.31/0.54 |
| 262 | Ir(L136)$_3$ | 7.2 | 19.4 | 0.28/0.50 |
| 263 | Ir(L137)$_3$ | 8.6 | 23.4 | 0.33/0.62 |
| 264 | Ir(L143)$_3$ | 7.7 | 22.8 | 0.36/0.60 |
| 265 | Ir(L166)$_3$ | 8.3 | 18.6 | 0.35/0.60 |
| 266 | Ir(L167)$_3$ | 7.9 | 19.5 | 0.36/0.59 |
| 267 | Ir(L168)$_3$ | 8.4 | 16.4 | 0.33/0.62 |
| 268 | Ir(L196)$_3$ | 8.8 | 12.7 | 0.63/0.37 |
| 269 | Ir(L197)$_3$ | 8.7 | 19.8 | 0.58/0.38 |
| 270 | Ir(L198)$_3$ | 7.9 | 8.4 | 0.66/0.34 |
| 271 | Ir(L199)$_3$ | 8.3 | 7.2 | 0.67/0.33 |

The invention claimed is:
1. A compound of the formula (1)

     formula (1)

containing a moiety M(L)$_n$ of the formula (3):

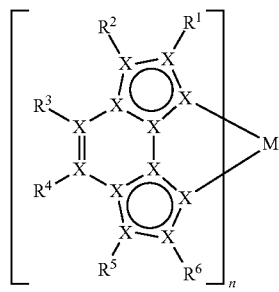     formula (3)

where the following applies to the symbols and indices used:

M is selected from the group consisting of iridium, platinum, copper and gold;

X is selected on each occurrence, identically or differently, from the group consisting of C and N; and all X together represent a 14π electron system;

R$^1$ to R$^6$ are on each occurrence, identically or differently, H, D, F, Cl, Br, I, N(R$^8$)$_2$, CN, NO$_2$, Si(R$^8$)$_3$, B(OR$^8$)$_2$, C(=O)R$^8$, P(=O)(R$^8$)$_2$, S(=O)R$^8$, S(=O)$_2$R$^8$, OSO$_2$R$^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^8$, where one or more non-adjacent CH$_2$ groups is optionally replaced by R$^8$C=CR$^8$, C≡C, Si(R$^8$)$_2$, Ge(R$^8$)$_2$, Sn(R$^8$)$_2$, C=O, C=S, C=Se, C=NR$^8$, P(=O)(R$^8$), SO, SO$_2$, NR$^8$, O, S or CONR$^8$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^8$, or an aryloxy or heteroaryloxy group having 5 to 60 aromatic ring atoms, which is optionally substituted by one or more radicals R$^8$, or an aralkyl or heteroaralkyl group having 5 to 60 aromatic ring atoms, which is optionally substituted by one or more radicals R$^8$, or a diarylamino group, diheteroarylamino group or arylheteroarylamino group having 10 to 40 aromatic ring atoms, which is optionally substituted by one or more radicals R$^8$; R$^1$ and R$^2$ and/or R$^2$ and R$^3$ and/or R$^4$ and R$^5$ and/or R$^5$ and R$^6$ here optionally forms a mono- or polycyclic, aliphatic, aromatic and/or benzo-fused ring system with one another; furthermore, R$^3$ and R$^4$ optionally form a mono- or polycyclic, aliphatic ring system with one another;

with the proviso that R$^1$ to R$^6$ represent a free electron pair if the group X to which these radicals R$^1$ to R$^6$ are bonded is a nitrogen atom with a saturated valence;

R$^8$ is on each occurrence, identically or differently, H, D, F, Cl, Br, I, N(R$^9$)$_2$, CN, NO$_2$, Si(R$^9$)$_3$, B(OR$^9$)$_2$, C(=O)R$^9$, P(=O)(R$^9$)$_2$, S(=O)R$^9$, S(=O)$_2$R$^9$, OSO$_2$R$^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals R$^9$, where one or more non-adjacent CH$_2$ groups is optionally replaced by R$^9$C=CR$^9$, C≡C, Si(R$^9$)$_2$, Ge(R$^9$)$_2$, Sn(R$^9$)$_2$, C=O, C=S, C=Se, C=NR$^9$, P(=O)(R$^9$), SO, SO$_2$, NR$^9$, O, S or CONR$^9$ and where one or more H atoms is optionally replaced by D, F, Cl, Br, I, CN or NO$_2$, or an aromatic or heteroaromatic ring system having 5 to 60 aromatic ring atoms, which optionally in each case be substituted by one or more radicals R$^9$, or an aryloxy or heteroaryloxy group having 5 to 60 aromatic ring atoms, which is optionally substituted by one or more radicals R$^9$, or an aralkyl or heteroaralkyl group having 5 to 60 aromatic ring atoms, which is optionally substituted by one or more radicals R$^9$, or a diarylamino group, diheteroarylamino group or arylheteroarylamino group having 10 to 40 aromatic ring atoms, which is optionally substituted by one or more radicals R$^9$; two or more adjacent radicals R$^8$ here may form a mono- or polycyclic, aliphatic or aromatic ring system with one another;

R$^9$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R$^9$ here may also form a mono- or polycyclic, aliphatic or aromatic ring system with one another;

L' is, identically or differently on each occurrence, any desired co-ligand;

n is 1, 2, 3 or 4;

m is 0, 1, 2, 3, 4, 5 or 6;

a plurality of ligands L, wherein the ligands L bond to the metal M via one carbon atom and one nitrogen atom or via two carbon atoms, and may also be linked to one another or L is optionally linked to L' via any desired bridge V, thus forming a tridentate, tetradentate, pentadentate or hexadentate ligand system, and wherein the compounds of formula (1) are uncharged.

2. The compound according to claim 1, wherein the ligands L bond to the metal M via one carbon atom and one nitrogen atom.

3. The compound according to claim 1, wherein the moiety of the formula (3) is selected from the formula (3b):

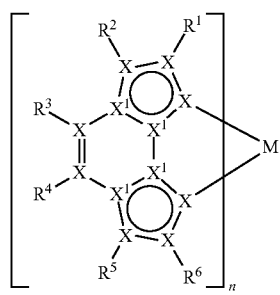

formula (3b)

where the symbols and indices used have the meanings given in claim 1, and furthermore:

$X^1$ is, identically or differently on each occurrence, C or N, with the proviso that at least one group $X^1$ stands for N.

4. The compound according to claim 1, wherein the moieties of the formulae (7) to (8) are selected from the structures of the following formulae (7a) to (8a):

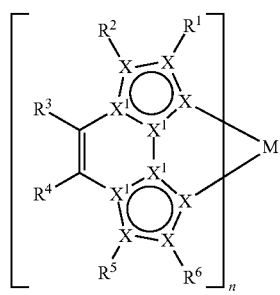

formula (7a)

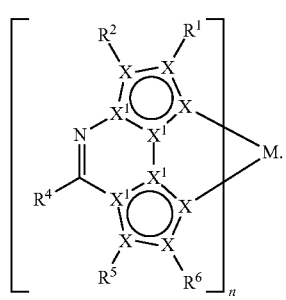

formula (8a)

5. The compound according to claim 1, wherein the moieties of the formula (3) are selected from the structures of the formulae (27)-(30), (50)-(53) and (73)-(76):

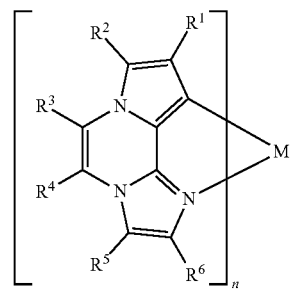

formula (27)

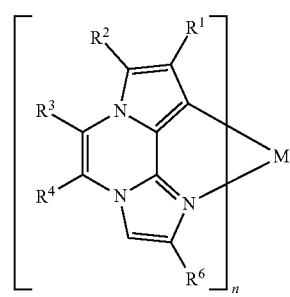

formula (28)

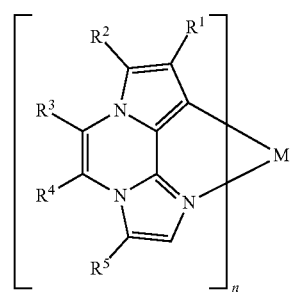

formula (29)

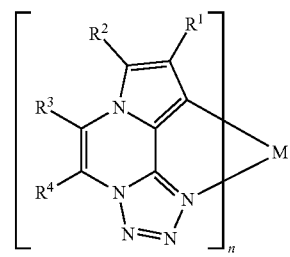

formula (30)

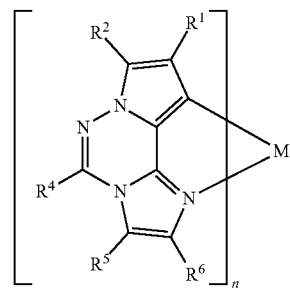

formula (50)

formula (51)
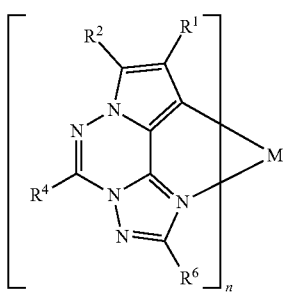

formula (52)
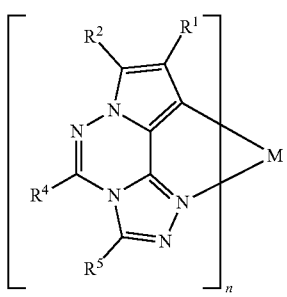

formula (53)
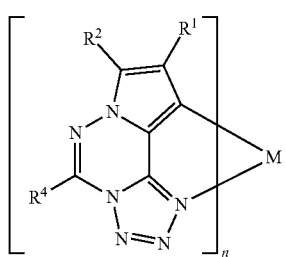

formula (73)
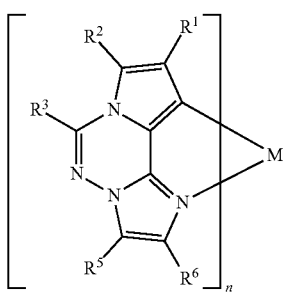

formula (74)
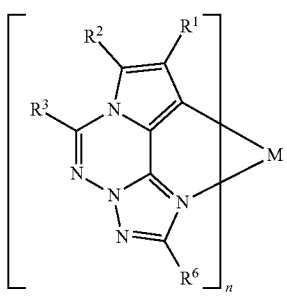

formula (75)
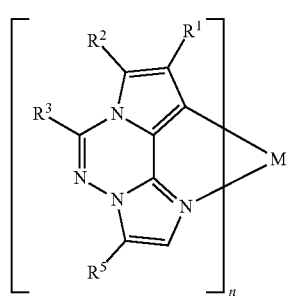

formula (76)
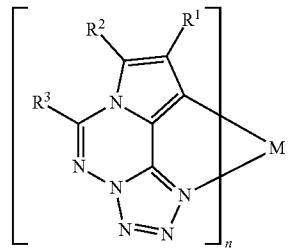

where the symbols and indices used have the meanings indicated in claim 1.

6. The compound according to claim 1, wherein at least one of the substituents $R^2$, $R^3$ and/or $R^4$, is a substituent not equal to hydrogen or deuterium.

7. The compound according to claim 1, wherein the substituent $R^6$ which is in the ortho-position to the metal coordination represents a coordinating group which coordinates to the metal M, and is aryl or heteroaryl groups, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides.

8. The compound according to claim 7, wherein the moiety of the formula (3) is selected from the structures of the formulae (94) to (97):

formula (94)
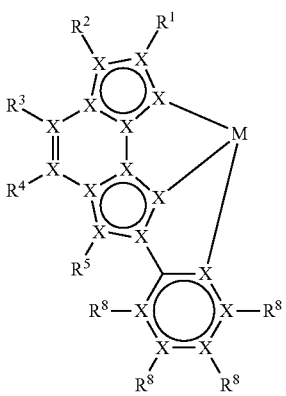

-continued formula (95)
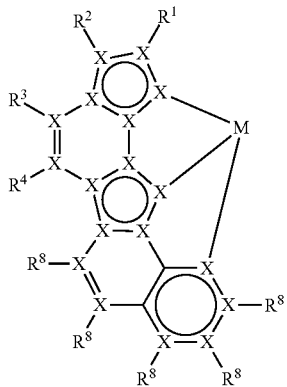

formula (96)
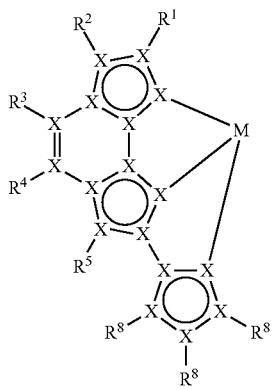

formula (97)
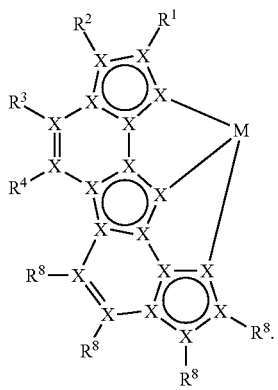

9. The compound according to claim 1, wherein the complexes contain a polydentate ligand, wherein the metal complexes are selected from the formulae (102), (103) and (105):

formula (102)
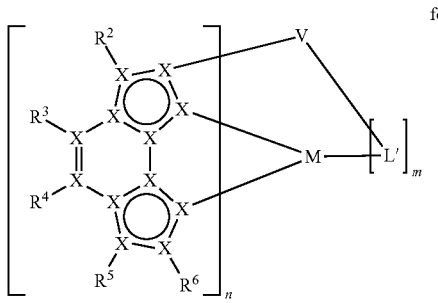

-continued formula (103)
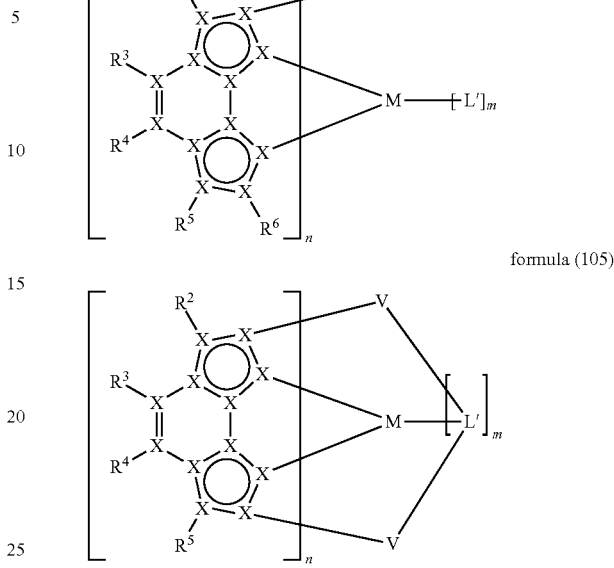

formula (105)
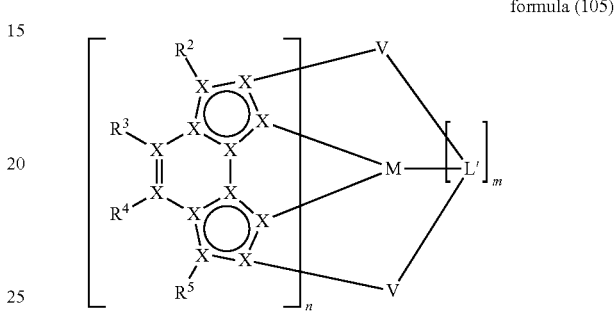

where the symbols used have the meanings given above, and V represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'.

10. The compound according to claim 9, wherein V, if it is a trivalent group, which bridges three ligands L to one another or two ligands L to L' or one ligand L to two ligands L', is selected, identically or differently on each occurrence, from the group consisting of B, $B(R^8)^-$, $B(C(R^8)_2)_3$, $(R^8)B(C(R^8)_2)_3^-$, $B(O)_3$, $(R^8)B(O)_3^-$, $B(C(R^8)_2C(R^8)_2)_3$, $(R^8)B(C(R^8)_2C(R^8)_2)_3^-$, $B(C(R^8)_2O)_3$, $(R^8)B(C(R^8)_2O)_3^-$, $B(OC(R^8)_2)_3$, $(R^8)B(OC(R^8)_2)_3^-$, $C(R^8)$, $CO^-$, $CN(R^8)_2$, $(R^8)C(C(R^8)_2)_3$, $(R^8)C(O)_3$, $(R^8)C(C(R^8)_2C(R^8)_2)_3$, $(R^8)C(C(R^8)_2O)_3$, $(R^8)C(OC(R^8)_2)_3$, $(R^8)C(Si(R^8)_2)_3$, $(R^8)C(Si(R^8)_2C(R^8)_2)_3$, $(R^8)C(C(R^8)_2Si(R^8)_2)_3$, $(R^8)C(Si(R^8)_2Si(R^8)_2)_3$, $Si(R^8)$, $(R^8)Si(C(R^8)_2)_3$, $(R^8)Si(O)_3$, $(R^8)Si(C(R^8)_2C(R^8)_2)_3$, $(R^8)Si(OC(R^8)_2)_3$, $(R^8)Si(C(R^8)_2O)_3$, $(R^8)Si(Si(R^8)_2)_3$, $(R^8)Si(Si(R^8)_2C(R^8)_2)_3$, $(R^8)Si(C(R^8)_2Si(R^8)_2)_3$, $(R^8)Si(Si(R^8)_2Si(R^8)_2)_3$, N, NO, $N(R^8)^+$, $N(C(R^8)_2)_3$, $(R^8)N(C(R^8)_2)_3^+$, $N(C=O)_3$, $N(C(R^8)_2C(R^8)_2)_3$, $(R^8)N(C(R^8)_2C(R^8)_2)_3^+$, P, $P(R^8)^+$, PO, PS, PSe, PTe, $P(O)_3$, $PO(O)_3$, $P(OC(R^8)_2)_3$, $PO(OC(R^8)_2)_3$, $P(C(R^8)_2)_3$, $P(R^8)(C(R^8)_2)_3^+$, $PO(C(R^8)_2)_3$, $P(C(R^8)_2C(R^8)_2)_3$, $P(R^8)(C(R^8)_2C(R^8)_2)_3^+$, $PO(C(R^8)_2C(R^8)_2)_3$, As, $As(R^8)^+$, AsO, AsS, AsSe, AsTe, $As(O)_3$, $AsO(O)_3$, $As(OC(R^8)_2)_3$, $AsO(OC(R^8)_2)_3$, $As(C(R^8)_2)_3$, $As(R^8)(C(R^8)_2)_3^+$, $AsO(C(R^8)_2)_3$, $As(C(R^8)_2C(R^8)_2)_3$, $As(R^8)(C(R^8)_2C(R^8)_2)_3^+$, $AsO(C(R^8)_2C(R^8)_2)_3$, Sb, $Sb(R^8)^+$, SbO, SbS, SbSe, SbTe, $Sb(O)_3$, $SbO(O)_3$, $Sb(OC(R^8)_2)_3$, $SbO(OC(R^8)_2)_3$, $Sb(C(R^8)_2)_3$, $Sb(R^8)(C(R^8)_2)_3^+$, $SbO(C(R^8)_2)_3$, $Sb(C(R^8)_2C(R^8)_2)_3$, $Sb(R^8)(C(R^8)_2C(R^8)_2)_3^+$, $SbO(C(R^8)_2C(R^8)_2)_3$, Bi, $Bi(R^8)^+$, BiO, BiS, BiSe, BiTe, $Bi(O)_3$, $BiO(O)_3$, $Bi(OC(R^8)_2)_3$, $BiO(OC(R^8)_2)_3$, $Bi(C(R^8)_2)_3$, $Bi(R^8)(C(R^8)_2)_3^+$, $BiO(C(R^8)_2)_3$, $Bi(C(R^8)_2C(R^8)_2)_3$, $Bi(R^8)(C(R^8)_2C(R^8)_2)_3^+$, $BiO(C(R^8)_2C(R^8)_2)_3$, $S^+$, $S(C(R^8)_2)_3^+$, $S(C(R^8)_2C(R^8)_2)_3^+$, $Se^+$, $Se(C(R^8)_2)_3^+$, $Se(C(R^8)_2C(R^8)_2)_3^+$, $Te^+$, $Te(C(R^8)_2)_3^+$, $Te(C(R^8)_2C(R^8)_2)_3^+$, or a unit of the formula (106), (107), (108) or (109):

formula (106)

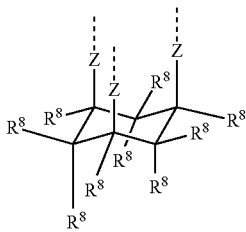

formula (107)

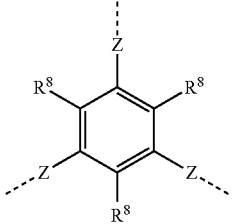

formula (108)

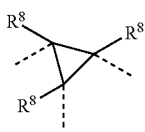

formula (109)

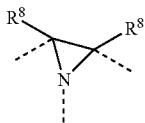

where the dashed bonds in each case indicate the bond to the part-ligands L or L', and Z is selected, identically or differently on each occurrence, from the group consisting of a single bond, O, S, S(=O), S(=O)$_2$, NR$^8$, PR$^8$, P(=O)R$^8$, P(=NR$^8$), C(R$^8$)$_2$, C(=O), C(=NR$^8$), C(=C(R$^8$)$_2$), Si(R$^8$)$_2$ and BR$^8$;

or in that V, if V is a divalent group, which bridges two ligands L to one another or one ligand L to L', is identically or differently on each occurrence, from the group consisting of BR$^8$, B(R$^8$)$_2^-$, C(R$^8$)$_2$, C(=O), Si(R$^8$)$_2$, NR$^8$, PR$^8$, P(R$^8$)$_2^+$, P(=O)(R$^8$), P(=S)(R$^8$), AsR$^8$, As(=O)(R$^8$), As(=S)(R$^8$), O, S, Se, or a unit of the formulae (110) to (119):

formula (110)

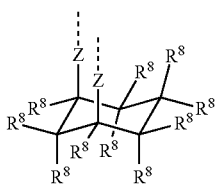

formula (111)

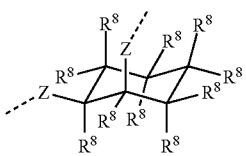

formula (112)

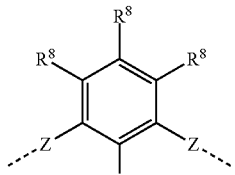

formula (113)

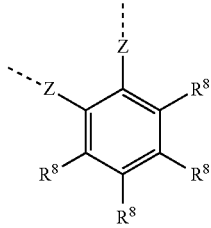

formula (114)

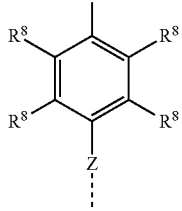

formula (115)

formula (116)

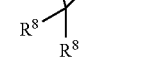

formula (117)

formula (118)

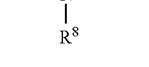

formula (119)

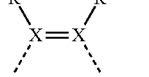

where the dashed bonds in each case indicate the bond to the part-ligands L or L', Z is selected, identically or differently on each occurrence, from the group consisting of a single bond, O, S, S(=O), S(=O)$_2$, NR$^8$, PR$^8$, P(=O)R$^8$, P(=NR$^8$), C(R$^8$)$_2$, C(=O), C(=NR$^8$), C(=C(R$^8$)$_2$), Si(R$^8$)$_2$ and BR$^8$, Y stands on each occurrence, identically or differently, for C(R$^8$)$_2$, N(R$^8$), O or S.

11. The compound according to claim 1, wherein the ligands L' are selected, identically or differently on each occurrence, from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, F⁻, Cl⁻, Br⁻ and I⁻, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, $\eta^5$-cyclopentadienyl, $\eta^5$-pentamethylcyclopentadienyl, $\eta^6$-benzene and $\eta^7$-cycloheptatrienyl, each of which is optionally substituted by one or more radicals $R^1$; and/or the ligands L' are, identically or differently on each occurrence, bidentate ligands L' which, with the metal, form a cyclometallated five- or six-membered ring, the combination of two groups, as depicted by the formulae (120) to (147), where one group bonds via a neutral nitrogen atom or a carbene atom and the other group bonds via a negatively charged carbon atom or a negatively charged nitrogen atom, where the aromatic rings in these groups in each case bond to one another at the position denoted by #, and the position at which the groups coordinate to the metal is denoted by *:

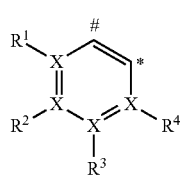

formula (120)

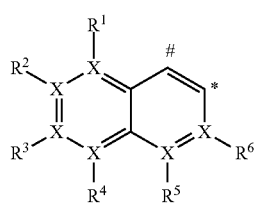

formula (121)

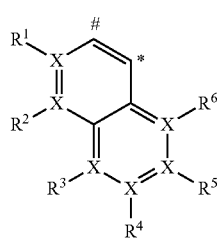

formula (122)

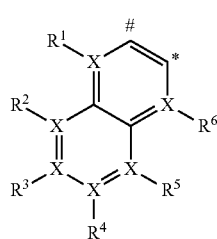

formula (123)

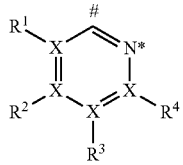

formula (124)

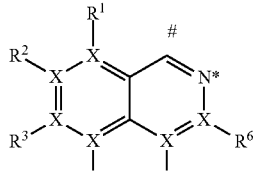

formula (125)

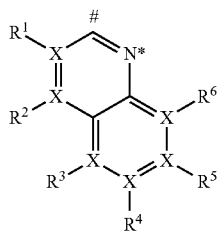

formula (126)

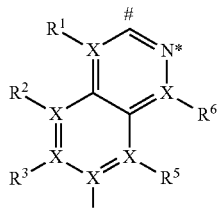

formula (127)

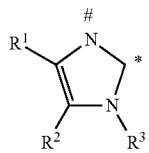

formula (128)

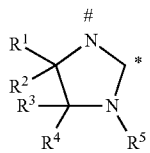

formula (129)

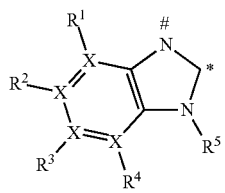

formula (130)

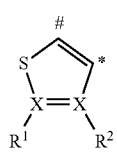

formula (131)

-continued formula (132)
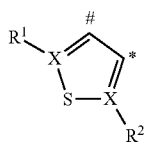

formula (133)
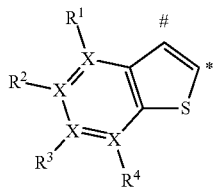

formula (134)
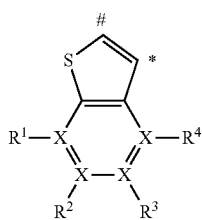

formula (135)
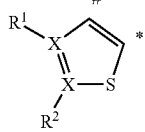

formula (136)
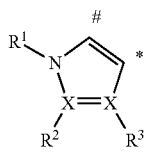

formula (137)
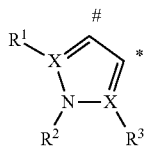

formula (138)
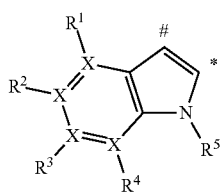

formula (139)
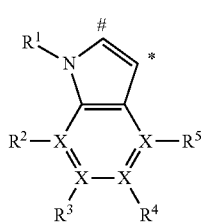

-continued formula (140)
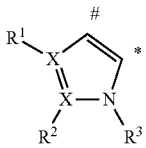

formula (141)
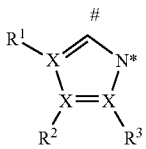

formula (142)
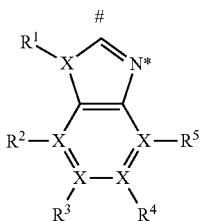

formula (143)
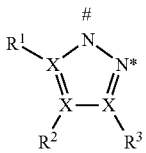

formula (144)
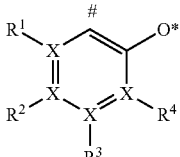

formula (145)
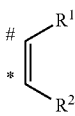

formula (146)
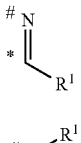

formula (147)
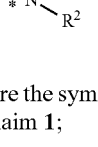

where the symbols used have the same meaning as described in claim 1;

and/or the ligands L' are 1,3,5-cis,cis-cyclohexane derivatives of the formula (148), 1,1,1-tri(methylene)methane derivatives of the formula (149), and 1,1,1-trisubstituted methanes of the formulae (150) and (151):

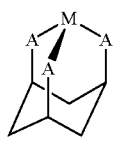

formula (148)

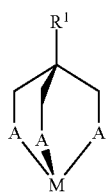

formula (149)

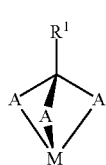

formula (150)

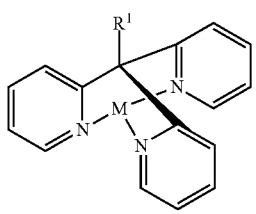

formula (151)

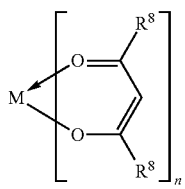

where the coordination to the metal M is shown in each of the formulae (148) to (151), $R^1$ has the meaning given in claim 1, and A stands, identically or differently on each occurrence, for $O^-$, $S^-$, $COO^-$, $P(R^1)_2$ or $N(R^1)_2$.

12. Process for the preparation of the compound according to claim 1 which comprises reacting the corresponding free ligands or a precursor of the ligand with metal alkoxides of the formula (152), with metal ketoketonates of the formula (153) or with metal halides of the formula (154):

$M(OR^8)_n$          formula (152)

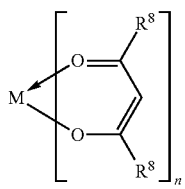

formula (153)

$MHal_n$          formula (154)

where the symbols M, n and $R^8$ have the meanings indicated above, and Hal=F, Cl, Br or I, or with metal compounds which carry both alkoxide and/or halide and/or hydroxyl radicals as well as ketoketonate radicals and may also be charged.

13. An oligomer, polymer or dendrimer comprising one or more of the compounds according to claim 1, where at least one of the radicals $R^1$ to $R^6$ and $R^8$ defined above represents a bond to the polymer or dendrimer.

14. An electronic device comprising at least one compound according to claim 1.

15. The electronic device as claimed in claim 14, wherein the electronic device selected from the group consisting of organic electroluminescent device (OLED, PLED), organic integrated circuit (O-IC), organic field-effect transistor (O-FET), organic thin-film transistor (O-TFT), organic light-emitting transistor (O-LET), organic solar cells (O-SCs), organic optical detector, organic photoreceptor, organic field-quench device (O-FQD), light-emitting electrochemical cell (LEC) and organic laser diode (O-laser).

16. An organic electroluminescent device which comprises the compound according to claim 1 is employed as emitting compound in one or more emitting layers.

17. The organic electroluminescent device according to claim 16, wherein the matrix material of the emitting layer is selected from ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives and zinc complexes.

18. A compound of the formula (1)

$M(L)_n(L')_m$          formula (1)

containing a moiety $M(L)_n$ of the formula (5) or formula (6)

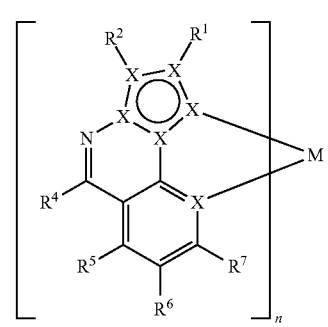

formula (5)

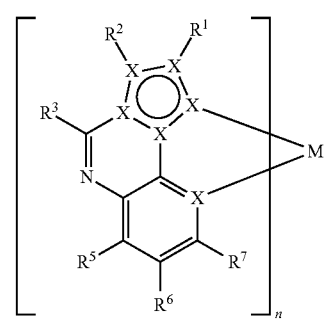

formula (6)

where the following applies to the symbols and indices used:

M is selected from the group consisting of iridium, platinum, copper and gold;

X is selected on each occurrence, identically or differently, from the group consisting of C and N; and all X together represent a 14π a electron system;

$R^1$ to $R^7$ are on each occurrence, identically or differently, H, D, F, Cl, Br, I, $N(R^8)_2$, CN, $NO_2$, $Si(R^8)_3$, $B(OR^8)_2$, $C(=O)R^8$, $P(=O)(R^8)_2$, $S(=O)R^8$, $S(=O)_2R^8$, $OSO_2R^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^8$, where one or more non-adjacent $CH_2$ groups is optionally replaced by $R^8C=CR^8$, $C≡C$, $Si(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which is optionally substituted by one or more radicals $R^8$, or an aralkyl or heteroaralkyl group having 5 to 60 aromatic ring atoms, which is optionally substituted by one or more radicals $R^8$, or a diarylamino group, diheteroarylamino group or arylheteroarylamino group having 10 to 40 aromatic ring atoms, which is optionally substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here optionally forms a mono- or polycyclic, aliphatic, aromatic and/or benzo-fused ring system with one another; furthermore, $R^3$ and $R^4$ optionally form a mono- or polycyclic, aliphatic ring system with one another;

with the proviso that $R^1$ to $R^7$ represent a free electron pair if the group X to which these radicals $R^1$ to $R^7$ are bonded is a nitrogen atom with a saturated valence;

$R^8$ is on each occurrence, identically or differently, H, D, F, Cl, Br, I, $N(R^9)_2$, CN, $NO_2$, $Si(R^9)_3$, $B(OR^9)_2$, $C(=O)R^9$, $P(=O)(R^9)_2$, $S(=O)R^9$, $S(=O)_2R^9$, $OSO_2R^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^9$, where one or more non-adjacent $CH_2$ groups is optionally replaced by $R^9C=CR^9$, $C≡C$, $Si(R^9)_2$, $Ge(R^9)_2$, $Sn(R^9)_2$, $C=O$, $C=S$, $C=Se$, $C=NR^9$, $P(=O)(R^9)$, SO, $SO_2$, $NR^9$, O, S or $CONR^9$ and where one or more H atoms is optionally replaced by D, F, Cl, Br, I, CN or $NO_2$, or an aromatic or heteroaromatic ring system having 5 to 60 aromatic ring atoms, which optionally in each case be substituted by one or more radicals $R^9$, or an aryloxy or heteroaryloxy group having 5 to 60 aromatic ring atoms, which is optionally substituted by one or more radicals $R^9$, or an aralkyl or heteroaralkyl group having 5 to 60 aromatic ring atoms, which is optionally substituted by one or more radicals $R^9$, or a diarylamino group, diheteroarylamino group or arylheteroarylamino group having 10 to 40 aromatic ring atoms, which is optionally substituted by one or more radicals $R^9$; two or more adjacent radicals $R^8$ here may form a mono- or polycyclic, aliphatic or aromatic ring system with one another;

$R^9$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^9$ here may also form a mono- or polycyclic, aliphatic or aromatic ring system with one another;

L' is, identically or differently on each occurrence, any desired co-ligand;

n is 1, 2, 3 or 4;

m is 0, 1, 2, 3, 4, 5 or 6;

a plurality of ligands L here may also be linked to one another or L is optionally linked to L' via any desired bridge V, thus &fulling a tridentate, tetradentate, pentadentate or hexadentate ligand system, and wherein the compounds of formula (1) are uncharged.

19. The compound according to claim 18, wherein the moieties of the formulae (5) to (6) are selected from the structures of the following formulae (5a) to (6a):

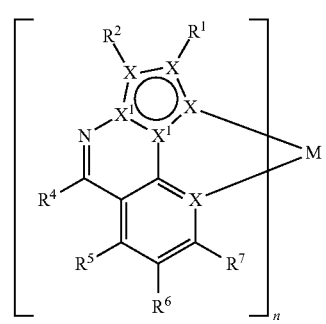

formula (5a)

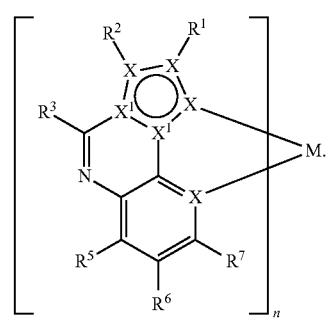

formula (6a)

20. The compound according to claim 18, wherein the ligands L bond to the metal M via one carbon atom and one nitrogen atom.

21. The compound according to claim 18, wherein at least one of the substituents $R^2$, $R^3$ and/or $R^4$, is a substituent not equal to hydrogen or deuterium.

22. The compound according to claim 18, wherein the ligands L' are selected, identically or differently on each occurrence, from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$ and $I^-$, alkylacetylides, arylacetylides, cyanide, cyanate, isocyanate, thio-cyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, $η^5$-cyclopenta-dienyl, $η^5$-pentamethylcyclopentadienyl, $η^6$-benzene and $η^7$-cycloheptatrienyl, each of which is optionally substituted by one or more radicals $R^1$; and/or the ligands L' are, identically or differently on each occurrence, bidentate ligands L' which, with the metal, form a cyclometallated five- or six-membered ring, the combination of two groups, as depicted by the formulae (120) to (147), where one group bonds via a neutral nitrogen atom or a carbene atom and the other group bonds via a negatively charged carbon atom or a negatively charged nitrogen atom, where the aromatic rings in these groups in each case bond to one another at the position denoted by #, and the position at which the groups coordinate to the metal is denoted by *:
formula (120)
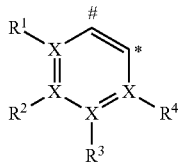
formula (121)
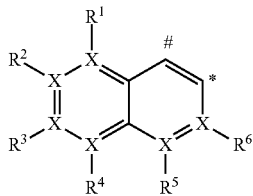
formula (122)
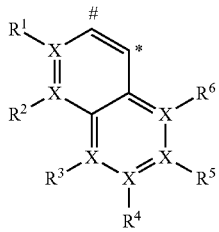
formula (123)
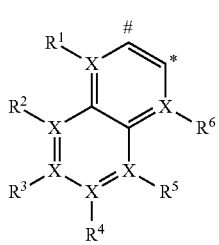
formula (124)
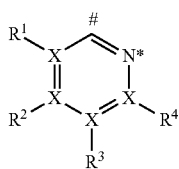
formula (125)
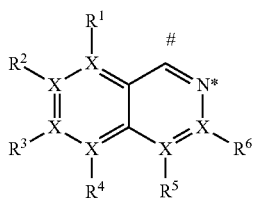
formula (126)
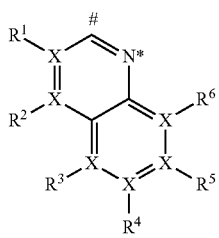
formula (127)
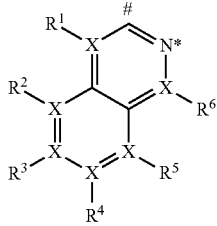
formula (128)
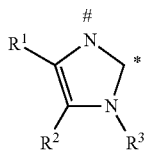
formula (129)
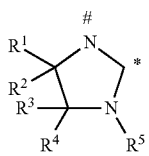
formula (130)
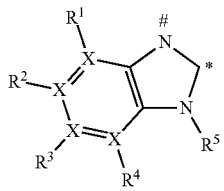
formula (131)
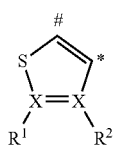
formula (132)
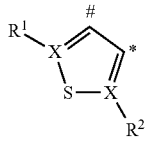
formula (133)
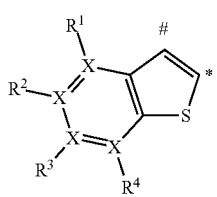
formula (134)
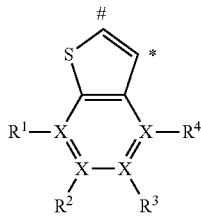

-continued formula (135)
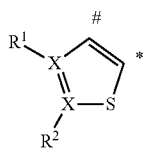

formula (136)
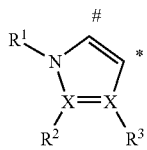

formula (137)
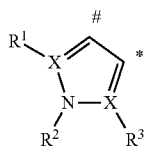

formula (138)
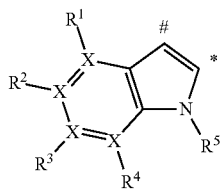

formula (139)
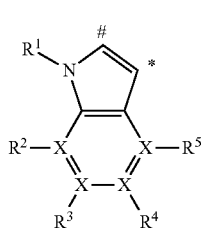

formula (140)
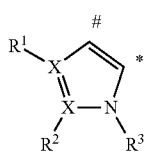

formula (141)
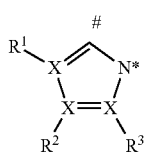

formula (142)
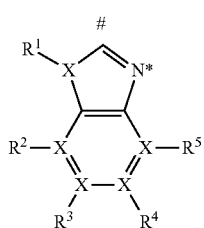

formula (143)
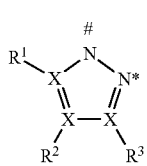

formula (144)
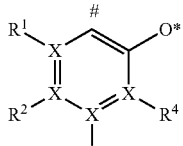

formula (145)
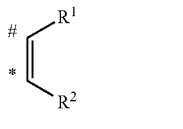

formula (146)
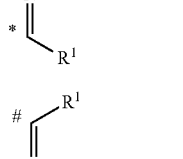

formula (147)
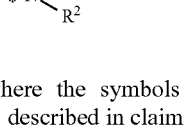

where the symbols used have the same meaning as described in claim 18;

and/or the ligands L' are 1,3,5-cis,cis-cyclohexane derivatives of the formula (148), 1,1,1-tri(methylene)methane derivatives of the formula (149), and 1,1,1-trisubstituted methanes of the formulae (150) and (151):

formula (148)
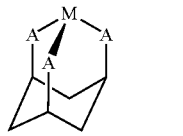

formula (149)
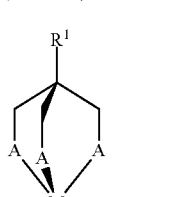

formula (150)
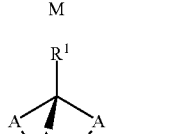

formula (151)
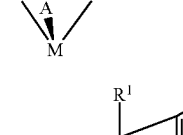

where the coordination to the metal M is shown in each of the formulae (148) to (151), $R^1$ has the meaning given in claim 18, and A stands, identically or differently on each occurrence, for $O^-$, $S^-$, $COO^-$, $P(R^1)_2$ or $N(R^1)_2$.

23. Process for the preparation of the compound according to claim 18 which comprises reacting the corresponding free ligands or a precursor of the ligand with metal alkoxides of the formula (152), with metal ketoketonates of the formula (153) or with metal halides of the folumla (154):

M(OR$^8$)$_n$            formula (152)

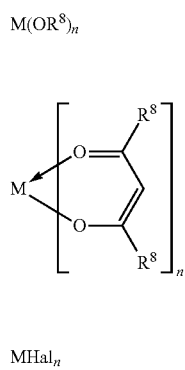

formula (153)

MHal$_n$            formula (154)

where the symbols M, n and R$^8$ have the meanings indicated above, and Hal=F, Cl, Br or I, or with metal compounds which carry both alkoxide and/or halide and/or hydroxyl radicals as well as ketoketonate radicals and may also be charged.

24. An oligomer, polymer or dendrimer comprising one or more of the compounds according to claim 18, where at least one of the radicals R$^1$ to R$^8$ defined above represents a bond to the polymer or dendrimer.

25. An electronic device comprising at least one compound according to claim 18.

26. The electronic device as claimed in claim 25, wherein the electronic device selected from the group consisting of organic electroluminescent device (OLED, PLED), organic integrated circuit (O-IC), organic field-effect transistor (O-FET), organic thin-film transistor (O-TFT), organic light-emitting transistor (O-LET), organic solar cells (O-SCs), organic optical detector, organic photoreceptor, organic field-quench device (O-FQD), light-emitting electrochemical cell (LEC) and organic laser diode (O-laser).

27. An organic electroluminescent device which comprises the compound according to claim 18 is employed as emitting compound in one or more emitting layers.

28. The organic electroluminescent device according to claim 27, wherein the one or more emitting layers further comprises a matrix material selected from ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives and zinc complexes.

29. A compound of the formula (1)

M(L)$_n$(L')$_m$            formula (1)

containing a moiety M(L)$_n$ selected from the structures of the foimulae (9) to (12), (14)-(17), (25), (26) or (31) to (77):

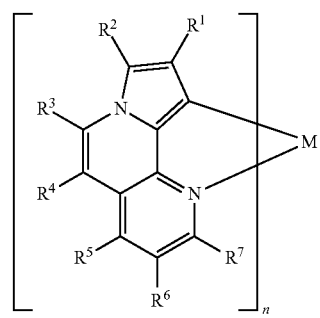

formula (9)

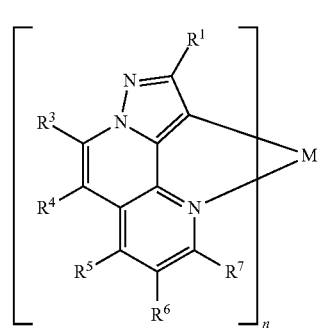

formula (10)

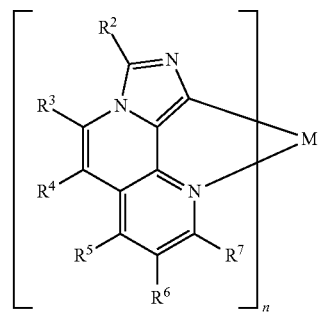

formula (11)

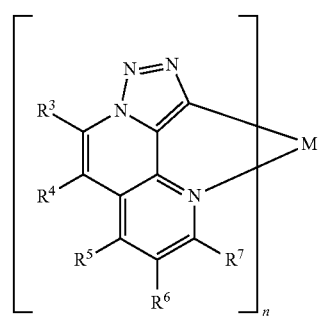

formula (12)

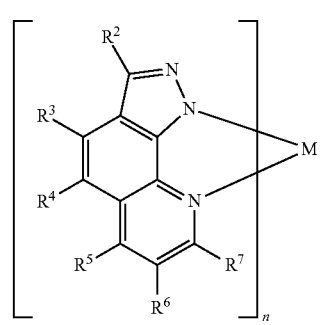

formula (14)

formula (15) 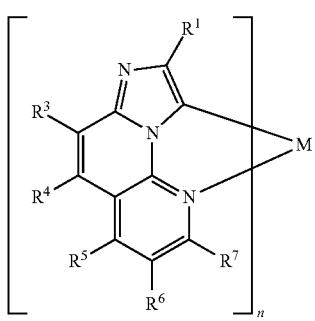
formula (16) 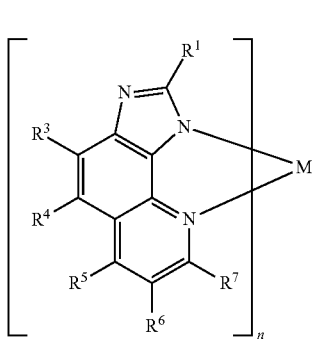
formula (17) 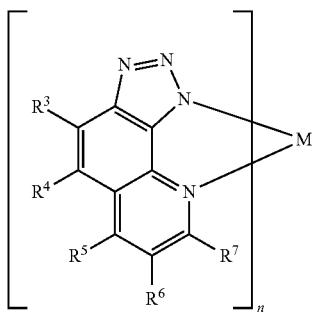
formula (25) 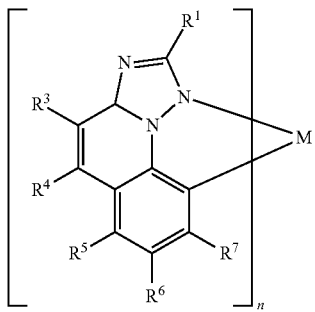
formula (26) 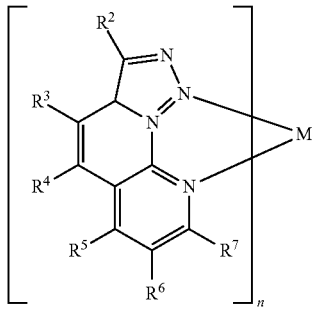
formula (31) 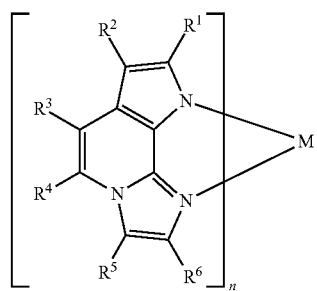
formula (32) 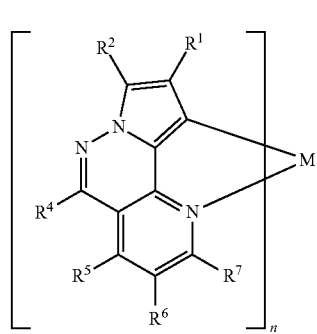
formula (33) 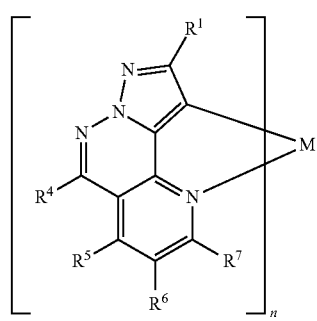
formula (34) 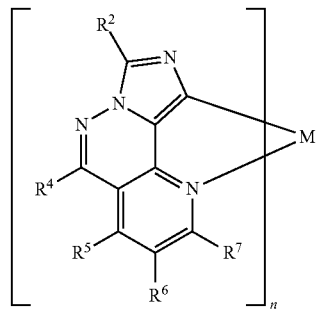
formula (35) 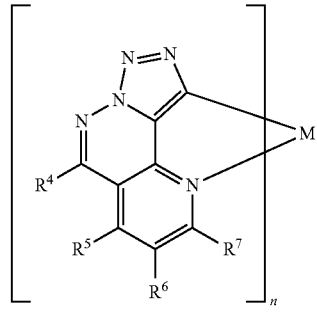

formula (36)
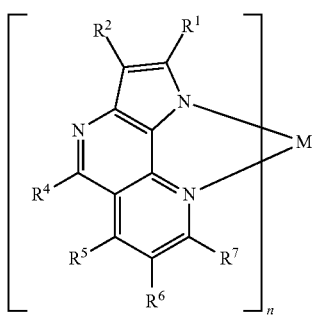
formula (37)
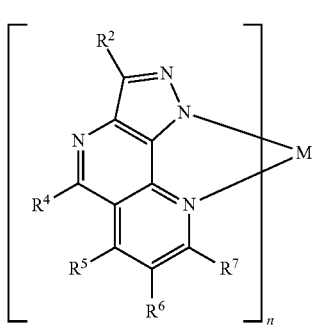
formula (38)
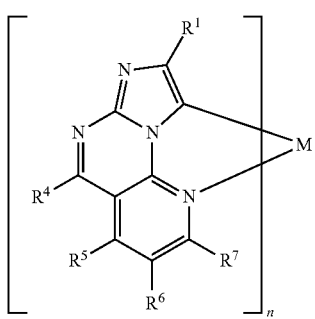
formula (39)
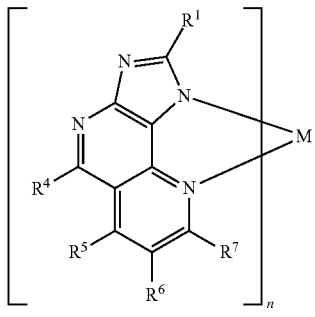
formula (40)
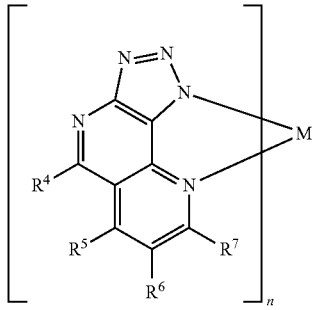
formula (41)
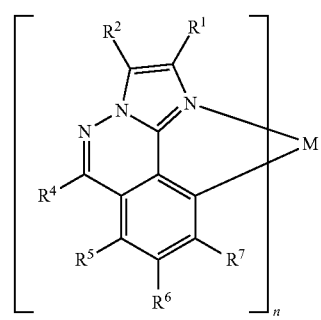
formula (42)
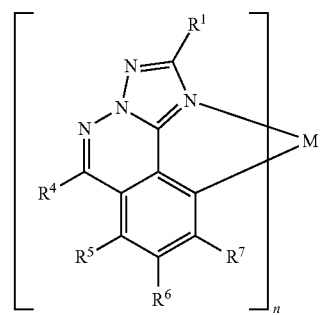
formula (43)
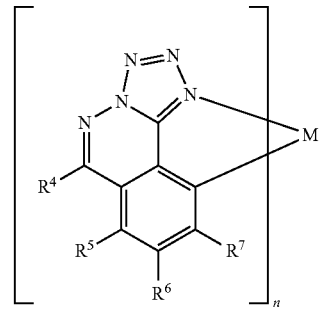
formula (44)
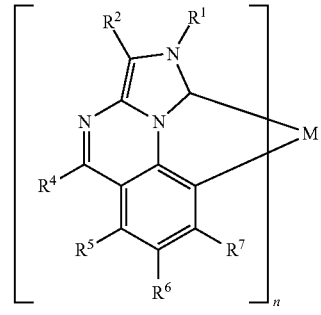
formula (45)
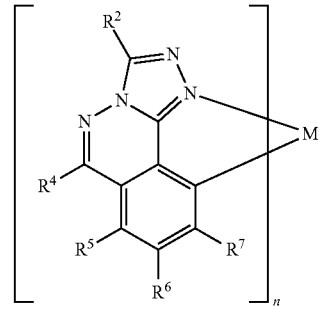

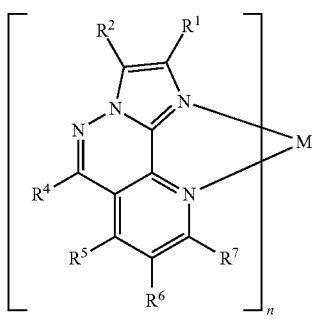
formula (46)
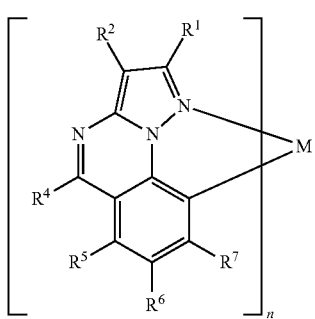
formula (47)
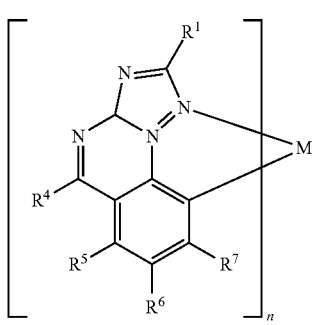
formula (48)
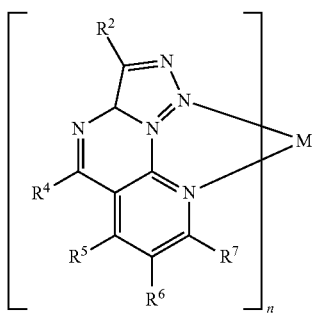
formula (49)
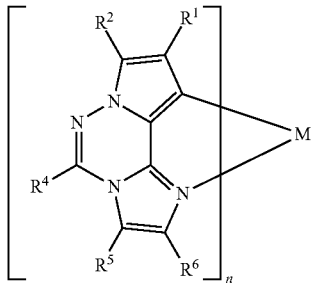
formula (50)
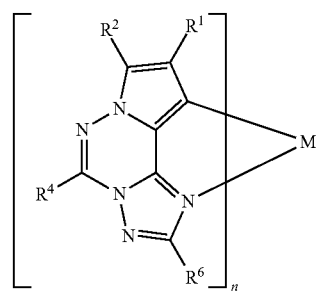
formula (51)
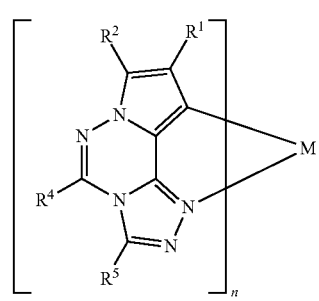
formula (52)
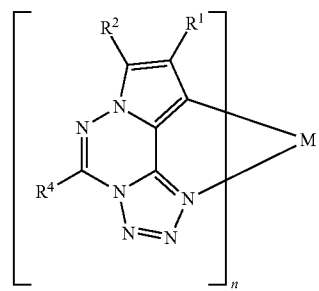
formula (53)
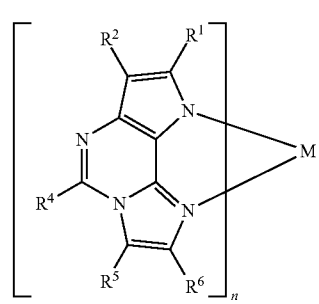
formula (54)
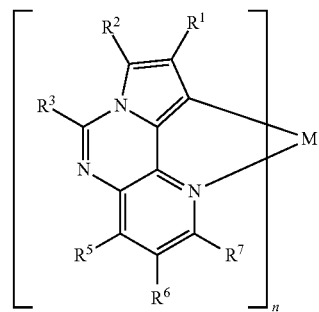
formula (55)

formula (56)
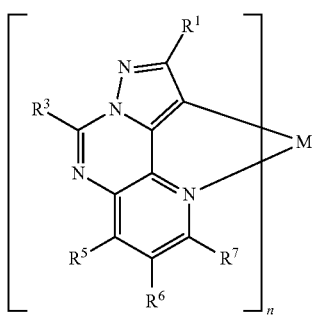
formula (57)
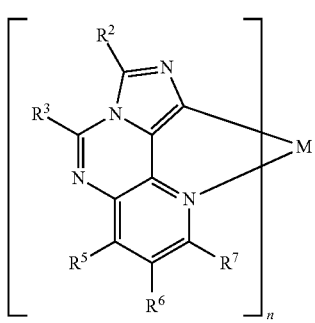
formula (58)
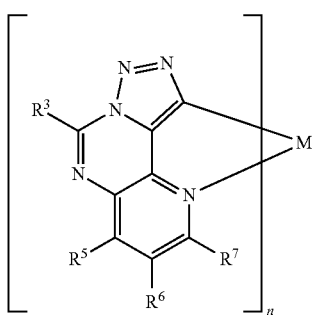
formula (59)
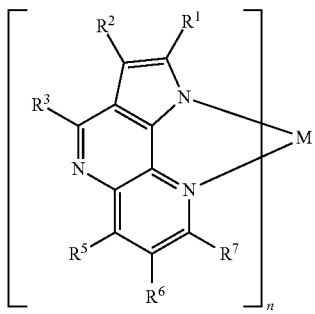
formula (60)
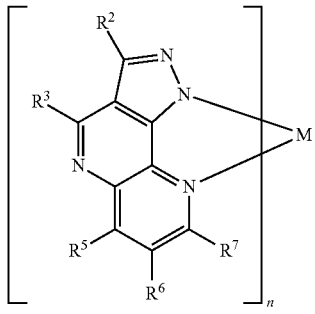
formula (61)
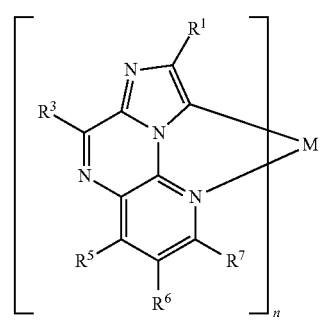
formula (62)
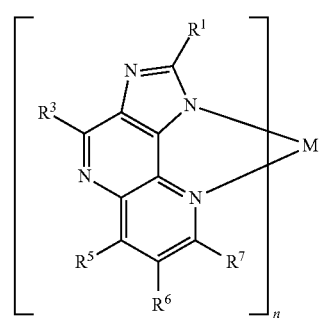
formula (63)
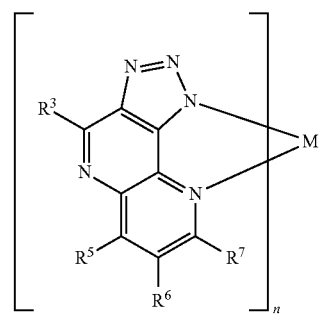
formula (64)
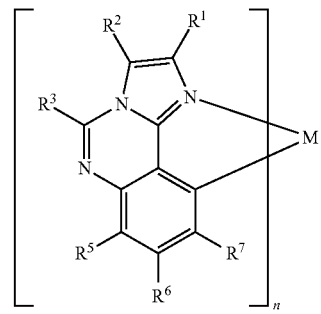
formula (65)
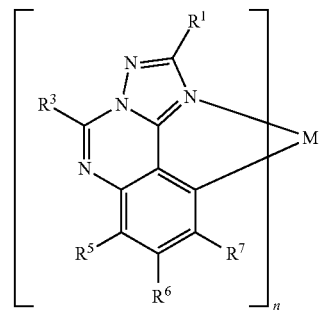

formula (66)
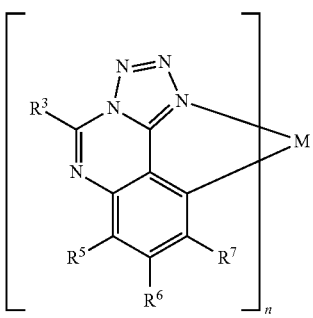
formula (67)
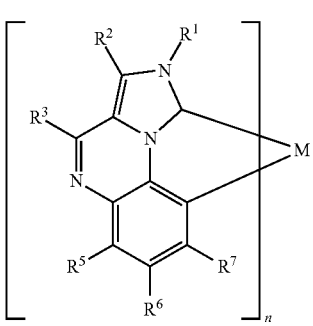
formula (68)
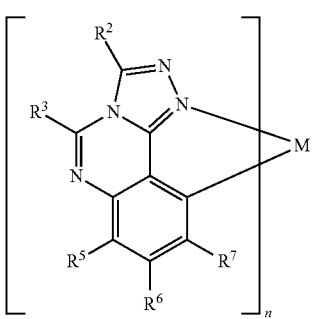
formula (69)
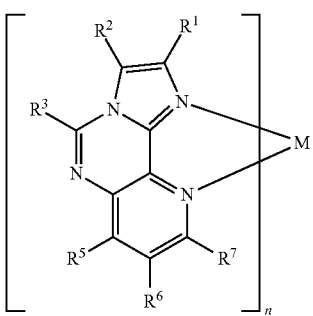
formula (70)
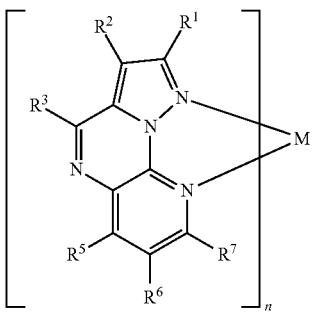
formula (71)
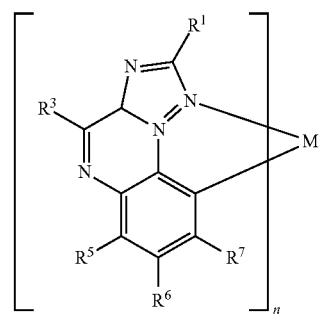
formula (72)
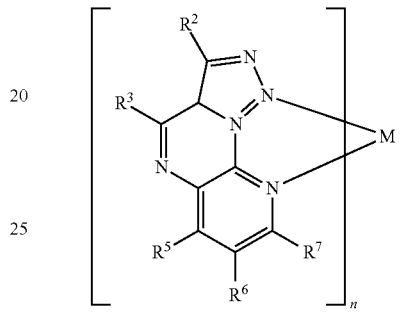
formula (73)
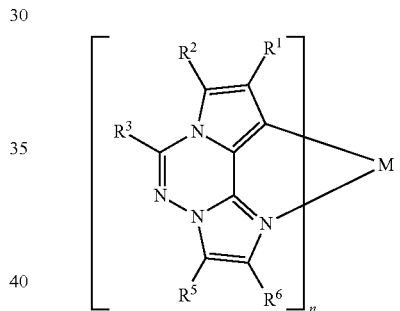
formula (74)
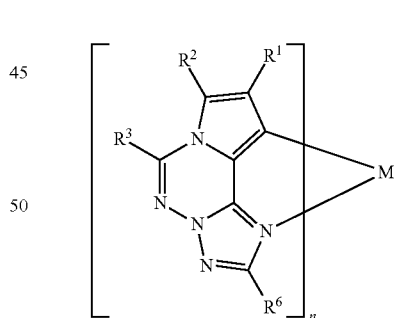
formula (75)
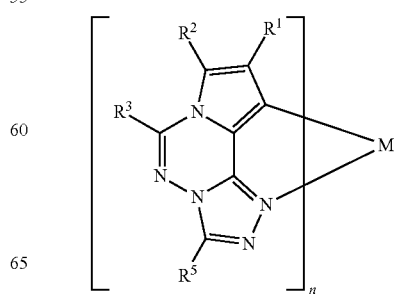

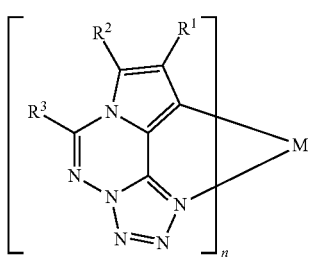

formula (76)

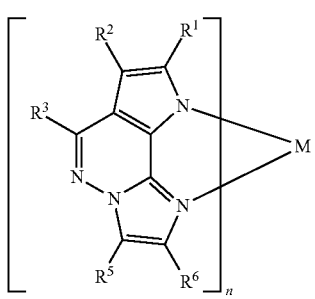

formula (77)

where the following applies to the symbols and indices used:

M is selected from the group consisting of iridium, platinum, copper and gold;

$R^1$ to $R^7$ are on each occurrence, identically or differently, H, D, F, Cl, Br, I, $N(R^8)_2$, CN, $NO_2$, $Si(R^8)_3$, $B(OR^8)_2$, $C(=O)R^8$, $P(=O)(R^8)_2$, $S(=O)R^8$, $S(=O)_2R^8$, $OSO_2R^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^8$, where one or more non-adjacent $CH_2$ groups is optionally replaced by $R^8C=CR^8$, $C\equiv C$, $Si(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which is optionally substituted by one or more radicals $R^8$, or an aralkyl or heteroaralkyl group having 5 to 60 aromatic ring atoms, which is optionally substituted by one or more radicals $R^8$, or a diarylamino group, diheteroarylamino group or arylheteroarylamino group having 10 to 40 aromatic ring atoms, which is optionally substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here optionally forms a mono- or polycyclic, aliphatic, aromatic and/or benzo-fused ring system with one another; furthermore, $R^3$ and $R^4$ optionally form a mono- or polycyclic, aliphatic ring system with one another;

with the proviso that $R^1$ to $R^7$ represent a free electron pair if the group X to which these radicals $R^1$ to $R^7$ are bonded is a nitrogen atom with a saturated valence;

$R^8$ is on each occurrence, identically or differently, H, D, F, Cl, Br, I, $N(R^9)_2$, CN, $NO_2$, $Si(R^9)_3$, $B(OR^9)_2$, $C(=O)R^9$, $P(=O)(R^9)_2$, $S(=O)R^9$, $S(=O)_2R^9$, $OSO_2R^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^9$, where one or more non-adjacent $CH_2$ groups is optionally replaced by $R^9C=CR^9$, $C\equiv C$, $Si(R^9)_2$, $Ge(R^9)_2$, $Sn(R^9)_2$, $C=O$, $C=S$, $C=Se$, $C=NR^9$, $P(=O)(R^9)$, SO, $SO_2$, $NR^9$, O, S or $CONR^9$ and where one or more H atoms is optionally replaced by D, F, Cl, Br, I, CN or $NO_2$, or an aromatic or heteroaromatic ring system having 5 to 60 aromatic ring atoms, which optionally in each case be substituted by one or more radicals $R^9$, or an aryloxy or heteroaryloxy group having 5 to 60 aromatic ring atoms, which is optionally substituted by one or more radicals $R^9$, or an aralkyl or heteroaralkyl group having 5 to 60 aromatic ring atoms, which is optionally substituted by one or more radicals $R^9$, or a diarylamino group, diheteroarylamino group or arylheteroarylamino group having 10 to 40 aromatic ring atoms, which is optionally substituted by one or more radicals $R^9$; two or more adjacent radicals $R^8$ here may form a mono- or polycyclic, aliphatic or aromatic ring system with one another;

$R^9$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^9$ here may also form a mono- or polycyclic, aliphatic or aromatic ring system with one another;

L' is, identically or differently on each occurrence, any desired co-ligand;

n is 1, 2, 3 or 4;

m is 0, 1, 2, 3, 4, 5 or 6;

a plurality of ligands L here may also be linked to one another or L is optionally linked to L' via any desired bridge V, thus forming a tridentate, tetradentate, pentadentate or hexadentate ligand system, and wherein the compounds of formmla (1) are uncharged.

30. The compound according to claim 29, wherein at least one of the substituents $R^2$, $R^3$ and/or $R^4$, is a substituent not equal to hydrogen or deuterium.

31. The compound according to claim 29, wherein the ligands L' are selected, identically or differently on each occurrence, from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$ and $I^-$, alkylacetylides, arylacetylides, cyanide, cyanate, isocyanate, thio-cyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates derived from dialcohols, dithiolates derived from dithiols, borates of nitrogen-containing heterocycles, $\eta^5$-cyclopenta-dienyl, $\eta^5$-pentamethylcyclopentadienyl, $\eta^6$-benzene and $\eta^7$-cycloheptatrienyl, each of which is optionally substituted by one or more radicals $R^1$; and/or the ligands L' are, identically or differently on each occurrence, bidentate ligands L' which, with the metal, form a cyclometallated five- or six-membered ring, the combination of two groups, as depicted by the folinulae (120) to (147), where one group bonds via a neutral nitrogen atom or a carbene atom and the other group bonds via a negatively charged carbon atom or a negatively charged nitrogen atom, where the aromatic rings in these groups in each case bond to one another at the position denoted by #, and the position at which the groups coordinate to the metal is denoted by *:
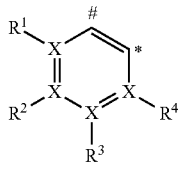
formula (120)
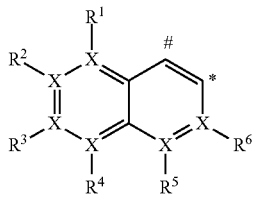
formula (121)
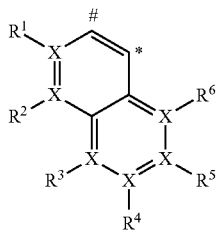
formula (122)
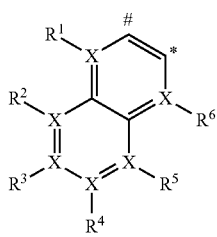
formula (123)
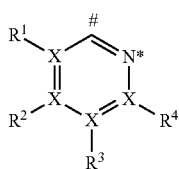
formula (124)
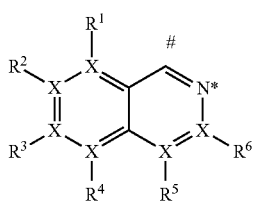
formula (125)
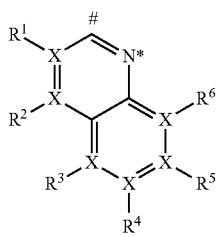
formula (126)
-continued
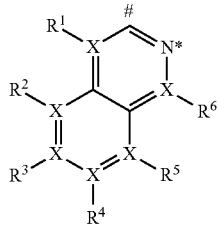
formula (127)
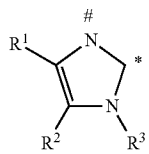
formula (128)
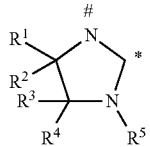
formula (129)
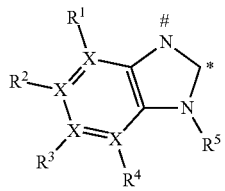
formula (130)
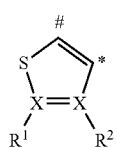
formula (131)
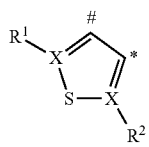
formula (132)
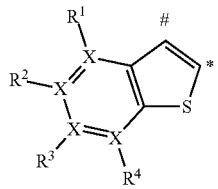
formula (133)
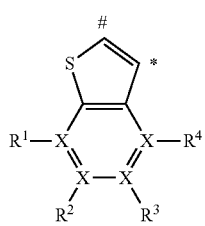
formula (134)

-continued

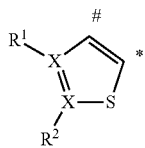
formula (135)

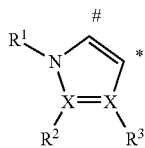
formula (136)

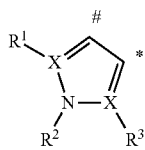
formula (137)

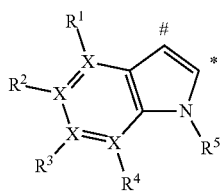
formula (138)

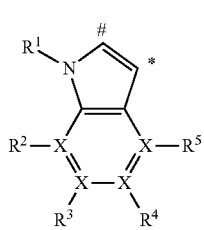
formula (139)

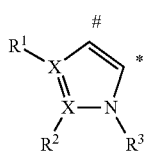
formula (140)

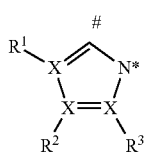
formula (141)

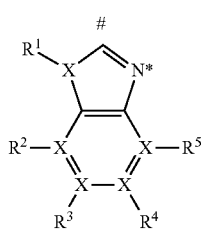
formula (142)

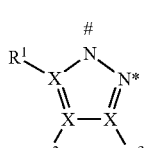
formula (143)

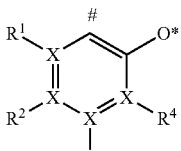
formula (144)

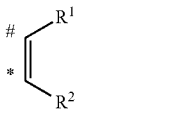
formula (145)

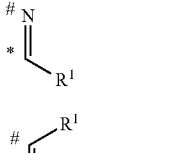
formula (146)

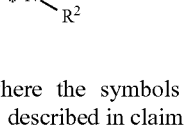
formula (147)

where the symbols used have the same meaning as described in claim 18;

and/or the ligands L' are 1,3,5-cis,cis-cyclohexane derivatives of the formula (148), 1,1,1-tri(methylene)methane derivatives of the formula (149), and 1,1,1-trisubstituted methanes of the formulae (150) and (151):

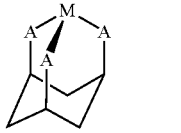
formula (148)

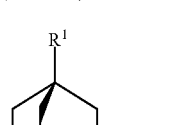
formula (149)

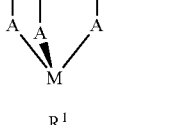
formula (150)

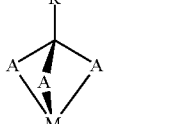
formula (151)

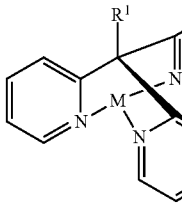

where the coordination to the metal M is shown in each of the formulae (148) to (151), $R^1$ has the meaning given in claim 29, and A stands, identically or differently on each occurrence, for $O^-$, $S^-$, $COO^-$, $P(R^1)_2$ or $N(R^1)_2$.

32. Process for the preparation of the compound according to claim 29 which comprises reacting the corresponding free ligands or a precursor of the ligand with metal alkoxides of the formula (152), with metal ketoketonates of the formula (153) or with metal halides of the formula (154):

$$M(OR^8)_n \quad \text{formula (152)}$$

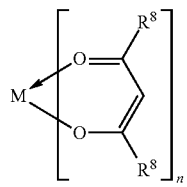

formula (153)

$$MHal_n \quad \text{formula (154)}$$

where the symbols M, n and $R^8$ have the meanings indicated above, and Hal=F, Cl, Br or I, or with metal compounds which carry both alkoxide and/or halide and/or hydroxyl radicals as well as ketoketonate radicals and may also be charged.

33. An oligomer, polymer or dendrimer comprising one or more of the compounds according to claim 29, where at least one of the radicals $R^1$ to $R^8$ defined above represents a bond to the polymer or dendrimer.

34. An electronic device comprising at least one compound according to claim 29.

35. The electronic device as claimed in claim 34, wherein the electronic device selected from the group consisting of organic electroluminescent device (OLED, PLED), organic integrated circuit (O-IC), organic field-effect transistor (O-FET), organic thin-film transistor (O-TFT), organic light-emitting transistor (O-LET), organic solar cells (O-SCs), organic optical detector, organic photoreceptor, organic field-quench device (O-FQD), light-emitting electrochemical cell (LEC) and organic laser diode (O-laser).

36. An organic electroluminescent device which comprises the compound according to claim 29 is employed as emitting compound in one or more emitting layers.

37. The organic electroluminescent device according to claim 36, wherein the one or more emitting layers further comprises a matrix material selected from ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives and zinc complexes.

38. A compound of the formula (1)

$$M(L)_n(L')_m \quad \text{formula (1)}$$

containing a moiety $M(L)_n$ selected from the structures of the formulae (90) to (93) or wherein the metal complexes are selected from the formulae (98) to (101) and (104):

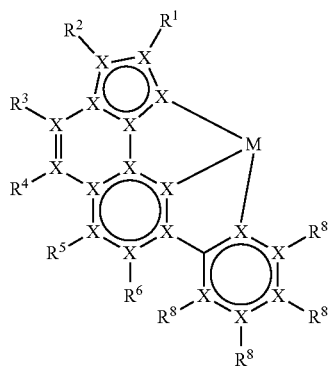

formula (90)

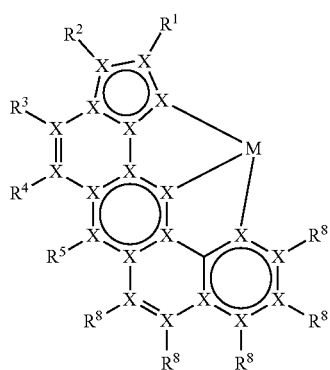

formula (91)

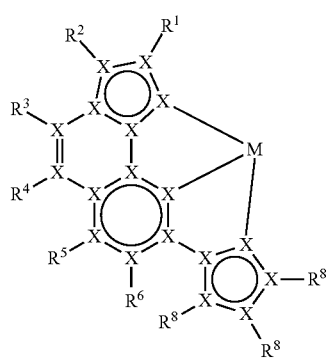

formula (92)

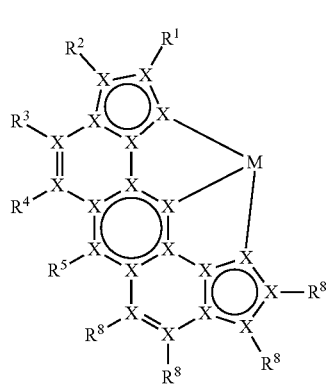

formula (93)

formula (98)

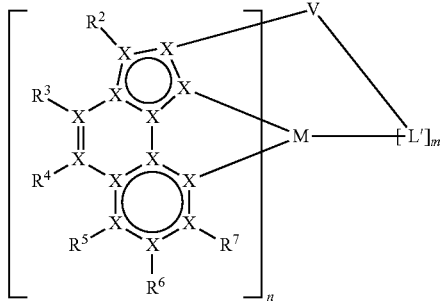

formula (99)

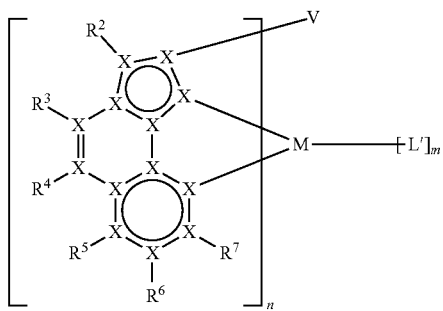

formula (100)

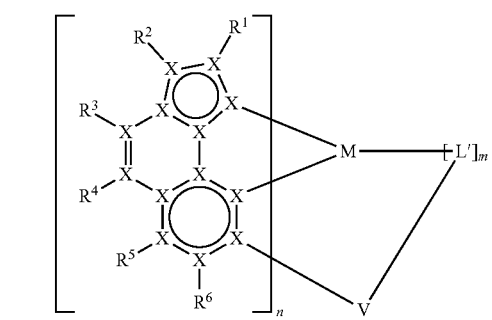

formula (101)

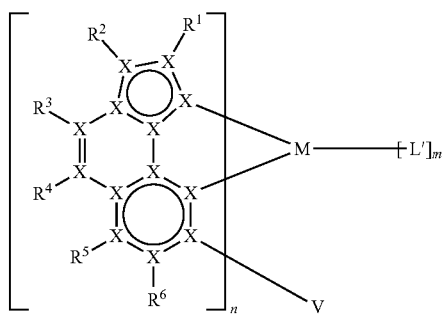

formula (104)

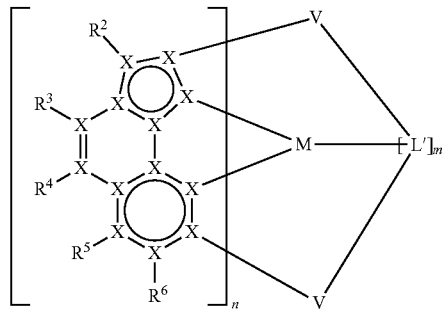

where the following applies to the symbols and indices used:

M is selected from the group consisting of iridium, platinum, copper and gold;

$R^1$ to $R^7$ are on each occurrence, identically or differently, H, D, F, Cl, Br, I, $N(R^8)_2$, CN, $NO_2$, $Si(R^8)_3$, $B(OR^8)_2$, $C(=O)R^8$, $P(=O)(R^8)_2$, $S(=O)R^8$, $S(=O)_2R^8$, $OSO_2R^8$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^8$, where one or more non-adjacent $CH_2$ groups is optionally replaced by $R^8C=CR^8$, $C\equiv C$, $Si(R^8)_2$, $Ge(R^8)_2$, $Sn(R^8)_2$, C=O, C=S, C=Se, $C=NR^8$, $P(=O)(R^8)$, SO, $SO_2$, $NR^8$, O, S or $CONR^8$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which is optionally substituted by one or more radicals $R^8$, or an aralkyl or heteroaralkyl group having 5 to 60 aromatic ring atoms, which is optionally substituted by one or more radicals $R^8$, or a diarylamino group, diheteroarylamino group or arylheteroarylamino group having 10 to 40 aromatic ring atoms, which is optionally substituted by one or more radicals $R^8$; $R^1$ and $R^2$ and/or $R^2$ and $R^3$ and/or $R^4$ and $R^5$ and/or $R^5$ and $R^6$ and/or $R^6$ and $R^7$ here optionally forms a mono- or polycyclic, aliphatic, aromatic and/or benzo-fused ring system with one another; furthermore, $R^3$ and $R^4$ optionally form a mono- or polycyclic, aliphatic ring system with one another;

with the proviso that $R^1$ to $R^7$ represent a free electron pair if the group X to which these radicals $R^1$ to $R^7$ are bonded is a nitrogen atom with a saturated valence;

$R^8$ is on each occurrence, identically or differently, H, D, F, Cl, Br, I, $N(R^9)_2$, CN, $NO_2$, $Si(R^9)_3$, $B(OR^9)_2$, $C(=O)R^9$, $P(=O)(R^9)_2$, $S(=O)R^9$, $S(=O)_2R^9$, $OSO_2R^9$, a straight-chain alkyl, alkoxy or thioalkoxy group having 1 to 40 C atoms or an alkenyl or alkynyl group having 2 to 40 C atoms or a branched or cyclic alkyl, alkoxy or thioalkoxy group having 3 to 40 C atoms, each of which is optionally substituted by one or more radicals $R^9$, where one or more non-adjacent $CH_2$ groups is optionally replaced by $R^9C=CR^9$, $C\equiv C$, $Si(R^9)_2$, $Ge(R^9)_2$, $Sn(R^9)_2$, C=O, C=S, C=Se, $C=NR^9$, $P(=O)(R^9)$, SO, $SO_2$, $NR^9$, O, S or $CONR^9$ and where one or more H atoms is optionally replaced by D, F, Cl, Br, I, CN or $NO_2$, or an aromatic or heteroaromatic ring system having 5 to 60 aromatic ring atoms, which optionally in each case be substituted by one or more radicals $R^9$, or an aryloxy or heteroaryloxy group having 5 to 60 aromatic ring atoms, which is optionally substituted by one or more radicals $R^9$, or an aralkyl or heteroaralkyl group having 5 to 60 aromatic ring atoms, which is optionally substituted by one or more radicals $R^9$, or a diarylamino group, diheteroarylamino group or arylheteroarylamino group having 10 to 40 aromatic ring atoms, which is optionally substituted by one or more radicals $R^9$; two or more adjacent radicals $R^8$ here may form a mono- or polycyclic, aliphatic or aromatic ring system with one another;

$R^9$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^9$ here may also form a mono- or polycyclic, aliphatic or aromatic ring system with one another;

L' is, identically or differently on each occurrence, any desired co-ligand;

n is 1, 2, 3 or 4;

m is 0, 1, 2, 3, 4, 5 or 6;

V represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L', and wherein the compounds of formula (1) are uncharged.

\* \* \* \* \*